US010301285B2

(12) United States Patent
Miller et al.

(10) Patent No.: US 10,301,285 B2
(45) Date of Patent: *May 28, 2019

(54) COMPOUNDS FOR TREATMENT OF CANCER

(71) Applicants: University of Tennessee Research Foundation, Knoxville, TN (US); GTx, Inc., Memphis, TN (US)

(72) Inventors: Duane D. Miller, Collierville, TN (US); Jianjun Chen, Knoxville, TN (US); James T. Dalton, Ann Arbor, MI (US); Chien-Ming Li, Fremont, CA (US); Sunjoo Ahn, Daejeon (KR); Wei Li, Germantown, TN (US)

(73) Assignees: GTX, INC., Memphis, TN (US); UNIVERSITY OF TENNESSEE RESEARCH FOUNDATION, Noxville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/692,597

(22) Filed: Apr. 21, 2015

(65) Prior Publication Data
US 2018/0093971 A1 Apr. 5, 2018

Related U.S. Application Data

(63) Continuation of application No. 14/049,950, filed on Oct. 9, 2013, now Pat. No. 9,029,408, which is a continuation-in-part of application No. 13/676,650, filed on Nov. 14, 2012, now Pat. No. 9,447,049, which is a continuation-in-part of application No. 13/216,927, filed on Aug. 24, 2011, now Pat. No. 8,822,513, which is a continuation-in-part of application No. 12/981,233, filed on Dec. 29, 2010, now Pat. No. 9,334,242, which is a continuation-in-part of application No. 12/485,881, filed on Jun. 16, 2009, now Pat. No. 8,592,465.

(60) Provisional application No. 61/376,675, filed on Aug. 24, 2010, provisional application No. 61/315,790, filed on Mar. 19, 2010, provisional application No. 61/309,360, filed on Mar. 1, 2010, provisional application No. 61/061,875, filed on Jun. 16, 2008.

(51) Int. Cl.
| C07D 403/04 | (2006.01) |
|---|---|
| A61K 31/4178 | (2006.01) |
| C07D 233/02 | (2006.01) |
| C07D 233/22 | (2006.01) |
| C07D 233/54 | (2006.01) |
| C07D 401/04 | (2006.01) |
| C07D 401/06 | (2006.01) |
| C07D 413/04 | (2006.01) |
| C07D 413/06 | (2006.01) |
| C07D 417/04 | (2006.01) |
| C07D 417/06 | (2006.01) |
| C07D 263/06 | (2006.01) |
| C07D 263/14 | (2006.01) |
| C07D 263/32 | (2006.01) |
| C07D 277/04 | (2006.01) |
| C07D 277/24 | (2006.01) |
| C07D 277/28 | (2006.01) |
| C07D 277/56 | (2006.01) |
| A61K 45/06 | (2006.01) |

(52) U.S. Cl.
CPC ........ *C07D 403/04* (2013.01); *A61K 31/4178* (2013.01); *A61K 45/06* (2013.01); *C07D 233/02* (2013.01); *C07D 233/22* (2013.01); *C07D 233/54* (2013.01); *C07D 263/06* (2013.01); *C07D 263/14* (2013.01); *C07D 263/32* (2013.01); *C07D 277/04* (2013.01); *C07D 277/24* (2013.01); *C07D 277/28* (2013.01); *C07D 277/56* (2013.01); *C07D 401/04* (2013.01); *C07D 401/06* (2013.01); *C07D 413/04* (2013.01); *C07D 413/06* (2013.01); *C07D 417/04* (2013.01); *C07D 417/06* (2013.01)

(58) Field of Classification Search
None
See application file for complete search history.

(56) References Cited

U.S. PATENT DOCUMENTS

| 3,772,315 A | 11/1973 | Regel et al. |
|---|---|---|
| 4,721,712 A | 1/1988 | Kadin |
| 4,987,132 A | 1/1991 | Mase et al. |
| 5,514,690 A | 5/1996 | Atwal et al. |
| 6,080,764 A | 6/2000 | Chihiro et al. |
| 6,706,717 B2 | 3/2004 | Barrish et al. |

(Continued)

FOREIGN PATENT DOCUMENTS

| EP | 0279681 A2 | 8/1988 |
|---|---|---|
| EP | 0499987 A1 | 8/1992 |

(Continued)

OTHER PUBLICATIONS

U.S. Appl. No. 14/773,265, filed Sep. 2015, Wang, Jin.*

(Continued)

*Primary Examiner* — Michael Barker
(74) *Attorney, Agent, or Firm* — Mark S. Cohen; Pearl Cohen Zedek Latzer Baratz LLP

(57) ABSTRACT

The present invention relates to a compound of formula XXII and a compound of formula 17ya, which are defined as anywhere in the specification, to a composition comprising the same, and to a method of using thereof in the treatment of various forms of cancer.

25 Claims, 32 Drawing Sheets

(56) References Cited

U.S. PATENT DOCUMENTS

| | | | |
|---|---|---|---|
| 6,828,344 B1 | 12/2004 | Seehra et al. | |
| 7,307,093 B2 | 11/2007 | Miller et al. | |
| 7,585,859 B2 | 9/2009 | Ibrahim et al. | |
| 9,029,408 B2* | 5/2015 | Miller | C07D 233/02 |
| | | | 514/370 |
| 10,022,356 B2* | 7/2018 | Wang | A61K 31/337 |
| 2003/0225102 A1 | 4/2003 | Sankaranarayanan | |
| 2003/0144329 A1 | 7/2003 | Pfahl et al. | |
| 2004/0192743 A1 | 9/2004 | Mjalli et al. | |
| 2004/0248957 A1 | 12/2004 | Lockhart et al. | |
| 2004/0267017 A1 | 12/2004 | Bierer et al. | |
| 2005/0131014 A1 | 6/2005 | Collini et al. | |
| 2005/0256170 A1 | 11/2005 | Oxford et al. | |
| 2006/0014740 A1 | 1/2006 | Miller et al. | |
| 2006/0040998 A1 | 2/2006 | Miller et al. | |
| 2006/0041006 A1 | 2/2006 | Ibrahim et al. | |
| 2006/0154915 A1 | 7/2006 | Corte et al. | |
| 2006/0189618 A1 | 8/2006 | Pelletier | |
| 2006/0211603 A1 | 9/2006 | Raju et al. | |
| 2006/0252793 A1 | 11/2006 | Ameriks et al. | |
| 2007/0155807 A1 | 5/2007 | Miller et al. | |
| 2007/0167622 A1 | 7/2007 | Gillespie et al. | |
| 2008/0125418 A1 | 5/2008 | Babin et al. | |
| 2008/0146555 A1 | 6/2008 | Caligiuri et al. | |
| 2008/0255213 A1 | 10/2008 | Miller et al. | |
| 2009/0143446 A1 | 4/2009 | Miller et al. | |
| 2009/0275575 A1 | 11/2009 | Choi et al. | |
| 2009/0326020 A1 | 12/2009 | Miller et al. | |
| 2011/0257196 A1 | 10/2011 | Lu et al. | |
| 2012/0053185 A1 | 3/2012 | Coopersmith et al. | |
| 2012/0071524 A1 | 3/2012 | Lu et al. | |
| 2012/0196879 A1 | 8/2012 | Dumble et al. | |
| 2013/0197049 A1 | 8/2013 | Li et al. | |

FOREIGN PATENT DOCUMENTS

| | | |
|---|---|---|
| EP | 0513387 | 11/1992 |
| EP | 549364 | 6/1993 |
| EP | 0585014 A2 | 3/1994 |
| EP | 535906 | 6/2005 |
| EP | 1637529 | 3/2006 |
| EP | 1832585 | 9/2007 |
| EP | 1834954 | 9/2007 |
| EP | 2050749 | 4/2009 |
| EP | 2 065 369 | 6/2009 |
| JP | 2001-240593 A | 9/2001 |
| KR | 20110062351 A | 6/2011 |
| RU | 2139283 C1 | 10/1999 |
| RU | 2141956 | 11/1999 |
| RU | 97114846 A | 11/1999 |
| WO | WO 92/14732 | 9/1992 |
| WO | WO 1999/033827 A1 | 7/1999 |
| WO | WO 01/17992 | 3/2001 |
| WO | WO 2001/047875 A1 | 7/2001 |
| WO | WO 01/85685 A1 | 11/2001 |
| WO | WO 02/085899 | 10/2002 |
| WO | WO 03/016338 A1 | 2/2003 |
| WO | WO 2006/018188 A2 | 2/2003 |
| WO | WO 03/027076 | 4/2003 |
| WO | WO 003/027085 A2 | 4/2003 |
| WO | WO 03/037332 | 5/2003 |
| WO | WO 2003/040107 A1 | 5/2003 |
| WO | WO 03/090680 | 11/2003 |
| WO | WO 2004/052280 | 6/2004 |
| WO | WO 2004/072068 A1 | 8/2004 |
| WO | WO 2004/091610 A1 | 10/2004 |
| WO | WO 2005/000940 A1 | 1/2005 |
| WO | WO 2005/009940 A1 | 2/2005 |
| WO | WO 2005/014534 A1 | 2/2005 |
| WO | WO 2005049591 A1 | 6/2005 |
| WO | WO 2005/086902 | 9/2005 |
| WO | WO 2006/018443 A1 | 2/2006 |
| WO | WO 2006/063585 | 6/2006 |
| WO | WO 2006/076706 | 7/2006 |
| WO | WO 2006/078287 | 7/2006 |
| WO | WO 2006/127587 | 11/2006 |
| WO | WO 2007/016979 | 2/2007 |
| WO | WO 2007/042546 A1 | 4/2007 |
| WO | WO 2007/058338 | 5/2007 |
| WO | WO 2007/096259 A1 | 8/2007 |
| WO | WO 2007/104558 | 9/2007 |
| WO | WO 2007/115805 | 10/2007 |
| WO | WO 2007/146230 A2 | 12/2007 |
| WO | WO 2008/006873 | 1/2008 |
| WO | WO 2008/014291 A2 | 1/2008 |
| WO | WO 2008/019357 A2 | 3/2008 |
| WO | WO 2008/030448 | 3/2008 |
| WO | WO 2008036067 A2 | 3/2008 |
| WO | WO 2008/038955 | 4/2008 |
| WO | WO 2008/079277 | 7/2008 |
| WO | WO 2008128179 A1 | 10/2008 |
| WO | WO 2009070645 A1 | 4/2009 |
| WO | WO 2009/076454 A2 | 6/2009 |
| WO | WO 2010/074776 A | 7/2010 |
| WO | WO 2011/047238 | 4/2011 |
| WO | WO 2011/109059 A1 | 9/2011 |
| WO | WO 2012/136776 A1 | 10/2012 |

OTHER PUBLICATIONS

Alvarez et al.; "Exploring the effect of 2,3,4-trimethoxy-phenyl moiety as a component of indolephenstatins", European journal of medicinal chemistry 2010, 45 (2), 588-97.

Bai et al.; "Identification of the cysteine residue of beta-tubulin alkylated by the antimitotic agent 2,4- dichlorobenzyl thiocyanate, facilitated by separation of the protein subunits of tubulin by hydrophobic column chromatography", Biochemistry 1989, 28 (13), 5606-12.

Bai et al.; "Mapping the binding site of colchicinoids on beta-tubulin. 2-Chloroacetyl-2-demethylthiocolchicine covalently reacts predominantly with cysteine 239 and secondarily with cysteine 354", J Biol Chem 2000, 275 (51), 40443-52.

Brancale et al.; "Indole, a core nucleus for potent inhibitors of tubulin polymerization", Med Res Rev 2007, 27 (2), 209-38.

Burns; "Analysis of the colchicine-binding site of beta-tubulin", FEBS letters 1992, 297 (3), 205-8.

Chen e al.; "Discovery of novel 2-aryl-4-benzoylimidazole (ABI-III) analogues targeting tubulin polymerization as antiproliferative agents", J Med Chem 2012, 55 (16), 7285-9.

Chen et al.; "Synthesis and antiproliferative activity of novel 2-aryl-4-benzoyl-imidazole derivatives targeting tubulin polymerization", Bioorg Med Chem 2011, 19 (16), 4782-95.

Cuccia et al.", A novel and efficient synthesis of 4-phenyl-2-chloropyrimidine from acetophenone cyanoimines", Synthetic Communications 2002, 32, (19), 3011-3018.

Fisher et al.; "Clinical studies with modulators of multidrug resistance",. Hematology/oncology clinics of North America 1995, 9, (2), 363-82.

Goncalves et al.; "Resistance to Taxol in lung cancer cells associated with increased microtubule dynamics", Proc Natl Acad Sci USA 2001, 98, (20), 11737-42.

Gottesman et al.; "The multidrug transporter, a double-edged sword",. J Biol Chem 1988, 263, (25), 12163-6.

Green et al. "Beta-Tubulin mutations in ovarian cancer using single strand conformation analysis-risk of false positive results from paraffin embedded tissues", Cancer letters 2006, 236, (1), 14854.

Hennenfent et al.; "Novel formulations of taxanes: a review. Old wine in a new bottle?", Ann Oncol 2006, 17, (5), 735-49.

Jordan et al.; "Microtubules as a target for anticancer drugs",. Nature reviews. Cancer 2004, 4 (4), 253-65.

Kiselyov et al.; "Recent progress in discovery and development of antimitotic agents",. Anticancer Agents Med Chem 2007, 7, (2), 189-208.

Kuo et al.; "BPR0L075, a novel synthetic indole compound with antimitotic activity in human cancer cells, exerts effective antitumoral activity in vivo",. Cancer Res 2004, 64 (13), 4621-8.

(56) References Cited

OTHER PUBLICATIONS

Leslie et al.; "Multidrug resistance proteins: role of P-glycoprotein, MRP1, MRP2, and BCRP (ABCG2) in tissue defense", Toxicology and Applied Pharmacology 2005, 204, (3), 216-237.
Li et al.; "Drug metabolism and pharmacokinetics of 4-substituted methoxybenzoyl-aryl-thiazoles. Drug metabolism and disposition: the biological fate of chemicals", 2010, 38 (11), 2032-9.
Li et al.; "Biological activity of 4-substituted methoxybenzoyl-aryl-thiazole: an active microtubule inhibitor", Cancer Res 2011, 71 (1), 216-24.
Liu et al.; "Antiproliferative properties of piperidinylchalcones", Bioorg Med Chem 2006, 14 (1), 153-63.
Llauger et al.; "Evaluation of 8-arylsulfanyl, 8-arylsulfoxyl, and 8-arylsulfonyl adenine derivatives as inhibitors of the heat shock protein 90",. J Med Chem 2005, 48, (8), 2892-905.
Lu et al.; "An overview of tubulin inhibitors that interact with the colchicine binding site",. Pharmaceutical research 2012, 29 (11), 2943-71.
Lu et al.; "Design, synthesis, and SAR studies of 4-substituted methoxybenzoyl-aryl-thiazoles analogues as potent and orally bioavailable anticancer agents",. J Med Chem 2011, 54 (13), 4678-93.
Lu et al.; "Discovery of 4-substituted methoxybenzoyl-aryl-thiazole as novel anticancer agents: synthesis, biological evaluation, and structure-activity relationships", J Med Chem 2009, 52 (6), 1701-11.
Lu et al.; "Synthesis, in vitro structure-activity relationship, and in vivo studies of 2-arylthiazolidine-4-carboxylic acid amides as anticancer agents",. Bioorg Med Chem 2010, 18, (2), 47795.
Luo et al.; ABT-751, "a novel tubulin-binding agent, decreases tumor perfusion and disrupts tumor vasculature", Anticancer Drugs 2009, 20, (6), 483-92.
Mauer et al.; "A phase II study of ABT-751 in patients with advanced non-small cell lung cancer", J Thorac Oncol 2008, 3, (6), 631-6.
Mickisch et al.; "Chemotherapy and chemosensitization of transgenic mice which express the human multidrug resistance gene in bone marrow: efficacy, potency, and toxicity", Cancer Res 1991, 51, (19), 5417-24.
Miller; "Tricyclic norephedrine analogs. Isomeric 9-hydroxy-10-amino-1,2,3,4,4a,9,10,10a-(trans-4a, 10a)octahydrophenanthrenes", 1969.
Monzo et al.; "Paclitaxel resistance in non-small-cell lung cancer associated with beta-tubulin gene mutations",. J Clin Oncol 1999, 17, (6), 1786-93.
Nam; "Combretastatin A-4 analogues as antimitotic antitumor agents", Curr Med Chem 2003, 10 (17), 1697-722.
Pettit et al.; "Antineoplastic agents. 379. Synthesis of phenstatin phosphate", J Med Chem 1998, 41 (10), 1688-95.
Pletnev et al.; "Carbopalladation of nitriles: synthesis of 2,3-diarylindenones and polycyclic aromatic ketones by the Pd-catalyzed annulation of alkynes and bicyclic alkenes by 2-iodoarenenitriles", J Org Chem 2002, 67, (26), 927687.
Ray et al.; "Role of B-ring of colchicine in its binding to tubulin", J Biol Chem 1981, 256 (12), 6241-4.
Rustin et al.; "A Phase Ib trial of CA4P (combretastatin A-4 phosphate), carboplatin, and paclitaxel in patients with advanced cancer", Br J Cancer 2010, 102, (9), 1355-60.).
Shan et al.; "Selective, covalent modification of beta-tubulin residue Cys-239 by T138067, an antitumor agent with in vivo efficacy against multidrug-resistant tumors", Proceedings of the National Academy of Sciences of the United States of America 1999, 96 (10), 5686-91.
Slominski et al.; The role of CYP11A1 in the production of vitamin D metabolites and their role in the regulation of epidermal functions, The Journal of steroid biochemistry and molecular biology 2013.
Sriram et al.; "Design, synthesis and biological evaluation of dihydronaphthalene and benzosuberene analogs of the combretastatins as inhibitors of tubulin polymerization in cancer chemotherapy", Bioorg Med Chem 2008, 16 (17), 8161-71.
Ten Tije et al; "Pharmacological effects of formulation vehicles : implications for cancer chemotherapy", Clin Pharmacokinet 2003, 42, (7), 665-85.
Wang et al.; "Paclitaxel resistance in cells with reduced beta-tubulin", Biochimica et Biophysica Acta, Molecular Cell Research 2005, 1744, (2), 245-255.
Wang et al.; "Novel tubulin polymerization inhibitors overcome multidrug resistance and reduce melanoma lung metastasis", Pharmaceutical research 2012, 29 (11), 3040-52.
Xiao et al.; "Discovery of 4-Aryl-2-benzoyl-imidazoles as tubulin polymerization inhibitor with potent antiproliferative properties", J Med Chem 2013, 56 (8), 3318-29.
Yoshino et al.; "Novel sulfonamides as potential, systemically active antitumor agents", *J Med Chem* 1992, 35, (13), 2496-7.
Aitken et al.; "", J. Chem. Res. 2:76, 1998.
Anderson et al., "Design, synthesis, antineoplastic activity, and chemical properties of bis(carbamate) derivatives of 4,5-bis(hydroxymethyl)imidazole" J. Med. Chem. 32(1), 119-127, 1989.
Bergeron et al., "Desazadesmethyldesferrethiocin analogues as orally effective iron chelators", J. Med. Chem. 42:95-108, 1999.
Bergeron et al., "Partition-variant desferrithiocin analogues: organ targeting and increased iron clearance" J. Med. Chem, vol. 48, pp. 821-831.
Bergeron, "Evaluation of Desferrethiocin and its synthetic analogs as orally effective iron chelators", J. Med. Chem. 34:2072-8, 1991.
Byrn et al.; "", Solid-State Chemistry of Drugs, $2^{nd}$, Chapter 11:Hydrates and Solvates, pp. 233-247, 1999.
Chen et al., "Synthesis and Antiproliferative Activity of Imidazole and Imidazoline Analogs for Melanoma," Bioorg. Med. Chem. Lett. 18(11 ):3183-3187 (2008).
Delgado et al.; "Synthesis and conformational assignment of cis- and trans-2-amino-1-arylcyclohexanols", Can. J. Chem. 63, 3186 (1985).
Deswal, S. et al.: 'Quantitative structure activity relationship studies of aryl heterocycle-based thrombin inhibitors' European Journal of Medicinal Chemistry vol. 41, 2006, pp. 1339-1346, XP024993923.
Dothager et al., "Synthesis and identification of small molecules that potently induce apoptosis in melanoma cells through G1 cell cycle arrest", J. Am. Chem. Soc. 127:8686-8696, 2005.
Giordano et al., New Strategy for Racemization of 2-Amino-1, 3-propanediols, Key Intermediates for the Synthesis of Antibiotic Drugs, Tetrahedron Letters, vol. 29, No. 43, 1988, pp. 5561-5564.
Gududuru et al., "Discovery of 2-Arylthiazolidine-4-Carboxylic Acid Amides as a New Class of Cytotoxic Agents for Prostate Cancer," J. Med. Chem. 48:2584-2588 (2005).
Gududuru et al., "SAR Studies of 2-Arylthiazolidine-4-Carboxylic Acid Amides: A Novel Class of Cytotoxic Agents for Prostate Cancer," Bioorg. Med. Chem. Lett. 15:4010-4013 (2005).
Gududuru et al., "Synthesis and Antiproliferactive Activity of 2-Aryl-4-Oxo-Thiazolidin-3-Yl-Amides for Prostate Cancer," Bioorg. Med. Chem. Lett. 14:5289-5293 (2004).
Guo et al., Expression and Function of Lysophosphatidic Acid LPA1 Receptor in Prostate Cancer Cells, Endocrinology, 2006, vol. 147, pp. 4883-4892.
Hilt et al.; "Synthesis of Hexahydrocyclopenta[c]furans by an Intramolecular Iron-Catalyzed Ring Expansion Reaction", Advanced Synthesis & Catalysis vol. 349, Issue 11-12, pp. 2018-2026, Aug. 6, 2007.
Holmes et al., "Reagents for Combinatorial Organic Synthesis: Development of a New o-Nitrobenzyl Photolabile Linker for Solid Phase Syntheses," J. Org. Chem. 60:2318-2319 (1995).
Hsu et al., Optically active derivatives of imidazolines. alpha-Adrenergic blocking properties J. Med. Chem., 1980, vol. 23(11), pp. 1232-1235.
International Search Report for International Application No. PCT/US09/47572 dated Jun. 9, 2010.
Jesberger et al., Synthesis, 2003, 1929-1958.
Jikken Kagaku Kouza 15 (Course of Experimental Chemistry 15) 5th edition—Synthesis of organic compounds III—Aldehydes, ketones and quinines, pp. 241-251, Nov. 30, 2003.
Jikken Kagaku Kouza 21 (Course of Experimental Chemistry 21) 4th edition—Synthesis of organic compounds III—Aldehydes, ketones and quinines, pp. 241-251, Feb. 5, 1991.

(56) References Cited

OTHER PUBLICATIONS

Kue et al., Essential Role for G Proteins in Prostate Cancer Cell Growth and Signaling, J. Urol., 2002, vol. 164, pp. 2162-2167.
Lange, U.E.W. et al: 'Orally active thrombin inhibitors. Part 2: Optimization of the P2-moiety' Bioorganic & Medicinal Chemistry Letters vol. 16, 2006, pp. 2648-2653, XP025106813.
Lee et al.; "The Safety, Tolerability, Pharmacokinetics, and Pharmacodynamics of Single Oral Doses of RO5068760, an MEK inhibitor, in Healthy Volunteers: Assessment of Target Suppression", Abstract, The Journal of clinical Pharmacology, 2010, vol. 50, Iss 12, pp. 1397-1405.
Li et al., "Structure-Activity Relationship Studies of Arythiazolidine Amides as Selective Cytotoxic Agents for Melanoma," Anticancer Research 27:883-888 (2007).
Li et al., "Synthesis and Antiproliferative Activity of Thiazolidine Analogs for Melanoma," Bioorg. Med. Chem. Lett. 17:4113-4117(2007).
Lu et al., "Discovery of 4-Substituted Methoxybenzoyl-aryl-thiazole as Novel Anticancer Agents: Synthesis, Biological Evaluation, and Structure-Activity Relationships," J. Med. Chem. 52:1701-1711 (2009).
Lu et al., Synthesis and Biological Evaluation of 2-Arylthiazolidine-4-Caboxylic Acid Amides for Melanoma and Prostate Cancer, Abstracts of Papers, 234th ACS National Meeting, Boston, MA, United Staes, Aug. 19-23, 2007, MEDI-304.
Mahboobi et al., Synthesis of Naturally Occurring Pyrazine and Imidazole Alkaloids from Botryllus Leachi, Monatshefte Fuer Chemie, vol. 135, No. 3, 2004, pp. 333-342.
Margolis et al., "Addition of colchicine-tubulin complex to microtubule ends: the mechanism of substroichiometric colchicine poisoning", Proc. Natl. Acad. Sci. 74:3466-3470, 1977.
Meyer et al., Tetrahedron: Asymmetry, 2003, vol. 14, pp. 2229-2238.
Morissette et al.; "", Adv. Drug Delivery Rev., 2004, 56, pp. 275-300.
Nahm et al., "N-methoxy-N-methylamides as effective acylating agents", Tetrahedron Letters, 22:3815-3818, 1981.
Office Action for Japanese Application No. 2012-072925 dated Nov. 19, 2013.
Schubert H et al: "N-Alkyl-Uno N-Alkoxyderivate Des 3-Hyd Roxy-2,5-0 I Phenyl-Pyrazine",Journal Fuer Praktische Chemie (Leipzig) vol. 33, 1966,pp. 265-276, XP008066209.
Schubert et al: "Kristallin-flussige Hydroxypyrazine", Zeitschrift Fuer Chemie (Stuttgart) vol. 4, 1964, p. 228, XP009190406.
Office Action EP Application No. 10 847 161.6 dated Jun. 16, 2016.
Patel et al. "Clinical Responses to Selumetinib (AZD6244; ARRY-142886)-Based Combination Therapy Startified by Gene Mutations in Patients With Metastatic Melanoma" Cancer, Feb. 2013, vol. 119, No. 4, pp. 799-805.
Haass et al. "The Mitogen-Activated Protein/Extracellular Signal-Regulated Kinase Kinase Inhibitor AZD6244 (ARRY-142886) Induces Growth Arrest in Melanoma Cells and Tumor Regression When Combined with Docetaxel" Clin. Cancer. Res., 2008, vol. 14(1), pp. 230-239.
Tesei et al. "Low-dose taxotere enhances the ability of sarafenib to induce apoptosis in gastric cancer models" J. Cell. Mol. Med., 2011, vol. 15(2), pp. 316-326.
Wang et al. "Novel Tubulin Polymerization Inhibitors Overcome Multidrug Resistance and Reduce Melanoma Lung Metastasis" Pharm. Res., 2012, vol. 29(11), pp. 3053-3063.
J. Wang et al: "Synergistic Combination of Novel Tubulin Inhibitor Abi-274 and Vemurafenib Overcomes Vemurafenib Acquired Resistance in Brafv600e Melanoma". Molecular Cancer Therapeutics. vol. 13. No. 1. Nov. 18, 2013 (Nov. 18, 2013). pp. 16-26
Chien-Ming Li et al: "Orally Bioavailable Tubulin Antagonists for Paclitaxel-Refractory Cancer". Pharmaceutical Research. Kluwer Academic Publishers-Plenum Publishers. Nl. vol. 29. No. 11.Jul. 4, 2012 (Jul. 4, 2012). pp. 3053-3063.
Jianjun Chen et al: "Discovery of Novel 2-Aryl-4-Benzoyl-Imidazole (Abi Iii) Analogues Targeting Tubulin Polymerization as Antiproliferative Agents". Journal of Medicinal Chemistry. vol. 55. No. 16. Aug. 23, 2012 (Aug. 23, 2012). pp. 7285-7289.
R. N. Amaria et al: "Therapeutic Options in Cutaneous Melanoma: Latest Developments". Therapeutic Advances in Medical Oncologyenglandjan 2016. vol. 3. No. 5. Sep. 1, 2011 (Sep. 1, 2011). pp. 245-25.
Qi et al., Lysophosphatidic Acid Stimulates Phospholipase D Activity and Cell Proliferation in PC-3 Human Prostate Cancer Cells, J. Cell, Physiol, 1998, vol. 174, pp. 261-272.
Raj et al., Guanosine Phosphate Binding Protein Coupled Receptors in Prostate Cancer: A Review, J. Urol., 2002, vol. 167, pp. 1458-1463.
Riedrich et al., "Peptide-embedded heterocycles by mild single and multiple Aza-Wittig ring closures" Angewandte Chemie, International Edition, 2007, vol. 46(15), .pp. 2701-2703.
Rouhi; "", A.M. Chem. & Eng. News, Feb. 24, 2003, 81(8), pp. 32-35.
Roy et al., Thiazole and Oxazole Peptides: biosynthesis and molecular machinery, Natural Product Reports, 1999, vol. 16, pp. 249-263; p. 249 scheme1.
Rubinstein et al., "Comparison of in vitro anticancer drug-screening data generated with a tetrazolium assay versus a protein assay against a diverse panel of human tumor cell lines", J. Natl. Cancer Inst. 82:1113-1118, 1990.
Sheppard et al., 3-(2-(3-Pyridinyl) thiazolidin-4-oyl) indoles, a Novel Series of Platelet Activating Factor Antagonists, Journal of Medicinal Chemistry, vol. 37, No. 13, 1997.
Staas, D. D.: 'Discovery of potent, selective 4-fluoroproline-based thrombin inhibitors with improved metabolic stability' Biorganic & Medicinal Chemistry vol. 14, 2006, pp. 6900-6916, XP025133602.
Stenhagen et al. Studies of Hydrocarbons Structurally Related to Phthiocerol, Journal Biological Chemistry, 1950, vol. 183, pp. 223-229; p. 224.
STN Search Report: Pavlova et al Khimiko-Farmatsevticheskii Zhurnal, 20(9), 1083-1088 (1986) (abstract only).
Supplementary Partial Search Report for European Patent Application No. EP 09 83 5407 dated Feb. 9, 2012.
Terasawa et al., "Cytotoxic activity of 5-benzoylimidazole and related compounds against human oral tumor cell lines", Anticancer Research, International Institute of Anticancer Research, vol. 21, 2001, pp. 1081-1086.
Tucker et al., Structure-Activity Relationships of Acyloxyamidine Cytomegalovirus DNA Polymerase Inhibitors, Bioorganic & Medical Chemistry, vol. 8, No. 3, 2000, pp. 601-615.
Williams et al., "Studies of mild dehydrogenations in heterocyclic systems", Tetrahedron Letters, 38:331-334, 1997.
Young, M.B. et al: 'Discovery and Evaluation of potent P1 Aryl Heterocycle-Based Thrombin Inhibitors' Journal of Medicinal Chemistry vol. 47, No. 12, 2004, pp. 2995-3008, XP003026047.
Zamri et al., "An improved stereocontrolled synthesis of pyochelin, siderophore of pseudomonas aeruginosa and burkholderia cepacia", Tetrahedron 56:249-256, 2000.
Duran et al.; "Novel alkaloids from the red ascidian botryllus leachi", Tetrahedron (Impact Factor: 2.8), Nov. 1999; 55(46):13225-13232.
Li et al.; "An Unusual Trifluoromethyl Elimination Reaction from the 4,4-Bis(trifluoromethyl)-5-hydroxyimidazoline Ring System", J Org Chem. Apr. 18, 1997;62(8):2550-2554.
Office Action for Russian Application No. 201 21 41 590 dated Dec. 25, 2014.
Office Action for U.S. Appl. No. 13/676,650 dated May 19, 2015.
Khalili B et al: "Novel one-pot synthesis of (4 or 5)-aryl-2-aryloyl-(1 H)imidazole in water and tauto-isomerization study using NMR", Tetrahedron, vol. 65, No. 34,Aug. 22, 2009, pp. 6882-6887, XP026348193.
Schubert et al: "Phasenbeziehungen zwischen Imidazolylketonen and Hydroxypyrazinen", Journal Fuer Praktische Chemie (Leipzig) vol. 24, 1964, pp. 125-130, XP009190407.
Greg Barsh et al: "Xviii Pasper 2013 Advances in Melanocyte and Melanoma Biology President Local Organizing Committee Past-President and Ifpcs Representative" Uw Hospital & Clinics. Sep. 1,

(56) References Cited

OTHER PUBLICATIONS 2013 (Sep. 1, 2013). Retrieved From The Internet: Url:Http//Onlinelibrary.Wiley.Com/Store/10.1111 Retrieved on Feb. 13, 2014 p. 762-783
Supplementary Partial European Search Report Corresponding to EP patent No. 14760577.8 dated Dec. 14, 2016.
Office Action for Chinese Patent Application No. 201480025267.4 dated Jun. 20, 2017.
Office Action for U.S. Appl. No. 14/773,265 dated Jul. 20, 2017.
Bellina, F et al., Novel imidazole-based combretastatin A-4 analogues: Evaluation of their in vitro antitumor activity and molecular modeling study of their binding to the colchicine site of tubulin, Bioorganic & Medicinal Chemistry Letters 16, pp. 5757-5762, 2006.
International Search Report for PCT Application PCT/US15/29270 dated Sep. 21, 2015.
Lu et al. "Design, Synthesis, and Biological Evaluation of Stable Colchicine Binding Site Tubulin Inhibitors as Potential Anticancer Agents" *J. Med. Chem.*, 2014, 57(17), pp. 7355-7366.
Office Action for U.S. Appl. No. 15/309,357 dated Jun. 21, 2017.
Office Action for Japanese Patent Application No. 2013-526130 dated Jun. 2, 2015.
Office Action for corresponding U.S. Appl. No. 15/270,359 dated Sep. 28, 2018.
Office Action for corresponding Japanes Application No. 2015-561618 dated Sep. 4, 2018.
Otsuka Kouki et al. "Cancer Gene Abnormalities and Frontier of Molecular Targeted Therapy" Journal of the Kyorin Medical Society, Jun. 2013, vol. 44 No. 2, pp. 71-80.

\* cited by examiner

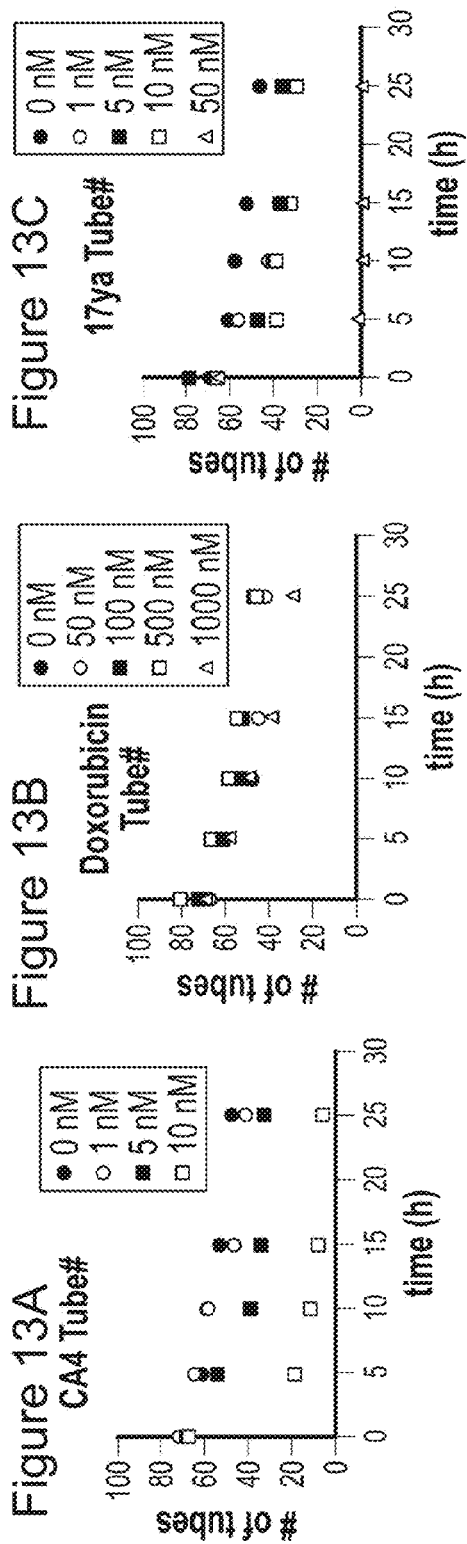
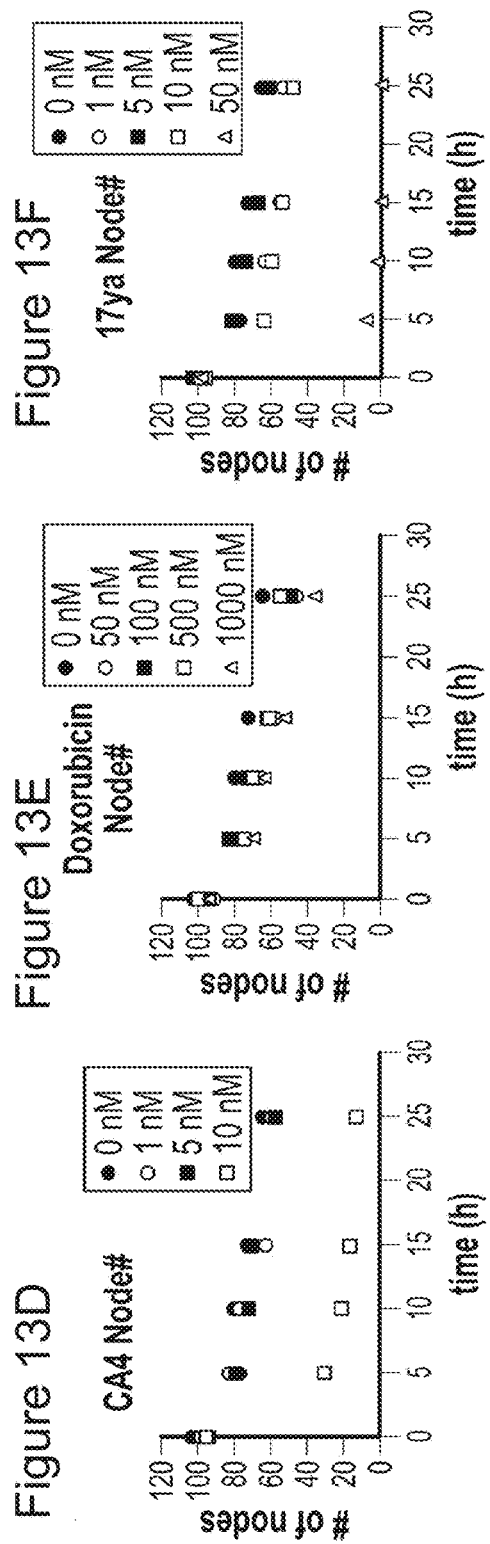

COMPOUNDS FOR TREATMENT OF CANCER

CROSS-REFERENCE TO RELATED APPLICATIONS

This Application is a Continuation Application of U.S. application Ser. No. 14/049,950 filed on Oct. 9, 2013 which is a Continuation-in-Part application of U.S. application Ser. No. 12/485,881 filed on Jun. 16, 2009, which claims the benefit of U.S. Provisional Patent Application Ser. No. 61/061,875, filed on Jun. 16, 2008, both of which are incorporated herein by reference in their entirety.

This Application is a Continuation-in-Part application of U.S. application Ser. No. 13/676,650, filed on Nov. 14, 2012, which is a continuation-in-part application of U.S. application Ser. No. 13/216,927, filed on Aug. 24, 2011, which is a continuation-in-part application of U.S. application Ser. No. 12/981,233, filed on Dec. 29, 2010, which claims the benefit of U.S. Provisional Application Ser. No. 61/376,675, filed on Aug. 24, 2010; U.S. Provisional Application Ser. No. 61/315,790, filed on Mar. 19, 2010; and U.S. Provisional Application Ser. No. 61/309,360, filed on Mar. 1, 2010, all of which are incorporated herein by reference in their entirety.

GOVERNMENT INTEREST STATEMENT

This invention was made in whole or in part with government support under Grant Number 1R15CA125623-01A2 and 1R01CA148706-01A1, awarded by the NIH (National Institutes of Health). This invention was also made with funding received from the U.S. Department of Defense under grant DAMD 17-01-1-0830 and the National Institutes of Health under Core Grant 21765. The U.S. government has certain rights in this invention.

FIELD OF THE INVENTION

The present invention relates to novel compounds having anti-cancer activity, compositions comprising the same, and their use for treating various forms of cancer.

BACKGROUND OF THE INVENTION

Cancer is the second most common cause of death in the United States, exceeded only by heart disease. In the United States, cancer accounts for 1 of every 4 deaths. The 5-year relative survival rate for all cancers patients diagnosed in 1996-2003 is 66%, up from 50% in 1975-1977 (*Cancer Facts & Figures* American Cancer Society: Atlanta, Ga. (2008)). This improvement in survival reflects progress in diagnosing at an earlier stage and improvements in treatment. Discovering highly effective anticancer agents with low toxicity is a primary goal of cancer research.

2-Aryl-thiazolidine-4-carboxylic acid amides (ATCAA) have been described as potent cytotoxic agents for both prostate cancer and melanoma (Li et al., "Synthesis and Antiproliferative Activity of Thiazolidine Analogs for Melanoma," *Bioorg. Med. Chem. Lett.* 17:4113-7 (2007); Li et al., "Structure-Activity Relationship Studies of Arylthiazolidine Amides as Selective Cytotoxic Agents for Melanoma," *Anticancer Res.* 27:883-888 (2007); Lu et al., "Synthesis and Biological Evaluation of 2-Arylthiazolidine-4-Carboxylic Acid Amides for Melanoma and Prostate Cancer," *Abstracts of Papers*, 234th ACS National Meeting, Boston, Mass., United States, Aug. 19-23, 2007, MEDI-304; Gududuru et al., "SAR Studies of 2-Arylthiazolidine-4-Carboxylic Acid Amides: A Novel Class of Cytotoxic Agents for Prostate Cancer," *Bioorg. Med. Chem. Lett.* 15:4010-4013 (2005); Gududuru et al., "Discovery of 2-Arylthiazolidine-4-Carboxylic Acid Amides as a New Class of Cytotoxic Agents for Prostate Cancer," *J. Med. Chem.* 48:2584-2588 (2005)). These 2-aryl-thiazolidine-4-carboxylic acid amides were designed from the lysophosphatidic acid (LPA) structure with a lipid chain. This design choice was directed toward inhibition of GPCR (guanine-binding protein-coupled receptor) signaling, which is involved in proliferation and survival of prostate cancer (Raj et al., "Guanosine Phosphate Binding Protein Coupled Receptors in Prostate Cancer: A Review," *J. Urol.* 167:1458-1463 (2002); Kue et al., "Essential Role for G Proteins in Prostate Cancer Cell Growth and Signaling," *J. Urol.* 164:2162-7 (2000); Guo et al., "Expression and Function of Lysophosphatidic Acid LPA1 Receptor in Prostate Cancer Cells," *Endocrinology* 147:4883-4892 (2006); Qi et al., "Lysophosphatidic Acid Stimulates Phospholipase D Activity and Cell Proliferation in PC-3 Human Prostate Cancer Cells," *J. Cell. Physiol.* 174:261-272 (1998)).

The most potent of the 2-aryl-thiazolidine-4-carboxylic acid amides could inhibit prostate cancer cells with an average $IC_{50}$ in the range from 0.7 to 1.0 μM and average $IC_{50}$ values against melanoma cells were 1.8-2.6 μM (Li et al., "Synthesis and Antiproliferative Activity of Thiazolidine Analogs for Melanoma," *Bioorg. Med. Chem. Lett.* 17:4113-7 (2007)). One preferred compound, (2RS, 4R)-2-phenyl-thiazolidine-4-carboxylic acid hexadecylamide, was sent to the United States National Cancer Institute 60 human tumor cell line anticancer drug screen (NCI-60). Results from NCI-60 assay showed that this compound could inhibit growth of all nine types of cancer cells with $IC_{50}$ values in the range from 0.124 μM (Leukemia, CCRF-CEM) to 3.81 μM (Non-Small Cell Lung Cancer, NCI-H522). Further improvement in anti-cancer activity of these compounds, in terms of their $IC_{50}$ values, would be desirable.

The present invention is directed to overcoming these and other deficiencies in the prior art.

SUMMARY OF THE INVENTION

In one aspect, the present invention provides a compound represented by formula XXII:

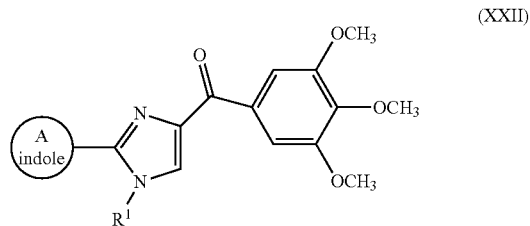

(XXII)

wherein
A is indolyl;
wherein said A is optionally substituted by substituted or unsubstituted O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, substituted or unsubstituted —$SO_2$-aryl, substituted or unsubstituted $C_1$-$C_5$ linear or branched alkyl, substituted or unsubstituted haloalkyl, substituted or unsubstituted alkylamino, substituted or unsubstituted aminoalkyl, —OCH$_2$Ph, substituted or unsubstituted —NHCO-alkyl, COOH, substituted or unsubstituted —C(O)Ph, substituted or unsubstituted C(O)O-alkyl, C(O)H, —C(O)NH$_2$, NO$_2$ or combination thereof; and i is an integer between 0-5;

R$_1$ is hydrogen, linear or branched, substituted or unsubstituted alkyl, substituted or unsubstituted aryl, —CH$_2$Ph, substituted benzyl, haloalkyl, aminoalkyl, —OCH$_2$Ph, substituted or unsubstituted SO$_2$-aryl, substituted or unsubstituted —(C=O)-aryl or OH; or an N-oxide thereof, or a pharmaceutically acceptable salt thereof.

In another aspect, the present invention provides a compound represented by formula 17ya:

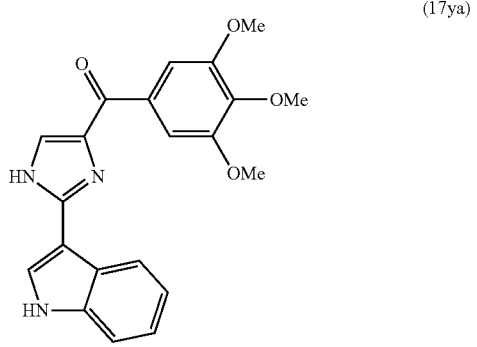 [SMILES: COc1cc(C(=O)c2c[nH]c(-c3c[nH]c4ccccc34)n2)cc(OC)c1OC]

(17ya)

or an N-oxide or a pharmaceutically acceptable salt thereof.

In another aspect, the present invention provides a compound represented by formula 17yab or 17yac:

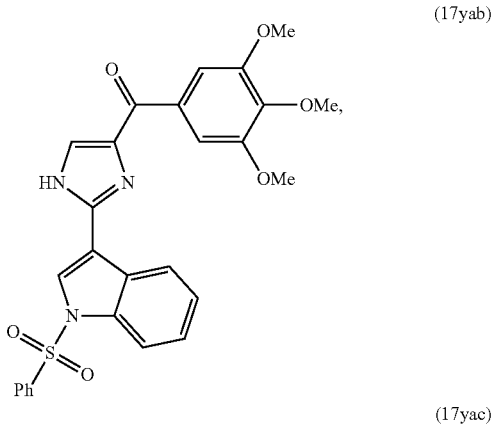

(17yab)

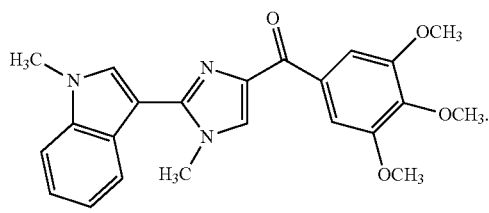

(17yac)

In another aspect, the present invention provides a pharmaceutical composition comprising a compound of formula XXII or 17ya, or an N-oxide thereof, or a pharmaceutically acceptable salt thereof, and at least one pharmaceutically acceptable carrier. In some embodiments, the pharmaceutical composition of the present invention is useful for the treatment of cancer.

In yet another aspect, the present invention provides a method of treating, suppressing, reducing the severity, reducing the risk, or inhibiting cancer comprising administering a compound of formula XXII or 17ya to a subject having cancer under conditions effective to treat the cancer. In some embodiments, said cancer is selected from the group consisting of prostate cancer, drug-resistant prostate cancer, breast cancer, ovarian cancer, drug-resistant ovarian cancer, skin cancer, melanoma, lung cancer, colon cancer, glioma, leukemia, renal cancer, CNS cancer, uterine cancer, drug-resistant uterine cancer, and combinations thereof. In some embodiments, said cancer is melanoma cancer. In certain embodiments, said cancer is metastatic melanoma. In other embodiments, said cancer is prostate cancer. In some embodiments, said cancer is ovarian cancer. In some embodiments, said administering is carried out in combination with another cancer therapy.

In yet another aspect, the present invention provides a method of treating a drug resistant tumor or tumors comprising administering a compound of formula XXII or 17ya to a subject suffering from cancer under conditions effective to treat the drug resistant tumor or tumors. In some embodiments, said cancer is melanoma cancer. In certain embodiments, said cancer is metastatic melanoma. In other embodiments, said cancer is prostate cancer. In some embodiments, said cancer is ovarian cancer. In some embodiments, said cancer is uterine cancer. In some embodiments, said administering is carried out in combination with another cancer therapy.

In yet another aspect, the present invention provides a method of destroying a cancerous cell comprising providing a compound of formula XXII or 17ya and contacting the cancerous cell with the compound under conditions effective to kill the cancer cell.

In one embodiment, the present invention provides a method of inhibiting, preventing, or slowing the progress of vascularization of a tumor comprising administering a compound of this invention to a subject having cancer under conditions effective to inhibit, prevent or slow the progress of vascularization of the tumor.

Other features and advantages of the present invention will become apparent from the following detailed description, examples, and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

FIG. 3A illustrates the effect of various dosages (10 nM, 50 nM, 200 nM, and 500 nM) of compound 8f relative to control. Amounts in excess of the $IC_{50}$ value illustrate a significant change in cell cycle distribution. FIG. 3B graphically illustrates the change in G2/M versus G1 cell cycle distribution.

FIG. 10A, competitive mass binding. Tubulin (1 mg/mL) and colchicine (1.2 µM) were incubated with various concentrations of podophyllotoxin, vinblastine, compounds 17ya, and 55. N=3; mean±SD. Podophyllotoxin and vinblastine were used as positive and negative controls, respectively. FIG. 10B, effect on tubulin polymerization. Tubulin (0.4 mg) was exposed to test compounds (5 µM). Colchicine was used as positive control. FIGS. 10C and 10D, ability of 17ya and 55 to enhance cytoplasmic DNA-Histone complex formation (apoptosis) at 24 h in PC-3 (C) and PC-3/TxR (D) cells (N=3); mean±SD. Docetaxel was used as positive control.

FIG. 11A, Nude mice bearing PC-3 tumors were treated with docetaxel (i.v., 10 or 20 mg/kg) on day 1 and 9. (N=5-6). Bars, SE. FIG. 11B, Nude mice bearing PC-3/TxR tumors were treated with docetaxel (i.v., 10 or 20 mg/kg) on day 1 and 9, or compound 17ya treatments (p.o., 6.7 mg/kg) once daily, five days a week. (N=4-5). Bars, SE. FIG. 11C, Nude mice bearing PC-3/TxR tumors were treated with compound 17ya (PO, 3.3 mg/kg) twice a day for four days in the first week, and then dosed once a day, five days a week for weeks 2-4 (N=7), or with compound 55 treatments (p.o., 10 or 30 mg/kg) twice a day, five days a week for four weeks (N=7). Bars, SE. FIG. 11D, Nude mice bearing PC-3/TxR tumors were treated with compound 17ya (PO, 10 mg/kg) three times a week for four weeks (N=5). Bars, SE.

FIG. 13 depicts the disruption of preformed capillary by 17ya. HUVEC cells loaded on Matrigel were allowed to make tube for 16 h and the test compound was treated to the preformed tubes. The number of tubes (A, B, and C) and nodes (D, E, and F) were counted up to 25 h after drug treatment. Panels A and D are conditions in the presence of CA4, panels B and E are conditions in the presence of doxorubicin and panels C and F are conditions in the presence of 17ya.

FIGS. 17A to 17D provides spectroscopic characteristic of compound 31a. FIG. 17A provides mass spectra. FIGS. 17B to 17D provides the proton NMR spectrum of compound 31a, with the chemical shift axis (x-axis) expanded in FIGS. 17C and 17D.

FIGS. 19A and 19B—rats were administered the indicated doses by injection and the concentration of 17ya and 31 in the blood was determined over time. The upper trace of (•) symbols in FIG. 19B correlate with 17ya blood levels when dosed intravenously, indicative of increased in vivo stability for the imidazole. FIG. 19C—rats were orally administered 5 mg/kg and the concentration of 17ya and 31 in the blood was determined over time.

FIGS. 20A and 20B: Nude mice bearing PC3 (prostate) tumors were orally administered 15 mg/kg 17ya (○) three times per week, intravenously administered 7 mg/kg 17ya (Δ) one time per week, or orally administered vehicle alone (•) three times per week, and the effect on tumor size (FIG. 20A) and body weight (FIG. 20B) was measured over time. Nude mice bearing PC3/TXR (prostate-paclitaxel-(multidrug) resistant) tumors were orally administered 15 mg/kg 17ya (○) three times per week, orally administered vehicle alone (Δ) three times per week, or orally administed vehicle alone (•) one time per week, and the effect on tumor size (FIG. 20C) and body weight (FIG. 20D) was measured over time.

(FIG. 23C, oral administration of 15 mg/kg 17ya (•-red) two times per week; oral administrations of vehicle alone (•-black) two times per week)

DETAILED DESCRIPTION OF THE INVENTION

Figure 1:
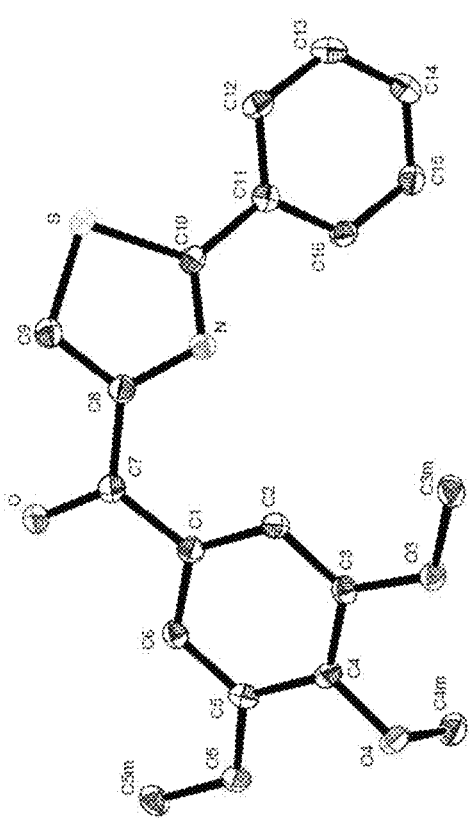
FIG. 1 is an Oak Ridge Thermal Ellipsoid Plot (ORTEP) drawing of compound 8f with thermal ellipsoids depicted at 50% probability level. The drawing was generated following X-ray crystallography studies.

One aspect of the present invention relates to compounds according to formula (I)

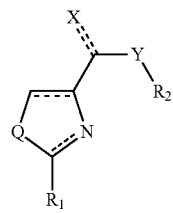

(I)

wherein

Q is S, N, or O;

X is optional, and can be S=, O=, =N—NH$_2$, =N—OH, or —OH;

Y is optional and can be —N(H)—, O, or C$_1$ to C$_{20}$ hydrocarbon; and

R$_1$ and R$_2$ are each independently substituted or unsubstituted single-, fused- or multiple-ring aryl or (hetero) cyclic ring systems, including saturated and unsaturated N-heterocycles, saturated and unsaturated S-heterocycles, and saturated and unsaturated O-heterocycles, saturated or unsaturated cyclic hydrocarbons, saturated or unsaturated mixed heterocycles, aliphatic straight- or branched-chain C$_1$ to C$_{30}$ hydrocarbons.

As used herein, "saturated or unsaturated cyclic hydrocarbons" can be any such cyclic hydrocarbon, including but not limited to phenyl, biphenyl, triphenyl, naphthyl, cycloalkyl, cycloalkenyl, cyclodienyl, fluorene, adamantane, etc.; "saturated or unsaturated N-heterocycles" can be any such N-containing heterocycle, including but not limited to aza- and diaza-cycloalkyls such as aziridinyl, azetidinyl, diazatidinyl, pyrrolidinyl, piperidinyl, piperazinyl, and azocanyl, pyrrolyl, pyrazolyl, imidazolyl, pyridinyl, pyrimidinyl, pyrazinyl, pyridazinyl, triazinyl, tetrazinyl, pyrrolizinyl, indolyl, quinolinyl, isoquinolinyl, benzimidazolyl, indazolyl, quinolizinyl, cinnolinyl, quinalolinyl, phthalazinyl, naphthyridinyl, quinoxalinyl, etc.; "saturated or unsaturated O-heterocycles" can be any such O-containing heterocycle including but not limited to oxiranyl, oxetanyl, tetrahydrofuranyl, tetrahydropyranyl, dioxanyl, furanyl, pyrylium, benzofuranyl, benzodioxolyl, etc.; "saturated or unsaturated S-heterocycles" can be any such S-containing heterocycle, including but not limited to thiranyl, thietanyl, tetrahydrothiophene-yl, dithiolanyl, tetrahydrothiopyranyl, thiophene-yl, thiepinyl, thianaphthenyl, etc.; "saturated or unsaturated mixed heterocycles" can be any heterocycle containing two or more S-, N-, or O-heteroatoms, including but not limited to oxathiolanyl, morpholinyl, thioxanyl, thiazolyl, isothiazolyl, thiadiazolyl, oxazolyl, isoxazolyl, oxadiazolyl, etc.

As noted above, the R$^1$ and R$^2$ groups can be substituted or unsubstituted. Thus, although the exemplary groups recited in the preceding paragraph are unsubstituted, it should be appreciated by those of skill in the art that these groups can be substituted by one or more, two or more, three or more, and even up to five substituents (other than hydrogen). Preferred R$^1$ and R$^2$ groups can be generically represented by the following structures:

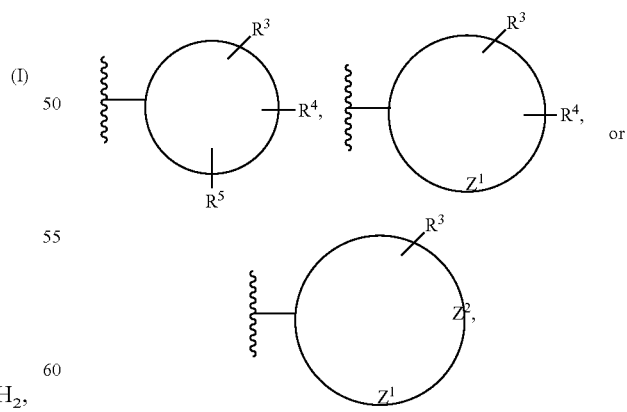

where Z$^1$ and Z$^2$ represent the one or more S-, N-, or O-heteroatoms present in the cyclic structure, and the rings are five- or six-member rings. In one embodiment, the R$^1$ and R$^2$ groups can have the structure:

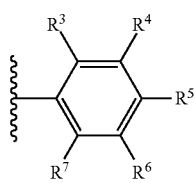

The substituents of these cyclic members (e.g., $R^3$, $R^4$, $R^5$, $R^6$, $R^7$) are independently selected from the group of hydrogen (e.g., no substitution at a particular position), hydroxyl, an aliphatic straight- or branched-chain $C_1$ to $C_{10}$ hydrocarbon, alkoxy, aryloxy, nitro, cyano, halo (e.g., chloro, fluoro, bromo, or iodo), haloalkyl, dihaloalkyl, trihaloalkyl, amino, alkylamino, mesylamino, dialkylamino, arylamino, amido, urea, alkyl-urea, alkylamido (e.g., acetamide), haloalkylamido, arylamido, aryl, and $C_5$ to $C_7$ cycloalkyl, arylalkyl, and combinations thereof. Single substituents can be present at the ortho, meta, or para positions. When two or more substituents are present, one of them is preferably, though not necessarily, at the para position.

As used herein, "aliphatic straight- or branched-chain hydrocarbon" refers to both alkylene groups that contain a single carbon and up to a defined upper limit, as well as alkenyl groups and alkynyl groups that contain two carbons up to the upper limit, whether the carbons are present in a single chain or a branched chain. Unless specifically identified, a hydrocarbon can include up to about 30 carbons, or up to about 20 hydrocarbons, or up to about 10 hydrocarbons. Alkenyl and alkynyl groups can be mono-unsaturated or polyunsaturated.

As used herein, the term "alkyl" can be any straight- or branched-chain alkyl group containing up to about 30 carbons unless otherwise specified. The alkyl group can be a sole substituent or it can be a component of a larger substituent, such as in an alkoxy, haloalkyl, arylalkyl, alkylamino, dialkylamino, alkylamido, alkylurea, etc. Preferred alkyl groups are methyl, ethyl, and propyl, and thus halomethyl, dihalomethyl, trihalomethyl, haloethyl, dihaloethyl, trihaloethyl, halopropyl, dihalopropyl, trihalopropyl, methoxy, ethoxy, propoxy, arylmethyl, arylethyl, arylpropyl, methylamino, ethylamino, propylamino, dimethylamino, diethylamino, methylamido, acetamido, propylamido, halomethylamido, haloethylamido, halopropylamido, methyl-urea, ethyl-urea, propyl-urea, etc.

As used herein, the term "aryl" refers to any aromatic ring substituent that is directly bonded to the $R^1$ or $R^2$ ring member(s). The aryl group can be a sole substituent, or the aryl group can be a component of a larger substituent, such as in an arylalkyl, arylamino, arylamido, etc. Exemplary aryl groups include, without limitation, phenyl, tolyl, xylyl, furanyl, naphthyl, pyridinyl, pyrimidinyl, pyridazinyl, pyrazinyl, triazinyl, thiazolyl, oxazolyl, isooxazolyl, pyrazolyl, imidazolyl, thiophene-yl, pyrrolyl, phenylmethyl, phenylethyl, phenylamino, phenylamido, etc.

As used herein, the term "aminoalkyl" refers to an amine group substituted by an alkyl group as defined above. Aminoalkyl refers to monoalkylamine, dialkylamine or trialkylamine. Nonlimiting examples of aminoalkyl groups are $-N(Me)_2$, $-NHMe$, $-NH_3$.

A "haloalkyl" group refers, in another embodiment, to an alkyl group as defined above, which is substituted by one or more halogen atoms, e.g. by F, Cl, Br or I. Nonlimiting examples of haloalkyl groups are $CF_3$, $CF_2CF_3$, $CH_2CF_3$.

Preferred $R^1$ and $R^2$ groups include substituted (with $R^3$-$R^7$ as defined above) and unsubstituted furanyl, indolyl, pyridinyl, phenyl, biphenyl, triphenyl, diphenylmethane, adamantane-yl, fluorene-yl, and other heterocyclic analogs such as those identified above (e.g., pyrrolyl, pyrazolyl, imidazolyl, pyridinyl, pyrimidinyl, pyrazinyl, pyridazinyl, triazinyl, tetrazinyl, pyrrolizinyl, indolyl, quinolinyl, isoquinolinyl, benzimidazolyl, indazolyl, quinolizinyl, cinnolinyl, quinalolinyl, phthalazinyl, naphthyridinyl, quinoxalinyl, oxiranyl, oxetanyl, tetrahydrofuranyl, tetrahydropyranyl, dioxanyl, furanyl, pyrylium, benzofuranyl, benzodioxolyl, thiranyl, thietanyl, tetrahydrothiophene-yl, dithiolanyl, tetrahydrothiopyranyl, thiophene-yl, thiepinyl, thianaphthenyl, oxathiolanyl, morpholinyl, thioxanyl, thiazolyl, isothiazolyl, thiadiazolyl, oxazolyl, isoxazolyl, oxadiaziolyl).

The most preferred $R^2$ group is 3,4,5-trimethoxyphenyl, and the most preferred $R^1$ groups include substituted and unsubstituted phenyl, substituted and unsubstituted thiophene-yl, and substituted and unsubstituted indolyl groups. The preferred substituents of these preferred $R^1$ groups are methyl, ethyl, fluoro, bromo, cyano, nitro, trifluoromethyl, and amino.

In certain embodiments, the compound of formula (I) is

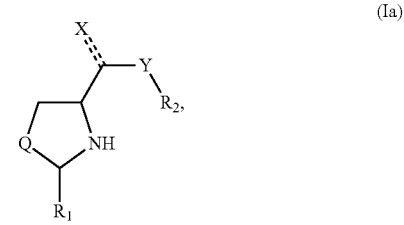

(Ia)

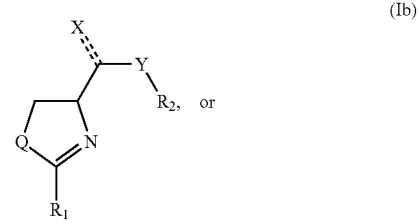

(Ib)

or

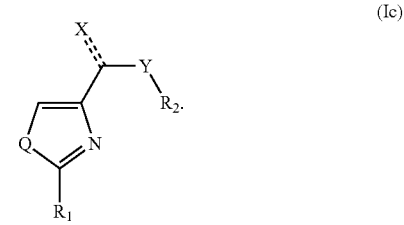

(Ic)

Depending on the definition of Q, therefore, the compounds of the present invention include thiazoles, dihydro-thiazoles, thiazolidines, oxazoles, dihydro-oxazoles, oxazolidines, imidazoles, dihydro-imidazoles, and imidazolidines.

According to a preferred embodiment, the class of compounds has a structure according to formula (II):

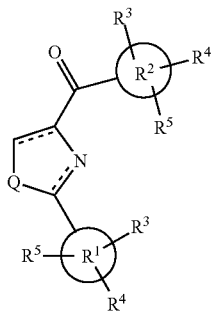

(II)

where Q and $R^1$-$R^5$ are defined as above for formula (I).

Exemplary compounds of formula (II) include, without limitation:
phenyl(2-phenylthiazol-4-yl)methanone (compound 8a);
phenyl(2-phenylthiazolidin-4-yl)methanone;
phenyl(2-phenyloxazolidin-4-yl)methanone;
(4,5-dihydro-2-phenyloxazol-4-yl)(phenyl)methanone;
phenyl(2-phenyloxazol-4-yl)methanone;
(4-methoxyphenyl)(2-phenylthiazol-4-yl)methanone (compound 8b);
(4-methoxyphenyl)(2-phenylthiazolidin-4-yl)methanone;
(4,5-dihydro-2-phenylthiazol-4-yl)(4-methoxyphenyl)methanone;
(4-methoxyphenyl)(2-phenyloxazol-4-yl)methanone;
(4-methoxyphenyl)(2-phenyloxazolidin-4-yl)methanone;
(4,5-dihydro-2-phenyloxazol-4-yl)(4-methoxyphenyl)methanone;
(4-methoxyphenyl)(2-phenyl-1H-imidazol-4-yl)methanone;
(4-methoxyphenyl)(2-phenylimidazolidin-4-yl)methanone;
(4,5-dihydro-2-phenyl-1H-imidazol-4-yl)(4-methoxyphenyl)methanone;
(3-methoxyphenyl)(2-phenylthiazol-4-yl)methanone (compound 8c);
(3-methoxyphenyl)(2-phenylthiazolidin-4-yl)methanone;
(4,5-dihydro-2-phenylthiazol-4-yl)(3-methoxyphenyl)methanone;
(3-methoxyphenyl)(2-phenyloxazol-4-yl)methanone;
(3-methoxyphenyl)(2-phenyloxazolidin-4-yl)methanone;
(4,5-dihydro-2-phenyloxazol-4-yl)(3-methoxyphenyl)methanone;
(3-methoxyphenyl)(2-phenyl-1H-imidazol-4-yl)methanone;
(3-methoxyphenyl)(2-phenylimidazolidin-4-yl)methanone;
(4,5-dihydro-2-phenyl-1H-imidazol-4-yl)(3-methoxyphenyl)methanone;
(2-methoxyphenyl)(2-phenylthiazol-4-yl)methanone (compound 8d);
(2-methoxyphenyl)(2-phenylthiazolidin-4-yl)methanone;
(4,5-dihydro-2-phenylthiazol-4-yl)(2-methoxyphenyl)methanone;
(2-methoxyphenyl)(2-phenyloxazol-4-yl)methanone;
(2-methoxyphenyl)(2-phenyloxazolidin-4-yl)methanone;
(4,5-dihydro-2-phenyloxazol-4-yl)(2-methoxyphenyl)methanone;
(2-methoxyphenyl)(2-phenyl-1H-imidazol-4-yl)methanone;
(2-methoxyphenyl)(2-phenylimidazolidin-4-yl)methanone;
(4,5-dihydro-2-phenyl-1H-imidazol-4-yl)(2-methoxyphenyl)methanone;
(3,4-dimethoxyphenyl)(2-phenylthiazol-4-yl)methanone (compound 8e);
(3,4-dimethoxyphenyl)(2-phenylthiazolidin-4-yl)methanone;
(4,5-dihydro-2-phenylthiazol-4-yl)(3,4-dimethoxyphenyl)methanone;
(3,4-dimethoxyphenyl)(2-phenyloxazol-4-yl)methanone;
(3,4-dimethoxyphenyl)(2-phenyloxazolidin-4-yl)methanone;
(4,5-dihydro-2-phenyloxazol-4-yl)(3,4-dimethoxyphenyl)methanone;
(3,4-dimethoxyphenyl)(2-phenyl-1H-imidazol-4-yl)methanone;
(3,4-dimethoxyphenyl)(2-phenylimidazolidin-4-yl)methanone;
(4,5-dihydro-2-phenyl-1H-imidazol-4-yl)(3,4-dimethoxyphenyl)methanone;
(3,4,5-trimethoxyphenyl)(2-phenylthiazol-4-yl)methanone (compound 8f);
(3,4,5-trimethoxyphenyl)(2-phenylthiazolidin-4-yl)methanone;
(4,5-dihydro-2-phenylthiazol-4-yl)(3,4,5-trimethoxyphenyl)methanone, which readily converts to compound 8f;
(3,4,5-trimethoxyphenyl)(2-phenyloxazolidin-4-yl)methanone;
(4,5-dihydro-2-phenyloxazol-4-yl)(3,4,5-trimethoxyphenyl)methanone;
(3,4,5-trimethoxyphenyl)(2-phenyloxazol-4-yl)methanone;
(4,5-dihydro-2-phenyl-1H-imidazol-4-yl)(3,4,5-trimethoxyphenyl)methanone;
(3,4,5-trimethoxyphenyl)(2-phenyl-1H-imidazol-4-yl)methanone;
(3,4,5-trimethoxyphenyl)(2-phenylimidazolidin-4-yl)methanone;
(3,5-dimethoxyphenyl)(2-phenylthiazol-4-yl)methanone (compound 8g);
(3,5-dimethoxyphenyl)(2-phenylthiazolidin-4-yl)methanone;
(4,5-dihydro-2-phenylthiazol-4-yl)(3,5-dimethoxyphenyl)methanone;
(3,5-dimethoxyphenyl)(2-phenyloxazol-4-yl)methanone;
(3,5-dimethoxyphenyl)(2-phenyloxazolidin-4-yl)methanone;
(4,5-dihydro-2-phenyloxazol-4-yl)(3,5-dimethoxyphenyl)methanone;
(3,5-dimethoxyphenyl)(2-phenyl-1H-imidazol-4-yl)methanone;
(3,5-dimethoxyphenyl)(2-phenylimidazolidin-4-yl)methanone;
(4,5-dihydro-2-phenyl-1H-imidazol-4-yl)(3,5-dimethoxyphenyl)methanone;
(2-fluorophenyl)(2-phenylthiazol-4-yl)methanone(compound 8h);
(2-fluorophenyl)(2-phenylthiazolidin-4-yl)methanone;
(4,5-dihydro-2-phenylthiazol-4-yl)(2-fluorophenyl)methanone;
(2-fluorophenyl)(2-phenyloxazol-4-yl)methanone;
(2-fluorophenyl)(2-phenyloxazolidin-4-yl)methanone;
(4,5-dihydro-2-phenyloxazol-4-yl)(2-fluorophenyl)methanone;
(2-fluorophenyl)(2-phenyl-1H-imidazol-4-yl)methanone;
(2-fluorophenyl)(2-phenylimidazolidin-4-yl)methanone;
(4,5-dihydro-2-phenyl-1H-imidazol-4-yl)(2-fluorophenyl)methanone;
(2-phenylthiazol-4-yl)(pyridin-2-yl)methanone(compound 8i);
(4,5-dihydro-2-phenylthiazol-4-yl)(pyridin-2-yl)methanone;
(2-phenylthiazolidin-4-yl)(pyridin-2-yl)methanone;
(2-phenyloxazol-4-yl)(pyridin-2-yl)methanone;

(4,5-dihydro-2-phenyloxazol-4-yl)(pyridin-2-yl)methanone;
(2-phenyloxazolidin-4-yl)(pyridin-2-yl)methanone;
(2-phenyl-1H-imidazol-4-yl)(pyridin-2-yl)methanone;
(4,5-dihydro-2-phenyl-1H-imidazol-4-yl)(pyridin-2-yl)methanone;
(2-phenylimidazolidin-4-yl)(pyridin-2-yl)methanone;
(2-p-tolylthiazol-4-yl)(3,4,5-trimethoxyphenyl)methanone (compound 8k);
(4,5-dihydro-2-p-tolylthiazol-4-yl)(3,4,5-trimethoxyphenyl)methanone;
(3,4,5-trimethoxyphenyl)(2-p-tolylthiazolidin-4-yl)methanone;
(2-p-tolyloxazol-4-yl)(3,4,5-trimethoxyphenyl)methanone;
(4,5-dihydro-2-p-tolyloxazol-4-yl)(3,4,5-trimethoxyphenyl)methanone;
(3,4,5-trimethoxyphenyl)(2-p-tolyloxazolidin-4-yl)methanone;
(2-p-tolyl-1H-imidazol-4-yl)(3,4,5-trimethoxyphenyl)methanone;
(4,5-dihydro-2-p-tolyl-1H-imidazol-4-yl)(3,4,5-trimethoxyphenyl)methanone;
(3,4,5-trimethoxyphenyl)(2-p-tolylimidazolidin-4-yl)methanone;
(2-(2-fluorophenyl)-thiazol-4-yl)-(3,4,5-trimethoxyphenyl)methanone (compound 8l);
(4,5-dihydro-2-(2-fluorophenyl)thiazol-4-yl)(3,4,5-trimethoxyphenyl)methanone;
(3,4,5-trimethoxyphenyl)(2-(2-fluorophenyl)thiazolidin-4-yl)methanone;
(2-(2-fluorophenyl)oxazol-4-yl)(3,4,5-trimethoxyphenyl)methanone;
(4,5-dihydro-2-(2-fluorophenyl)oxazol-4-yl)(3,4,5-trimethoxyphenyl)methanone;
(3,4,5-trimethoxyphenyl)(2-(2-fluorophenyl)oxazolidin-4-yl)methanone;
(2-(2-fluorophenyl)-1H-imidazol-4-yl)(3,4,5-trimethoxyphenyl)methanone;
(4,5-dihydro-2-(2-fluorophenyl)-1H-imidazol-4-yl)(3,4,5-trimethoxyphenyl)methanone;
(3,4,5-trimethoxyphenyl)(2-(2-fluorophenyl)imidazolidin-4-yl)methanone;
(2-(3-fluorophenyl)-thiazol-4-yl)(3,4,5-trimethoxyphenyl)methanone (compound 8m);
(4,5-dihydro-2-(3-fluorophenyl)thiazol-4-yl)(3,4,5-trimethoxyphenyl)methanone;
(3,4,5-trimethoxyphenyl)(2-(3-fluorophenyl)thiazolidin-4-yl)methanone;
(2-(3-fluorophenyl)oxazol-4-yl)(3,4,5-trimethoxyphenyl)methanone;
(4,5-dihydro-2-(3-fluorophenyl)oxazol-4-yl)(3,4,5-trimethoxyphenyl)methanone;
(3,4,5-trimethoxyphenyl)(2-(3-fluorophenyl)oxazolidin-4-yl)methanone;
(2-(3-fluorophenyl)-1H-imidazol-4-yl)(3,4,5-trimethoxyphenyl)methanone;
(4,5-dihydro-2-(3-fluorophenyl)-1H-imidazol-4-yl)(3,4,5-trimethoxyphenyl)methanone;
(3,4,5-trimethoxyphenyl)(2-(3-fluorophenyl)imidazolidin-4-yl)methanone;
(2-(4-fluorophenyl)-thiazol-4-yl)(3,4,5-trimethoxyphenyl)methanone (compound 8n);
(4,5-dihydro-2-(4-fluorophenyl)thiazol-4-yl)(3,4,5-trimethoxyphenyl)methanone;
(3,4,5-trimethoxyphenyl)(2-(4-fluorophenyl)thiazolidin-4-yl)methanone;
(2-(4-fluorophenyl)oxazol-4-yl)(3,4,5-trimethoxyphenyl)methanone;
(4,5-dihydro-2-(4-fluorophenyl)oxazol-4-yl)(3,4,5-trimethoxyphenyl)methanone;
(3,4,5-trimethoxyphenyl)(2-(4-fluorophenyl)oxazolidin-4-yl)methanone;
(2-(4-fluorophenyl)-1H-imidazol-4-yl)(3,4,5-trimethoxyphenyl)methanone;
(4,5-dihydro-2-(4-fluorophenyl)-1H-imidazol-4-yl)(3,4,5-trimethoxyphenyl)methanone;
(3,4,5-trimethoxyphenyl)(2-(4-fluorophenyl)imidazolidin-4-yl)methanone;
(2-(3,4-dimethoxyphenyl)-thiazol-4-yl)(3,4,5-trimethoxyphenyl)methanone (compound 8o);
(4,5-dihydro-2-(3,4-dimethoxyphenyl)thiazol-4-yl)(3,4,5-trimethoxyphenyl)methanone;
(3,4,5-trimethoxyphenyl)(2-(3,4-dimethoxyphenyl)thiazolidin-4-yl)methanone;
(2-(3,4-dimethoxyphenyl)oxazol-4-yl)(3,4,5-trimethoxyphenyl)methanone;
(4,5-dihydro-2-(3,4-dimethoxyphenyl)oxazol-4-yl)(3,4,5-trimethoxyphenyl)methanone;
(3,4,5-trimethoxyphenyl)(2-(3,4-dimethoxyphenyl)oxazolidin-4-yl)methanone;
(2-(3,4-dimethoxyphenyl)-1H-imidazol-4-yl)(3,4,5-trimethoxyphenyl)methanone;
(4,5-dihydro-2-(3,4-dimethoxyphenyl)-1H-imidazol-4-yl)(3,4,5-trimethoxyphenyl)methanone;
(3,4,5-trimethoxyphenyl)(2-(3,4-dimethoxyphenyl)imidazolidin-4-yl)methanone;
(2-(4-nitrophenyl)-thiazol-4-yl)(3,4,5-trimethoxyphenyl)methanone (compound 8p);
(4,5-dihydro-2-(4-nitrophenyl)thiazol-4-yl)(3,4,5-trimethoxyphenyl)methanone;
(3,4,5-trimethoxyphenyl)(2-(4-nitrophenyl)thiazolidin-4-yl)methanone;
(2-(4-nitrophenyl)oxazol-4-yl)(3,4,5-trimethoxyphenyl)methanone;
(4,5-dihydro-2-(4-nitrophenyl)oxazol-4-yl)(3,4,5-trimethoxyphenyl)methanone;
(3,4,5-trimethoxyphenyl)(2-(4-nitrophenyl)oxazolidin-4-yl)methanone;
(2-(4-nitrophenyl)-1H-imidazol-4-yl)(3,4,5-trimethoxyphenyl)methanone;
(4,5-dihydro-2-(4-nitrophenyl)-1H-imidazol-4-yl)(3,4,5-trimethoxyphenyl)methanone;
(3,4,5-trimethoxyphenyl)(2-(4-nitrophenyl)imidazolidin-4-yl)methanone;
(2-(4-cyanophenyl)-thiazol-4-yl)(3,4,5-trimethoxyphenyl)methanone (compound 8q);
(4,5-dihydro-2-(4-cyanophenyl)thiazol-4-yl)(3,4,5-trimethoxyphenyl)methanone;
(3,4,5-trimethoxyphenyl)(2-(4-cyanophenyl)thiazolidin-4-yl)methanone;
(2-(4-cyanophenyl)oxazol-4-yl)(3,4,5-trimethoxyphenyl)methanone;
(4,5-dihydro-2-(4-cyanophenyl)oxazol-4-yl)(3,4,5-trimethoxyphenyl)methanone;
(3,4,5-trimethoxyphenyl)(2-(4-cyanophenyl)oxazolidin-4-yl)methanone;
(2-(4-cyanophenyl)-1H-imidazol-4-yl)(3,4,5-trimethoxyphenyl)methanone;
(4,5-dihydro-2-(4-cyanophenyl)-1H-imidazol-4-yl)(3,4,5-trimethoxyphenyl)methanone;
(3,4,5-trimethoxyphenyl)(2-(4-cyanophenyl)imidazolidin-4-yl)methanone;

4-(4-(3,4,5-trimethoxybenzoyl)-thiazol-2-yl)-benzoic acid (compound 8r);
4-(4-(3,4,5-trimethoxybenzoyl)-(1,3-dihydro)thiazol-2-yl)-benzoic acid;
4-(4-(3,4,5-trimethoxybenzoyl)-4,5-dihydrothiazol-2-yl) benzoic acid;
4-(4-(3,4,5-trimethoxybenzoyl)-thiazolidin-2-yl)-benzoic acid;
4-(4-(3,4,5-trimethoxybenzoyl)-oxazol-2-yl)-benzoic acid;
4-(4-(3,4,5-trimethoxybenzoyl)-(1,3-dihydro)oxazol-2-yl)-benzoic acid;
4-(4-(3,4,5-trimethoxybenzoyl)-4,5-dihydrooxazol-2-yl) benzoic acid;
4-(4-(3,4,5-trimethoxybenzoyl)-oxazolidin-2-yl)-benzoic acid;
4-(4-(3,4,5-trimethoxybenzoyl)-1H-imidazol-2-yl)-benzoic acid;
4-(4-(3,4,5-trimethoxybenzoyl)-(1,3-dihydro)-1H-imidazol-2-yl)-benzoic acid;
4-(4-(3,4,5-trimethoxybenzoyl)-4,5-dihydrothiazol-2-yl) benzoic acid;
4-(4-(3,4,5-trimethoxybenzoyl)-imidazolidin-2-yl)-benzoic acid;
methyl-4-(4-(3,4,5-trimethoxybenzoyl)-thiazol-2-yl)-benzoate (compound 8s);
methyl-4-(4-(3,4,5-trimethoxybenzoyl)-(1,3-dihydro)thiazol-2-yl)-benzoate;
methyl 4-(4-(3,4,5-trimethoxybenzoyl)-4,5-dihydrothiazol-2-yl)benzoate;
methyl-4-(4-(3,4,5-trimethoxybenzoyl)-thiazolidin-2-yl)-benzoate;
methyl-4-(4-(3,4,5-trimethoxybenzoyl)-oxazol-2-yl)-benzoate;
methyl-4-(4-(3,4,5-trimethoxybenzoyl)-(1,3-dihydro)oxazol-2-yl)-benzoate;
methyl 4-(4-(3,4,5-trimethoxybenzoyl)-4,5-dihydrooxazol-2-yl)benzoate;
methyl-4-(4-(3,4,5-trimethoxybenzoyl)-oxazolidin-2-yl)-benzoate;
methyl-4-(4-(3,4,5-trimethoxybenzoyl)-1H-imidazol-2-yl)-benzoate;
methyl-4-(4-(3,4,5-trimethoxybenzoyl)-(1,3-dihydro)-1H-imidazol-2-yl)-benzoate;
methyl 4-(4-(3,4,5-trimethoxybenzoyl)-4,5-dihydro-1H-imidazol-2-yl)benzoate;
methyl-4-(4-(3,4,5-trimethoxybenzoyl)-imidazolidin-2-yl)-benzoate;
(2-(4-(trifluoromethyl)-phenyl)-thiazol-4-yl)(3,4,5-trimethoxyphenyl)methanone (compound 8t);
(4,5-dihydro-2-(4-(trifluoromethyl)-phenyl)thiazol-4-yl)(3,4,5-trimethoxyphenyl)methanone;
(3,4,5-trimethoxyphenyl)(2-(4-cyanophenyl)thiazolidin-4-yl)methanone;
(2-(4-(trifluoromethyl)-phenyl)oxazol-4-yl)(3,4,5-trimethoxyphenyl)methanone;
(4,5-dihydro-2-(4-(trifluoromethyl)-phenyl)oxazol-4-yl)(3,4,5-trimethoxyphenyl)methanone;
(3,4,5-trimethoxyphenyl)(2-(4-(trifluoromethyl)-phenyl)oxazolidin-4-yl)methanone;
(2-(4-(trifluoromethyl)-phenyl)-1H-imidazol-4-yl)(3,4,5-trimethoxyphenyl)methanone;
(4,5-dihydro-2-(4-(trifluoromethyl)-phenyl)-1H-imidazol-4-yl)(3,4,5-trimethoxyphenyl)methanone;
(3,4,5-trimethoxyphenyl)(2-(4-(trifluoromethyl)-phenyl)imidazolidin-4-yl)methanone;
(2-(4-bromophenyl)-thiazol-4-yl)-(3,4,5-trimethoxyphenyl)methanone (compound 8u);
(4,5-dihydro-2-(4-bromophenyl)thiazol-4-yl)(3,4,5-trimethoxyphenyl)methanone;
(3,4,5-trimethoxyphenyl)(2-(4-bromophenyl)thiazolidin-4-yl)methanone;
(2-(4-bromophenyl)oxazol-4-yl)(3,4,5-trimethoxyphenyl)methanone;
(4,5-dihydro-2-(4-bromophenyl)oxazol-4-yl)(3,4,5-trimethoxyphenyl)methanone;
(3,4,5-trimethoxyphenyl)(2-(4-bromophenyl)oxazolidin-4-yl)methanone;
(2-(4-bromophenyl)-1H-imidazol-4-yl)(3,4,5-trimethoxyphenyl)methanone;
(4,5-dihydro-2-(4-bromophenyl)-1H-imidazol-4-yl)(3,4,5-trimethoxyphenyl)methanone;
(3,4,5-trimethoxyphenyl)(2-(4-bromophenyl)imidazolidin-4-yl)methanone;
(2-(4-ethylphenyl)-thiazol-4-yl)-(3,4,5-trimethoxy-phenyl)methanone (compound 8v);
(4,5-dihydro-2-(4-ethylphenyl)thiazol-4-yl)(3,4,5-trimethoxyphenyl)methanone;
(3,4,5-trimethoxyphenyl)(2-(4-ethylphenyl)thiazolidin-4-yl)methanone;
(2-(4-ethylphenyl)oxazol-4-yl)(3,4,5-trimethoxyphenyl)methanone;
(4,5-dihydro-2-(4-ethylphenyl)oxazol-4-yl)(3,4,5-trimethoxyphenyl)methanone;
(3,4,5-trimethoxyphenyl)(2-(4-ethylphenyl)oxazolidin-4-yl)methanone;
(2-(4-ethylphenyl)-1H-imidazol-4-yl)(3,4,5-trimethoxyphenyl)methanone;
(4,5-dihydro-2-(4-ethylphenyl)-1H-imidazol-4-yl)(3,4,5-trimethoxyphenyl)methanone;
(3,4,5-trimethoxyphenyl)(2-(4-ethylphenyl)imidazolidin-4-yl)methanone;
(2-(4-aminophenyl)-thiazol-4-yl)-(3,4,5-trimethoxy-phenyl)methanone (compound 8w);
(2-(4-aminophenyl)thiazolidin-4-yl)(3,4,5-trimethoxyphenyl)methanone;
(2-(4-aminophenyl)-4,5-dihydrothiazol-4-yl)(3,4,5-trimethoxyphenyl)methanone;
(2-(4-aminophenyl)-oxazol-4-yl)-(3,4,5-trimethoxyphenyl)methanone;
(2-(4-aminophenyl)oxazolidin-4-yl)(3,4,5-trimethoxyphenyl)methanone;
(2-(4-aminophenyl)-4,5-dihydrooxazol-4-yl)(3,4,5-trimethoxyphenyl)methanone;
(2-(4-aminophenyl)-1H-imidazol-4-yl)-(3,4,5-trimethoxyphenyl)methanone;
(2-(4-aminophenyl)-1H-imidazolidin-4-yl)(3,4,5-trimethoxyphenyl)methanone;
(2-(4-aminophenyl)-4,5-dihydroimidazol-4-yl)(3,4,5-trimethoxyphenyl)methanone;
(2-(4-acetamidophenyl)thiazolidin-4-yl)(3,4,5-trimethoxyphenyl)methanone;
(2-(4-acetamidophenyl)-4,5-dihydrothiazol-4-yl)(3,4,5-trimethoxyphenyl)methanone;
(2-(4-acetamidophenyl)-thiazol-4-yl)-(3,4,5-trimethoxyphenyl)methanone;
(3,4,5-trimethoxyphenyl)(2-(3,4,5-trimethoxyphenyl)thiazol-4-yl)methanone;
(4,5-dihydro-2-(3,4,5-trimethoxyphenyl)thiazol-4-yl)(3,4,5-trimethoxyphenyl)methanone;
(3,4,5-trimethoxyphenyl)(2-(3,4,5-trimethoxyphenyl)thiazolidin-4-yl)methanone;
(3,4,5-trimethoxyphenyl)(2-(3,4-dimethoxyphenyl)thiazol-4-yl)methanone;

(4,5-dihydro-2-(3,4-dimethoxyphenyl)thiazol-4-yl)(3,4,5-trimethoxyphenyl)methanone;
(3,4,5-trimethoxyphenyl)(2-(3,4-dimethoxyphenyl)thiazolidin-4-yl)methanone;
(2-(4-fluorophenyl)thiazolidin-4-yl)(3,4,5-trimethoxyphenyl)methanone;
(2-(4-fluorophenyl)-4,5-dihydrothiazol-4-yl)(3,4,5-trimethoxyphenyl)methanone;
(2-(4-fluorophenyl)-thiazol-4-yl)(3,4,5-trimethoxyphenyl)methanone;
(3,4,5-trimethoxyphenyl)(2-(2-methoxyphenyl)thiazol-4-yl)methanone;
(4,5-dihydro-2-(2-methoxyphenyl)thiazol-4-yl)(3,4,5-trimethoxyphenyl)methanone;
(3,4,5-trimethoxyphenyl)(2-(2-methoxyphenyl)thiazolidin-4-yl)methanone;
(2-(pyridin-4-yl)-thiazol-4-yl)-(3,4,5-trimethoxyphenyl)methanone (compound 8x);
(4,5-dihydro-2-(pyridin-4-yl)thiazol-4-yl)(3,4,5-trimethoxyphenyl)methanone;
(3,4,5-trimethoxyphenyl)(2-(pyridin-4-yl)thiazolidin-4-yl)methanone;
(2-(pyridin-4-yl)-oxazol-4-yl)-(3,4,5-trimethoxyphenyl)methanone;
(4,5-dihydro-2-(pyridin-4-yl)oxazol-4-yl)(3,4,5-trimethoxyphenyl)methanone;
(3,4,5-trimethoxyphenyl)(2-(pyridin-4-yl)oxazolidin-4-yl)methanone;
(2-(pyridin-4-yl)-1H-imidazol-4-yl)-(3,4,5-trimethoxyphenyl)methanone;
(4,5-dihydro-2-(pyridin-4-yl)-1H-imidazol-4-yl)(3,4,5-trimethoxyphenyl)methanone;
(3,4,5-trimethoxyphenyl)(2-(pyridin-4-yl)imidazolidin-4-yl)methanone;
(2-(pyrimidin-2-yl)-thiazol-4-yl)-(3,4,5-trimethoxyphenyl)methanone (compound 8y);
(4,5-dihydro-2-(pyrimidin-4-yl)thiazol-4-yl)(3,4,5-trimethoxyphenyl)methanone;
(3,4,5-trimethoxyphenyl)(2-(pyrimidin-4-yl)thiazolidin-4-yl)methanone;
(2-(pyrimidin-4-yl)-oxazol-4-yl)-(3,4,5-trimethoxyphenyl)methanone;
(4,5-dihydro-2-(pyrimidin-4-yl)oxazol-4-yl)(3,4,5-trimethoxyphenyl)methanone;
(3,4,5-trimethoxyphenyl)(2-(pyrimidin-4-yl)oxazolidin-4-yl)methanone;
(2-(pyrimidin-4-yl)-1H-imidazol-4-yl)-(3,4,5-trimethoxyphenyl)methanone;
(4,5-dihydro-2-(pyrimidin-4-yl)-1H-imidazol-4-yl)(3,4,5-trimethoxyphenyl)methanone;
(3,4,5-trimethoxyphenyl)(2-(pyrimidin-4-yl)imidazolidin-4-yl)methanone;
(2-(thiophen-2-yl)-thiazol-4-yl)-(3,4,5-trimethoxyphenyl)methanone (compound 8z);
(4,5-dihydro-2-(thiophen-2-yl)thiazol-4-yl)(3,4,5-trimethoxyphenyl)methanone;
(3,4,5-trimethoxyphenyl)(2-(thiophen-2-yl)thiazolidin-4-yl)methanone;
(2-(thiophen-2-yl)-oxazol-4-yl)-(3,4,5-trimethoxyphenyl)methanone;
(4,5-dihydro-2-(thiophen-2-yl)oxazol-4-yl)(3,4,5-trimethoxyphenyl)methanone;
(3,4,5-trimethoxyphenyl)(2-(thiophen-2-yl)oxazolidin-4-yl)methanone;
(2-(thiophen-2-yl)-1H-imidazol-4-yl)-(3,4,5-trimethoxyphenyl)methanone;
(4,5-dihydro-2-(thiophen-2-yl)-1H-imidazol-4-yl)(3,4,5-trimethoxyphenyl)methanone;
(3,4,5-trimethoxyphenyl)(2-(thiophen-2-yl)imidazolidin-4-yl)methanone;
(2-(1H-indol-5-yl)thiazol-4-yl)(3,4,5-trimethoxyphenyl)methanone (compound 31);
[(2-(1-methyl-1H-indol-5-yl)thiazol-4-yl)(3,4,5-trimethoxyphenyl)methanone](compound 31a);
(2-(1H-indol-5-yl)thiazolidin-4-yl)(3,4,5-trimethoxyphenyl)methanone;
(4,5-dihydro-2-(1H-indol-5-yl)thiazol-4-yl)(3,4,5-trimethoxyphenyl)methanone;
(2-(1H-indol-5-yl)oxazol-4-yl)(3,4,5-trimethoxyphenyl)methanone;
(2-(1H-indol-5-yl)oxazolidin-4-yl)(3,4,5-trimethoxyphenyl)methanone;
(4,5-dihydro-2-(1H-indol-5-yl)oxazol-4-yl)(3,4,5-trimethoxyphenyl)methanone;
(2-(1H-indol-5-yl)imidazol-4-yl)(3,4,5-trimethoxyphenyl)methanone;
(2-(1H-indol-5-yl)imidazolidin-4-yl)(3,4,5-trimethoxyphenyl)methanone;
(4,5-dihydro-2-(1H-indol-5-yl)imidazol-4-yl)(3,4,5-trimethoxyphenyl)methanone;
(2-(1H-indol-2-yl)thiazol-4-yl)(3,4,5-trimethoxyphenyl)methanone (compound 32);
(4,5-dihydro-2-(1H-indol-2-yl)thiazol-4-yl)(3,4,5-trimethoxyphenyl)methanone;
(2-(1H-indol-2-yl)thiazolidin-4-yl)(3,4,5-trimethoxyphenyl)methanone;
(2-(1H-indol-2-yl)oxazol-4-yl)(3,4,5-trimethoxyphenyl)methanone;
(4,5-dihydro-2-(1H-indol-2-yl)oxazol-4-yl)(3,4,5-trimethoxyphenyl)methanone;
(2-(1H-indol-2-yl)oxazolidin-4-yl)(3,4,5-trimethoxyphenyl)methanone;
(2-(1H-indol-2-yl)imidazol-4-yl)(3,4,5-trimethoxyphenyl)methanone;
(4,5-dihydro-2-(1H-indol-2-yl)imidazol-4-yl)(3,4,5-trimethoxyphenyl)methanone;
(2-(1H-indol-2-yl)imidazolidin-4-yl)(3,4,5-trimethoxyphenyl)methanone;
(2-(1H-indol-1-yl)thiazol-4-yl)(3,4,5-trimethoxyphenyl)methanone;
(4,5-dihydro-2-(1H-indol-1-yl)thiazol-4-yl)(3,4,5-trimethoxyphenyl)methanone;
(2-(1H-indol-1-yl)thiazolidin-4-yl)(3,4,5-trimethoxyphenyl)methanone;
(2-(1H-indol-1-yl)oxazol-4-yl)(3,4,5-trimethoxyphenyl)methanone;
(4,5-dihydro-2-(1H-indol-1-yl)oxazol-4-yl)(3,4,5-trimethoxyphenyl)methanone;
(2-(1H-indol-1-yl)oxazolidin-4-yl)(3,4,5-trimethoxyphenyl)methanone;
(2-(1H-indol-1-yl)imidazol-4-yl)(3,4,5-trimethoxyphenyl)methanone;
(4,5-dihydro-2-(1H-indol-1-yl)imidazol-4-yl)(3,4,5-trimethoxyphenyl)methanone;
(2-(1H-indol-1-yl)imidazolidin-4-yl)(3,4,5-trimethoxyphenyl)methanone;
(2-(1H-indol-3-yl)thiazol-4-yl)(3,4,5-trimethoxyphenyl)methanone;
(4,5-dihydro-2-(1H-indol-3-yl)thiazol-4-yl)(3,4,5-trimethoxyphenyl)methanone;
(2-(1H-indol-3-yl)thiazolidin-4-yl)(3,4,5-trimethoxyphenyl)methanone;

(2-(1H-indol-3-yl)oxazol-4-yl)(3,4,5-trimethoxyphenyl)
  methanone;
(4,5-dihydro-2-(1H-indol-3-yl)oxazol-4-yl)(3,4,5-
  trimethoxyphenyl)methanone;
(2-(1H-indol-3-yl)oxazolidin-4-yl)(3,4,5-trimethoxyphenyl)
  methanone;
(2-(1H-indol-3-yl)imidazol-4-yl)(3,4,5-trimethoxyphenyl)
  methanone (Compound 17ya);
(4,5-dihydro-2-(1H-indol-3-yl)imidazol-4-yl)(3,4,5-
  trimethoxyphenyl)methanone;
(2-(1H-indol-3-yl)imidazolidin-4-yl)(3,4,5-trimethoxyphe-
  nyl)methanone;
(2-(1H-indol-4-yl)thiazol-4-yl)(3,4,5-trimethoxyphenyl)
  methanone;
(4,5-dihydro-2-(1H-indol-4-yl)thiazol-4-yl)(3,4,5-
  trimethoxyphenyl)methanone;
(2-(1H-indol-4-yl)thiazolidin-4-yl)(3,4,5-trimethoxyphe-
  nyl)methanone;
(2-(1H-indol-4-yl)oxazol-4-yl)(3,4,5-trimethoxyphenyl)
  methanone;
(4,5-dihydro-2-(1H-indol-4-yl)oxazol-4-yl)(3,4,5-
  trimethoxyphenyl)methanone;
(2-(1H-indol-4-yl)oxazolidin-4-yl)(3,4,5-trimethoxyphenyl)
  methanone;
(2-(1H-indol-4-yl)imidazol-4-yl)(3,4,5-trimethoxyphenyl)
  methanone;
(4,5-dihydro-2-(1H-indol-4-yl)imidazol-4-yl)(3,4,5-
  trimethoxyphenyl)methanone;
(2-(1H-indol-4-yl)imidazolidin-4-yl)(3,4,5-trimethoxyphe-
  nyl)methanone;
(2-(1H-indol-6-yl)thiazol-4-yl)(3,4,5-trimethoxyphenyl)
  methanone;
(4,5-dihydro-2-(1H-indol-6-yl)thiazol-4-yl)(3,4,5-
  trimethoxyphenyl)methanone;
(2-(1H-indol-6-yl)thiazolidin-4-yl)(3,4,5-trimethoxyphe-
  nyl)methanone;
(2-(1H-indol-6-yl)oxazol-4-yl)(3,4,5-trimethoxyphenyl)
  methanone;
(4,5-dihydro-2-(1H-indol-6-yl)oxazol-4-yl)(3,4,5-
  trimethoxyphenyl)methanone;
(2-(1H-indol-6-yl)oxazolidin-4-yl)(3,4,5-trimethoxyphenyl)
  methanone;
(2-(1H-indol-6-yl)imidazol-4-yl)(3,4,5-trimethoxyphenyl)
  methanone;
(4,5-dihydro-2-(1H-indol-6-yl)imidazol-4-yl)(3,4,5-
  trimethoxyphenyl)methanone;
(2-(1H-indol-6-yl)imidazolidin-4-yl)(3,4,5-trimethoxyphe-
  nyl)methanone;
(2-(1H-indol-7-yl)thiazol-4-yl)(3,4,5-trimethoxyphenyl)
  methanone;
(4,5-dihydro-2-(1H-indol-7-yl)thiazol-4-yl)(3,4,5-
  trimethoxyphenyl)methanone;
(2-(1H-indol-7-yl)thiazolidin-4-yl)(3,4,5-trimethoxyphe-
  nyl)methanone;
(2-(1H-indol-7-yl)oxazol-4-yl)(3,4,5-trimethoxyphenyl)
  methanone;
(4,5-dihydro-2-(1H-indol-7-yl)oxazol-4-yl)(3,4,5-
  trimethoxyphenyl)methanone;
(2-(1H-indol-7-yl)oxazolidin-4-yl)(3,4,5-trimethoxyphenyl)
  methanone;
(2-(1H-indol-7-yl)imidazol-4-yl)(3,4,5-trimethoxyphenyl)
  methanone;
(4,5-dihydro-2-(1H-indol-7-yl)imidazol-4-yl)(3,4,5-
  trimethoxyphenyl)methanone; and
(2-(1H-indol-7-yl)imidazolidin-4-yl)(3,4,5-trimethoxyphe-
  nyl)methanone.

Preferably, the $R^1$ group is substituted or unsubstituted phenyl, substituted or unsubstituted thiophene-yl, or substituted or unsubstituted indolyl; and the $R^2$ group is 3,4,5-trimethoxyphenyl. Thus, of the above-listed compounds,
(3,4,5-trimethoxyphenyl)(2-phenylthiazol-4-yl)methanone
  (compound 8f);
(2-p-tolylthiazol-4-yl)(3,4,5-trimethoxyphenyl)methanone
  (compound 8k);
(2-(4-fluorophenyl)-thiazol-4-yl)(3,4,5-trimethoxyphenyl)
  methanone (compound 8n);
(2-(4-nitrophenyl)-thiazol-4-yl)(3,4,5-trimethoxyphenyl)
  methanone (compound 8p);
(2-(4-cyanophenyl)-thiazol-4-yl)(3,4,5-trimethoxyphenyl)
  methanone (compound 8q);
(2-(4-(trifluoromethyl)-phenyl)-thiazol-4-yl)(3,4,5-
  trimethoxyphenyl)methanone (compound 8t);
(2-(4-bromophenyl)-thiazol-4-yl)-(3,4,5-trimethoxyphenyl)
  methanone (compound 8u);
(2-(4-ethylphenyl)-thiazol-4-yl)-(3,4,5-trimethoxy-phenyl)
  methanone (compound 8v);
(2-(4-aminophenyl)-thiazol-4-yl)-(3,4,5-trimethoxy-phenyl)
  methanone (compound 8w);
(2-(thiophen-2-yl)-thiazol-4-yl)-(3,4,5-trimethoxyphenyl)
  methanone (compound 8z);
(2-(1H-indol-5-yl)thiazol-4-yl)(3,4,5-trimethoxyphenyl)
  methanone (compound 31);
(2-(1-methyl-1H-indol-5-yl)thiazol-4-yl)(3,4,5-trimethoxy-
  phenyl)methanone) (compound 31a);
(2-(1H-indol-2-yl)thiazol-4-yl)(3,4,5-trimethoxyphenyl)
  methanone (compound 32);
(2-(1H-indol-1-yl)thiazol-4-yl)(3,4,5-trimethoxyphenyl)
  methanone;
(2-(1H-indol-3-yl)thiazol-4-yl)(3,4,5-trimethoxyphenyl)
  methanone;
(2-(1H-indol-4-yl)thiazol-4-yl)(3,4,5-trimethoxyphenyl)
  methanone;
(2-(1H-indol-6-yl)thiazol-4-yl)(3,4,5-trimethoxyphenyl)
  methanone; and
(2-(1H-indol-7-yl)thiazol-4-yl)(3,4,5-trimethoxyphenyl)
  methanone are preferred.

According to another embodiment, the class of compounds has a structure according to formula (III):

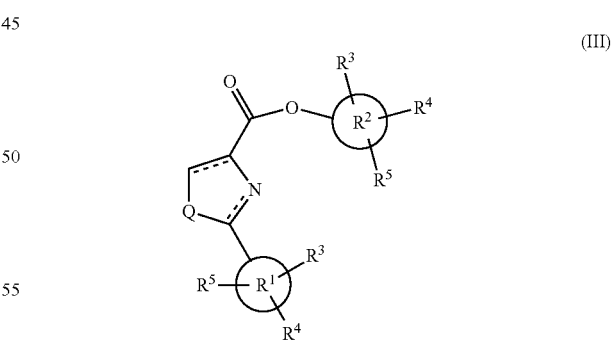

where Q and $R^1$-$R^5$ are defined as above for formula (I).
Exemplary compounds of formula (III) include, without limitation:
3,4,5-trimethoxyphenyl 4,5-dihydro-2-phenylthiazole-4-carboxylate;
3,4,5-trimethoxyphenyl 2-phenylthiazole-4-carboxylate;
3,4,5-trimethoxyphenyl 2-phenylthiazolidine-4-carboxylate;
3,4,5-trimethoxyphenyl 2-phenyloxazolidine-4-carboxylate;

3,4,5-trimethoxyphenyl 4,5-dihydro-2-phenyloxazole-4-carboxylate;
3,4,5-trimethoxyphenyl 2-phenyloxazole-4-carboxylate;
3,4,5-trimethoxyphenyl 2-phenylimidazolidine-4-carboxylate;
3,4,5-trimethoxyphenyl 4,5-dihydro-2-phenyl-1H-imidazole-4-carboxylate; and
3,4,5-trimethoxyphenyl 2-phenyl-1H-imidazole-4-carboxylate.

According to another embodiment, the class of compounds has a structure according to formula (IV):

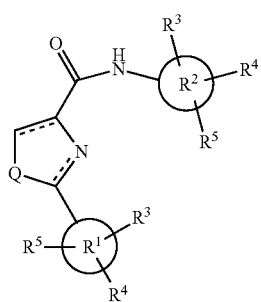

(IV)

where Q and $R^1$-$R^5$ are defined as above for formula (I).

Exemplary compounds of formula (IV) include, without limitation:
N-(3,4,5-trimethoxyphenyl)-2-phenyloxazolidine-4-carboxamide;
4,5-dihydro-N-(3,4,5-trimethoxyphenyl)-2-phenyloxazole-4-carboxamide;
N-(3,4,5-trimethoxyphenyl)-2-phenyloxazole-4-carboxamide;
N-(3,4,5-trimethoxyphenyl)-2-phenyl-1H-imidazole-4-carboxamide;
4,5-dihydro-N-(3,4,5-trimethoxyphenyl)-2-phenyl-1H-imidazole-4-carboxamide;
N-(3,4,5-trimethoxyphenyl)-2-phenylimidazolidine-4-carboxamide;
4,5-dihydro-N-(3,4,5-trimethoxyphenyl)-2-phenylthiazole-4-carboxamide;
N-(3,4,5-trimethoxyphenyl)-2-phenylthiazole-4-carboxamide; and
N-(3,4,5-trimethoxyphenyl)-2-phenylthiazolidine-4-carboxamide.

According to another embodiment, the class of compounds has a structure according to formula (V):

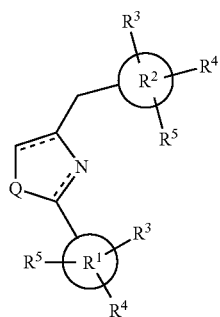

(V)

where Q and $R^1$-$R^5$ are defined as above for formula (I).

Exemplary compounds of formula (V) include, without limitation:
4-(3,4,5-trimethoxybenzyl)-2-phenylthiazolidine;
4-(3,4,5-trimethoxybenzyl)-4,5-dihydro-2-phenylthiazole;
4-(3,4,5-trimethoxybenzyl)-2-phenylthiazole;
4-(3,4,5-trimethoxybenzyl)-2-phenyloxazole;
4-(3,4,5-trimethoxybenzyl)-4,5-dihydro-2-phenyloxazole;
4-(3,4,5-trimethoxybenzyl)-2-phenyloxazolidine;
4-(3,4,5-trimethoxybenzyl)-2-phenylimidazolidine;
4-(3,4,5-trimethoxybenzyl)-4,5-dihydro-2-phenyl-1H-imidazole; and
4-(3,4,5-trimethoxybenzyl)-2-phenyl-1H-imidazole.

According to another embodiment, the class of compounds has a structure according to formula (VI):

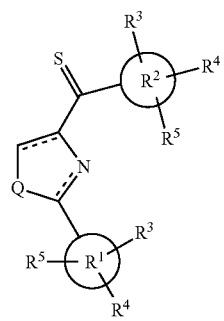

(VI)

where Q and $R^1$-$R^5$ are defined as above for formula (I).

Exemplary compounds of formula (VI) include, without limitation:
phenyl(2-phenylthiazolidin-4-yl)methanethione;
phenyl(2-phenyloxazolidin-4-yl)methanethione;
(4,5-dihydro-2-phenyloxazol-4-yl)(phenyl)methanethione;
phenyl(2-phenyloxazol-4-yl)methanethione;
(3,4,5-trimethoxyphenyl)(2-phenylthiazol-4-yl)methanethione;
(3,4,5-trimethoxyphenyl)(2-phenylthiazolidin-4-yl)methanethione;
(3,4,5-trimethoxyphenyl)(2-phenyloxazolidin-4-yl)methanethione;
(4,5-dihydro-2-phenyloxazol-4-yl)(3,4,5-trimethoxyphenyl)methanethione;
(3,4,5-trimethoxyphenyl)(2-phenyloxazol-4-yl)methanethione;
(4,5-dihydro-2-phenyl-1H-imidazol-4-yl)(3,4,5-trimethoxyphenyl)methanethione;
(3,4,5-trimethoxyphenyl)(2-phenyl-1H-imidazol-4-yl)methanethione; and
(3,4,5-trimethoxyphenyl)(2-phenylimidazolidin-4-yl)methanethione.

According to another preferred embodiment, the class of compounds has a structure according to formula (VII):

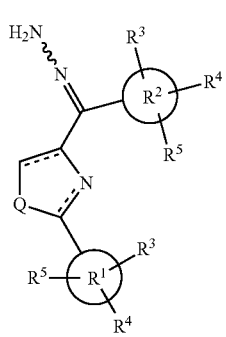

(VII)

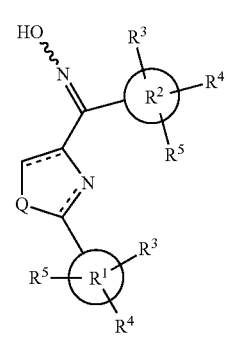

(VIII)

where Q and $R^1$-$R^5$ are defined as above for formula (I).

Exemplary compounds according to formula (VII) include, without limitation, (Z)-1-((3,4,5-trimethoxyphenyl)(2-phenylthiazol-4-yl)methylene)hydrazine (compound 33);

(E)-1-((3,4,5-trimethoxyphenyl)(2-phenylthiazol-4-yl)methylene)hydrazine (compound 34);

(Z)-1-((4,5-dihydro-2-phenylthiazol-4-yl)(3,4,5-trimethoxyphenyl)methylene)hydrazine;

(E)-1-((4,5-dihydro-2-phenylthiazol-4-yl)(3,4,5-trimethoxyphenyl)methylene)hydrazine;

(Z)-1-((3,4,5-trimethoxyphenyl)(2-phenylthiazolidin-4-yl)methylene)hydrazine;

(E)-1-((3,4,5-trimethoxyphenyl)(2-phenylthiazolidin-4-yl)methylene)hydrazine;

(Z)-1-((3,4,5-trimethoxyphenyl)(2-phenyloxazol-4-yl)methylene)hydrazine;

(E)-1-((3,4,5-trimethoxyphenyl)(2-phenyloxazol-4-yl)methylene)hydrazine;

(Z)-1-((4,5-dihydro-2-phenyloxazol-4-yl)(3,4,5-trimethoxyphenyl)methylene)hydrazine;

(E)-1-((4,5-dihydro-2-phenyloxazol-4-yl)(3,4,5-trimethoxyphenyl)methylene)hydrazine;

(Z)-1-((3,4,5-trimethoxyphenyl)(2-phenyloxazolidin-4-yl)methylene)hydrazine;

(E)-1-((3,4,5-trimethoxyphenyl)(2-phenyloxazolidin-4-yl)methylene)hydrazine;

(Z)-1-((3,4,5-trimethoxyphenyl)(2-phenyl-1H-imidazol-4-yl)methylene)hydrazine;

(E)-1-((3,4,5-trimethoxyphenyl)(2-phenyl-1H-imidazol-4-yl)methylene)hydrazine;

(Z)-1-((4,5-dihydro-2-phenyl-1H-imidazol-4-yl)(3,4,5-trimethoxyphenyl)methylene) hydrazine;

(E)-1-((4,5-dihydro-2-phenyl-1H-imidazol-4-yl)(3,4,5-trimethoxyphenyl)methylene)hydrazine;

(Z)-1-((3,4,5-trimethoxyphenyl)(2-phenylimidazolidin-4-yl)methylene)hydrazine; and (E)-1-((3,4,5-trimethoxyphenyl)(2-phenylimidazolidin-4-yl)methylene)hydrazine.

According to another preferred embodiment, the class of compounds has a structure according to formula (VIII):

where Q and $R^1$-$R^5$ are defined as above for formula (I).

Exemplary compounds according to formula (VIII) include, without limitation, (Z)-(2-phenylthiazol-4-yl)(3,4,5-trimethoxyphenyl)methanone oxime (compound 35);

(E)-(2-phenylthiazol-4-yl)(3,4,5-trimethoxyphenyl)methanone oxime (compound 36);

(Z)-1-(4,5-dihydro-2-phenylthiazol-4-yl)(3,4,5-trimethoxyphenyl)methanone oxime;

(E)-1-(4,5-dihydro-2-phenylthiazol-4-yl)(3,4,5-trimethoxyphenyl)methanone oxime;

(Z)-1-(3,4,5-trimethoxyphenyl)(2-phenylthiazolidin-4-yl)methanone oxime;

(E)-1-(3,4,5-trimethoxyphenyl)(2-phenylthiazolidin-4-yl)methanone oxime;

(Z)-1-(3,4,5-trimethoxyphenyl)(2-phenyloxazol-4-yl)methanone oxime;

(E)-1-(3,4,5-trimethoxyphenyl)(2-phenyloxazol-4-yl)methanone oxime;

(Z)-1-(4,5-dihydro-2-phenyloxazol-4-yl)(3,4,5-trimethoxyphenyl)methanone oxime;

(E)-1-(4,5-dihydro-2-phenyloxazol-4-yl)(3,4,5-trimethoxyphenyl)methanone oxime;

(Z)-1-(3,4,5-trimethoxyphenyl)(2-phenyloxazolidin-4-yl)methanone oxime;

(E)-1-(3,4,5-trimethoxyphenyl)(2-phenyloxazolidin-4-yl)methanone oxime;

(Z)-1-(3,4,5-trimethoxyphenyl)(2-phenyl-1H-imidazol-4-yl)methanone oxime;

(E)-1-(3,4,5-trimethoxyphenyl)(2-phenyl-1H-imidazol-4-yl)methanone oxime;

(Z)-1-(4,5-dihydro-2-phenyl-1H-imidazol-4-yl)(3,4,5-trimethoxyphenyl)methanone oxime;

(E)-1-(4,5-dihydro-2-phenyl-1H-imidazol-4-yl)(3,4,5-trimethoxyphenyl)methanone oxime;

(Z)-1-(3,4,5-trimethoxyphenyl)(2-phenylimidazolidin-4-yl)methanone oxime; and (E)-1-(3,4,5-trimethoxyphenyl)(2-phenylimidazolidin-4-yl)methanone oxime.

In one aspect, the present invention provides a compound of formula XI:

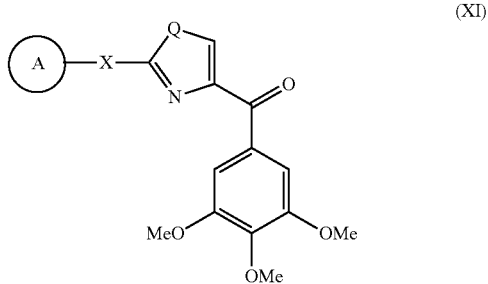

(XI)

wherein
X is a bond, NH or S;
Q is O, NH or S; and
A is substituted or unsubstituted single-, fused- or multiple-ring aryl or (hetero)cyclic ring systems; substituted or unsubstituted, saturated or unsaturated N-heterocycles; substituted or unsubstituted, saturated or unsaturated S-heterocycles; substituted or unsubstituted, saturated or unsaturated O-heterocycles; substituted or unsubstituted, saturated or unsaturated cyclic hydrocarbons; or substituted or unsubstituted, saturated or unsaturated mixed heterocycles; wherein said A ring is optionally substituted by 1-5 substituents which are independently O-alkyl, O-haloalkyl, F, Cl, Br, I, haloalkyl, $CF_3$, CN, —$CH_2CN$, $NH_2$, hydroxyl, —$(CH_2)_i$NHCH_3$, —$(CH_2)_i NH_2$, —$(CH_2)_i N(CH_3)_2$, —$OC(O)CF_3$, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or $NO_2$; and
i is an integer from 0-5;
or its pharmaceutically acceptable salt, hydrate, polymorph, metabolite, tautomer or isomer.

In one embodiment, the present invention provides a compound of formula XI, or an N-oxide thereof, or a pharmaceutically acceptable salt thereof.

In one embodiment, the A group is substituted or unsubstituted furanyl, benzofuranyl, benzothiophenyl, indolyl, pyridinyl, phenyl, biphenyl, triphenyl, diphenylmethane, adamantane-yl, fluorene-yl, or other heterocyclic analogs such as, e.g., pyrrolyl, pyrazolyl, imidazolyl, pyridinyl, pyrimidinyl, pyrazinyl, pyridazinyl, triazinyl, tetrazinyl, pyrrolizinyl, indolyl, isoquinolinyl, quinolinyl, benzimidazolyl, indazolyl, quinolizinyl, cinnolinyl, quinalolinyl, phthalazinyl, naphthyridinyl, quinoxalinyl, oxiranyl, oxetanyl, tetrahydrofuranyl, tetrahydropyranyl, dioxanyl, furanyl, pyrylium, benzodioxolyl, thiranyl, thietanyl, tetrahydrothiophene-yl, dithiolanyl, tetrahydrothiopyranyl, thiophene-yl, thiepinyl, thianaphthenyl, oxathiolanyl, morpholinyl, thioxanyl, thiazolyl, isothiazolyl, thiadiazolyl, oxazolyl, isoxazolyl, and oxadiazolyl.

In one embodiment, the A group is substituted or unsubstituted phenyl. In another embodiment, the A group is phenyl substituted by Cl, F or methyl. In one embodiment, A is substituted or unsubstituted isoquinolinyl. In one embodiment, the A group includes substituted or unsubstituted indolyl groups, for example, substituted or unsubstituted 3-indolyl, 4-indolyl and 5-indolyl. In another embodiment, the A group is an indolyl substituted with a methyl. In another embodiment, the A group is substituted or unsubstituted 3-indolyl. In certain embodiments, the A group is unsubstituted 3-indolyl. In certain embodiments, the A group is unsubstituted 5-indolyl. In certain embodiments, the A group is substituted 5-indolyl.

In one embodiment, the A group can be substituted or unsubstituted. Thus, although the exemplary groups recited in the preceding paragraph are unsubstituted, it should be appreciated by those of skill in the art that these groups can be substituted by one or more, two or more, three or more, and even up to five substituents (other than hydrogen).

In one embodiment, the A group is 3,4,5-trimethoxyphenyl. In another embodiment the A group is substituted by alkoxy. In another embodiment the A group is substituted by methoxy. In another embodiment the A group is substituted by alkyl. In another embodiment the A group is substituted by methyl. In another embodiment the A group is substituted by halogen. In another embodiment, the A group is substituted by F. In another embodiment, the A group is substituted by Cl. In another embodiment, the A group is substituted by Br.

In one embodiment, the substituents of the A groups of formula XI are independently selected from the group consisting of hydrogen (e.g., no substitution at a particular position), hydroxyl, an aliphatic straight- or branched-chain $C_1$ to $C_{10}$ hydrocarbon, alkoxy, haloalkoxy, aryloxy, nitro, cyano, alkyl-CN, halo, haloalkyl, dihaloalkyl, trihaloalkyl, COOH, C(O)Ph, C(O)-alkyl, C(O)O-alkyl, C(O)H, C(O)$NH_2$, —$OC(O)CF_3$, —$OCH_2Ph$, amino, aminoalkyl, alkylamino, mesylamino, dialkylamino, arylamino, amido, NHC(O)-alkyl, urea, alkyl-urea, alkylamido (e.g., acetamide), haloalkylamido, arylamido, aryl, and $C_5$ to $C_7$ cycloalkyl, arylalkyl, and combinations thereof. Single substituents can be present at the ortho, meta, or para positions. In some embodiments, when two or more substituents are present, one of them is at the para position.

In one embodiment if Q of Formula XI is S, then X is not a bond.

In one embodiment, Q is NH. In another embodiment, Q is O.

In one embodiment, X is a bond. In another embodiment, X is NH. In certain embodiments, X is S.

In one embodiment, Q is NH and X is a bond.

In another embodiment, Q is NH, X is a bond and A is a substituted or unsubstituted indolyl. In another embodiment, Q is NH, X is a bond and A is a substituted or unsubstituted 3-indolyl.

In another aspect, this invention provides a compound of formula XI(e):

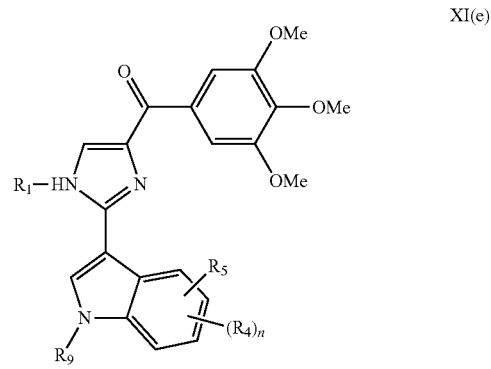

XI(e)

wherein $R_4$ and $R_5$ are independently hydrogen, O-alkyl, O-haloalkyl, F, Cl, Br, I, haloalkyl, $CF_3$, CN, —$CH_2CN$, $NH_2$, hydroxyl, —$(CH_2)_i NHCH_3$, —$(CH_2)_i NH_2$, —$(CH_2)_i N(CH_3)_2$, —$OC(O)CF_3$, $C_1$-$C_5$ linear or branched alkyl, haloalkyl, alkylamino, aminoalkyl, —OCH$_2$Ph, —NHCO-alkyl, COOH, —C(O)Ph, C(O)O-alkyl, C(O)H, —C(O)NH$_2$ or NO$_2$;

R$_9$ and R$_1$ are independently H, linear or branched, substituted or unsubstituted alkyl, substituted or unsubstituted aryl, —CH$_2$Ph, substituted benzyl, haloalkyl, aminoalkyl, —OCH$_2$Ph, substituted or unsubstituted SO$_2$-aryl, substituted or unsubstituted —(C=O)-aryl or OH;

i is an integer from 0-5; and n is an integer between 1-3;

or its pharmaceutically acceptable salt, hydrate, polymorph, metabolite, tautomer or isomer.

In one embodiment, the present invention provides a compound of formula XI(e), or an N-oxide thereof, or a pharmaceutically acceptable salt thereof.

In one embodiment, n is 1. In another embodiment, n is 2.

In one embodiment, R$_4$ and R$_5$ are independently H.

In another embodiment, R$_4$ and R$_5$ of formula XI(e) are independently H, O-alkyl, O-haloalkyl, F, Cl, Br, I, haloalkyl, CN, NH$_2$, or OH. In one embodiment, R$_4$ and R$_5$ are independently H, OCH$_3$, F, Cl, CF$_3$, or OH. In certain embodiments, R$_4$ and R$_5$ are independently H or OCH$_3$. In another embodiment, R$_4$ and R$_5$ are independently H, F, or Cl. In another embodiment, R$_4$ and R$_5$ are independently H or CF$_3$. In another embodiment, R$_4$ and R$_5$ are independently H or OH.

In another embodiment, R$_1$ and R$_9$ of formula XI(e) are independently are independently H, linear or branched, substituted or unsubstituted alkyl, substituted or unsubstituted aryl, —CH$_2$Ph, substituted benzyl, haloalkyl, aminoalkyl, —OCH$_2$Ph, substituted or unsubstituted SO$_2$-aryl, substituted or unsubstituted —(C=O)-aryl or OH. In one embodiment, R$_1$ and R$_9$ are independently hydrogen. In one embodiment, R$_1$ and R$_9$ are independently branched, substituted or unsubstituted alkyl. In one embodiment, R$_1$ and R$_9$ are independently substituted or unsubstituted aryl. In one embodiment, R$_1$ and R$_9$ are independently —CH$_2$Ph. In one embodiment, R$_1$ and R$_9$ are independently substituted benzyl. In one embodiment, R$_1$ and R$_9$ are independently haloalkyl. In one embodiment, R$_1$ and R$_9$ are independently aminoalkyl. In one embodiment, R$_1$ and R$_9$ are independently —OCH$_2$Ph. In one embodiment, R$_1$ and R$_9$ are independently substituted or unsubstituted SO$_2$-aryl. In one embodiment, R$_1$ and R$_9$ are independently hydrogen or substituted or unsubstituted —(C=O)-aryl. In one embodiment, R$_1$ and R$_9$ are independently OH.

In another aspect, the present invention provides a compound of formula (17ya):

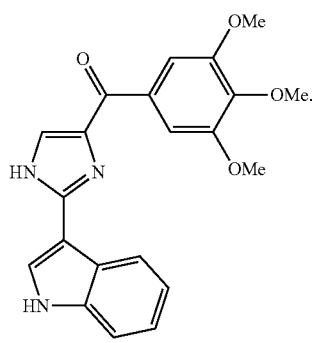

(17ya)

In another embodiment, a compound of formula XI(e) is represented by the structure of compound 17yab:

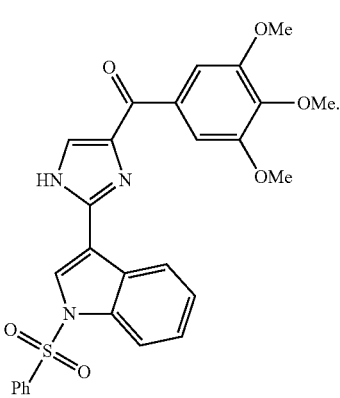

(17yab)

In another embodiment, a compound of formula XI(e) is represented by the structure of compound 17yac:

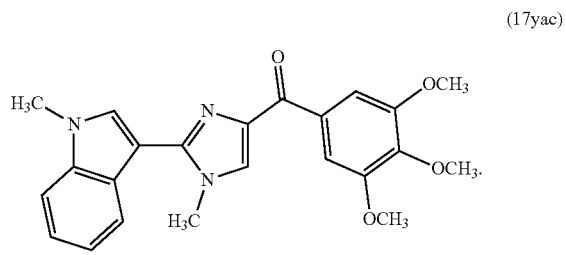 [SMILES: COc1cc(C(=O)c2cn(C)c(-c3cn(C)c4ccccc34)n2)cc(OC)c1OC]

(17yac)

In another aspect, the present invention provides a compound of formula XXI:

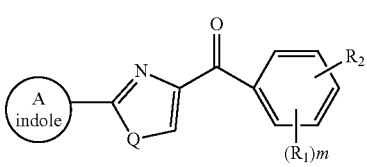

(XXI)

wherein

A is indolyl;

Q is NH, O or S;

R$_1$ and R$_2$ are independently H, O-alkyl, I, Br, Cl, F, alkyl, haloalkyl, aminoalkyl, —(CH$_2$)$_i$NHCH$_3$, —(CH$_2$)$_i$NH$_2$, —(CH$_2$)$_i$N(CH$_3$)$_2$, —OCH$_2$Ph, OH, CN, NO$_2$, —NHCO-alkyl, COOH, C(O)O-alkyl or C(O)H; and wherein said A is optionally substituted by substituted or unsubstituted O-alkyl, O-haloalkyl, F, Cl, Br, I, haloalkyl, CF$_3$, CN, —CH$_2$CN, NH$_2$, hydroxyl, —(CH$_2$)$_i$NHCH$_3$, —(CH$_2$)$_i$NH$_2$, —(CH$_2$)$_i$N(CH$_3$)$_2$, —OC(O)CF$_3$, substituted or unsubstituted —SO$_2$-aryl, substituted or unsubstituted C$_1$-C$_5$ linear or branched alkyl, substituted or unsubstituted haloalkyl, substituted or unsubstituted alkylamino, substituted or unsubstituted aminoalkyl, —OCH$_2$Ph, substituted or unsubstituted —NHCO-alkyl, COOH, substituted or unsubstituted —C(O)Ph, substituted or unsubstituted C(O) O-alkyl, C(O)H, —C(O)NH$_2$, NO$_2$ or combination thereof;

i is an integer between 0-5; and m is an integer between 1-4;

or its pharmaceutically acceptable salt, hydrate, polymorph, metabolite, tautomer or isomer.

In one embodiment, the present invention provides a compound of formula (XXI), or an N-oxide thereof, or a pharmaceutically acceptable salt thereof.

In one embodiment, $R_1$ of compound of formula XXI is $OCH_3$; m is 3 and $R_2$ is hydrogen. In another embodiment, $R_1$ is F; m is 1 and $R_2$ is hydrogen.

In one embodiment, Q of formula XXI is O. In another embodiment Q of formula XXI is NH. In another embodiment, Q of formula XXI is S.

In one embodiment, A ring of compound of formula XXI is substituted 5-indolyl. In another embodiment, the substitution is —(C=O)-aryl. In another embodiment, the aryl is 3,4,5-$(OCH_3)_3$-Ph. In another embodiment, the substitution is methyl.

In another embodiment, A ring of compound of formula XXI is 3-indolyl. In another embodiment, A ring of compound of formula XXI is 5-indolyl. In another embodiment, A ring of compound of formula XXI is 2-indolyl. Non limiting examples of compounds of formula XXI are selected from:
(5-(4-(3,4,5-trimethoxybenzoyl)-1H-imidazol-2-yl)-1H-indol-2-yl)(3,4,5-trimethoxyphenyl)methanone (15xaa);
(1-(phenylsulfonyl)-2-(1-(phenylsulfonyl)-2-(3,4,5-trimethoxybenzoyl)-1H-indol-5-yl)-1H-imidazol-4-yl)(3,4,5-trimethoxyphenyl)methanone (16xaa);
2-(1H-indol-3-yl)-1H-imidazol-4-yl)(3,4,5-trimethoxyphenyl)methanone (17ya);
(2-(1H-indol-2-yl)thiazol-4-yl)(3,4,5-trimethoxyphenyl)methanone (32);
(2-(1H-indol-5-yl)thiazol-4-yl)(3,4,5-trimethoxyphenyl)methanone (31); and
(2-(1-methyl-1H-indol-5-yl)thiazol-4-yl)(3,4,5-trimethoxyphenyl)methanone)] (31a).

In another aspect, the present invention provides a compound of formula XXIa:

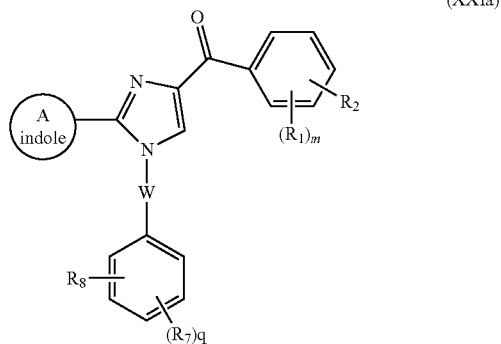

(XXIa)

wherein
W is C=O, C=S, $SO_2$, S=O;
A is indolyl;
$R_1$ and $R_2$ are independently H, O-alkyl, I, Br, Cl, F, alkyl, haloalkyl, aminoalkyl, —$(CH_2)_iNHCH_3$, —$(CH_2)_iNH_2$, —$(CH_2)_iN(CH_3)_2$, —$OCH_2Ph$, OH, CN, $NO_2$, —NHCO-alkyl, COOH, C(O)O-alkyl or C(O)H;
$R_7$ and $R_8$ are independently H, O-alkyl, I, Br, Cl, F, alkyl, haloalkyl, aminoalkyl, —$(CH_2)_iNHCH_3$, —$(CH_2)_iNH_2$, —$(CH_2)_iN(CH_3)_2$, —$OCH_2Ph$, OH, CN, $NO_2$, —NHCO-alkyl, COOH, C(O)O-alkyl or C(O)H;

wherein said A is optionally substituted by substituted or unsubstituted O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, substituted or unsubstituted —$SO_2$-aryl, substituted or unsubstituted $C_1$-$C_5$ linear or branched alkyl, substituted or unsubstituted haloalkyl, substituted or unsubstituted alkylamino, substituted or unsubstituted aminoalkyl, —$OCH_2Ph$, substituted or unsubstituted —NHCO-alkyl, COOH, substituted or unsubstituted —C(O)Ph, substituted or unsubstituted C(O)O-alkyl, C(O)H, —C(O)$NH_2$, $NO_2$ or combination thereof;
i is an integer between 0-5; and
m is an integer between 1-3;
q is an integer between 1-3;
or its pharmaceutically acceptable salt, hydrate, polymorph, metabolite, tautomer or isomer.

In one embodiment, the invention provides a compound of formula (XXIa), or an N-oxide thereof, or a pharmaceutically acceptable salt thereof.

In one embodiment, $R_1$ of compound of formula XXIa is $OCH_3$; m is 3 and $R_2$ is hydrogen. In another embodiment, $R_1$ is F; m is 1 and $R_2$ is hydrogen.

In another embodiment, A ring of compound of formula XXIa is substituted 5-indolyl. In another embodiment, A ring of compound of formula XXIa is 3-indolyl. Non limiting examples of compounds of formula XXIa are selected from:
(1-(phenylsulfonyl)-2-(1-(phenylsulfonyl)-2-(3,4,5-trimethoxybenzoyl)-1H-indol-5-yl)-1H-imidazol-4-yl)(3,4,5-trimethoxyphenyl)methanone (16xaa); and
(1-(phenylsulfonyl)-2-(1-(phenylsulfonyl)-1H-indol-3-yl)-1H-imidazol-4-yl)(3,4,5-trimethoxyphenyl)methanone (17yaa).

In another aspect, the present invention provides a compound of formula XXII:

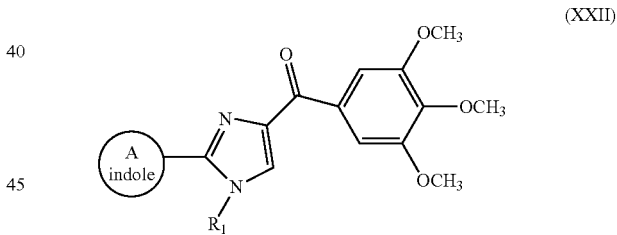

(XXII)

wherein
A is indolyl;
wherein said A is optionally substituted by substituted or unsubstituted O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, substituted or unsubstituted —$SO_2$-aryl, substituted or unsubstituted $C_1$-$C_5$ linear or branched alkyl, substituted or unsubstituted haloalkyl, substituted or unsubstituted alkylamino, substituted or unsubstituted aminoalkyl, —$OCH_2Ph$, substituted or unsubstituted —NHCO-alkyl, COOH, substituted or unsubstituted —C(O)Ph, substituted or unsubstituted C(O)O-alkyl, C(O)H, —C(O)$NH_2$, $NO_2$ or combination thereof;
i is an integer between 0-5;
$R_1$ is hydrogen, linear or branched, substituted or unsubstituted alkyl, substituted or unsubstituted aryl, —$CH_2Ph$, substituted benzyl, haloalkyl, aminoalkyl, —$OCH_2Ph$, substituted or unsubstituted $SO_2$-aryl, substituted or unsubstituted —(C=O)-aryl or OH;

or its pharmaceutically acceptable salt, hydrate, polymorph, metabolite, tautomer or isomer.

In one embodiment, the invention provides a compound of formula XXII, or an N-oxide thereof, or a pharmaceutically acceptable salt thereof.

In one embodiment, A ring of compound of formula XXII is substituted 5-indolyl. In another embodiment the substitution is —(C=O)-aryl. In another embodiment, the aryl is 3,4,5-(OCH$_3$)$_3$-Ph.

In another embodiment, A ring of compound of formula XXII is substituted 3-indolyl. In another embodiment, A ring of compound of formula XXII is 3-indolyl. Non limiting examples of compounds of formula XXII are selected from:

(5-(4-(3,4,5-trimethoxybenzoyl)-1H-imidazol-2-yl)-1H-indol-2-yl)(3,4,5-trimethoxyphenyl)methanone (15xaa); and (2-(1H-indol-3-yl)-1H-imidazol-4-yl)(3,4,5-trimethoxyphenyl)methanone (17ya).

In another aspect, the present invention provides a compound of formula (17ya):

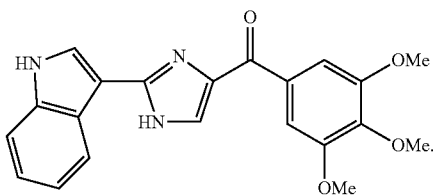

(17ya)

In one embodiment, this invention provides a compound of this invention or its isomer, metabolite, pharmaceutically acceptable salt, pharmaceutical product, tautomer, hydrate, N-oxide, polymorph, or crystal or combinations thereof. In one embodiment, this invention provides an isomer of the compound of this invention. In another embodiment, this invention provides a metabolite of the compound of this invention. In another embodiment, this invention provides a pharmaceutically acceptable salt of the compound of this invention. In another embodiment, this invention provides a pharmaceutical product of the compound of this invention. In another embodiment, this invention provides a tautomer of the compound of this invention. In another embodiment, this invention provides a hydrate of the compound of this invention. In another embodiment, this invention provides an N-oxide of the compound of this invention. In another embodiment, this invention provides a polymorph of the compound of this invention. In another embodiment, this invention provides a crystal of the compound of this invention. In another embodiment, this invention provides composition comprising a compound of this invention, as described herein, or, in another embodiment, a combination of an isomer, metabolite, pharmaceutically acceptable salt, pharmaceutical product, tautomer, hydrate, N-oxide, polymorph, or crystal of the compound of this invention.

In another embodiment, the invention provides a compound of this invention or an N-oxide thereof, or a pharmaceutically acceptable salt thereof.

In one embodiment, this invention provides a compound of formula 17ya or its isomer, metabolite, pharmaceutically acceptable salt, pharmaceutical product, tautomer, hydrate, N-oxide, polymorph, or crystal or combinations thereof. In one embodiment, this invention provides an isomer of a compound of formula 17ya. In another embodiment, this invention provides a metabolite of a compound of formula 17ya. In another embodiment, this invention provides a pharmaceutically acceptable salt of a compound of formula 17ya. In another embodiment, this invention provides a pharmaceutical product of a compound of formula 17ya. In another embodiment, this invention provides a tautomer of a compound of formula 17ya. In another embodiment, this invention provides a hydrate of a compound of formula 17ya. In another embodiment, this invention provides an N-oxide of a compound of formula 17ya. In another embodiment, this invention provides a polymorph of a compound of formula 17ya. In another embodiment, this invention provides a crystal of a compound of formula 17ya. In another embodiment, this invention provides composition comprising a compound of formula 17ya, as described herein, or, in another embodiment, a combination of an isomer, metabolite, pharmaceutically acceptable salt, pharmaceutical product, tautomer, hydrate, N-oxide, polymorph, or crystal of a compound of formula 17ya.

In another embodiment, the invention provides a compound of formula 17ya or an N-oxide thereof, or a pharmaceutically acceptable salt thereof.

In one embodiment, the term "isomer" includes, but is not limited to, optical isomers and analogs, structural isomers and analogs, conformational isomers and analogs, and the like.

In one embodiment, the compounds of this invention are the pure (E)-isomers. In another embodiment, the compounds of this invention are the pure (Z)-isomers. In another embodiment, the compounds of this invention are a mixture of the (E) and the (Z) isomers. In one embodiment, the compounds of this invention are the pure (R)-isomers. In another embodiment, the compounds of this invention are the pure (S)-isomers. In another embodiment, the compounds of this invention are a mixture of the (R) and the (S) isomers.

The compounds of the present invention can also be present in the form of a racemic mixture, containing substantially equivalent amounts of stereoisomers. In another embodiment, the compounds of the present invention can be prepared or otherwise isolated, using known procedures, to obtain a stereoisomer substantially free of its corresponding stereoisomer (i.e., substantially pure). By substantially pure, it is intended that a stereoisomer is at least about 95% pure, more preferably at least about 98% pure, most preferably at least about 99% pure.

Compounds of the present invention can also be in the form of a hydrate, which means that the compound further includes a stoichiometric or non-stoichiometric amount of water bound by non-covalent intermolecular forces.

Compounds of the present invention may exist in the form of one or more of the possible tautomers and depending on the particular conditions it may be possible to separate some or all of the tautomers into individual and distinct entities. It is to be understood that all of the possible tautomers, including all additional enol and keto tautomers and/or isomers are hereby covered. For example the following tautomers, but not limited to these, are included.

Tautomerization of the Imidazole Ring

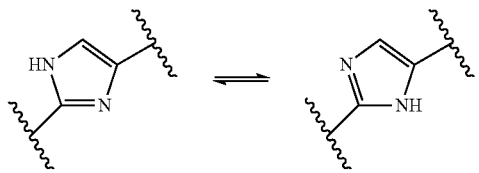 [SMILES: *c1c[nH]c(*)n1 ; *c1cnc(*)[nH]1]

The tautomers of this invention are freely interconverting tautomers, not unresolved mixtures. The imidazoles and other ring systems of this invention are tautomerizable. All tautomers are considered as part of the invention.

The invention includes "pharmaceutically acceptable salts" of the compounds of this invention, which may be produced, by reaction of a compound of this invention with an acid or base. Certain compounds, particularly those possessing acid or basic groups, can also be in the form of a salt, preferably a pharmaceutically acceptable salt. The term "pharmaceutically acceptable salt" refers to those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

Suitable pharmaceutically-acceptable salts of amines of the compounds of this invention may be prepared from an inorganic acid or from an organic acid. In one embodiment, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In one embodiment, examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates gluconates, glutamates, glycolates, glucorate, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, naphthalenesulfonates, 2-naphthalenesulfonates, nicotinates, nitrates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartrates, theophyllineacetates, p-toluenesulfonates (tosylates), trifluoroacetates, terephthalates, tannates, teoclates, trihaloacetates, triethiodide, tricarboxylates, undecanoates and valerates.

In one embodiment, examples of inorganic salts of carboxylic acids or hydroxyls may be selected from ammonium, alkali metals to include lithium, sodium, potassium, cesium; alkaline earth metals to include calcium, magnesium, aluminium; zinc, barium, cholines, quaternary ammoniums.

In another embodiment, examples of organic salts of carboxylic acids or hydroxyl may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines and ureas.

In one embodiment, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

The compounds of the present invention may also be administered as prodrugs. Thus, certain derivatives which may have little or no pharmacological activity themselves can, when administered into or onto the body, be converted into compounds of the present invention having the desired activity, for example, by hydrolytic cleavage. Further information on the use of prodrugs may be found in *Pro-drugs as Novel Delivery Systems*, Vol. 14, ACS Symposium Series (Higuchi and Stella); and *Bioreversible Carriers in Drug Design*, Pergamon Press (ed. E B Roche, American Pharmaceutical Association) (1987), each of which is hereby incorporated by reference in its entirety.

Prodrugs can, for example, be produced by replacing appropriate functionalities present in the compounds of the present invention with certain moieties known to those skilled in the art as pro-moieties. Examples of such prodrugs include, without limitation, replacement of hydrogen in an alcohol functionality (—OH) by a C1 to C6 alkyl to form an ether; and (ii) replacement of hydrogen in a secondary amino functionality with a C1 to C10 alkanoyl to form an amide.

A further aspect of the present invention relates to a method of making the compounds according to formula (I). Furthermore, the present invention discloses synthetic methodologies for the preparation of amide, alkoxyamides, ketone, hydrazine, and oxime derivatives of thiazolidines, thiazolines, thiazoles, imidazolines, imidazoles, oxazolidines, oxazolines, and oxazoles.

To synthesize thiazoline and thiazole series compounds, L- or D-cysteine can be reacted with substituted or unsubstituted benzonitrile in methanol and pH 6.4 phosphate buffer solution at ambient temperature for several days (Bergeron et al., "Evaluation of Desferrithiocin and its Synthetic Analogs as Orally Effective Iron Chelators," *J. Med. Chem.* 34:2072-8 (1991); Bergeron et al., "Desazadesmethyldesferrithiocin Analogues as Orally Effective Iron Chelators," *J. Med. Chem.* 42:95-108 (1999); Zamri et al., "An Improved Stereocontrolled Synthesis of Pyochelin, Siderophore of Pseudomonas aeruginosa and Burkholderia cepacia," *Tetrahedron* 56:249-256 (2000), each of which is hereby incorporated by reference in its entirety). The resulting carboxylic acid intermediates can be easily converted to corresponding Weinreb amides (Nahm et al., "N-Methoxy-N-methylamides as Effective Acylating Agents," *Tetrahedron Lett.* 22:3815-18 (1981), which is hereby incorporated by reference in its entirety) using EDCI/HOBt as coupling reagents. Thiazole intermediates can be obtained from BrCCl$_3$/DBU dehydrogenation of the Weinreb amides. The thiazole intermediates can be reacted with appropriate lithium reagents or Grignard reagents (i.e., bearing the corresponding "C" ring, see Scheme 3 infra) in anhydrous THF to give the final thiazoles (Nahm et al., "N-Methoxy-N-methylamides as Effective Acylating Agents," *Tetrahedron Lett.* 22:3815-18 (1981), which is hereby incorporated by reference in its entirety). Alternatively, the thiazoline Weinreb amides can be reacted directly with appropriate lithium reagents or Grignard reagents, after quenching with saturated NH$_4$Cl solution, which affords mixtures of thiazoline compounds and the corresponding thiazole compounds.

Figure 2:
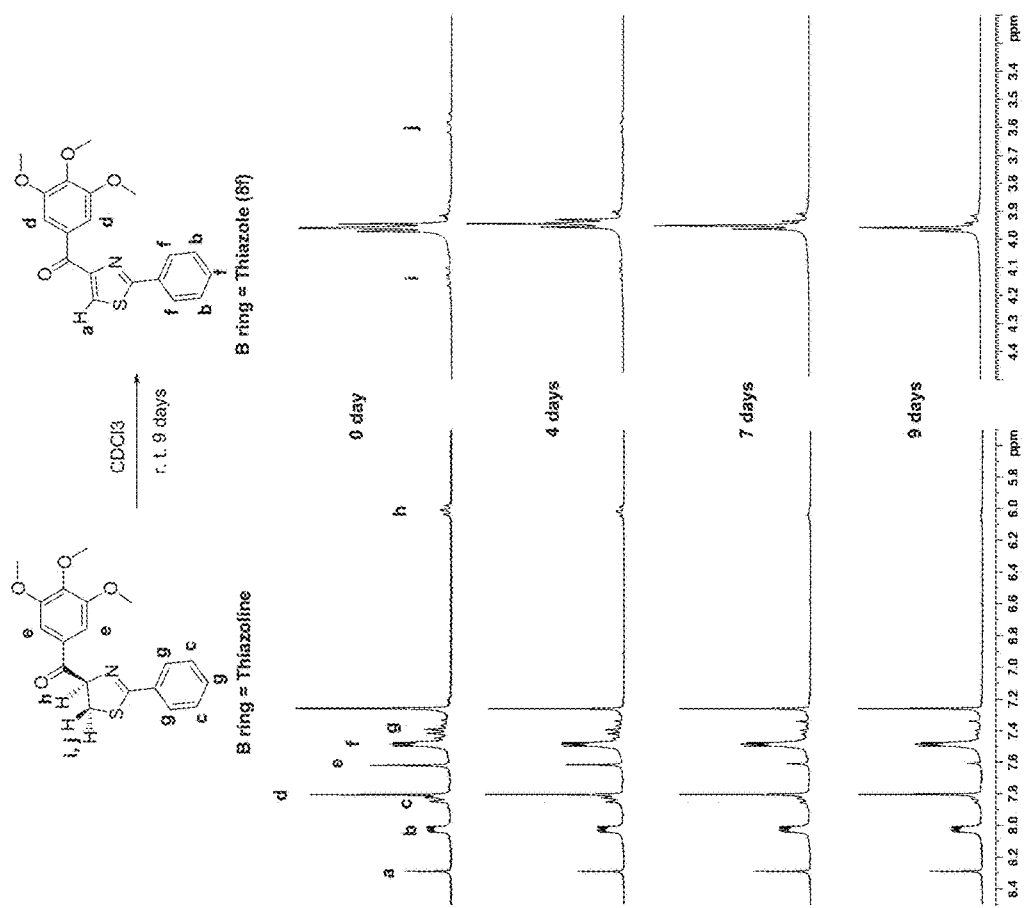
FIG. 2 illustrates NMR studies measuring the auto-dehydrogenation from thiazoline to thiazole compound 8f. At 0 day, NMR sample contained thiazoline and thiazole mixtures in CDCl$_3$; ratio is about 3: 2. At 9$^{th}$ day, thiazoline compound was nearly completely converted to thiazole compound 8f.

When thiazoline/thiazole mixtures were placed in the solvent and exposed to air under ambient atmosphere for some time (overnight to several days), the thiazoline ring spontaneously dehydrogenated to thiazoles. As an example, in solution with deuterated chloroform, mixtures of thiazoline/thiazole compounds can be slowly converted to almost pure thiazole compounds after roughly 9 days (see, e.g., FIG. 2).

Formation of thiazolidine compounds is described in U.S. Pat. No. 7,307,093 to Miller et al. and U.S. Pat. No. 7,662,842 to Miller et al., each of which is hereby incorporated by reference in its entirety.

Oxazoline derivatives (carboxylic acids, carboxamides, methanones) according to the present invention are prepared via condensation of imine derivatives (benzonitrile and 1-phenyl-2-methoxy-ethanimine) with enantioneric (L or D) or racemic cysteine or serine ester while using triethylamine as a base (Meyer et al., *Tetrahedron: Asymmetry* 14:2229-2238 (2003), which is hereby incorporated by reference in its entirety).

Imidazoline derivatives are prepared using L-tartaric acid in a condensation reaction with substituted or unsubstituted arylaldehyde to form the imidazoline ring system (Anderson et al., *J. Med. Chem.* 32(1), 119-127 (1989), which is hereby incorporated by reference in its entirety).

Syntheses of thiazole, oxazole, and imidazole can be carried out by dehydrogenation of corresponding thiazoline, oxazoline, and imidazoline. Dehydrogenation according to the present invention can be achieved by initial halogenation of these core ring systems (thiazoline, imidazoline, and oxazoline) followed by elimination to yield the desired thiazole, oxazole, and imidazole derivatives.

Formation of thiocarbonyl linker group (from carbonyl) can be carried out using Lawesson's reagent (Jesberger et al., *Synthesis* 1929-1958 (2003), which is hereby incorporated by reference in its entirety). The thioketone structure with conjugated aromatic rings is stable relative to unhindered thioketones.

The carbonyl linker group can also be reduced to an alcohol using Grignard reaction of an intermediate aldehyde with according Grignard reagents. Alternatively, the carbonyl group can be completely removed with Clemmensen reduction to form the corresponding hydrocarbon (e.g., methylene group). When carbonyl is reduced to an alcohol or methylene, the strong hydrogen acceptor C=O reverses to strong hydrogen donor O—H or hydrocarbon, which totally loses hydrogen bond effects.

The ester and carboxamide linkages can be prepared from the same intermediate acids used to form the ketone linkage, except that the reactants (acid and "C" ring precursor) are exposed to suitable conditions for formation of the respective ester (DCC, NMM) or amide (EDCl, HOBt, Et$_3$N) linkages. Carboxamide linkages are also taught in U.S. Pat. No. 7,307,093 to Miller et al. and U.S. Pat. No. 7,662,842 to Miller et al., each of which is hereby incorporated by reference in its entirety.

It is also appreciated that the compounds and synthetic intermediates of the present invention can be prepared by synthetic processes known to those skilled in the art. Functional groups of intermediates and compounds of the present invention may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl (t-Boc or Boc), benzyloxycarbonyl, phenylsulfonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein. The use of protecting groups is described in detail in Green et al., *Protective Groups in Organic Synthesis,* 2nd Ed., Wiley-Interscience (1991), which is hereby incorporated by reference in its entirety.

Pharmaceutical Composition

Another aspect of the present invention relates to a pharmaceutical composition including a pharmaceutically acceptable carrier and a compound according to the aspects of the present invention. The pharmaceutical composition can contain one or more of the above-identified compounds of the present invention. Typically, the pharmaceutical composition of the present invention will include a compound of the present invention or its pharmaceutically acceptable salt, as well as a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, or emulsions.

Typically, the composition will contain from about 0.01 to 99 percent, preferably from about 20 to 75 percent of active compound(s), together with the adjuvants, carriers and/or excipients. While individual needs may vary, determination of optimal ranges of effective amounts of each component is within the skill of the art. Typical dosages comprise about 0.01 to about 100 mg/kg body wt. The preferred dosages comprise about 0.1 to about 100 mg/kg body wt. The most preferred dosages comprise about 1 to about 100 mg/kg body wt. Treatment regimen for the administration of the compounds of the present invention can also be determined readily by those with ordinary skill in art. That is, the frequency of administration and size of the dose can be established by routine optimization, preferably while minimizing any side effects.

The solid unit dosage forms can be of the conventional type. The solid form can be a capsule and the like, such as an ordinary gelatin type containing the compounds of the present invention and a carrier, for example, lubricants and inert fillers such as, lactose, sucrose, or cornstarch. In another embodiment, these compounds are tabulated with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, these active compounds can be incorporated with excipients and used in the form of tablets, capsules, elixirs, suspensions, syrups, and the like. Such compositions and preparations should contain at least 0.1% of active compound. The percentage of the compound in these compositions can, of course, be varied and can conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 mg and 800 mg of active compound.

The active compounds of the present invention may be orally administered, for example, with an inert diluent, or with an assimilable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

In one embodiment, the compounds of this invention are administered in combination with an anti-cancer agent. In one embodiment, the anti-cancer agent is a monoclonal antibody. In some embodiments, the monoclonal antibodies are used for diagnosis, monitoring, or treatment of cancer. In one embodiment, monoclonal antibodies react against specific antigens on cancer cells. In one embodiment, the monoclonal antibody acts as a cancer cell receptor antagonist. In one embodiment, monoclonal antibodies enhance the patient's immune response. In one embodiment, monoclonal antibodies act against cell growth factors, thus blocking cancer cell growth. In one embodiment, anti-cancer monoclonal antibodies are conjugated or linked to anti-cancer drugs, radioisotopes, other biologic response modifiers, other toxins, or a combination thereof. In one embodiment, anti-cancer monoclonal antibodies are conjugated or linked to a compound of this invention as described hereinabove.

Yet another aspect of the present invention relates to a method of treating cancer that includes selecting a subject in need of treatment for cancer, and administering to the subject a pharmaceutical composition comprising a compound according to the first aspect of the present invention and a pharmaceutically acceptable carrier under conditions effective to treat cancer.

When administering the compounds of the present invention, they can be administered systemically or, alternatively, they can be administered directly to a specific site where cancer cells or precancerous cells are present. Thus, administering can be accomplished in any manner effective for delivering the compounds or the pharmaceutical compositions to the cancer cells or precancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Biological Activity

The compounds of the present invention are useful in the treatment or prevention of various forms of cancer, particularly prostate cancer, breast cancer, ovarian, skin cancer (e.g., melanoma), lung cancer, colon cancer, leukemia, renal cancer, CNS cancer (e.g., glioma, glioblastoma). Treatment of these different cancers is supported by the Examples herein. Moreover, based upon their mode of action as tubulin inhibitors, other forms of cancer will likewise be treatable or preventable upon administration of the compounds or compositions of the present invention to a patient. Preferred compounds of the present invention are selectively disruptive to cancer cells, causing ablation of cancer cells but preferably not normal cells. Significantly, harm to normal cells is minimized because the cancer cells are susceptible to disruption at much lower concentrations of the compounds of the present invention.

Thus, a further aspect of the present invention relates to a method of destroying a cancerous cell that includes: providing a compound of the present invention and then contacting a cancerous cell with the compound under conditions effective to destroy the contacted cancerous cell. According to various embodiments of destroying the cancerous cells, the cells to be destroyed can be located either in vivo or ex vivo (i.e., in culture).

A still further aspect of the present invention relates to a method of treating or preventing a cancerous condition that includes: providing a compound of the present invention and then administering an effective amount of the compound to a patient in a manner effective to treat or prevent a cancerous condition.

According to one embodiment, the patient to be treated is characterized by the presence of a precancerous condition, and the administering of the compound is effective to prevent development of the precancerous condition into the cancerous condition. This can occur by destroying the precancerous cell prior to or concurrent with its further development into a cancerous state.

According to another embodiment, the patient to be treated is characterized by the presence of a cancerous condition, and the administering of the compound is effective either to cause regression of the cancerous condition or to inhibit growth of the cancerous condition, i.e., stopping its growth altogether or reducing its rate of growth. This preferably occurs by destroying cancer cells, regardless of their location in the patient body. That is, whether the cancer cells are located at a primary tumor site or whether the cancer cells have metastasized and created secondary tumors within the patient body.

When the compounds or pharmaceutical compositions of the present invention are administered to treat or prevent a cancerous condition, the pharmaceutical composition can also contain, or can be administered in conjunction with, other therapeutic agents or treatment regimen presently known or hereafter developed for the treatment of various types of cancer. Examples of other therapeutic agents or treatment regimen include, without limitation, radiation therapy, immunotherapy, chemotherapy, surgical intervention, and combinations thereof.

In one embodiment, the invention provides compounds and compositions, including any embodiment described herein, for use in any of the methods of this invention. In one embodiment, use of a compound of this invention or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound of this invention is being administered.

In one embodiment, this invention is directed to a method of treating, suppressing, reducing the severity, reducing the risk of developing or inhibiting cancer comprising administering a compound of this invention to a subject suffering from cancer under conditions effective to treat the cancer.

Drug resistance is the major cause of cancer chemotherapy failure. One major contributor to multidrug resistance is overexpression of P-glycoprotein (P-gp). This protein is a clinically important transporter protein belonging to the ATP-binding cassette family of cell membrane transporters. It can pump substrates including anticancer drugs out of tumor cells through an ATP-dependent mechanism.

In one embodiment, this invention provides methods for: a) treating, suppressing, reducing the severity, reducing the risk, or inhibiting drug resistant tumors; b) treating, suppressing, reducing the severity, reducing the risk, or inhibiting metastatic cancer; c) treating, suppressing, reducing the severity, reducing the risk, or inhibiting drug resistant cancer; d) treating, suppressing, reducing the severity, reducing the risk, or inhibiting a drug resistant cancer wherein the cancer is melanoma; e) treating, suppressing, reducing the severity, reducing the risk, or inhibiting a drug resistant cancer wherein the cancer is prostate cancer; f) treating, suppressing, reducing the severity, reducing the risk, or inhibiting a drug resistant cancer wherein the cancer is uterine cancer; g) treating, suppressing, reducing the severity, reducing the risk, or inhibiting a drug resistant cancer wherein the cancer is ovarian cancer; h) treating, suppressing, reducing the severity, reducing the risk, or inhibiting metastatic melanoma; i) treating, suppressing, reducing the severity, reducing the risk, or inhibiting prostate cancer; j) treating, suppressing, reducing the severity, reducing the risk, or inhibiting uterine cancer; k) treating, suppressing, reducing the severity, reducing the risk, or inhibiting ovarian cancer; l) treating, suppressing, reducing the severity, reducing the risk, or inhibiting lung cancer; m) treating, suppressing, reducing the severity, reducing the risk, or inhibiting colon cancer; n) treating, suppressing, reducing the severity, reducing the risk, or inhibiting leukemia; o) treating, suppressing, reducing the severity, reducing the risk, or inhibiting breast cancer; p) treating, suppressing, reducing the severity, reducing the risk, or inhibiting glioma; and/or q) treating, suppressing, reducing the severity, reducing the risk, or inhibiting cancer in a subject, wherein the subject has been previously treated with chemotherapy, radiotherapy, or biological therapy; comprising the step of administering to said subject a compound of this invention and/or an isomer, metabolite, pharmaceutically acceptable salt, pharmaceutical product, tautomer, hydrate, N-oxide, polymorph, or crystal of said compound, or any combination thereof.

The compounds of the present invention are useful in the treatment, reducing the severity, reducing the risk, or inhibition of cancer, metastatic cancer, drug resistant tumors, drug resistant cancer and various forms of cancer. In a preferred embodiment the cancer is prostate cancer, drug-resistant prostate cancer, breast cancer, ovarian cancer, drug-resistant ovarian cancer, uterine cancer, drug-resistant uterine cancer, skin cancer (e.g., melanoma), lung cancer, colon cancer, leukemia, lymphoma, head and neck, pancreatic, esophageal, renal cancer or CNS cancer (e.g., glioma, glioblastoma). Treatment of these different cancers is supported by the Examples herein. Moreover, based upon their mode of action as tubulin inhibitors, other forms of cancer will likewise be treatable or preventable upon administration of the compounds or compositions of the present invention to a patient. Preferred compounds of the present invention are selectively disruptive to cancer cells, causing ablation of cancer cells but preferably not normal cells. Significantly, harm to normal cells is minimized because the cancer cells are susceptible to disruption at much lower concentrations of the compounds of the present invention.

In some embodiments, this invention provides for the use of a compound as herein described, or its isomer, metabolite, pharmaceutically acceptable salt, pharmaceutical product, tautomer, polymorph, crystal, N-oxide, hydrate or any combination thereof, for treating, suppressing, reducing the severity, reducing the risk, or inhibiting cancer in a subject. In another embodiment, the cancer is adrenocortical carcinoma, anal cancer, bladder cancer, brain tumor, brain stem tumor, breast cancer, glioma, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic leukemia, oral cavity cancer, liver cancer, lung cancer, non-small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian cancer, ovarian epithelial cancer, ovarian germ cell tumor, ovarian low malignant potential tumor, drug-resistant ovarian cancer, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, drug-resistant prostate cancer, rhabdomyosarcoma, rectal cancer, renal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, drug-resistant uterine cancer, sarcoma, unusual cancer of childhood, vaginal cancer, vulvar cancer, Wilms' tumor, or any combination thereof. In another embodiment the subject has been previously treated with chemotherapy, radiotherapy or biological therapy.

In some embodiments, this invention provides for the use of a compound as herein described, or its isomer, metabolite, pharmaceutically acceptable salt, pharmaceutical product, tautomer, polymorph, crystal, N-oxide, hydrate or any combination thereof, for treating, suppressing, reducing the severity, reducing the risk, or inhibiting a metastatic cancer in a subject. In another embodiment, the cancer is adrenocortical carcinoma, anal cancer, bladder cancer, brain tumor, brain stem tumor, breast cancer, glioma, cerebellar astrocytoma, cerebral astrocytoma, ependymoma, medulloblastoma, supratentorial primitive neuroectodermal, pineal tumors, hypothalamic, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non-small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian cancer, ovarian epithelial cancer, ovarian germ cell tumor, ovarian low malignant potential tumor, drug-resistant ovarian cancer, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, drug-resistant prostate cancer, rhabdomyosarcoma, rectal cancer, renal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, drug-resistant uterine cancer, sarcoma, unusual cancer of childhood, vaginal cancer, vulvar cancer, Wilms' tumor, or any combination thereof.

In some embodiments, this invention provides for the use of a compound as herein described, or its isomer, metabolite, pharmaceutically acceptable salt, pharmaceutical product, tautomer, polymorph, crystal, N-oxide, hydrate or any combination thereof, for treating, suppressing, reducing the severity, reducing the risk, or inhibiting a drug-resistant cancer or resistant cancer in a subject. In another embodiment, the cancer is adrenocortical carcinoma, anal cancer, bladder cancer, brain tumor, brain stem tumor, breast cancer, glioma, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non-small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian cancer, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, or any combination thereof.

In one embodiment "metastatic cancer" refers to a cancer that spread (metastasized) from its original site to another area of the body. Virtually all cancers have the potential to spread. Whether metastases develop depends on the complex interaction of many tumor cell factors, including the type of cancer, the degree of maturity (differentiation) of the tumor cells, the location and how long the cancer has been present, as well as other incompletely understood factors. Metastases spread in three ways—by local extension from the tumor to the surrounding tissues, through the bloodstream to distant sites or through the lymphatic system to neighboring or distant lymph nodes. Each kind of cancer may have a typical route of spread. The tumor is called by the primary site (ex. breast cancer that has spread to the brain is called metastatic breast cancer to the brain).

In one embodiment "drug-resistant cancer" refers to cancer cells that acquire resistance to chemotherapy. Cancer cells can acquire resistance to chemotherapy by a range of mechanisms, including the mutation or overexpression of the drug target, inactivation of the drug, or elimination of the drug from the cell. Tumors that recur after an initial response to chemotherapy may be resistant to multiple drugs (they are multidrug resistant). In the conventional view of drug resistance, one or several cells in the tumor population acquire genetic changes that confer drug resistance. Accordingly, the reasons for drug resistance, inter alia, are: a) some of the cells that are not killed by the chemotherapy mutate (change) and become resistant to the drug. Once they multiply, there may be more resistant cells than cells that are sensitive to the chemotherapy; b) Gene amplification. A cancer cell may produce hundreds of copies of a particular gene. This gene triggers an overproduction of protein that renders the anticancer drug ineffective; c) cancer cells may pump the drug out of the cell as fast as it is going in using a molecule called p-glycoprotein; d) cancer cells may stop taking in the drugs because the protein that transports the drug across the cell wall stops working; e) the cancer cells may learn how to repair the DNA breaks caused by some anti-cancer drugs; f) cancer cells may develop a mechanism that inactivates the drug. One major contributor to multidrug resistance is overexpression of P-glycoprotein (P-gp). This protein is a clinically important transporter protein belonging to the ATP-binding cassette family of cell membrane transporters. It can pump substrates including anticancer drugs out of tumor cells through an ATP-dependent mechanism. Thus, the resistance to anticancer agents used in chemotherapy is the main cause of treatment failure in malignant disorders, provoking tumors to become resistant. Drug resistance is the major cause of cancer chemotherapy failure.

In one embodiment "resistant cancer" refers to drug-resistant cancer as described herein above. In another embodiment "resistant cancer" refers to cancer cells that acquire resistance to any treatment such as chemotherapy, radiotherapy or biological therapy.

In one embodiment, this invention is directed to treating, suppressing, reducing the severity, reducing the risk, or inhibiting cancer in a subject, wherein the subject has been previously treated with chemotherapy, radiotherapy or biological therapy.

In one embodiment "Chemotherapy" refers to chemical treatment for cancer such as drugs that kill cancer cells directly. Such drugs are referred as "anti-cancer" drugs or "antineoplastics." Today's therapy uses more than 100 drugs to treat cancer. To cure a specific cancer. Chemotherapy is used to control tumor growth when cure is not possible; to shrink tumors before surgery or radiation therapy; to relieve symptoms (such as pain); and to destroy microscopic cancer cells that may be present after the known tumor is removed by surgery (called adjuvant therapy). Adjuvant therapy is given to prevent a possible cancer reoccurrence.

In one embodiment, "Radiotherapy" refers to high energy x-rays and similar rays (such as electrons) to treat disease. Many people with cancer will have radiotherapy as part of their treatment. This can be given either as external radiotherapy from outside the body using x-rays or from within the body as internal radiotherapy. Radiotherapy works by destroying the cancer cells in the treated area. Although normal cells can also be damaged by the radiotherapy, they can usually repair themselves. Radiotherapy treatment can cure some cancers and can also reduce the chance of a cancer coming back after surgery. It may be used to reduce cancer symptoms.

In one embodiment "Biological therapy" refers to substances that occur naturally in the body to destroy cancer cells. There are several types of treatment including: monoclonal antibodies, cancer growth inhibitors, vaccines and gene therapy. Biological therapy is also known as immunotherapy.

In one embodiment, this invention provides a method of treating a subject suffering from prostate cancer, metastatic prostate cancer, resistant prostate cancer or drug-resistant prostate cancer comprising the step of administering to said subject a compound of this invention, or its isomer, metabolite, pharmaceutically acceptable salt, pharmaceutical product, tautomer, hydrate, N-oxide, polymorph, crystal or any combination thereof, or a composition comprising the same in an amount effective to treat prostate cancer in the subject. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In another embodiment, the compound is compound 31. In yet another embodiment, the compound is compound 31a.

In one embodiment, this invention provides a method for suppressing, reducing the severity, reducing the risk, delaying the progression, or inhibiting prostate cancer, metastatic prostate cancer, resistant prostate cancer or drug-resistant prostate cancer in a subject, comprising administering to the subject a compound of this invention and/or its isomer, metabolite, pharmaceutically acceptable salt, pharmaceutical product, tautomer, hydrate, N-oxide, polymorph, crystal or any combination thereof or a composition comprising the same. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiment, the compound is compound 31. In yet another embodiment, the compound is compound 31a.

In one embodiment, this invention provides a method of treating a subject suffering from breast cancer, metastatic breast cancer, resistant breast cancer or drug-resistant breast cancer comprising the step of administering to said subject a compound of this invention, or its isomer, metabolite, pharmaceutically acceptable salt, pharmaceutical product, tautomer, hydrate, N-oxide, polymorph, crystal or any combination thereof, or a composition comprising the same. In another embodiment, the subject is a male or female. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiment, the compound is compound 31. In yet another embodiment, the compound is compound 31a.

In one embodiment, this invention provides a method of suppressing, reducing the severity, reducing the risk, delaying the progression, or inhibiting breast cancer, metastatic breast cancer, resistant breast cancer or drug-resistant breast cancer in a subject comprising the step of administering to said subject a compound of this invention or its isomer, metabolite, pharmaceutically acceptable salt, pharmaceutical product, tautomer, hydrate, N-oxide, polymorph, crystal or any combination thereof, or a composition comprising the same. In another embodiment, the subject is a male or female. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiment, the compound is compound 31. In yet another embodiment, the compound is compound 31a.

In another embodiment, this invention provides for the use of a compound as herein described, or its isomer, metabolite, pharmaceutically acceptable salt, pharmaceutical product, tautomer, hydrate, N-oxide, polymorph, crystal or any combination thereof, for treating, suppressing, reducing the severity, reducing the risk, delaying the progression, or inhibiting ovarian cancer, metastatic ovarian cancer, resistant ovarian cancer or drug-resistant ovarian cancer in a subject. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiment, the compound is compound 31. In yet another embodiment, the compound is compound 31a.

In one embodiment, this invention provides a method for treating, suppressing, reducing the severity, reducing the risk or inhibiting melanoma, metastatic melanoma, resistant melanoma or drug-resistant melanoma in a subject, comprising administering to the subject a compound of this invention and/or its isomer, metabolite, pharmaceutically acceptable salt, pharmaceutical product, tautomer, hydrate, N-oxide, polymorph, crystal or any combination thereof. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiment, the compound is compound 31. In yet another embodiment, the compound is compound 31a.

In another embodiment, this invention provides for the use of a compound as herein described, or isomer, metabolite, pharmaceutically acceptable salt, pharmaceutical product, tautomer, hydrate, N-oxide, polymorph, crystal or any combination thereof, for treating, suppressing, reducing the severity, reducing the risk, delaying the progression, or inhibiting lung cancer, metastatic lung cancer, resistant lung cancer or drug-resistant lung cancer. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiment, the compound is compound 31. In yet another embodiment, the compound is compound 31a.

In another embodiment, this invention provides for the use of a compound as herein described, or isomer, metabolite, pharmaceutically acceptable salt, pharmaceutical product, tautomer, hydrate, N-oxide, polymorph, crystal any combination thereof, for treating, suppressing, reducing the severity, reducing the risk, delaying the progression, or inhibiting non-small cell lung cancer, metastatic small cell lung cancer, resistant small cell lung cancer or drug-resistant small cell lung cancer. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiment, the compound is compound 31. In yet another embodiment, the compound is compound 31a.

In another embodiment, this invention provides for the use of a compound as herein described, or isomer, metabolite, pharmaceutically acceptable salt, pharmaceutical product, tautomer, hydrate, N-oxide, polymorph, crystal any combination thereof, for treating, suppressing, reducing the severity, reducing the risk, delaying the progression, or inhibiting colon cancer, metastatic colon cancer, resistant colon cancer or drug-resistant colon cancer. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiment, the compound is compound 31. In yet another embodiment, the compound is compound 31a.

In another embodiment, this invention provides for the use of a compound as herein described, or isomer, metabolite, pharmaceutically acceptable salt, pharmaceutical product, tautomer, hydrate, N-oxide, polymorph, crystal any combination thereof, for treating, suppressing, reducing the severity, reducing the risk, delaying the progression, or inhibiting of leukemia, metastatic leukemia, resistant leukemia or drug-resistant leukemia. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiment, the compound is compound 31. In yet another embodiment, the compound is compound 31a.

In another embodiment, this invention provides for the use of a compound as herein described, or isomer, metabolite, pharmaceutically acceptable salt, pharmaceutical product, tautomer, hydrate, N-oxide, polymorph, crystal any combination thereof, for treating, suppressing, reducing the severity, reducing the risk, delaying the progression, or inhibiting glioma, metastatic glioma, resistant glioma or drug-resistant glioma. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiment, the compound is compound 31. In yet another embodiment, the compound is compound 31a.

In another embodiment, this invention provides for the use of a compound as herein described, or isomer, metabolite, pharmaceutically acceptable salt, pharmaceutical product, tautomer, hydrate, N-oxide, polymorph, crystal any combination thereof, for treating, suppressing, reducing the severity, reducing the risk, delaying the progression, or inhibiting lymphoma, metastatic lymphoma, resistant lymphoma or drug-resistant lymphoma. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiment, the compound is compound 31. In yet another embodiment, the compound is compound 31a.

In another embodiment, this invention provides for the use of a compound as herein described, or isomer, metabolite, pharmaceutically acceptable salt, pharmaceutical product, tautomer, hydrate, N-oxide, polymorph, crystal any combination thereof, for treating, suppressing, reducing the severity, reducing the risk, delaying the progression, or inhibiting head and neck cancer, metastatic head and neck cancer, resistant head and neck cancer or drug-resistant head and neck cancer. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiment, the compound is compound 31. In yet another embodiment, the compound is compound 31a.

In another embodiment, this invention provides for the use of a compound as herein described, or isomer, metabolite, pharmaceutically acceptable salt, pharmaceutical product, tautomer, hydrate, N-oxide, polymorph, crystal any combination thereof, for treating, suppressing, reducing the severity, reducing the risk, delaying the progression, or inhibiting of pancreatic cancer, metastatic pancreatic cancer, resistant pancreatic cancer or drug-resistant pancreatic cancer. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiment, the compound is compound 31. In yet another embodiment, the compound is compound 31a.

In another embodiment, this invention provides for the use of a compound as herein described, or isomer, metabolite, pharmaceutically acceptable salt, pharmaceutical product, tautomer, hydrate, N-oxide, polymorph, crystal any combination thereof, for treating, suppressing, reducing the severity, reducing the risk, delaying the progression, or inhibiting esophageal cancer, metastatic esophageal cancer, resistant esophageal cancer or drug-resistant esophageal cancer. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiment, the compound is compound 31. In yet another embodiment, the compound is compound 31a.

In another embodiment, this invention provides for the use of a compound as herein described, or isomer, metabolite, pharmaceutically acceptable salt, pharmaceutical product, tautomer, hydrate, N-oxide, polymorph, crystal any combination thereof, for treating, suppressing, reducing the severity, reducing the risk, delaying the progression, or inhibiting renal cancer, metastatic renal cancer, resistant renal cancer or drug-resistant renal cancer. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiment, the compound is compound 31. In yet another embodiment, the compound is compound 31a.

In another embodiment, this invention provides for the use of a compound as herein described, or isomer, metabolite, pharmaceutically acceptable salt, pharmaceutical product, tautomer, hydrate, N-oxide, polymorph, crystal any combination thereof, for treating, suppressing, reducing the severity, reducing the risk, delaying the progression, or inhibiting CNS cancer, metastatic CNS cancer, resistant CNS cancer or drug-resistant CNS cancer. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiment, the compound is compound 31. In yet another embodiment, the compound is compound 31a.

In some embodiments, this invention provides for the use of a compound as herein described, or its isomer, metabolite, pharmaceutically acceptable salt, pharmaceutical product, tautomer, polymorph, crystal, N-oxide, hydrate or any combination thereof, for treating, suppressing, reducing the severity, reducing the risk, or inhibiting a drug resistant cancerous tumor or tumors in a subject. In another embodiment, the cancer is adrenocortical carcinoma, anal cancer, bladder cancer, brain tumor, brain stem tumor, breast cancer, glioma, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non-small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian cancer, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, or any combination thereof. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiment, the compound is compound 31. In yet another embodiment, the compound is compound 31a.

In another embodiment, the tumor is prostate cancer tumor. In another embodiment, the tumor is a multidrug resistant (MDR) prostate cancer tumor. In another embodiment, the tumor is ovarian cancer tumor. In yet another embodiment, the tumor is a multidrug (MDR) resistant ovarian cancer tumor. In another embodiment, the tumor is uterine cancer tumor. In yet another embodiment, the tumor is a multidrug (MDR) resistant uterine cancer tumor. In another embodiment, the tumor is a melanoma tumor. In another embodiment, the tumor is a multidrug resistant (MDR) melanoma tumor. In another embodiment, the tumor is a lung cancer tumor. In still another embodiment, the tumor is a colon cancer tumor. In another embodiment, the tumor is a breast cancer tumor. In another embodiment, the tumor is a glioma tumor. In another embodiment, the tumor is a leukemia tumor.

In one embodiment, this invention is directed to a method of destroying a cancerous cell comprising: providing a compound of this invention and contacting the cancerous cell with the compound under conditions effective to destroy the contacted cancerous cell. According to various embodiments of destroying the cancerous cells, the cells to be destroyed can be located either in vivo or ex vivo (i.e., in culture). In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiment, the compound is compound 31. In yet another embodiment, the compound is compound 31a.

In another embodiment, the cancer is selected from the group consisting of prostate cancer, drug-resistant prostate cancer, breast cancer, drug-reistant breast cancer, ovarian cancer, drug-reistant ovarian cancer, skin cancer, melanoma, lung cancer, colon cancer, leukemia, glioma, renal cancer, CNS cancer, uterine cancer, drug-resistant uterine cancer, and combinations thereof.

In one embodiment, this invention is directed to a method of inhibiting, preventing, or slowing the progress of vascularization of a tumor comprising administering a compound of this invention to a subject having cancer under conditions effective to inhibit, prevent or slow the progress of vascularization of said tumor. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiment, the compound is compound 31. In yet another embodiment, the compound is compound 31a.

In one embodiment, this invention is directed to a method of inhibiting, preventing, or slowing the progress of vascularization of a metastatic tumor comprising administering a compound of this invention to a subject having cancer under conditions effective to inhibit, prevent or slow the progress of vascularization of said tumor. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiment, the compound is compound 31. In yet another embodiment, the compound is compound 31a.

In another embodiment, the tumor is selected from the group consisting of prostate cancer tumor, drug-resistant prostate cancer tumor, breast cancer tumor, glioma tumor, ovarian cancer tumor, drug-resistant ovarian cancer tumor, skin cancer tumor, melanoma tumor, lung cancer tumor, colon cancer tumor, lymphoma tumor, renal cancer tumor, CNS cancer tumor, uterine cancer tumor, drug-resistant uterine cancer tumor, and combinations thereof.

A still further aspect of the present invention relates to a method of treating or preventing a cancerous condition that includes: providing a compound of the present invention and then administering an effective amount of the compound to a patient in a manner effective to treat or prevent a cancerous condition.

According to one embodiment, the patient to be treated is characterized by the presence of a precancerous condition, and the administering of the compound is effective to prevent development of the precancerous condition into the cancerous condition. This can occur by destroying the precancerous cell prior to or concurrent with its further development into a cancerous state.

According to another embodiment, the patient to be treated is characterized by the presence of a cancerous condition, and the administering of the compound is effective either to cause regression of the cancerous condition or to inhibit growth of the cancerous condition, i.e., stopping its growth altogether or reducing its rate of growth. This preferably occurs by destroying cancer cells, regardless of their location in the patient body. That is, whether the cancer cells are located at a primary tumor site or whether the cancer cells have metastasized and created secondary tumors within the patient body.

As used herein, subject or patient refers to any mammalian patient, including without limitation, humans and other primates, dogs, cats, horses, cows, sheep, pigs, rats, mice, and other rodents. In one embodiment, the subject is human. In one embodiment, the subject is male. In another embodiment, the subject is female. In some embodiments, while the methods as described herein may be useful for treating either males or females.

When administering the compounds of the present invention, they can be administered systemically or, alternatively, they can be administered directly to a specific site where cancer cells or precancerous cells are present. Thus, administering can be accomplished in any manner effective for delivering the compounds or the pharmaceutical compositions to the cancer cells or precancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

The compounds of the present invention are useful in the treatment or prevention of various forms of cancer, particularly prostate cancer, drug-resistant prostate cancer, breast cancer, drug resistant breat cancer, ovarian cancer, drug-resistant ovarian cancer, skin cancer (e.g., melanoma), lung cancer, colon cancer, glioma, leukemia, lymphoma, renal cancer, uterine cancer, drug-resistant uterine cancer, and CNS cancer (e.g., glioma, glioblastoma). Treatment of these different cancers is supported by the Examples herein. Moreover, based upon their mode of action as tubulin inhibitors, other forms of cancer will likewise be treatable or preventable upon administration of the compounds or compositions of the present invention to a patient. Preferred compounds of the present invention are selectively disruptive to cancer cells, causing ablation of cancer cells but preferably not normal cells. Significantly, harm to normal cells is minimized because the cancer cells are susceptible to disruption at much lower concentrations of the compounds of the present invention.

The compounds of the present invention are useful in the treatment, reducing the severity, reducing the risk, or inhibition of cancer, metastatic cancer, resistant cancer or drug-resistant cancer. In another embodiment, the cancer is prostate cancer, breast cancer, ovarian cancer, skin cancer (e.g., melanoma), lung cancer, colon cancer, glioma, leukemia, lymphoma, head and neck, pancreatic, esophageal, renal cancer, uterine cancer or CNS cancer, or combinations thereof. Treatment of these different cancers is supported by the Examples herein. Moreover, based upon their mode of action as tubulin inhibitors, other forms of cancer will likewise be treatable or preventable upon administration of the compounds or compositions of the present invention to a patient. Preferred compounds of the present invention are selectively disruptive to cancer cells, causing ablation of cancer cells but preferably not normal cells. Significantly, harm to normal cells is minimized because the cancer cells are susceptible to disruption at much lower concentrations of the compounds of the present invention. In one embodiment, the compound is a compound of formula XI, XI(e), XXI, XXIa, XXII, or 17ya. In another embodiment, the compound is compound 17ya. In one embodiment, the compound is compound 17yab. In another embodiment, the compound is compound 32. In other embodiments, the compound is compound 31. In yet another embodiment, the compound is compound 31a.

In one embodiment, the compound is administered in combination with an anti-cancer agent by administering the compounds as herein described, alone or in combination with other agents.

When the compounds or pharmaceutical compositions of the present invention are administered to treat, suppress, reduce the severity, reduce the risk, or inhibit a cancerous condition, the pharmaceutical composition can also contain, or can be administered in conjunction with, other therapeutic agents or treatment regimen presently known or hereafter developed for the treatment of various types of cancer. Examples of other therapeutic agents or treatment regimen include, without limitation, radiation therapy, immunotherapy, chemotherapy, surgical intervention, and combinations thereof.

The following examples are presented in order to more fully illustrate the embodiments of the invention. They should in no way, however, be construed as limiting the broad scope of the invention.

EXAMPLES

Materials and Methods:
General:
All reagents were purchased from Sigma-Aldrich Chemical Co., Fisher Scientific (Pittsburgh, Pa.), AK Scientific (Mountain View, Calif.), Oakwood Products (West Columbia, S.C.), etc. and were used without further purification. Moisture-sensitive reactions were carried under an argon atmosphere. Routine thin layer chromatography (TLC) was performed on aluminum backed Uniplates. (Analtech, Newark, Del.). Melting points were measured with Fisher-Johns melting point apparatus (uncorrected). NMR spectra were obtained on a Bruker ARX 300 (Billerica, Mass.) spectrometer or Varian Inova-500 spectrometer. Chemical shifts are reported as parts per million (ppm) relative to TMS in $CDCl_3$. Mass spectral data was collected on a Bruker ESQUIRE electrospray/ion trap instrument in positive and negative ion modes. Elemental analyses were performed by Atlantic Microlab Inc., (Norcross, Ga.).

Cell Culture and Cytotoxicity Assay of Prostate Cancer, Ovarian Cancer, and Melanoma.

All cell lines were obtained from ATCC (American Type Culture Collection, Manassas, Va., USA) unless otherwise specified, while cell culture supplies were purchased from Cellgro Mediatech (Herndon, Va., USA). We examined the antiproliferative activity of our anti-tubulin compounds in four human prostate cancer cell lines (LNCaP, DU 145, PC-3, and PPC-1) and two human melanoma cell lines (A375 and WM-164). Human ovarian cell line OVCAR-8 and its resistant cell line that over-expresses P-gp (NCI/ADR-RES) were used as MDR models. Both ovarian cell lines were obtained from National Cancer Institutes (NCI). All cell lines were tested and authenticated by either ATCC or NCI. All prostate cancer and ovarian cancer cell lines were cultured in RPMI 1640, supplemented with 10% fetal bovine serum (FBS). Melanoma cells were cultured in DMEM, supplemented with 5% FBS, 1% antibiotic/antimycotic mixture (Sigma-Aldrich, Inc., St. Louis, Mo., USA) and bovine insulin (5 µg/mL; Sigma-Aldrich). The cytotoxic potential of the anti-tubulin compounds was evaluated using the sulforhodamine B (SRB) assay after 96 h of treatment.

Aqueous Solubility.

The solubility of drugs was determined by Multiscreen Solubility Filter Plate (Millipore Corporate, Billerica, Mass.) coupled with LC-MS/MS. Briefly, 198 µL of phosphate buffered saline (PBS) buffer (pH 7.4) was loaded into 96-well plate, and 2 µL of 10 mM test compounds (in DMSO) was dispensed and mixed with gentle shaking (200-300 rpm) for 1.5 h at RT (N=3). The plate was centrifuged at 800 g for 5 min, and the filtrate was used to determine its concentration and solubility of test compound by LC-MS/MS as described below.

Pharmacokinetic Study.

Female Sprague-Dawley rats (n=3 or 4; 254±4 g) were purchased from Harlan Inc. (Indianapolis, Ind.). Rat thoracic jugular vein catheters were purchased from Braintree Scientific Inc. (Braintree, Mass.). On arrival at the animal facility, the animals were acclimated for 3 days in a temperature-controlled room (20-22° C.) with a 12 h light/dark cycle before any treatment. Compound 1-h was administered intravenously (i.v.) into the jugular vein catheters at a dose of 2.5 mg/kg (in DMSO/PEG300, 2/8), whereas 5-Ha and 5-Hc were dosed at 5 mg/kg (in DMSO/PEG300, 1/9). An equal volume of heparinized saline was injected to replace the removed blood, and blood samples (250 µL) were collected via the jugular vein catheters at 10, 20, 30 min, and 1, 2, 4, 8, 12, 24 h. Compounds 1-h, 5-Ha and 5-Hc were given (p.o.) by oral gavage at 10 mg/kg (in Tween80/DMSO/$H_2O$, 2/1/7). All blood samples (250 µL) after oral administration were collected via the jugular vein catheters at 30, 60, 90 min, 120 min, 150 min, 180 min, 210 min, 240 min, and 8, 12, 24 h. Heparinized syringes and vials were prepared prior to blood collection. Plasma samples were prepared by centrifuging the blood samples at 8,000 g for 5 min. All plasma samples were stored immediately at −80° C. until analyzed.

Analytes were extracted from 100 µL of plasma with 200 µL of acetonitrile containing 200 nM the internal standard ((3,5-dimethoxyphenyl)(2-phenyl-1H-imidazol-4-yl)methanone). The samples were thoroughly mixed, centrifuged, and the organic extract was transferred to autosampler for LC-MS/MS analysis. Multiple reaction monitoring (MRM) mode, scanning m/z 356→188 (compound 1-h), m/z 371→203 (compound 5-Ha), m/z 389→221 (compound 5-Hc), and m/z 309→171 (the internal standard), was used to obtain the most sensitive signals. The pharmacokinetic parameters were determined using non-compartmental analysis (WinNonlin, Pharsight Corporation, Mountain View, Calif.).

Analytical Method.

Sample solution (10 µL) was injected into an Agilent series HPLC system (Agilent 1100 Series Agilent 1100 Chemstation, Agilent Technology Co, Ltd). All analytes were separated on a narrow-bore C18 column (Alltech Alltima HP, 2.1×100 mm, 3 µm, Fisher, Fair Lawn, N.J.). Two gradient modes were used. Gradient mode was used to achieve the separation of analytes using mixtures of mobile phase A [ACN/H$_2$O (5%/95%, v/v) containing 0.1% formic acid] and mobile phase B [ACN/H$_2$O (95%/5%, v/v) containing 0.1% formic acid] at a flow rate of 300 µL/min. Mobile phase A was used at 15% from 0 to 1 min followed by a linearly programmed gradient to 100% of mobile phase B within 6 min, 100% of mobile phase B was maintained for 0.5 min before a quick ramp to 15% mobile phase A. Mobile phase A was continued for another 12 min towards the end of analysis.

In Vitro Tubulin Polymerization Assay.

Bovine brain tubulin (0.4 mg, >97% pure) (Cytoskeleton, Denver, Colo.) was mixed with 10 µM of the test compounds and incubated in 100 µL of general tubulin buffer (80 mM PIPES, 2.0 mM MgCl$_2$, 0.5 mM EGTA, and 1 mM GTP) at pH 6.9. The absorbance of wavelength at 340 nm was monitored every 1 min for 20 min by the SYNERGY 4 Microplate Reader (Bio-Tek Instruments, Winooski, Vt.). The spectrophotometer was set at 37° C. for tubulin polymerization.

A triple-quadruple mass spectrometer, API Qtrap 4000™ (Applied Biosystems/MDS SCIEX, Concord, Ontario, Canada), operating with a TurbolonSpray source was used. The spraying needle voltage was set at 5 kV for positive mode. Curtain gas was set at 10; Gas 1 and gas 2 were set 50. Collision-Assisted-Dissociation (CAD) gas at medium and the source heater probe temperature at 500° C. Data acquisition and quantitative processing were accomplished using Analyst™ software, Ver. 1.4.1 (Applied Biosystems).

The purity of the final compounds was tested via RP-HPLC on a Waters 2695 HPLC system installed with a Photodiode Array Detector. Two RP-HPLC methods were conducted using a Supelco Ascentis™ 5 µM C-18 column (250×4.6 mm) at ambient temperature, and a flow rate of 0.7 mL/min. HPLC1: Gradient: Solvent A (water) and Solvent B (methanol): 0-20 min 40-100% B (linear gradient), 20-27 min 100% B. HPLC2: Gradient: Solvent A (water) and Solvent B (methanol): 0-15 min 40-100% B (linear gradient), 15-25 min 100% B. UV detection at 254 nm.

Example 1: Synthesis of Thiazole, Thiazoline, and Thiazolidine Carboxamides

The synthesis of thiazole and thiazolidine carboxamides is generally disclosed in U.S. Pat. No. 7,307,093 to Miller et al. and U.S. Pat. No. 7,662,842 to Miller et al., each of which is hereby incorporated by reference in its entirety. The synthesis of various thiazole, dihydrothiazole, and thiazolidine carboxamides of the present invention is also illustrated in Scheme 1 below.

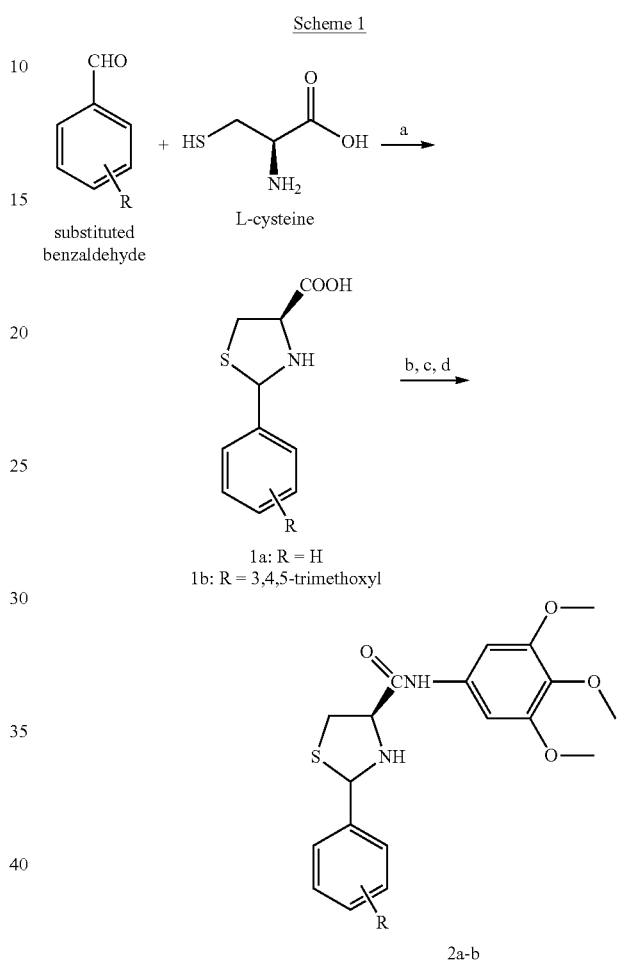

Reagents and conditions:
(a) C$_2$H$_5$OH, H$_2$O, r.t.;
(b) Boc$_2$O, 1N NaOH, 1,4-dioxane, H$_2$O;
(c) EDCI, HOBt, TEA, 3,4,5-trimethoxyaniline;
(d) TFA, CH$_2$Cl$_2$.

General Procedure for the Preparation of (2RS, 4R)-2-aryl-thiazolidine-4-carboxylic acid 1.

A mixture of L-cysteine (3.16 g, 26.11 mmol) and appropriate aldehyde (26.15 mmol) in ethanol (300 mL) and water (30 mL) was stirred at room temperature for 6-15 h, and the solid that precipitated out was collected, washed with diethyl ether, and dried to afford the according (2RS, 4R)-2-aryl-thiazolidine-4-carboxylic acid 1 with yields of 70-99%. At 0° C., 1 (5.95 mmol) was dissolved in 1 N NaOH (6 mL) and 1,4-dioxane (15 mL), then di-tert-butyl-dicarbonate (2.80 g, 12.80 mmol) was added slowly and stirred at room temperature for 1 h. The reaction mixture was concentrated in vacuum and washed with ethyl acetate (20 mL). The aqueous phase was adjusted to pH=4 by adding 1 N HCl or 5% KHSO$_4$, then extracted with ethyl acetate, dried with magnesium sulfate, filtered and concentrated on vacuum to give corresponding BOC protected acids as white foam-solids, which were used for next step without further purification.

General Procedure for the Preparation of (2RS,4R)-2-Aryl-N-(3,4,5-trimethoxyphenyl)thiazolidine-4-carboxamides 2a,2b A mixture of appropriate BOC protected carboxylic acids (0.3-0.5 g), EDCI (1.2 equiv) and HOBT (1.05 equiv) in $CH_2Cl_2$ (20 mL) was stirred at room temperature for 10 min. To this solution, 3,4,5-trimethoxyaniline (1.05 equiv) and $Et_3N$ (1.2 equiv) were added and stirring continued at room temperature (RT or r.t.) for 6-8 h. The reaction mixture was diluted with $CH_2Cl_2$ (30 mL) and sequentially washed with water, satd. $NaHCO_3$, brine and dried over $MgSO_4$. The solvent was removed under reduced pressure to yield a crude oil, which were stirred with TFA (0.6-1 mL) in 20 mL $CH_2Cl_2$ at RT for 1-8 h to cleave the BOC group. The reaction mixture was concentrated, washed with satd. $NaHCO_3$ and dried over $MgSO_4$. The solvent was removed to yield a crude solid, and compounds 2a-2b were purified by column chromatography. Yield was reported as 2 steps yield.

(2RS,4R)-2-Phenyl-N-(3,4,5-trimethoxyphenyl)thiazolidine-4-carboxamide (compound 2a)

Yield: 69.5%. M. p. 158-159° C. $^1$H NMR (300 MHz, $CDCl_3$) δ 9.14 (s, 0.8H), 8.61 (s, 0.2H), 7.58-7.32 (m, 5H), 6.90 (s, 1.6H), 6.71 (s, 0.4H), 5.71 (dd, 0.2H, J=9.0 Hz), 5.42 (dd, 0.8H, J=11.7 Hz), 4.53 (dt, 0.8H), 4.19 (m, 0.2H), 3.87, 3.80 (s, s, 6H), 3.82, 3.78 (s, s, 3H), 3.80-3.78 (m, 0.4H), 3.62-3.42 (m, 1.6H), 2.96 (t, 0.2H, J=9.0 Hz), 2.74 (dd, 0.8H, J=11.7 Hz). MS (ESI) m/z 375.1 [M+H]$^+$, 397.1 [M+Na]$^+$. Anal. ($C_{19}H_{22}N_2O_4S$) C, H, N.

(2RS,4R)—N,2-bis(3,4,5-trimethoxyphenyl)thiazolidine-4-carboxamide (Compound 2b)

Yield: 34.5%. M. p. 147-149° C. $^1$H NMR (300 MHz, $CDCl_3$) δ 9.10 (s, 0.7H), 8.59 (s, 0.3H), 6.90 (s, 1.4H), 6.80 (s, 0.6H), 6.74 (s, 1.4H), 6.71 (s, 0.6H), 5.66 (br, 0.3H), 5.35 (d, br, 0.7H, J=7.5 Hz), 4.52 (br, 0.7H), 4.21 (br, 0.3H), 3.90, 3.87, 3.86, 3.84, 3.82, 3.81, 3.79, 3.78 (all s, 18H), 3.66-3.61, 3.54-3.38 (m, 1.6H), 2.98, 2.72 (br, 1H). MS (ESI) m/z 465.1 [M+H]$^+$, 487.1 [M+Na]$^+$. Anal. ($C_{22}H_{28}N_2O_7S$) C, H, N.

To enhance the activity and to develop more selective agents, this synthesis was extended and, as discussed in the subsequent examples, biological studies were performed to examine the nature of the substituents attached to the carbonyl at the 4 position. The synthesis of these additional compounds is shown in Scheme 2 below.

Scheme 2

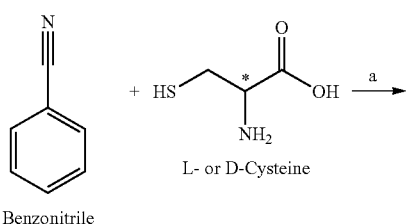

Benzonitrile    L- or D-Cysteine

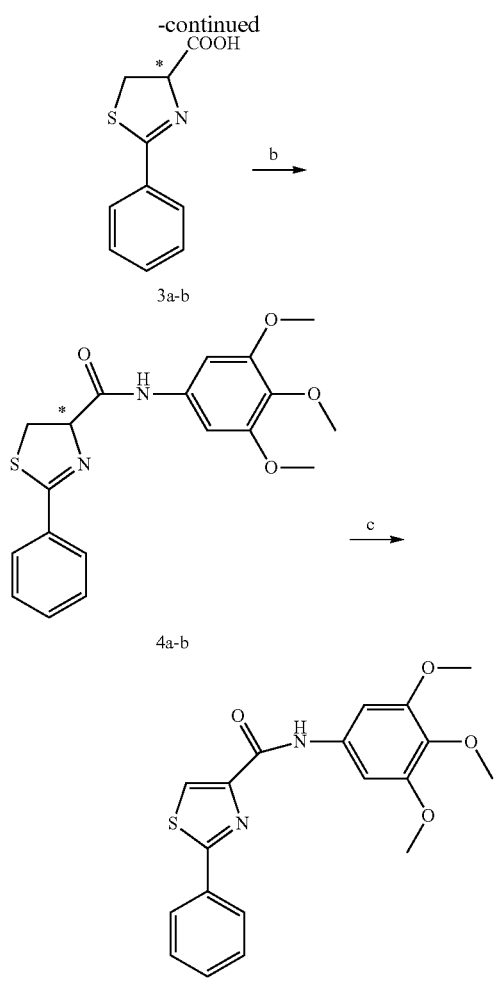

a: R-isomer
b: S-isomer
Reagents and conditions:
(a) MeOH/pH = 6.4 phosphate buffer, r.t.;
(b) EDCI, HOBt, TEA, 3,4,5-trimethoxyaniline;
(c) $CBrCl_3$, DBU.

Synthesis of 2-Phenyl-N-(3,4,5-trimethoxyphenyl)-4,5-dihydrothiazole-4-carboxamides 4a-4b, 5

Unsubstituted (or substituted) benzonitrile (40 mmol) was combined with L- or D-cysteine (45 mmol) in 100 mL of 1:1 MeOH/pH6.4 phosphate buffer solution. The reaction was stirred at 40° C. for 3 days (Bergeron et al., "Evaluation of Desferrithiocin and its Synthetic Analogs as Orally Effective Iron Chelators," *J. Med. Chem.* 34:2072-8 (1991), which is hereby incorporated by reference in its entirety). Precipitate was removed through filtration, and MeOH was removed using rotary evaporation. To the remaining solution was added 1 M HCl to adjust pH=4 under 0° C. The resulting precipitate was extracted into $CH_2Cl_2$, dried and concentrated (Scheme 2). The carboxylic acids 3a,3b were reacted with 3,4,5-trimethoxyaniline using the same procedures as described for preparation of compounds 2a,2b, thereby forming compounds 4a,4b. Conversion of the dihydrothiazoles 4a,4b to the thiazolidine 5 was carried out by oxidation with $BrCCl_3$/DBU (Williams et al., "Studies of Mild Dehydrogenations in Heterocyclic Systems," *Tetrahedron Lett.* 38:331-334 (1997), which is hereby incorporated by reference in its entirety).

(4R)-2-Phenyl-4,5-dihydrothiazole-4-carboxylic acid (Compound 3a)

Yield: 58.3%. $^1$H NMR (300 MHz, CDCl$_3$) δ 9.31 (br, 1H), 7.88-7.85 (m, 2H), 7.55-7.41 (m, 3H), 5.38 (t, 1H, J=9.6 Hz), 3.75 (dt, 2H, J=9.6 Hz, 2.7 Hz). MS (ESI) m/z 162.0 [M−COOH]$^−$.

(4S)-2-Phenyl-4,5-dihydrothiazole-4-carboxylic acid (Compound 3b)

Yield: 53.9%. $^1$H NMR (300 MHz, CDCl$_3$) δ 7.89-7.85 (m, 2H), 7.55-7.41 (m, 3H), 5.38 (t, 1H, J=9.3 Hz), 3.75 (dt, 2H, J=9.3 Hz, 2.7 Hz). MS (ESI) m/z 162.0 [M−COOH]$^−$.

(4R)-2-Phenyl-N-(3,4,5-trimethoxyphenyl)-4,5-dihydrothiazole-4-carboxamide (Compound 4a)

Yield: 98.7%. M. p. 121-122° C. $^1$H NMR (300 MHz, CDCl$_3$) δ 8.98 (s, 1H), 8.02-7.94, 7.62-7.48 (m, 5H), 6.93 (s, 2H), 5.38 (t, 1H, J=9.6 Hz), 3.92-3.85 (m, 2H), 3.87 (s, 6H), 3.82 (s, 3H). MS (ESI) m/z 373.1 [M+H]$^+$. Anal. (C$_{19}$H$_{20}$N$_2$O$_4$S) C, H, N.

(4R)-2-Phenyl-N-(3,4,5-trimethoxyphenyl)-4,5-dihydrothiazole-4-carboxamide (Compound 4b)

Yield: 70.7%. M. p. 122-123° C. $^1$H NMR (300 MHz, CDCl$_3$) δ 8.62 (s, 1H), 7.93-7.90 (m, 2H), 7.55-7.45 (m, 3H), 6.88 (s, 2H), 5.31 (t, 1H, J=9.6 Hz), 3.86 (s, 6H), 3.79 (s, 3H), 3.83-3.70 (m, 2H). MS (ESI) m/z 395.1 [M+Na]$^+$, 370.9 [M−1]$^−$. Anal. (C$_{19}$H$_{20}$N$_2$O$_4$S) C, H, N.

2-Phenyl-N-(3,4,5-trimethoxyphenyl)thiazole-4-carboxamide (Compound 5)

Yield: 89.7%. M. p. 157-158° C. $^1$H NMR (300 MHz, CDCl$_3$) δ 9.30 (s, 1H), 8.20 (s, 1H), 8.04-8.01 (m, 2H), 7.53-7.51 (m, 3H), 7.08 (s, 2H), 3.92 (s, 6H), 3.86 (s, 3H). MS (ESI) m/z 393.1 [M+Na]$^+$. Anal. (C$_{19}$H$_{18}$N$_2$O$_4$S) C, H, N.

Example 2: Synthesis of Thiazole and Thiazolidine Methanone Derivatives 2-(Substituted-phenyl)-4,5-dihydrothiazole-4-carboxylic acid methoxymethylamide intermediates As shown in Scheme 3 below, 2-(substituted-phenyl)- and unsubstituted 2-phenyl-4,5-dihydrothiazole-4-carboxylic acids 3 were prepared from appropriate nitriles (e.g., benzonitrile, pyridinyl-nitrile, pyrimidinyl-nitrile, thiophene-yl-nitrile) and L-cysteine as described above. The obtained carboxylic acids were then used for the synthesis of the methoxymethylamide intermediates. A mixture of appropriate the appropriate carboxylic acid 3 (5 mmol), EDCI (6 mmol) and HOBt (5 mmol) in CH$_2$Cl$_2$ (50 mL) was stirred for 10 min. To this solution, NMM (5 mmol) and HNCH$_3$OCH$_3$ (5 mmol) was added and stirring continued at room temperature for 6-8 hours. The reaction mixture was diluted with CH$_2$Cl$_2$ (100 mL) and sequentially washed with water, Satd. NaHCO$_3$, brine and dried over MgSO$_4$. The solvent was removed under reduced pressure to yield a crude product 6, which was purified by column chromatography.

Scheme 3

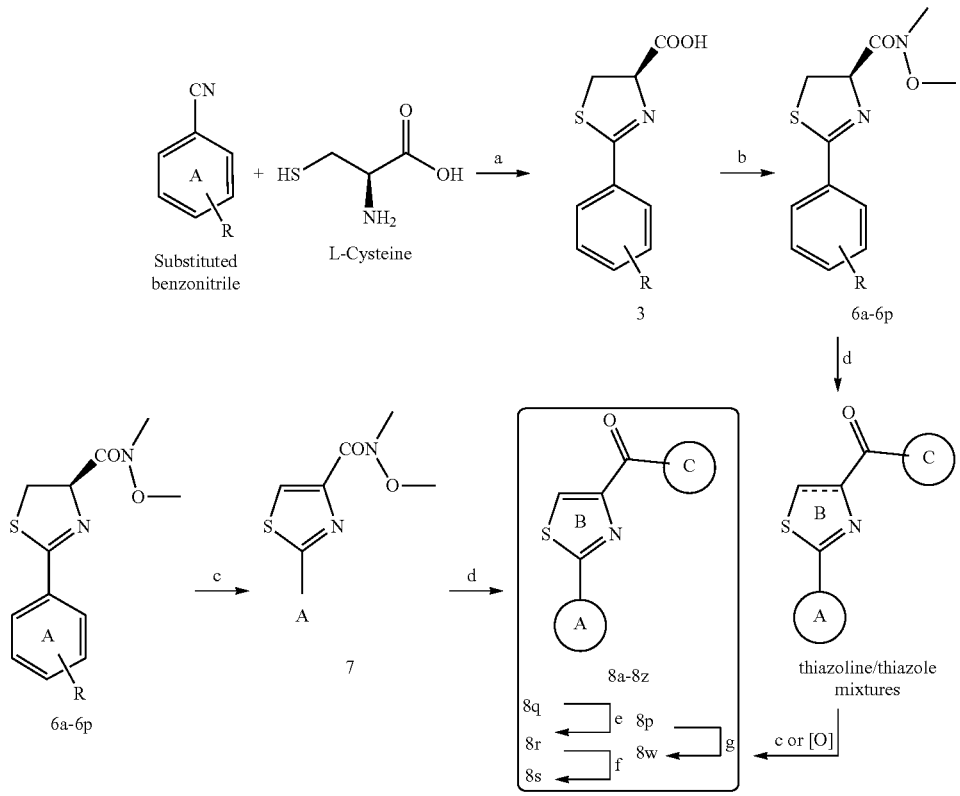

-continued
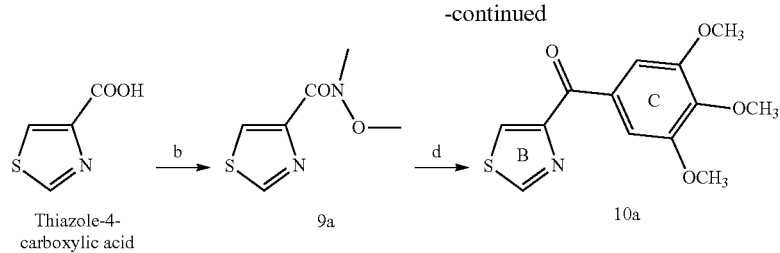
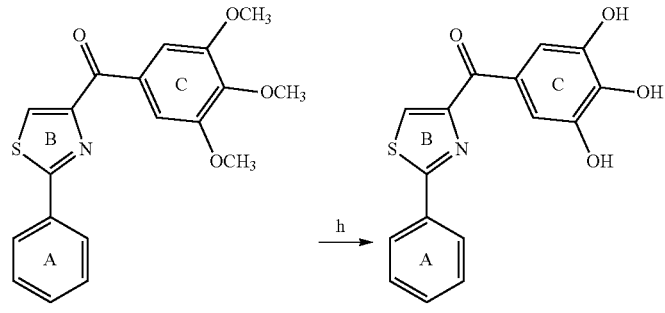
R or A ring
6a R = H
6b R = p-CH$_3$
6c R = o-F
6d R = m-F
6e R = p-F
6f R = 3,4-dimethoxyl
6g R = p-NO$_2$
6h R = p-CN
6i R = p-CF$_3$
6j R = p-Br
6k R = p-C$_2$H$_5$
6l A-ring = 4-pyridine
6m A-ring = 2-pyrimidine
6p A-ring = 2-thiophene
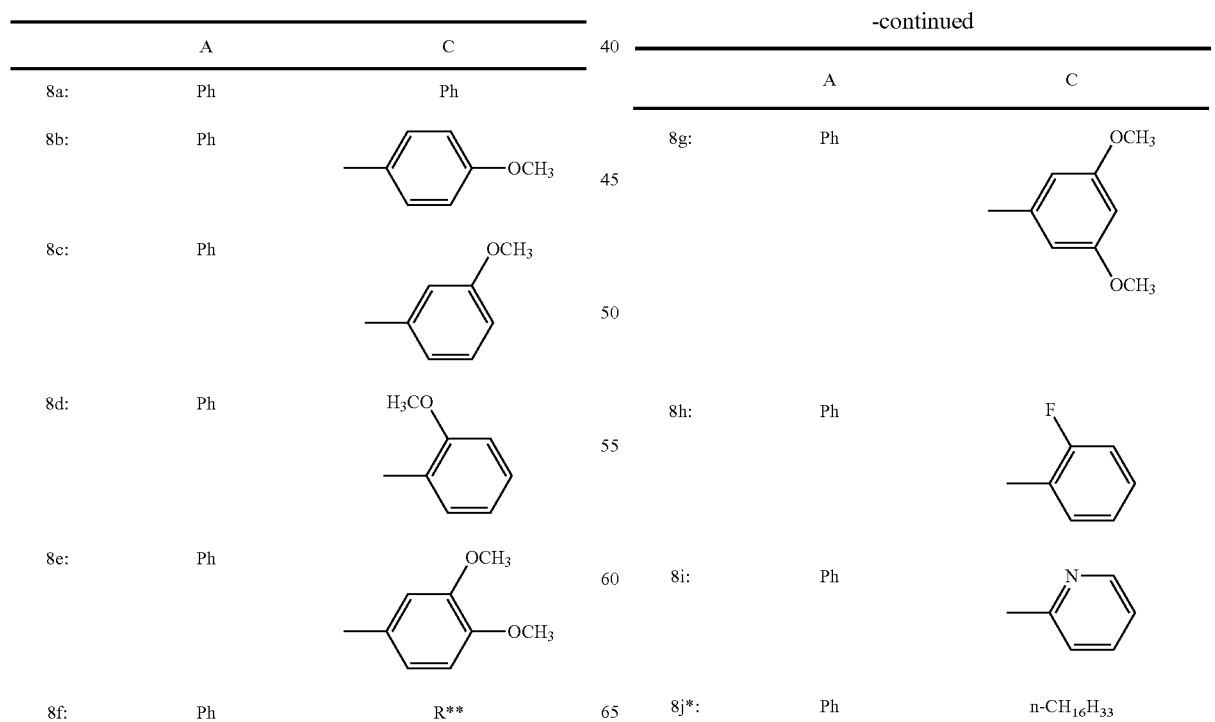

-continued

| | A | C |
|---|---|---|
| 8k: | 4-methylphenyl (CH₃) | R |
| 8l: | 2-fluoro-methylphenyl | R |
| 8m: | 3-fluoro-methylphenyl | R |
| 8n: | 4-fluoro-methylphenyl | R |
| 8o: | 3,4-dimethoxy-methylphenyl | R |
| 8p: | 4-nitro-methylphenyl (NO₂) | R |
| 8q: | 4-cyano-methylphenyl (CN) | R |
| 8r: | 4-carboxy-methylphenyl (COOH) | R |

-continued

| | A | C |
|---|---|---|
| 8s: | 4-(COOCH₃)-methylphenyl | R |
| 8t: | 4-(CF₃)-methylphenyl | R |
| 8u: | 4-bromo-methylphenyl (Br) | R |
| 8v: | 4-ethyl-methylphenyl (C₂H₅) | R |
| 8w: | 4-amino-methylphenyl (NH₂) | R |
| 8x: | 4-methylpyridyl | R |
| 8y: | 2-methylpyrimidyl | R |

-continued

| A | C |
|---|---|
| 8z: 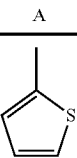 | R |

*Compound 8j contains a lipid at "C" position
**R = 3,4,5-trimethoxyphenyl
Reagents and conditions:
(a) MeOH/pH = 6.4 phosphate buffer, r.t.;
(b) EDCI, HOBt, NMM, HNCH$_3$OCH$_3$;
(c) CBrCl$_3$, DBU;
(d) ArBr/BuLi or ArMgBr, THF;
(e) HCl/HOAc;
(f) MeOH/CH$_3$COCl;
(g) Fe/HOAc;
(h) BBr$_3$, CH$_2$Cl$_2$.

(R)—N-Methoxy-N-methyl-2-phenyl-4,5-dihydrothiazole-4-carboxamide (Compound 6a)

Yield: 92.0%. $^1$H NMR (300 MHz, CDCl$_3$) δ 7.85-7.83 (m, 2H), 7.48-7.36 (m, 3H), 5.66 (t, 1H, J=9.0 Hz), 3.90 (s, 3H), 3.88-3.80 (br, 1H), 3.55-3.47 (dd, 1H, J=10.8 Hz, 9.0 Hz), 3.30 (s, 3H). MS (ESI) m/z 251.0 [M+H]$^+$, 273.0 [M+Na]$^+$.

(R)—N-Methoxy-N-methyl-2-p-tolyl-4,5-dihydrothiazole-4-carboxamide (Compound 6b)

Yield: 55.8%. $^1$H NMR (300 MHz, CDCl$_3$) δ 7.79 (d, 2H, J=7.8 Hz), 7.22 (d, 2H, J=7.8 Hz), 5.68 (t, 1H, J=8.7 Hz), 3.91 (s, 3H), 3.80 (t, 1H, J=9.3 Hz), 3.55 (t, 1H, J=9.3 Hz), 3.30 (s, 3H), 2.93 (s, 3H). MS (ESI) m/z 265.0 [M+H]$^+$, 287.0 [M+Na]$^+$.

(R)-2-(2-Fluorophenyl)-N-methoxy-N-methyl-4,5-dihydrothiazole-4-carboxamide (Compound 6c)

Yield: 39.6%. $^1$H NMR (300 MHz, CDCl$_3$) δ 7.91 (dt, 1H, J=7.5 Hz, 1.8 Hz), 7.43 (m, 1H), 7.19-7.09 (m, 2H), 5.63 (t, 1H), 3.88 (s, 3H), 3.83 (br, 1H), 3.48 (dd, 1H, J=11.1 Hz, 9.6 Hz), 3.30 (s, 3H). MS (ESI) m/z 291.0 [M+Na]$^+$.

(R)-2-(3-Fluorophenyl)-N-methoxy-N-methyl-4,5-dihydrothiazole-4-carboxamide (Compound 6d)

Yield: 84.3%. $^1$H NMR (300 MHz, CDCl$_3$) δ 7.60-7.56 (m, 2H), 7.38 (dt, 1H, J=8.1 Hz, 6.0 Hz), 7.16 (dt, 1H, J=8.1 Hz, 2.4 Hz), 5.67 (t, 1H), 3.90 (s, 3H), 3.86-3.83 (br, 1H), 3.52 (dd, 1H, J=10.8 Hz, 9.3 Hz), 3.30 (s, 3H). MS (ESI) m/z 291.0 [M+Na]$^+$.

(R)-2-(4-Fluorophenyl)-N-methoxy-N-methyl-4,5-dihydrothiazole-4-carboxamide (Compound 6e)

Yield: 66.0%. $^1$H NMR (300 MHz, CDCl$_3$) δ 7.90 (d, 2H), 7.13 (d, 2H), 5.63 (t, 1H), 3.88 (s, 3H), 3.83 (br, 1H), 3.46 (dd, 1H), 3.31 (s, 3H). MS (ESI) m/z 269.0 [M+H]$^+$.

(R)-2-(3,4-Dimethoxyphenyl)-N-methoxy-N-methyl-4,5-dihydrothiazole-4-carboxamide (Compound 6f)

Yield: 36.7%. $^1$H NMR (300 MHz, CDCl$_3$) δ 8.11 (d, 1H), 7.93 (s, 1H), 7.19-7.09 (d, 1H), 5.41 (t, 1H), 3.97 (s, 6H), 3.89 (s, 3H), 3.73 (br, 1H), 3.39 (d, 1H), 3.31 (s, 3H). MS (ESI) m/z 333.1 [M+Na]$^+$.

(R)—N-Methoxy-N-methyl-2-(4-nitrophenyl)-4,5-dihydrothiazole-4-carboxamide (Compound 6g)

Yield: 53.7%. $^1$H NMR (300 MHz, CDCl$_3$) δ 8.25 (d, 2H, J=9.0 Hz), 8.01 (d, 2H, J=9.0 Hz), 5.73 (t, 1H), 3.90 (s, 3H), 3.87 (br, 1H), 3.59 (dd, 1H, J=11.1 Hz, 9.3 Hz), 3.31 (s, 3H). MS (ESI) m/z 318.1 [M+Na]$^+$.

(R)-2-(4-Cyanophenyl)-N-methoxy-N-methyl-4,5-dihydrothiazole-4-carboxamide (Compound 6h)

Yield: 26.7%. $^1$H NMR (300 MHz, CDCl$_3$) δ 7.94 (d, 2H, J=8.1 Hz), 7.69 (d, 2H, J=8.1 Hz), 5.71 (t, 1H, J=9.3 Hz), 3.89 (s, 3H), 3.87 (br, 1H), 3.56 (dd, 1H, J=10.8 Hz, 9.3 Hz), 3.30 (s, 3H). MS (ESI) m/z 298.0 [M+Na]$^+$.

(R)—N-Methoxy-N-methyl-2-(4-trifluoromethylphenyl)-4,5-dihydrothiazole-4-carboxamide (Compound 6i)

Yield: 62.0%. $^1$H NMR (300 MHz, CDCl$_3$) δ 7.95 (d, 2H, J=8.1 Hz), 7.65 (d, 2H, J=8.1 Hz), 5.70 (t, 1H, J=9.6 Hz), 3.89 (s, 3H), 3.85 (br, 1H), 3.55 (dd, 1H, J=10.8 Hz, 9.6 Hz), 3.30 (s, 3H). MS (ESI) m/z 341.0 [M+Na]$^+$.

(R)-2-(4-Bromophenyl)-N-methoxy-N-methyl-4,5-dihydrothiazole-4-carboxamide (Compound 6j)

Yield: 20.0%. $^1$H NMR (300 MHz, CDCl$_3$) δ 7.71, 7.53 (d, d, 4H, J=8.4 Hz), 5.63 (t, 1H, J=9.6 Hz), 3.88 (s, 3H), 3.84 (t, 1H, J=9.6 Hz), 3.52 (dd, 1H, J=10.8 Hz, 9.6 Hz), 3.30 (s, 3H). MS (ESI) m/z 351.0 [M+Na]$^+$.

(R)—N-Methoxy-N-methyl-2-(4-ethylphenyl)-4,5-dihydrothiazole-4-carboxamide (Compound 6k)

Yield: 77.7%. $^1$H NMR (300 MHz, CDCl$_3$) δ 7.75 (d, 2H, J=8.4 Hz), 7.21 (d, 2H, J=8.4 Hz), 5.64 (t, 1H), 3.89 (s, 3H), 3.81 (m, 1H), 3.48 (dd, 1H, J=10.8 Hz, 9.3 Hz), 3.29 (s, 3H), 2.67 (q, 2H), 1.24 (t, 3H). MS (ESI) m/z 301.0 [M+Na]$^+$.

(R)—N-Methoxy-N-methyl-2-(pyridin-4-yl)-4,5-dihydrothiazole-4-carboxamide (Compound 6l)

Yield: 66.6%. $^1$H NMR (300 MHz, CDCl$_3$) δ 8.70 (d, 2H, J=9.0 Hz), 7.67 (d, 2H, J=9.0 Hz), 5.71 (t, 1H, J=9.6 Hz), 3.90 (s, 3H), 3.73 (t, 1H), 3.55 (dd, 1H, J=10.8 Hz, 9.6 Hz), 3.30 (s, 3H). MS (ESI) m/z 252.1 [M+H]$^+$, 274.0 [M+Na]$^+$.

(R)—N-Methoxy-N-methyl-2-(pyrimidin-2-yl)-4,5-dihydrothiazole-4-carboxamide (Compound 6m)

Yield: 32.5%. $^1$H NMR (300 MHz, CDCl$_3$) δ 8.88 (d, 2H, J=4.8 Hz), 7.38 (t, 1H, J=4.8 Hz), 5.83 (t, 1H, J=9.0 Hz), 3.87 (s, 3H), 3.56 (dd, 2H, J=9.0 Hz), 3.30 (s, 3H). MS (ESI) m/z 275.0 [M+Na]$^+$.

(R)—N-Methoxy-N-methyl-2-(thiophen-2-yl)-4,5-dihydrothiazole-4-carboxamide (Compound 6p)

Yield: 58.5%. $^1$H NMR (300 MHz, CDCl$_3$) δ 7.57 (br, 1H), 7.49 (d, 1H, J=4.8 Hz), 7.09 (dd, 1H, J=3.6 Hz, 4.8 Hz), 5.64 (t, 1H, J=9.0 Hz), 3.90 (s, 3H), 3.85 (br, 1H), 3.57 (dd, 1H, J=9.9 Hz, 9.0 Hz), 3.29 (s, 3H). MS (ESI) m/z 279.0 [M+Na]$^+$.

N-Methoxy-N-methylthiazole-4-carboxamide (Compound 9a)

Yield: 58.7%. $^1$H NMR (300 MHz, CDCl$_3$) δ 8.82 (d, 1H, J=2.1 Hz), 8.10 (d, 1H, J=2.1 Hz), 3.79 (s, 3H), 3.45 (s, 3H). MS (ESI) m/z 194.9 [M+Na]$^+$.

2-(Substituted-phenyl)-thiazole-4-carboxylic acid methoxymethylamides 7a-p

A solution of the resulting dihydrothiazole-4-carboxylic acid methoxymethylamides 6a-6p (1 equiv) in CH$_2$Cl$_2$ was cooled to 0° C., distilled, and DBU (2 equiv) was added. Bromotrichloromethane (1.7 equiv) was then introduced dropwise via syringe over 10 min. The reaction mixtures were allowed to warm to room temperature and stirred overnight. Upon washing with satd. aqueous NH$_4$Cl (2×50 mL), the aqueous phase was extracted with EtOAc (3×50 mL). The combined organic layers were dried on MgSO$_4$, filtered and concentrated in vacuo. The residue was purified by flash chromatography as needed providing compounds 7a-p.

2-Phenyl-thiazole-4-carboxylic acid methoxymethylamide (Compound 7a)

Yield: 73.6%. $^1$H NMR (300 MHz, CDCl$_3$) δ 8.01 (s, 1H), 7.99-7.96 (m, 2H), 7.47-7.44 (m, 3H), 3.88 (s, 3H), 3.49 (s, 3H). MS (ESI) m/z 271.0 [M+Na]$^+$.

(2-(Substituted-phenyl)-thiazol-4-yl)-(substituted-phenyl)-methanones

As shown in Scheme 3 above, three different methods were utilized for the synthesis of the methanones 8a-8z.

Method 1:
To a solution of n-BuLi (1.6 M, 0.713 mL) in 8 mL THF was added a solution of 3,4,5-trimethoxybromobenzene (1.09 mmol) in 3 mL THF under −78° C. The mixture was stirred for 2 h and a solution of amides 6 or 7 (1.14 mmol) in 3 mL THF was charged. The mixture was allowed to warm to room temperature and stirred overnight. The reaction mixture was quenched with satd. NH$_4$Cl, extracted with ethyl ether, dried with MgSO$_4$, and exposed in air atmosphere overnight. The solvent was removed under reduced pressure to yield a crude product, which was purified by column chromatography to obtain pure compounds 8a-8z.

Method 2:
To a solution of corresponding Grignard reagents (0.5 M, 3 mL) in 2 mL THF was charged a solution of amides 6 or 7 (1 mmol) in 3 mL THF at 0° C. The mixtures were stirred for 30 min to 2 hours until amides disappeared on TLC plates. The reaction mixture was quenched with satd. NH$_4$Cl, extracted with ethyl ether, dried with MgSO$_4$ and to set in air atmosphere overnight to yield 6 as starting material. The solvent was removed under reduced pressure to yield a crude product, which was purified by column chromatography to obtain pure compound 8a-8z.

Hydrochloride salts of compounds 8i, 8x, and 8w were also prepared. At 0° C., to a solution of 10 mL HCl in ethyl ether (2 M) solution was added 8i, 8x or 8w (100 mg) in 5 mL CH$_2$Cl$_2$ (5 mL) and stirred overnight. The hydrochloride precipitate was filtered and washed with ethyl ether. Drying under high vacuum yielded the corresponding salts.

Phenyl (2-phenylthiazol-4-yl)-methanone (Compound 8a)

Yield: 76.3%. M. p. 65-66° C. $^1$H NMR (300 MHz, CDCl$_3$) δ 8.32-8.29 (m, 2H), 8.24 (s, 1H), 8.04-8.00 (m, 2H), 7.64-7.52 (m, 3H), 7.50-7.46 (m, 3H). MS (ESI) m/z 288.0 [M+Na]$^+$. Anal. (C$_{16}$H$_{11}$NOS) C, H, N.

(4-Methoxyphenyl)(2-phenylthiazol-4-yl)-methanone (Compound 8b)

Yield: 74.8%. M. p. 105-106° C. $^1$H NMR (300 MHz, CDCl$_3$) δ 8.41 (d, 2H), 8.22 (s, 1H), 8.02 (dd, 2H), 7.47 (m, 3H), 7.01 (d, 2H), 3.80 (s, 3H). MS (ESI) m/z 318.1 [M+Na]$^+$. Anal. (C$_{17}$H$_{13}$NO$_2$S) C, H, N.

(3-Methoxyphenyl)(2-phenylthiazol-4-yl)-methanone (Compound 8c)

Yield: 58.8%. M. p. 43-44° C. 1H NMR (300 MHz, CDCl$_3$) δ 8.23 (s, 1H), 8.05-8.01 (m, 2H), 7.93 (d, 1H), 7.84 (m, 1H), 7.49-7.40 (m, 4H), 7.16-7.15 (m, 1H), 3.89 (s, 3H). MS (ESI) m/z 318.1 [M+Na]$^+$. Anal. (C$_{17}$H$_{13}$NO$_2$S) C, H, N.

(2-Methoxyphenyl)(2-phenylthiazol-4-yl)-methanone (Compound 8d)

Yield: 57.4%. Colorless oil. $^1$H NMR (300 MHz, CDCl$_3$) δ 8.03 (s, 1H), 7.98-7.95 (m, 2H), 7.57-7.47 (m, 2H), 7.47-7.42 (m, 3H), 7.08-7.01 (m, 2H), 3.78 (s, 3H). MS (ESI) m/z 318.1 [M+Na]$^+$. Anal. (C$_{17}$H$_{13}$NO$_2$S) C, H, N.

(3,4-Dimethoxyphenyl)(2-phenylthiazol-4-yl)-methanone (Compound 8e)

Yield: 15.3%. M. p. 89-91° C. $^1$H NMR (500 MHz, CDCl$_3$) δ 8.24 (s, 1H), 8.22 (dd, 1H, J=8.5 Hz, 2.0 Hz), 8.04-8.02 (m, 2H), 7.99 (d, 1H, J=2.0 Hz), 7.49-7.47 (m, 3H), 6.98 (d, 1H, J=8.5 Hz), 3.99 (s, 6H). MS (ESI) m/z 348.0 [M+Na]$^+$. Anal. (C$_{18}$H$_{15}$NO$_3$S) C, H, N.

(2-Phenyl-thiazol-4-yl)-(3,4,5-trimethoxy-phenyl)-methanone (Compound 8f)

Yield: 27.3%. M. p. 133-135° C. $^1$H NMR (300 MHz, CDCl$_3$) δ 8.29 (s, 1H), 8.03 (q, 2H), 7.80 (s, 2H), 7.49-7.47 (m, 3H), 3.96 (s, 6H), 3.97 (s, 3H). MS (ESI) m/z 378.1 [M+Na]$^+$. Anal. (C$_{19}$H$_{17}$NO$_4$S) C, H, N.

(3,5-Dimethoxyphenyl)(2-phenylthiazol-4-yl)-methanone (Compound 8g)

Yield: 41.5%. M. p. 84-85° C. $^1$H NMR (300 MHz, CDCl$_3$) δ 8.23 (s, 1H), 8.04-8.01 (m, 2H), 7.99 (d, 2H, J=2.4 Hz), 7.49-7.43 (m, 3H), 6.72 (t, 1H, J=2.4 Hz), 3.87 (s, 6H). MS (ESI) m/z 348.3 [M+Na]$^+$. Anal. (C$_{18}$H$_{15}$NO$_3$S) C, H, N.

(2-Fluorophenyl)(2-phenylthiazol-4-yl)-methanone (Compound 8h)

Yield: 66.4%. M. p. 77-79° C. $^1$H NMR (300 MHz, CDCl$_3$) δ 8.48-8.41 (m, 2H), 8.28 (s, 2H), 8.04-7.98 (m, 2H), 7.50-7.46 (m, 3H), 7.26-7.16 (m, 2H). MS (ESI) m/z 306.0 [M+Na]$^+$, 283.9 [M−H]$^-$. Anal. (C$_{16}$H$_{10}$FNOS) C, H, N.

(2-Phenylthiazol-4-yl)-(pyridin-2-yl)-methanone (Compound 8i)

Yield: 20.7%. M. p. 95-97° C. $^1$H NMR (300 MHz, CDCl$_3$) δ 9.01 (s, 1H), 8.77 (d, 1H, J=4.8 Hz), 8.28 (d, 1H, J=7.8 Hz), 8.08-8.05 (m, 2H), 7.92 (dt, 1H, J=7.8 Hz, 1.2 Hz), 7.52 (ddd, 1H, J=7.8 Hz, 4.8 Hz, 1.2 Hz), 7.48-7.46 (m, 3H). (compound 8i.HCl salt): Yield: 70.6%. M. p. 105-107° C. $^1$H NMR (300 MHz, DMSO-d$_6$) δ 9.03 (s, 1H), 8.79 (d, 1H, J=4.8 Hz), 8.10 (br, 1H), 8.08 (br, 1H), 8.03-8.00 (m, 2H), 7.73-7.69 (m, 1H), 7.56-7.54 (m, 3H). MS (ESI) m/z 267.0 [M+H]$^+$. Anal. ($C_{15}H_{10}N_2OS$, $C_{15}H_{10}N_2OS.HCl$) C, H, N.

1-(2-Phenylthiazol-4-yl)-heptadecan-1-one (Compound 8j)

Yield: 66.4%. M. p. 63-64° C. $^1$H NMR (300 MHz, CDCl$_3$) δ 8.12 (s, 1H), 8.02-7.99 (m, 2H), 7.49-7.47 (m, 3H), 3.16 (t, 2H, J=7.5 Hz), 1.82-1.72 (m, 2H), 1.26 (s, 26H), 0.88 (t, 3H, J=6.9 Hz). MS (ESI) m/z 414.4 [M+H]$^+$. Anal. ($C_{26}H_{39}NOS$) C, H, N.

(2-p-Tolylthiazol-4-yl)-(3,4,5-trimethoxyphenyl)-methanone (Compound 8k)

Yield: 53.2%. M. p. 116-119° C. $^1$H NMR (300 MHz, CDCl$_3$) δ 8.25 (s, 1H), 7.91 (d, 2H, J=8.1 Hz), 7.80 (s, 2H), 7.28 (d, 2H, J=8.1 Hz), 3.96 (s, 3H), 3.95 (s, 6H). MS (ESI) m/z 392.1 [M+Na]$^+$. Anal. ($C_{20}H_{19}NO_4S$) C, H, N.

[2-(2-Fluorophenyl)-thiazol-4-yl]-(3,4,5-trimethoxyphenyl)-methanone (Compound 8l)

Yield: 39.6%. M. p. 90-102° C. $^1$H NMR (500 MHz, CDCl$_3$) δ 8.40 (s, 1H), 8.33 (dt, 1H, J=1.5 Hz, 8.0 Hz), 7.78 (s, 2H), 7.49-7.44 (m, 1H), 7.30-7.23 (m, 2H), 3.97 (s, 3H), 3.95 (s, 6H). MS (ESI) m/z 396.1 [M+Na]$^+$. Anal. ($C_{19}H_{16}FNO_4S$) C, H, N.

[2-(3-Fluorophenyl)-thiazol-4-yl](3,4,5-trimethoxyphenyl)-methanone (Compound 8m)

Yield: 14.1%. M. p. 122-124° C. $^1$H NMR (300 MHz, CDCl$_3$) δ 8.31 (s, 1H), 7.79 (s, 2H), 7.76-7.74 (m, 2H), 7.45 (dt, 1H, J=6.0 Hz, 8.4 Hz), 7.18 (dt, 1H, J=1.8 Hz, 8.4 Hz), 3.97 (s, 3H), 3.96 (s, 6H). MS (ESI) m/z 396.1 [M+Na]$^+$. Anal. ($C_{19}H_{16}FNO_4S$) C, H, N.

[2-(4-Fluorophenyl)-thiazol-4-yl]-(3,4,5-trimethoxyphenyl)-methanone (Compound 8n)

Yield: 40.2%. M. p. 153-155° C. $^1$H NMR (300 MHz, CDCl$_3$) δ 8.27 (s, 1H), 8.04-8.00 (dd, 2H, J=8.4 Hz, 5.7 Hz), 7.75 (s, 2H), 7.21-7.15 (t, 3H, J=8.4 Hz), 3.97 (s, 3H), 3.95 (s, 6H). MS (ESI) m/z 396.1 [M+Na]$^+$. Anal. ($C_{19}H_{16}FNO_4S$) C, H, N.

[2-(3,4-Dimethoxyphenyl)-thiazol-4-yl]-(3,4,5-trimethoxyphenyl)-methanone (Compound 8o)

Yield: 46.6%. M. p. 145-147° C. $^1$H NMR (300 MHz, CDCl$_3$) δ 8.20 (s, 1H), 7.76 (s, 2H), 7.58-7.54 (m, 2H), 6.94 (d, 2H, J=8.1 Hz), 3.96 (s, 6H), 3.95 (s, s, 9H). MS (ESI) m/z 438.1 [M+Na]$^+$. Anal. ($C_{21}H_{21}NO_6S.1/4H_2O$) C, H, N.

[2-(4-Nitrophenyl)-thiazol-4-yl]-(3,4,5-trimethoxyphenyl)-methanone (Compound 8p)

Yield: 46.4%. M. p. 199-200° C. $^1$H NMR (300 MHz, CDCl$_3$) δ 8.38 (d, 2H, J=8.7 Hz), 8.34 (s, 1H), 8.20 (d, 2H, J=8.7 Hz), 7.73 (s, 2H), 3.98 (s, 3H), 3.95 (s, 6H). MS (ESI) m/z 423.1 [M+Na]$^+$. Anal. ($C_{19}H_{16}N_2O_6S$) C, H, N.

4-[4-(3,4,5-Trimethoxybenzoyl)-thiazol-2-yl]-benzonitrile (Compound 8q)

Yield: 45.9%. M. p. 181-182° C. $^1$H NMR (300 MHz, CDCl$_3$) δ 8.37 (s, 1H), 8.13 (d, 2H, J=8.4 Hz), 7.78 (d, 2H, J=8.4 Hz), 7.72 (s, 2H), 3.97 (s, 3H), 3.94 (s, 6H). MS (ESI) m/z 403.1 [M+Na]$^+$. Anal. ($C_{20}H_{16}N_2O_4S$) C, H, N.

4-[4-(3,4,5-Trimethoxybenzoyl)-thiazol-2-yl]-benzoic acid (Compound 8r)

Yield: 61.9%. M. p. >220° C. (dec.). $^1$H NMR (300 MHz, CDCl$_3$) δ 8.65 (s, 1H), 8.00 (d, 4H), 7.65 (s, 2H), 3.88 (s, 6H), 3.80 (s, 3H). MS (ESI) m/z 397.9 [M−H]$^-$, 353.9 [M−COOH]$^-$. Anal. ($C_{20}H_{17}NO_6S$) C, H, N.

Methyl-4-[4-(3,4,5-trimethoxybenzoyl)-thiazol-2-yl]-benzoate (Compound 8s)

Yield: 72.5%. M. p. 172-174° C. $^1$H NMR (300 MHz, CDCl$_3$) δ 8.35 (s, 1H), 8.12 (dd, 4H, J=8.4 Hz), 7.78 (s, 2H), 3.97 (s, 3H), 3.96 (s, 3H), 3.95 (s, 6H). MS (ESI) m/z 436.1 [M+Na]$^+$. Anal. ($C_{21}H_{19}NO_6S$) C, H, N.

(2-(4-(Trifluoromethyl)-phenyl)-thiazol-4-yl)(3,4,5-trimethoxyphenyl)-methanone (Compound 8t)

Yield: 45.5%. M. p. 144-145° C. $^1$H NMR (300 MHz, CDCl$_3$) δ 8.35 (s, 1H), 8.14, 7.65 (d, d, 4H, J=8.1 Hz), 7.76 (s, 2H), 3.97 (s, 3H), 3.95 (s, 6H). MS (ESI) m/z 446.1 [M+Na]$^+$. Anal. ($C_{20}H_{16}F_3NO_4S$) C, H, N.

[2-(4-Bromophenyl)-thiazol-4-yl]-(3,4,5-trimethoxyphenyl)-methanone (Compound 8u)

Yield: 51.8%. M. p. 149-150° C. $^1$H NMR (300 MHz, CDCl$_3$) δ 8.28 (s, 1H), 7.89, 7.62 (d, d, 4H, J=8.1 Hz), 7.75 (s, 2H), 3.97 (s, 3H), 3.94 (s, 6H). MS (ESI) m/z 456.0, 458.0 [M+Na]$^+$. Anal. ($C_{19}H_{16}BrNO_4S$) C, H, N.

[2-(4-Ethyl-phenyl)-thiazol-4-yl]-(3,4,5-trimethoxyphenyl)-methanone (Compound 8v)

Yield: 40.0%. M. p. 86-87° C. $^1$H NMR (300 MHz, CDCl$_3$) δ 8.25 (s, 1H), 7.93, 7.31 (d, d, 4H, J=8.4 Hz), 7.81 (s, 2H), 3.97 (s, 3H), 3.95 (s, 6H). MS (ESI) m/z 406.1 [M+Na]$^+$. Anal. ($C_{21}H_{21}NO_4S$) C, H, N.

[2-(4-Amino-phenyl)-thiazol-4-yl]-(3,4,5-trimethoxy-phenyl)-methanone (Compound 8w)

Yield: 61.8%. M. p. 177-179° C. $^1$H NMR (300 MHz, CDCl$_3$) δ 8.14 (s, 1H), 7.82, 7.65 (d, d, 4H, J=8.4 Hz), 7.78 (s, 2H), 3.96 (s, 3H), 3.94 (s, 6H). (compound 8w.HCl salt): Yield: 50.1%. M. p. 166-169° C. $^1$H NMR (300 MHz, DMSO-d$_6$) δ 8.49 (s, 1H), 7.84, 6.94 (d, d, 4H, J=8.4 Hz), 7.62 (s, 2H), 3.86 (s, 3H), 3.79 (s, 6H). MS (ESI) m/z 393.1 [M+Na]$^+$. Anal. ($C_{19}H_{18}N_2O_4S$, $C_{19}H_{18}N_2O_4S.HCl$) C, H, N.

[2-(Pyridin-4-yl)-thiazol-4-yl]-(3,4,5-trimethoxyphenyl)-methanone (Compound 8x)

Yield: 29.3%. M. p. 178-180° C. $^1$H NMR (300 MHz, CDCl$_3$) δ 8.77 (dd, 2H, J=6.0 Hz, 1.5 Hz), 8.40 (s, 1H), 7.87

(dd, 2H, J=6.0 Hz, 1.8 Hz), 7.75 (s, 2H), 3.98 (s, 3H), 3.95 (s, 6H). (compound 8x.HCl salt): Yield: 92.7%. M. p. 182-184° C. $^1$H NMR (300 MHz, CDCl$_3$) δ 8.85 (br, 2H), 8.52 (s, 1H), 8.22 (br, 2H), 7.66 (s, 2H), 3.98 (s, 3H), 3.94 (s, 6H). MS (ESI) m/z 379.1 [M+Na]$^+$. Anal. (C$_{18}$H$_{16}$N$_2$O$_4$S, C$_{18}$H$_{16}$N$_2$O$_4$S.HCl) C, H, N.

[2-(Pyrimidin-2-yl)-thiazol-4-yl]-(3,4,5-trimethoxy-phenyl)-methanone (Compound 8y)

Yield: 51.9%. M. p. 190-191° C. $^1$H NMR (300 MHz, CDCl$_3$) δ 8.88 (d, 2H, J=4.8 Hz), 8.44 (s, 1H), 7.73 (s, 2H), 7.37 (t, 1H, J=4.8 Hz), 3.95 (s, 3H), 3.94 (s, 6H). MS (ESI) m/z 380.1 [M+Na]$^+$. Anal. (C$_{17}$H$_{15}$N$_3$O$_4$S) C, H, N.

[2-(Thiophen-2-yl)-thiazol-4-yl]-(3,4,5-trimethoxy-phenyl)-methanone (Compound 8z)

Yield: 30.5%. M. p. 111-113° C. $^1$H NMR (300 MHz, CDCl$_3$) δ 8.25 (s, 1H), 7.90 (s, 2H), 7.58 (dd, 1H, J=3.6, 0.9 Hz), 7.46 (dd, 1H, J=5.4, 0.9 Hz), 7.12 (dd, 1H, J=5.4, 3.6 Hz), 3.98 (s, 6H), 3.97 (s, 3H). MS (ESI) m/z 384.1 [M+Na]$^+$. Anal. (C$_{17}$H$_{15}$NO$_4$S$_2$) C, H, N.

Thiazol-4-yl-(3,4,5-trimethoxy-phenyl)-methanone (Compound 10a)

Yield: 49.4%. M. p. 106-108° C. $^1$H NMR (300 MHz, CDCl$_3$) δ 8.92 (d, 1H, J=2.1 Hz), 8.34 (d, 1H, J=2.1 Hz), 7.61 (s, 2H), 3.94 (s, 3H), 3.93 (s, 6H). MS (ESI) m/z 302.0 [M+Na]$^+$. Anal. (C$_{13}$H$_{13}$NO$_4$S) C, H, N.

Method 3:

(2-Phenyl-thiazol-4-yl)-(3,4,5-trihydroxy-phenyl)-methanone (11f) was synthesized beginning with compound 8f. To a solution of compound 8f (123 mg, 0.35 mmol) in 5 mL anh. CH$_2$Cl$_2$ was added BBr$_3$ (1 M solution in CH$_2$Cl$_2$, 1.75 mL, 5 mmol) under −78° C. The mixture was stirred for 2 h and a solution of amide 7 (1.14 mmol) in 3 mL THF was charged. The mixture was allowed to warm to room temperature slowly and stirred overnight. The reaction mixture was quenched with satd. NH$_4$Cl, extracted with ethyl acetate, dried with MgSO$_4$. The solvent was removed under reduced pressure to yield a crude product, which was purified by column chromatography to obtain pure compound as red crystalline solid. Yield: 50.9%. M. p. 175-176° C. 1H NMR (300 MHz, DMSO-d$_6$) δ 8.44 (d, 1H), 8.07-8.04 (m, 2H), 7.57-7.55 (m, 3H), 7.33 (s, 2H). MS (ESI) m/z 336.1 [M+Na]$^+$. Anal. (C$_{16}$H$_{11}$NO$_4$S) C, H, N.

Example 3: X-ray Crystallography Structure Determination for Compound 8f

Compound 8f was recrystallized from hexane and ethyl acetate, and single colorless crystals suitable for X-ray diffraction were obtained. X-ray crystallographic data for 8f were collected from a single crystal mounted with paratone oil on a nylon cryoloop. Data were collected at 100K on a Bruker Proteum CCD area detector, controlled by Proteum2 software (Proteum2, Bruker AXS Inc., Madison, Wis., USA (2005)), using a rotating-anode generator and Osmic mirrors to generate Cu radiation (λ=1.54178 Å). The data were reduced using SAINT (SAINT, Bruker AXS Inc., Madison, Wis., USA. (1998)), with an absorption correction applied using SADABS (SADABS, Bruker AXS Inc., Madison, Wis., USA. (2000)) based on redundant reflections; this correction included a spherical component. The structure was solved using direct methods (SHELXS$^{x4}$), which revealed all of the heavy atoms. Structure refinement with SHELXL (SHELXL-97, G. M. Sheldrick, University of Gittingen, Germany (1997)) was carried out using full-matrix methods based on F$^2$, and proceeded smoothly. Hydrogen atoms were added to the structural model assuming ideal C—H distances and isotropic ADPs constrained to be similar to that of the bonded carbon atom. In the final model, anisotropic ADPs were refined for all heavy atoms, and isotropic ADPs for chemically-similar hydrogens (e.g. methyl H) were constrained to be identical. The final refinement parameters are: wR2=0.084 for 228 parameters and 3066 independent observations, R1=0.031, S (goodness-of-fit)=1.057.

An ORTEP drawing of 8f with the atom labeling scheme is shown in FIG. 1. The X-ray structure showed that 8f molecule contained a conjugated system composed of three aromatic rings and a carbonyl group linker between "B" and "C" ring as expected ("A" ring=phenyl; "B" ring=thiazole; "C" ring=3,4,5-trimethoxyphenyl). As a result, two C—C bonds adjacent to C═O and C—C— bond between "A" phenyl and "B" thiazole ring display (C1-C7=1.496(2) Å; C7-C8=1.492(2) Å; C10-C11=1.471(2) Å) shorter bond lengths than normal C—C single bond (1.54 Å) and longer than normal C═C double bond (1.34 Å) (see Table 1 below). Thus, conjugation of the π system is possible for "A", "B", "C" rings and carbonyl group. The carbonyl group is nearly coplanar with the adjacent "B" thiazole ring (O-C7-C1-C6 16.2(2)°, O—C7-C8-C9 9.7(2)°).

TABLE 1

Selected Geometric Parameters of Compound 8f (Å, °)

| C1—C7 | 1.496(2) | O—C7—C1 | 120.1(2) |
|---|---|---|---|
| C7—O | 1.224(2) | C8—C7—C1 | 121.9(2) |
| C7—C8 | 1.492(2) | C9—C8—N | 115.1(2) |
| C8—C9 | 1.371(2) | C9—C8—C7 | 121.7(2) |
| C8—N | 1.380(2) | N—C8—C7 | 123.0(2) |
| C9—S | 1.711(2) | C8—C9—S | 110.0(1) |
| S—C10 | 1.747(2) | C9—S—C10 | 89.6(1) |
| C10—N | 1.303(2) | N—C10—C11 | 123.5(2) |
| C10—C11 | 1.471(2) | N—C10—S | 113.9(1) |
| C2—C1—C6 | 121.2(2) | C11—C10—S | 122.6(1) |
| C2—C1—C7 | 122.3(2) | C10—N—C8 | 111.4(2) |
| C6—C1—C7 | 116.4(2) | C12—C11—C10 | 122.3(2) |
| O—C7—C8 | 118.0(2) | C16—C11—C10 | 118.5(2) |

Example 4: In Vitro Assays for Anti-Cancer Cytotoxicity

In vitro assays were tested against both melanoma cell lines and prostate cancer cells lines. In each case, standard sulforhodamine B assay was used. Cells were seeded into 96-well plates at 1000 to 5000 cells/well depending on growth rates. After 12 hours, media were changed and serial dilutions of compounds were added. Cells were incubated with each compound for 48 hours. Fresh media containing the test compound were changed ever 24 hours. Thereafter, total cell proteins corresponding to cell numbers (both viable and non-viable cells) were measured using the sulforhodamine B (SRB) assay according to manufacturer's protocol (Sigma-Aldrich, Inc.) (Rubinstein et al., "Comparison of in vitro Anticancer Drug-screening Data Generated with a Tetrazolium Assay Versus a Protein Assay Against a Diverse Panel of Human Tumor Cell Lines," *J. Natl. Cancer Inst.* 82:1113-1118 (1990); Dothager et al., "Synthesis and Identification of Small Molecules that Potently Induce Apoptosis in Melanoma Cells Through G1 Cell Cycle Arrest," *J. Am.*

*Chem. Soc.* 127:8686-8696 (2005), each of which is hereby incorporated by reference in their entirety).

For melanoma assays, one human melanoma cell line (A375) and one mouse melanoma cell line (B16-F1) were used. A375 cells and B16-F1 cells were purchased from ATCC (American Type Culture Collection, Manassas, Va., USA). Fibroblast cells were used as a control to determine the selectivity of these compounds against melanoma. Human dermal fibroblast cells were purchased from Cascade Biologics, Inc., Portland, Oreg., USA. All cell lines were cultured in DMEM (Cellgro Mediatech, Inc., Herndon, Va., USA), supplemented with 5% FBS (Cellgro Mediatech), 1% antibiotic/antimycotic mixture (Sigma-Aldrich, Inc., St. Louis, Mo., USA) and bovine insulin (5 µg/ml; Sigma-Aldrich). Cultures were maintained at 37° C. in a humidified atmosphere containing 5% $CO_2$. Cells were exposed to a wide range of concentrations for 48 h in round-bottomed 96-well plates. Cells were fixed with 10% trichloroacetic acid and washed five times with water. After cells were air-dried overnight and stained with SRB solution, total proteins were measured at 560 nm with a plate reader. $IC_{50}$ (i.e., concentration which inhibited cell growth by 50% of no treatment controls) values were obtained by nonlinear regression analysis with GraphPad Prism (GraphPad Software, San Diego, Calif.).

For prostate cancer assays, four human prostate cancer cell lines (LNCaP, DU 145, PC-3, and PPC-1) were selected. LNCaP, PC-3 and DU 145 cells were purchased from ATCC (American Type Culture Collection, Manassas, Va., USA). Dr. Mitchell Steiner at University of Tennessee Health Science Center kindly provided PPC-1 cells. All prostate cancer cell lines were cultured in RPMI 1640 (Cellgro Mediatech, Inc., Herndon, Va., USA), and supplemented with 10% FBS (Cellgro Mediatech). Cultures were maintained at 37° C. in a humidified atmosphere containing 5% $CO_2$. 1000 to 5000 cells were plated into each well of 96-well plates depending on growth rate and exposed to different concentrations of a test compound for 96 h in three to five replicates. Cell numbers at the end of the drug treatment were measured by the SRB assay. Briefly, the cells were fixed with 10% of trichloroacetic acid and stained with 0.4% SRB, and the absorbances at 540 nm were measured using a plate reader (DYNEX Technologies, Chantilly, Va.). Percentages of cell survival versus drug concentrations were plotted and the $IC_{50}$ (concentration that inhibited cell growth by 50% of untreated control) values were obtained by nonlinear regression analysis using WinNonlin (Pharsight Corporation, Mountain View, Calif.).

The results of these assays are provided in Tables 2-4 below.

Modifications of the "B" ring from a thiazolidine to thiazole system and the linker from an amide to a ketone. In prior ATCAA compounds, the thiazolidine ring, which contained a free NH at its 3-position, was shown to be important for cytotoxicity. Once the "B" ring thiazolidine moiety was replaced by a thiazoline ring, the antiproliferative activity decreased sharply from 0.6 µM to over 50 µM on WM-164 cell lines (Li et al., "Synthesis and Antiproliferative Activity of Thiazolidine Analogs for Melanoma," *Bioorg. Med. Chem. Lett.* 17:4113-7 (2007), which is hereby incorporated by reference in its entirety). The ATCAA-1 fatty amide derivative that was most effective against melanoma and prostate cancer cell lines were examined and shown to have an $IC_{50}$ 0.4-2.2 µM (see Table 2). Replacement of the long fatty chain with a certain aromatic bulky substituent such as fluorene (ATCAA-2) showed inhibitory activity on both cancer cell lines ($IC_{50}$=1.6-3.9 µM). The fluorene group in 4-carboxylic amide position was also replaced by 3,4,5-trimethoxylphenyl group (2a and 2b), but the potency against both cancer cell lines was lost. The subsequent "B" ring modification from saturated thiazolidine compound 2a to unsaturated thiazole 5 did not show any cytotoxicity against either cancer cell line tested. But thiazoline enantiomers 4a and 4b (R-isomer and S-isomer, with similar antiproliferative activities) showed improved activity ($IC_{50}$=3.4-38.3 µM) compared with 2a, 2b and 5. When the amide CONH linkage between "B" ring and "C" ring was replaced by a carbonyl linker, the mixtures of thiazoline/thiazole ketone 8f were obtained instead of desired thiazoline ketone, because the auto-dehydrogenation between thiazoline and thiazole occurred (the conversion was shown in FIG. 2). Surprisingly, introduction of the carbonyl group linker and thiazole "B" ring led to a significant enhancement of growth inhibition of examined cancer cell lines with a low nanomolar level (8f, $IC_{50}$=0.021-0.071 µM) that is comparable to the natural anticancer agent colchicine. Consequently, a series of the related compounds with "B" as a thiazole ring were designed and synthesized based on the discovery of 8f. Their anticancer activity was also evaluated against melanoma and prostate cancer.

Modifications of the "C" ring also had significant effects. Variation of the phenyl substituents has a remarkable change in effect on potency. The in vitro assay results shown in Table 3 provide interesting results, but only the 3,4,5-trimethoxylphenyl "C" ring (8f) showed excellent inhibition against all cancer cells ($IC_{50}$=21-71 nM, average $IC_{50}$=41 nM). Compound 8g, with a 3,5-dimethoxyphenyl group, showed 6-fold average cytotoxicity lower than 8f against six different cell lines ($IC_{50}$=170-424 nM, calcd. average $IC_{50}$=261 nM). Modifications of 8f by removal of one methoxy at meta-position (8e) or two methoxy groups (8b, 8c and 8d) from 8f led to a dramatic loss in activity ($IC_{50}$>20 µM). Although ortho-substituted monomethoxy compound 8d exhibited weak activity against a certain cell lines compared with meta-/para-MeO substituted 8c/8b and dimethoxyphenyl compound 8e, none of them showed significant potency in inhibition compared with 8f. Similar trends were also seen in 8h and 8j with 2-fluorophenyl and hexadecyl in "C" ring modifications.

Modifications of the "A" ring using different para-substituted electron withdrawing groups (EWG) and electron donor groups (EDG) did not show clear influence on antiproliferative activity. Introduction of a weak EWG (4-F in 8n, $IC_{50}$ values: 6-43 nM) or weak EDG (4-$CH_3$ in 8k, $IC_{50}$s: 5-21 nM), both increased the potency compared with 8f (see Table 4). The replacement of para-position with strong EWG such as $NO_2$ (8p), CN (8q), $CF_3$ (8t) or introducing strong EDG (3,4-dimethoxy) to "A" phenyl ring (8o) exhibited comparable antiproliferative activity.

To compare the effects of ortho-, meta- and para-substitutions, a fluoro atom was introduced to different positions of "A" phenyl ring (8l, 8m, and 8n). The various o-, m-, p-substituents did not exhibit equal activities. p-Fluoro substituted 8n has the best activity for examined prostate cancer cells (6-13 nM) while o-fluoro substituted 8l showed the lowest $IC_{50}$ values (27-30 nM) against melanoma cells. 8n has similar average $IC_{50}$ values (33-43 nM) against melanoma compared with 8l. But o-fluoro substituted 8l has lowest potency ($IC_{50}$ values: 52-114 nM) among the three substituted compounds on prostate cancer cells. Meta-substituted compound 8m showed lowest activity on melanoma cells ($IC_{50}$ values: 287-304 nM) but showed moderate inhibition on prostate cancer cells ($IC_{50}$ values: 23-46 nM).

Turning to the effects of steric hindrance group on the "A" phenyl ring substituents, it was found that p-bromo (8u, $IC_{50}$ values: 18-44 nM) caused a decrease in antiproliferative activity relative to p-fluoro position (8n, $IC_{50}$ values: 6-12 nM) but only against prostate cancer cells. Reduced activity against both cancer cell lines occurred when p-methyl (8k, $IC_{50}$ values: 5-21 nM) was replaced with a p-ethyl group (8v, $IC_{50}$ values: 17-70 nM).

To investigate if the phenyl ring played an essential role at the "A" ring site, phenyl at 2-thiazole position was removed and compound 10 was obtained. This modification caused a total loss of activity compared with 8f. The replacement of the "A" ring by pyridine (compound 8x) had the same effect. Moreover, substituting 2-pyrimidine in "A" ring (compound 8y) also caused a significant loss of activity ($IC_{50}$s: 11.8-41.0 µM). However, introducing the thiophene replacement of phenyl (8z) into "A" position improved the potency calcd. 1-3 folds on all examined cell lines ($IC_{50}$s: 9-38 nM) compared to 8f ($IC_{50}$s: 21-71 nM).

Because many of the compounds show poor water-solubility, three water-soluble salts were prepared after introducing a hydrophilic group such as $NH_2$ (8w) and COOH (8r) into "A" ring to form HCl or sodium salts. Another modification is replacing "A"/"C" rings in 8a with pyridine (8i, 8x, 8y) or pyrimidine rings, which could also be converted into HCl salts. These modifications reduced the calculated Log P values (Log P=2.74-3.90) compared with 8a and 8f (Log P=4.46 and 4.08). Introducing p-amino to "A" phenyl (8w) is the only case to increase the antiproliferative activity (HCl salt, $IC_{50}$ values: 11-29 nM) compared with 8f against all cell lines. Although replacing phenyl with pyrimidine (8y) kept partial activity against both cancer cells, the potency range was markedly reduced from nM to M compared with 8f. Unfortunately, introducing COOH to para-phenyl "A" ring and pyridine to "A" or "C" rings (8i, 8r, 8x) all resulted in the total loss of the anti-cancer activity. A total loss of potency was seen in the methyl ester 8s of acid 8r against both cancer cell lines. Demethylation of compound 8f afforded water soluble 3,4,5-trihydroxyphenyl at "C" ring compound 11f, but this demethylation results in complete loss of antiproliferative activity against all tested cancer cells, which also points out the importance of 3,4,5-trimethoxyphenyl at "C" position of the methanones.

Given these results, compound 8f was also subjected to in vitro testing in an NCI-60 screening assay, which measures the ability of the compound to act against six leukemia cell lines, eight non-small cell lung cancer cell lines, seven colon cancer cell lines, six CNS cancer (e.g., glioma/glioblastoma) cell lines, eight melanoma cell lines, six ovarian cancer cell lines, seven renal cancer cell lines, two prostate cancer cell lines, and eight breast cancer cell lines. The results of the NCI-60 assay showed broad activity against all of these cancers, with $GI_{50}$ values in the nanomolar range ($<1.0\times10^{-8}$) against most cell lines and TGI values in the micromolar range against most cell lines. TGI values in the nanomolar range were obtained against several leukemia cell lines, one lung cancer cell line, several colon cancer cell lines, several ovarian cancer cell lines, and several breast cancer cell lines.

TABLE 2

In Vitro Inhibitory Effects of Modified ATCAA Compounds against the Proliferation of Melanoma (A375, B16-F1) and Prostate Cancer Cells (DU145, PC-3, LNCaP, PPC-1)

|  | A ring | B ring[a] | C ring[b] | X |
|---|---|---|---|---|
| ATCAA-1 | p-NHAc—Ph | TZD | $C_{16}H_{33}$ | CONH |
| ATCAA-2 | p-NHAc—Ph | TZD | 9H-fluoren-1-yl | CONH |
| 2a | Ph | TZD | 3,4,5-triMeO—Ph | CONH |
| 2b | 3,4,5-triMeO—Ph | TZD | 3,4,5-triMeO—Ph | CONH |
| 4a(4R) | Ph | TZL | 3,4,5-triMeO—Ph | CONH |
| 4b(4S) | Ph | TZL | 3,4,5-triMeO—Ph | CONH |
| 5 | Ph | TZ | 3,4,5-triMeO—Ph | CONH |
| 8f | Ph | TZ | 3,4,5-triMeO—Ph | CO |
| Colchicine |  |  |  |  |

| | $IC_{50} \pm$ SEM (µM) | | | | | |
|---|---|---|---|---|---|---|
|  | B16-F1 | A375 | DU 145 | PC-3 | LNCaP | PPC-1 |
| ATCAA-1 | 2.2 ± 0.3 | 2.1 ± 0.2 | 1.7 ± 0.1 | 1.2 ± 0.1 | 1.0 ± 0.1 | 0.4 ± 0.1 |
| ATCAA-2 | 3.9 ± 0.3 | 2.1 ± 0.1 | 1.9 ± 0.3 | 2.1 ± 0.1 | 3.5 ± 0.7 | 1.6 ± 0.1 |

TABLE 2-continued

In Vitro Inhibitory Effects of Modified ATCAA Compounds against the Proliferation of Melanoma (A375, B16-F1) and Prostate Cancer Cells (DU145, PC-3, LNCaP, PPC-1)

| | | | | | | |
|---|---|---|---|---|---|---|
| 2a | >100 | >100 | >20 | >20 | >20 | >20 |
| 2b | >100 | >100 | >20 | >20 | >20 | >20 |
| 4a(4R) | 38.3 ± 3.2 | 22.8 ± 1.6 | >20 | >20 | >20 | 5.3 ± 0.3 |
| 4b(4S) | 30.4 ± 2.8 | 13.6 ± 1.2 | >20 | 13.2 ± 2.1 | 16.8 ± 1.8 | 3.4 ± 0.2 |
| 5 | >100 | >100 | >20 | >20 | >20 | >20 |
| 8f | 0.055 ± 0.005 | 0.028 ± 0.005 | 0.071 ± 0.004 | 0.021 ± 0.001 | 0.028 ± 0.004 | 0.043 ± 0.005 |
| Colchicine | 0.029 ± 0.005 | 0.020 ± 0.003 | 0.010 ± 0.002 | 0.011 ± 0.001 | 0.016 ± 0.004 | 0.020 ± 0.001 |

[a]TZD = Thiazolidine, TZL = Thiazoline, TZ = Thiazole;
[b]For ATCAA-1, "C" position contains a lipid chain. ATCAA-1 and ATCAA-2 were prepared using appropriate starting materials according to Scheme 1 of Example 1 (see also Li et al., "Synthesis and Antiproliferative Activity of Thiazolidine Analogs for Melanoma," *Bioorg. Med. Chem. Lett.* 17:4113-7 (2007); Gududuru et al., "Discovery of 2-Arylthiazolidine-4-Carboxylic Acid Amides as a New Class of Cytotoxic Agents for Prostate Cancer," *J. Med. Chem.* 48:2584-2588 (2005), each of which is hereby incorporated by reference in its entirety).

TABLE 3

In Vitro Growth Inhibitory Effects of Compounds 8a-8j with Different "C" Rings against Proliferation of Melanoma (A 375, B16-F1) and Prostate Cancer Cells (DU145, PC-3, LNCaP, PPC-1)

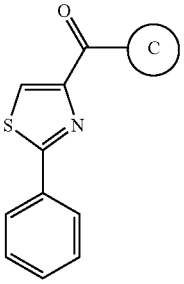

| Compounds 8 | | C Ring | IC$_{50}$ ± SEM (μM) | | | | | |
|---|---|---|---|---|---|---|---|---|
| | | | B16-F1 | A375 | DU 145 | PC-3 | LNCaP | PPC-1 |
| | 8a | Ph | >100 | >100 | >20 | >20 | >20 | >20 |
| | 8b | 4-MeO—Ph | >100 | >100 | >20 | >20 | >20 | >20 |
| | 8c | 3-MeO—Ph | >100 | >100 | >20 | >20 | >20 | >20 |
| | 8d | 2-MeO—Ph | 59.4 ± 21.2 | 70.3 ± 32.5 | >20 | >20 | >20 | >20 |
| | 8e | 3,4-diMeO—Ph | >100 | >100 | >20 | >20 | >20 | >20 |
| | 8f | 3,4,5-triMeO—Ph | 0.055 ± 0.005 | 0.028 ± 0.005 | 0.071 ± 0.004 | 0.021 ± 0.001 | 0.028 ± 0.004 | 0.043 ± 0.005 |
| | 8g | 3,5-diMeO—Ph | 0.350 ± 0.2 | 0.170 ± 0.1 | 0.424 ± 0.098 | 0.301 ± 0.030 | 0.343 ± 0.041 | 0.242 ± 0.014 |
| | 8h | 2-Fluoro-Ph | >100 | >100 | >20 | >20 | >20 | >20 |
| | 8j | Hexadecyl[a] | 18.6 ± 17.5 | 16.0 ± 15.2 | >20 | >20 | >20 | >20 |

[a]Compound 8j has a lipid chain at "C" ring position.

TABLE 4

In Vitro Growth Inhibitory Effects of Compounds 8f, 8k-8q, 8t-v, 8x-z, and 10 with different "A" Rings against the Proliferation of Melanoma (A375, B16-F1) and Prostate Cancer Cells (DU145, PC-3, LNCaP, PPC-1)

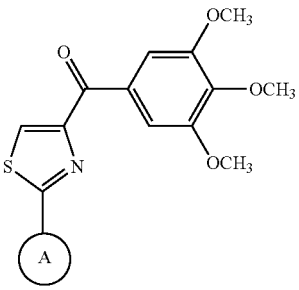

| Compounds 8 | | A Ring | IC$_{50}$ ± SEM (μM) | | | | | |
|---|---|---|---|---|---|---|---|---|
| | | | B16-F1 | A375 | DU 145 | PC-3 | LNCaP | PPC-1 |
| | 8f | Ph | 55 ± 5 | 28 ± 5 | 71 ± 4 | 21 ± 1 | 28 ± 4 | 43 ± 5 |
| | 8k | 4-Methyl-Ph | 21 ± 10 | 11 ± 5 | 7 ± 1 | 5 ± 1 | 6 ± 1 | 6 ± 1 |
| | 8l | 2-Fluoro-Ph | 27 ± 11 | 30 ± 9 | 114 ± 3 | 82 ± 9 | 53 ± 4 | 52 ± 3 |
| | 8m | 3-Fluoro-Ph | 287 ± 36 | 304 ± 25 | 35 ± 3 | 24 ± 2 | 11 ± 2 | 21 ± 1 |
| | 8n | 4-Fluoro-Ph | 43 ± 21 | 33 ± 14 | 12 ± 1 | 13 ± 1 | 6 ± 1 | 8 ± 1 |
| | 8o | 3,4-diMeO—Ph | 161 ± 29 | 34 ± 10 | 102 ± 2 | 69 ± 3 | 38 ± 6 | 56 ± 2 |
| | 8p | 4-Nitro-Ph | 56 ± 12 | 38 ± 9 | 95 ± 5 | 56 ± 1 | 39 ± 4 | 34 ± 1 |
| | 8q | 4-Cyano-Ph | 53 ± 16 | 59 ± 24 | 52 ± 2 | 30 ± 7 | 15 ± 4 | 19 ± 2 |
| | 8t | 4-Trifluoro-methyl-Ph | 92 ± 16 | 23 ± 5 | 50 ± 5 | 58 ± 4 | 94 ± 1 | 76 ± 1 |
| | 8u | 4-Bromo-Ph | 32 ± 5 | 13 ± 2 | 21 ± 4 | 18 ± 3 | 44 ± 3 | 21 ± 5 |
| | 8v | 4-Ethyl-Ph | 70 ± 8 | 17 ± 2 | 31 ± 4 | 27 ± 4 | 60 ± 5 | 22 ± 3 |
| | 8x | 4-Pyridine | >100000 | >100000 | >20000 | >20000 | >20000 | >20000 |
| | 8y | 2-Pyrimidine | 2300 ± 860 | 4100 ± 740 | 2813 ± 92 | 2657 ± 40 | 2370 ± 85 | 1186 ± 22 |
| | 8z | 2-Thienyl | 38 ± 15 | 20 ± 7 | 20 ± 1 | 17 ± 2 | 9 ± 1 | 13 ± 1 |
| | 10 | H[a] | >100000 | >100000 | >20000 | >20000 | >20000 | >20000 |

[a]Compound 10 has a proton at "A" ring position.

Example 5: Synthesis and In Vitro Cytotoxicity of Additional Methanone Compounds The A ring indole of compounds 31 and 32 was synthesized using the same approach as 8f described in Scheme 3 above from 1H-indole-5-carbonitrile or 1H-indole-2-carbonitrile as starting material. Crude product was purified by column chromatography. Description of synthesis of compounds 31 and 32 is provided below in Example 11.

(2-(1H-Indol-5-yl)thiazol-4-yl)(3,4,5-trimethoxyphenyl)methanone (Compound 31)

Yield: 36.3%. $^1$H NMR (300 MHz, CDCl$_3$) δ 8.36 (br, 1H), 8.31 (br, 1H), 8.21 (s, 1H), 7.92-7.89 (dd, 1H), 7.83 (s, 2H), 7.47 (d, 1H), 7.29 (t, 1H), 6.64 (t, br, 1H), 3.98 (s, 3H), 3.97 (m, 6H). MS (ESI) m/z 417.1 [M+Na]$^+$, 392.9 [M−H]$^−$.

(2-(1H-Indol-2-yl)thiazol-4-yl)(3,4,5-trimethoxyphenyl)methanone (Compound 32)

Yield: 45.8%. $^1$H NMR (500 MHz, CDCl$_3$) δ 9.26 (br, 1H), 8.11 (s, 1H), 7.67 (d, 2H), 7.46 (s, 2H), 7.42 (d, 1H), 7.29 (t, 1H), 7.16 (t, 1H), 7.10 (s, 1H), 3.97 (s, 3H), 3.93 (m, 6H). MS (ESI) m/z 417.1 [M+Na]$^+$, 392.9 [M−H]$^−$.

The activity of compound 31 was assessed by in vitro cytotoxicity assay as described in Example 4 above. It was determined that compound 31 exhibited enhanced activity against the PC-3, A375, and B16 cell lines.

TABLE 5

In Vitro Growth Inhibitory Effects of Compounds 31-32 Against Proliferation of Prostate and Melanoma Cancer Cells

| Compound | Structure | IC$_{50}$ (nM) | | | | | | |
|---|---|---|---|---|---|---|---|---|
| | | RH7777 | DU 145 | PC-3 | LNCaP | PPC-1 | A375 | B16 |
| 31 | C$_{21}$H$_{18}$N$_2$O$_4$S Mol. Wt.: 394.44 C, 63.94; H, 4.60; N, 7.10; O, 16.22; S, 8.13 | ND | ND | 7.6 | ND | ND | 25.0 | 8.3 |
| 32 | C$_{21}$H$_{18}$N$_2$O$_4$S Mol. Wt.: 394.44 C, 63.94; H, 4.60; N, 7.10; O, 16.22; S, 8.13 | ND | ND | ND | ND | ND | ND | ND |

ND = not determined.

Example 6: Determining Mechanism of Action for Compound 8f

Figure 3A:
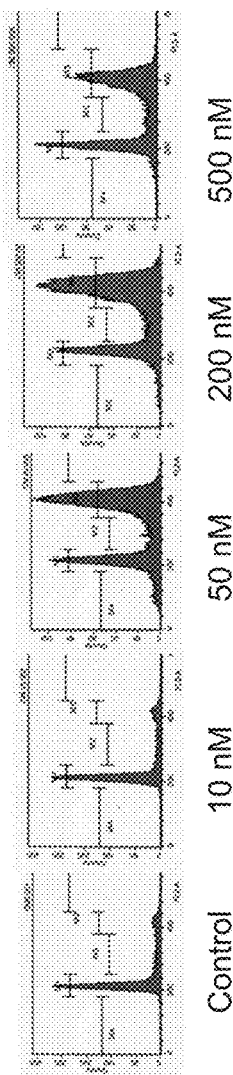
FIGS. 3A and 3B illustrate the effect of compound 8f on cell cycle distribution of LNCaP prostate cancer cells.
Figure 3B:
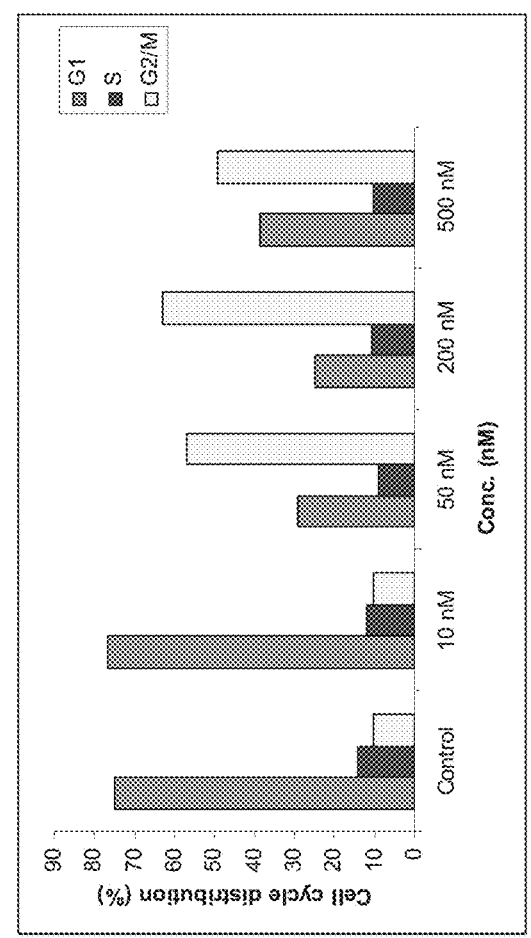

To understand the target for these highly potent compounds, cell cycle analysis was performed using compound 8f. LNCaP prostate cancer cells were exquisitely sensitive to compound 8f ($IC_{50}$=29 nM). LNCaP cells were treated with compound 8f (10 to 500 nM) for 24 h prior to staining with propidium iodide and performing cell cycle analysis. Although compound 8f had no effect on cell cycle distribution at a 10 nM (below the $IC_{50}$), the proportion of cells in G2/M phase increased in proportion to the concentration of compound 8f at higher concentrations. About 10% of untreated cells were observed in G2/M phase, whereas the cells treated with more than 50 nM showed a greater proportion of cells in G2/M phase (57, 63, and 49%, respectively, for 50, 200, and 500 nM). The results are shown in FIGS. 3A-B. The increase in G2/M phase cells was accompanied by a decrease in G1 populations, relative to control. These data indicate that compound 8f may inhibit tubulin action in a manner similar to paclitaxel, the *vinca* alkaloids, and cochicine (Margolis et al., "Addition of Colchicine-Tubulin Complex to Microtubule Ends: The Mechanism of Substoichiometric Colchicine Poisoning," *Proc. Nat'l Acad. Sci. USA* 74:3466-70 (1977), which is hereby incorporated by reference in its entirety).

Figure 4:
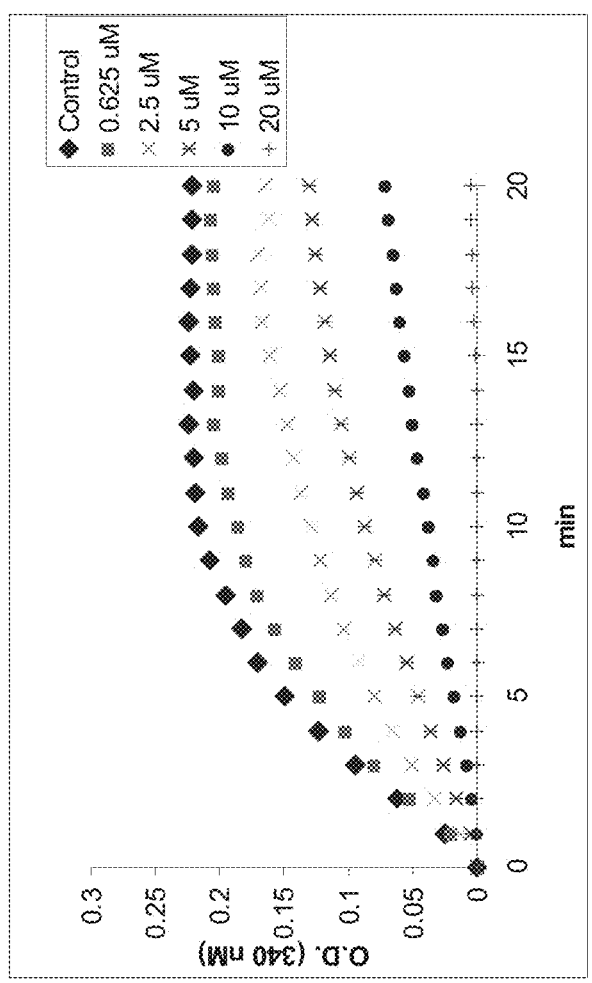
FIG. 4 is a graph illustrating the effect of compound 8f on tubulin assembly.

Based on these results, an in vitro microtubule polymerization assay was performed. Bovine brain tubulin (0.4 mg) (Cytoskeleton, Denver, Colo.) was mixed with various concentrations (0.625-20 µM) of compound 8f and incubated in 120 µl of general tubulin buffer (80 mM PIPES, 2.0 mM $MgCl_2$, 0.5 mM EGTA, pH 6.9 and 1 mM GTP). The absorbance of wavelength at 340 nm was monitored every 60s for 20 min by the SYNERGY 4 Microplate Reader (Bio-Tek Instruments, Winooski, Vt.). The spectrophotometer was set at 37° C. for tubulin polymerization. The $IC_{50}$ value was defined as the concentration which can inhibit 50% of microtubule polymerization. The results are shown in FIG. 4. Compared with non-treated control, compound 8f inhibits tubulin polymerization. The effect of 8f on tubulin assembly was examined at concentrations from 0.625 µM to 20 µM. The observed results demonstrate that compound 8f inhibited tubulin polymerization in a dose-dependent manner with an $IC_{50}$ value of 4.23 µM.

Figure 5B:
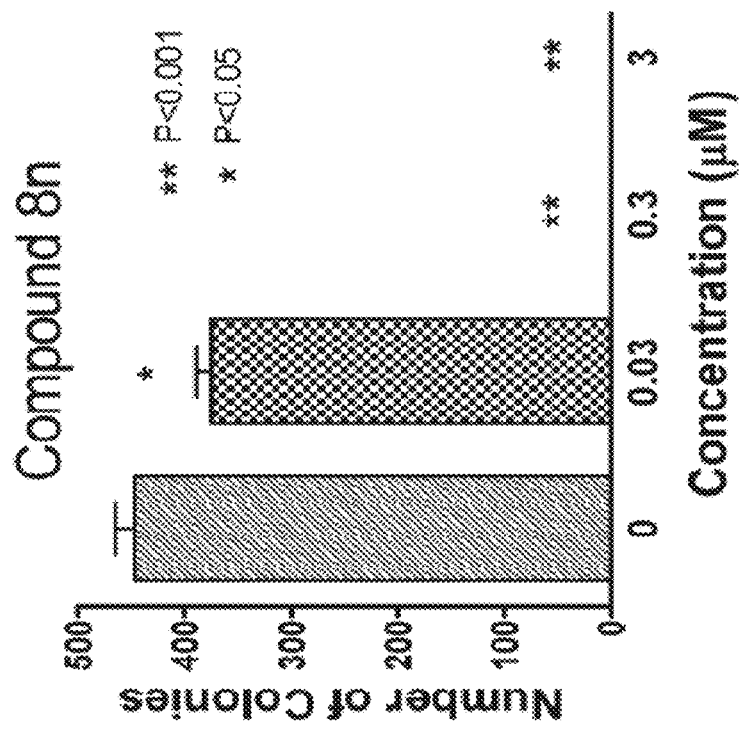
FIGS. 5A and 5B are graphs illustrating the ability of compounds 8f and 8n to significantly inhibit A375 melanoma colony formation in an in vitro assay. At 0.3 µM or above, colony formation is completely inhibited.
Figure 5A:
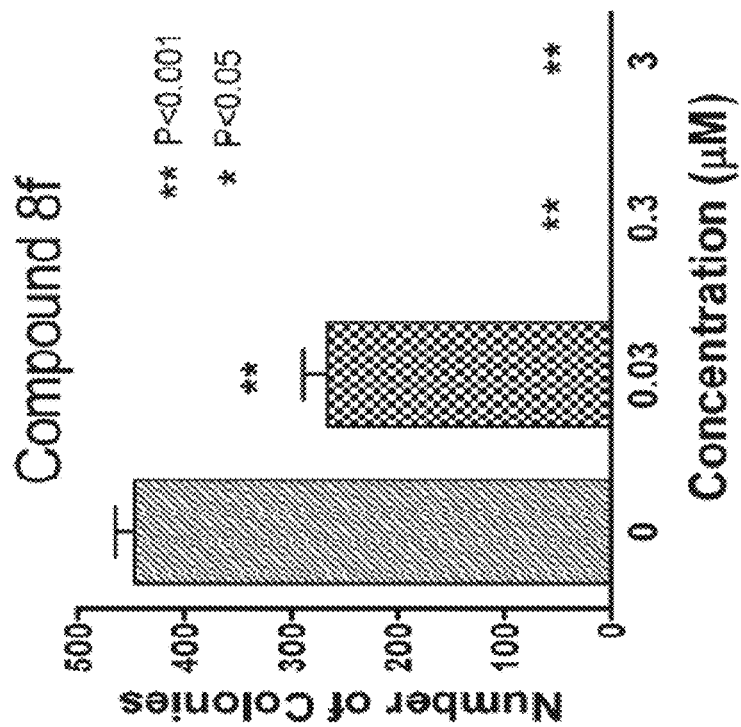

Example 7: In Vitro Cytotoxicity of Compounds 8f and 8n Against A375 Melanoma Cell Line Human A375 malignant melanoma cells were plated at a colony-forming density (200 cells per well on six well plates). Cells were grown in DMEM medium (GIBCO, Invitrogen Corp., Carlsbad, Calif.) supplemented with charcoal-stripped fetal bovine serum (HyClone, Logan, Utah) and an antibiotic-antimycotic solution (Sigma, St. Louis, Mo.) at 37° C. in an atmosphere of 95% air and 5% $CO_2$. Cells were treated with compounds 8f and 8n at different concentrations (0, 0.03, 0.3, and 3 µM). Cells were grown for 10 days and colonies were fixed with 4% paraformaldehyde in PBS at 4° C. The fixed colonies were washed with distilled water, stained with 0.1% crystalline blue for 30 min and rinsed with distilled water to remove excess of the dye. Plates were photographed and colony formations were examined by eye and under the microscope. Both of compounds 8f and 8n significantly inhibit melanoma colony formation at 0.03 µM. At the two higher concentrations tested (0.3 and 3 µM), colony formations were completely inhibited, with no colonies visible under the microscope (FIGS. 5A-B).

Figure 6:
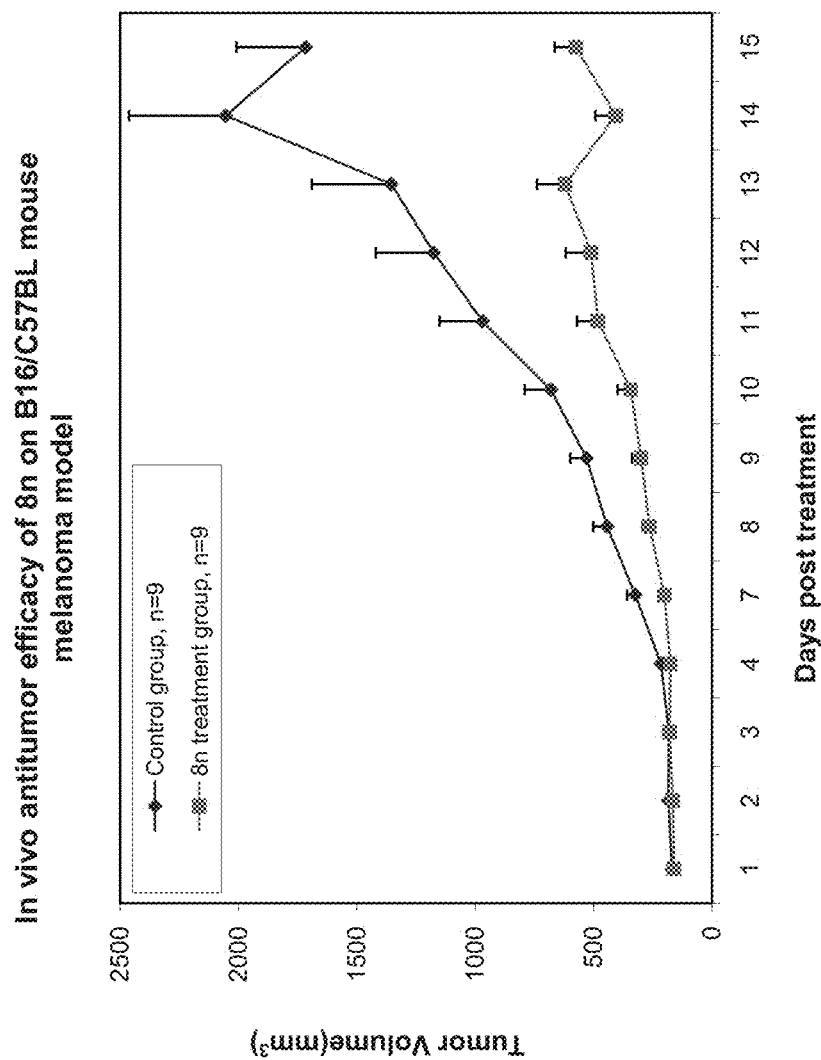
FIG. 6 is a graph illustrating the ability of compound 8n (6 mg/kg, IP daily injection) to inhibit B16 melanoma tumor growth in vivo.

Example 8: In Vivo Cytotoxicity of Compound 8n Against Melanoma Xenograft Tumor The efficacy of compound 8n was assessed using B16-F1 mouse melanoma cells injected in C57 black mice. B16 tumors will grow in a fully immunocompetent host, in which case the tumor progression may more accurately replicate melanoma growth. Logarithmic growth phase B16-F1 (3.8× $10^5$) cells were injected s.c. into the right dorsal flank of C57BL/6 mice. When tumors were palpable, mice were randomized into a control and a treatment group (n=9). Mice were dosed by daily i.p. injection with 30 µl of vehicle (control group) or 8n solution (treatment group, 6 mg/kg). Tumor volume was measured once daily with a Traceable® electronic digital caliper and calculated by using the formula a×$b^2$×0.5, where a and b represented the larger and smaller diameters, respectively. Body weights were also recorded. Tumor volume was expressed as cubic millimeters. Data were expressed as Mean±SE for each group and plotted as a function of time. At the end of treatment, all mice were euthanized by $CO_2$ inhalation followed by cervical dislocation. Compound 8n showed significant tumor growth inhibition at this relatively low dose (6 mg/kg) as shown in FIG. 6. There was no significant body weight loss (<5%), and all mice had normal activities during the experiments.

Example 9: Synthesis of Compound 8f Derivatives with Hydrazine or Oxime

Carbonyl group linkers were modified into oxime and hydrazine linkers (compounds 33-36) as illustrated in Scheme 4. Compound 8f was used as starting material.

Scheme 4

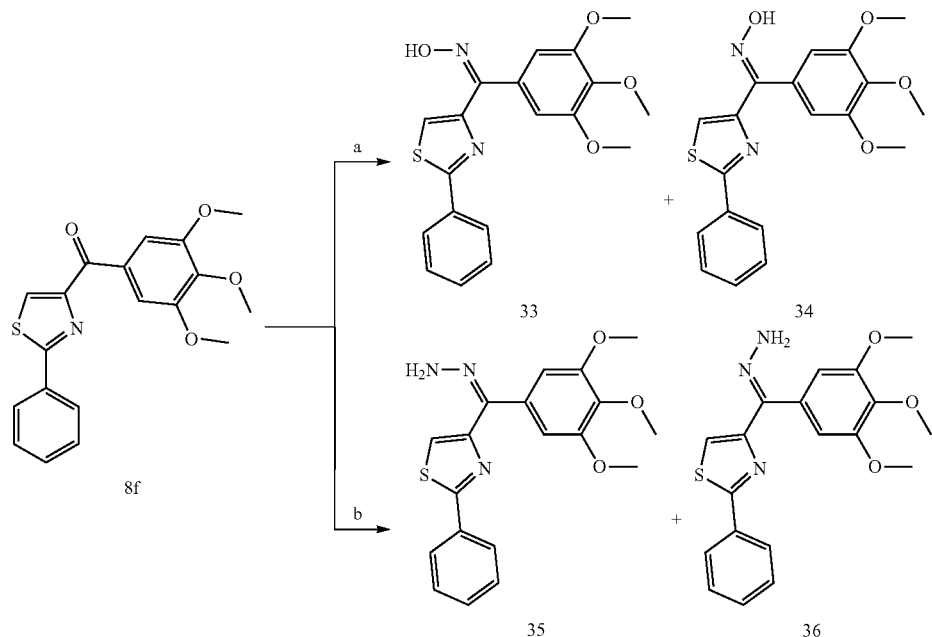

Reagents (a) NH₂OH·HCl, C₂H₅OH, H₂O, NaOH, 51%; (b) NH₂NH₂ xH₂O, CH₂Cl₂, C₂H₅OH, 57%.

To a suspension of 50 mg 8f in 2 mL ethyl alcohol was added a 0.5 mL aqueous solution of 34 mg hydroxylamine hydrochloride. Then 13 mg sodium hydroxide in 0.5 mL H$_2$O was added and stirred at room temperature for 10 min. Then heating to 60° C. and stirred for 3 h. Oxime isomers 33 and 34 were separated from the reaction mixtures by flash chromatograph as white crystals with a 50% overall yield.

(Z)-(2-Phenylthiazol-4-yl)(3,4,5-trimethoxyphenyl) methanone oxime (Compound 33)

M.p 150-153° C. $^1$H NMR (300 MHz, CDCl$_3$) δ 11.94 (br, 1H), 8.35 (br, 1H), 7.91-7.89 (m, 2H), 7.81-7.75 (d, 1H), 7.50-7.49 (m, 3H), 6.85 (s, 2H), 3.73 (s, 6H), 3.71 (s, 3H). MS (ESI) m/z 393.3 [M+Na]$^+$, 368.9 [M–H]$^-$.

(E)-(2-Phenylthiazol-4-yl)(3,4,5-trimethoxyphenyl) methanone oxime (Compound 34)

M.p 176-177° C. $^1$H NMR (500 MHz, DMSO-d$_6$) δ 11.48 (br, 1H), 7.92-7.90 (m, 2H), 7.64 (br, 1H), 7.52-7.48 (d, 1H), 7.52-7.48 (m, 3H), 6.75 (s, 2H), 3.75 (s, 6H), 3.72 (s, 3H). MS (ESI) m/z 393.1 [M+Na]$^+$, 368.9 [M–H]$^-$.

To a solution of 2 mL hydrazine in 6 mL ethyl alcohol was added a solution of 230 mg 8f in 2 mL methylene chloride. The mixtures was refluxed overnight and absorbed on silicon gel. Hydrazone isomers 35 and 36 was separated from the flash chromatograph as white crystals with a 56.9% overall yield.

(Z)-4-(Hydrazono(3,4,5-trimethoxyphenyl)methyl)-2-phenylthiazole (Compound 35)

M.p 117-119° C. $^1$H NMR (300 MHz, CDCl$_3$) δ 8.01-7.98 (m, 2H), 7.49-7.46 (m, 5H), 7.33 (s, 1H), 6.82 (s, 2H), 3.87 (s, 3H), 3.85 (s, 6H). MS (ESI) m/z 370.1 [M+H]$^+$.

(E)-4-(Hydrazono(3,4,5-trimethoxyphenyl)methyl)-2-phenylthiazole (Compound 36)

M.p 65-66° C. $^1$H NMR (300 MHz, CDCl$_3$) δ 8.04-8.00 (m, 2H), 7.44-7.40 (m, 3H), 6.95 (s, 1H), 6.62 (s, 2H), 5.62 (s, 2H), 3.93 (s, 3H), 3.87 (s, 6H). MS (ESI) m/z 370.1 [M+H]$^+$.

TABLE 6

Antiproliferative effects of compounds 33-36

| Compound | IC$_{50}$ (µM) | | | | | | |
|---|---|---|---|---|---|---|---|
| | B16 | A375 | Fibroblast | DU145 | PC-3 | LNCaP | PPC-1 |
| 33 | 0.32 | 0.18 | 0.36 | 0.10 | 0.12 | 0.19 | 0.16 |
| 34 | 11.4 | 7.8 | 10.1 | >1 | >1 | >1 | >1 |
| 35 | 2.0 | 0.9 | 1.9 | 1.21 | 1.12 | 1.80 | 0.87 |
| 36 | 1.8 | 0.6 | 1.0 | 1.21 | 1.04 | 1.30 | 0.97 |

Example 10: Design of Additional Derivatives

Compound 8f will be further modified to thioketone analogs 41 and 42 (Scheme 5 below). Compounds 8a-z will be similarly modified. The carbonyl group can be converted into a thiocarbonyl group by the action of Lawesson's reagent (Jesberger et al., Synthesis 1929-1958 (2003), which is hereby incorporated by reference in its entirety). The thioketone structure with conjugated aromatic rings is stable relative to unhindered thioketones. The thiazole compound can be obtained after dehydrogenation. (Riedrich et al., Angewandte Chemie, International Edition, 46(15):2701-2703 (2007), which is hereby incorporated by reference in its entirety). This conversion will decrease the hydrogen bond acceptor ability from O . . . H in ketone to S . . . H in thione. It will be helpful to examine the importance of hydrogen acceptor position in these molecules.

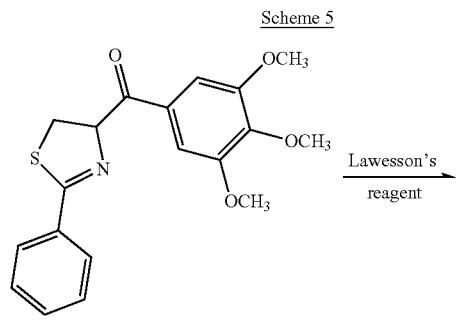

Scheme 5

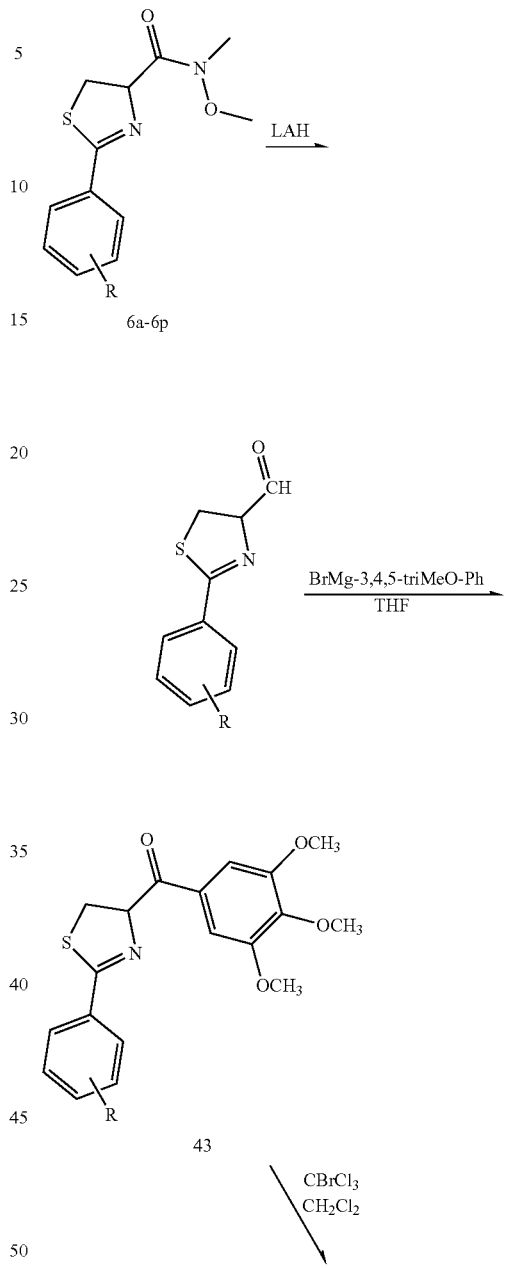

Scheme 6A

New analogs in which the carbonyl has been reduced to an alcohol (43 and 44, Scheme 6A below) or reduced to methylene (45 and 46, Scheme 6B below) will be synthesized. The alcohol 43 and 44 can be obtained using Grignard reaction of intermediate aldehyde with according Grignard reagents. Analogs 45 and 46 can be prepared with Clemmensen reduction of ketone function group to produce the corresponding hydrocarbon. When carbonyl is reduced to an alcohol or methylene, the strong hydrogen acceptor C=O reverses to strong hydrogen donor O—H or hydrocarbon, which totally loses hydrogen bond effects. This modification will provide insight as to the importance of carbonyl group and if it has a specific function in the anti-cancer activity.

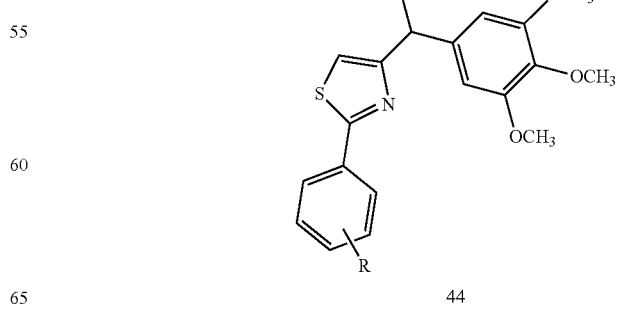

Scheme 6B

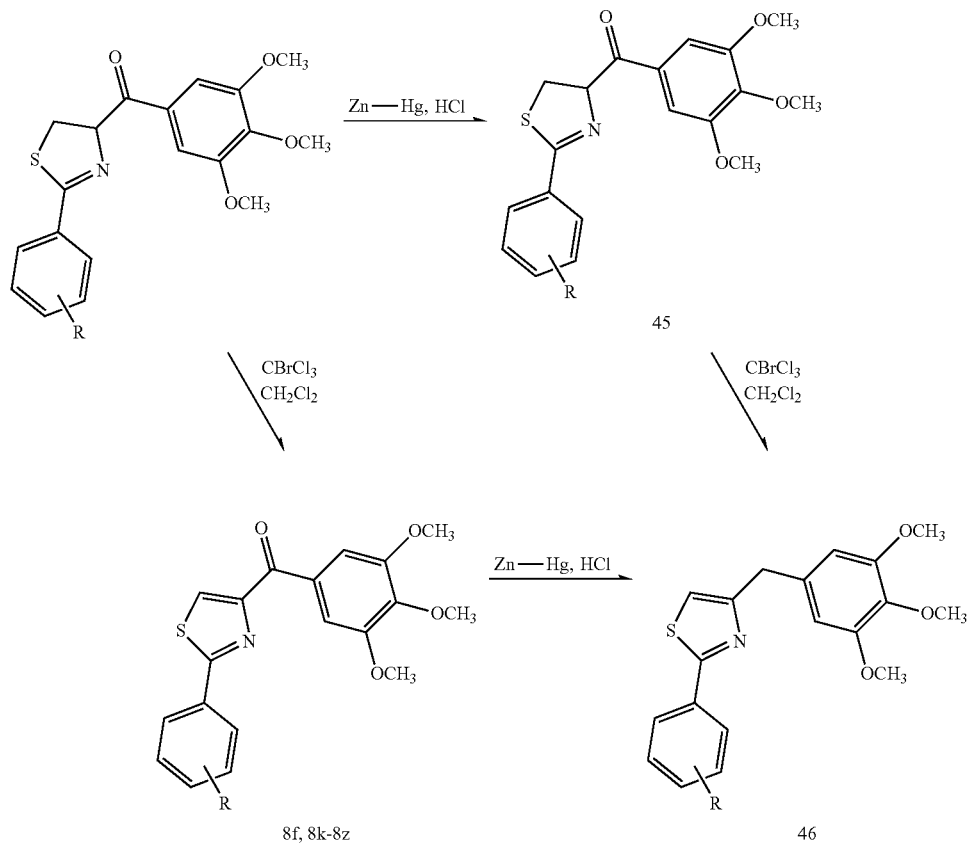

To examine the importance of ketone on antiproliferation in cancer cells, this linker will be converted into amide and ester analogs (47-50, Scheme 7 below). Finding activity in any of these series of analogs, the different linkages between the rings optimized to enhance activity and metabolic stability. As Scheme 7 below shows, consistent with the results demonstrated in the preceding examples, thiazoline and thiazole rings will be obtained from reaction of benzonitrile (including substituted benzonitrile) and cysteine (Bergeron et al., *J. Med. Chem.* 48:821-831 (2005), which is hereby incorporated by reference in its entirety). The resulting acid intermediates will be used to prepare the ester and amide linkages. These analogs will be compared for antiproliferation activity on prostate cancer cells and/or melanoma cells, and control cells, and compared to Compounds 8f and 8n.

Scheme 7

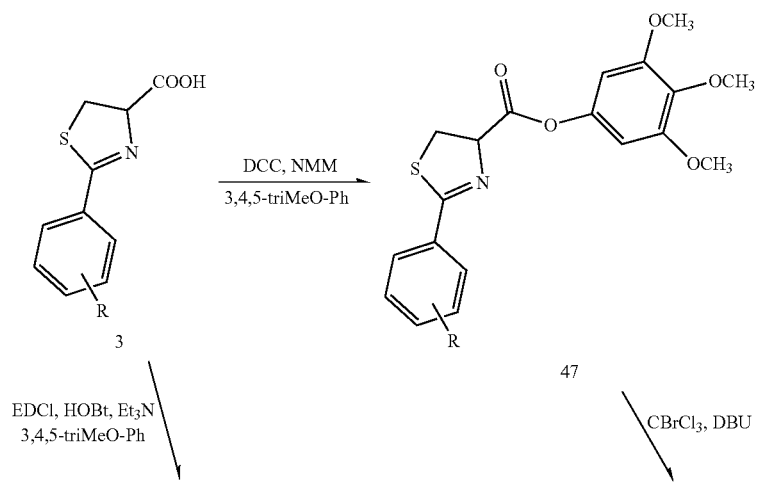

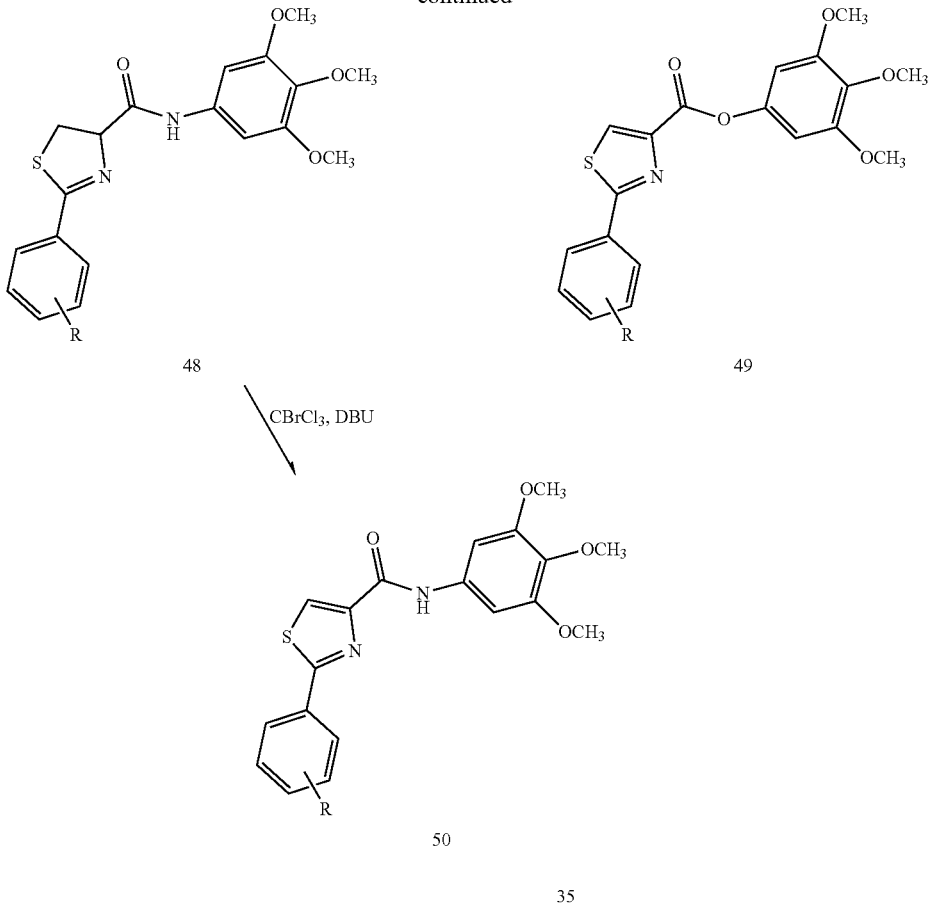

Compounds will also be prepared with the trimethoxylphenyl group replaced with different substituted aromatic rings, saturated or unsaturated alkyls and various heterocyclic groups as defined herein. This can be accomplished by using different Grignard reagents. These analogs will allow for optimization of the "C" ring with best activities, lowest toxicity, and best metabolic stability for prostate cancer, melanoma, and other cancers.

Replacement of the central thiazoline and thiazole rings with corresponding imidazoline (51), imidazole (52), oxazoline (53) and oxazole (54) ring systems will also be performed. Ethyl benzimidate hydrochloride salt reacted with 2,3-diaminopropanoic acid to give imidazoline ring system (see Scheme 8A below). (Hsu et al., *J. Med. Chem.* 23(11), 1232-1235 (1980), which is hereby incorporated by reference in its entirety). Dehydrogenation of imidazolines will afford desired imidazole compounds. Oxazolines can be prepared according to the classical condensation of phenyl imino ether with serine ester using triethylamine as a base (see Scheme 8B below) (Meyer et al., *Tetrahedron: Asymmetry* 14:2229-2238 (2003), which is hereby incorporated by reference in its entirety). Dehydrogenation of oxazolines will give the desired oxazole compounds.

Scheme 8A

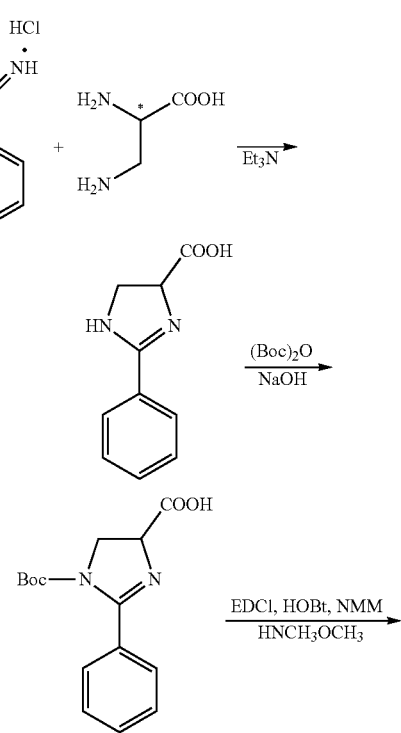

91
-continued
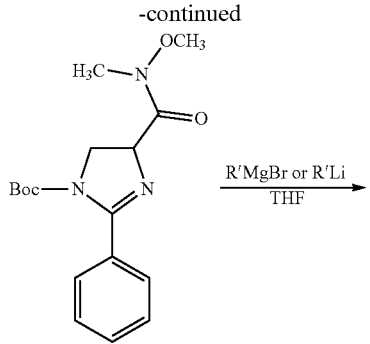
92
Scheme 8B
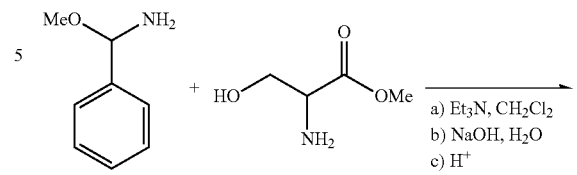
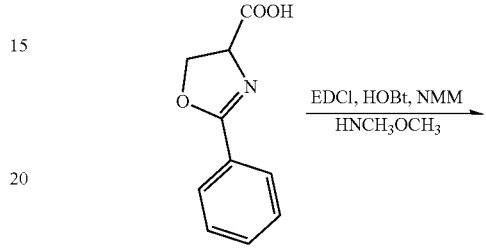
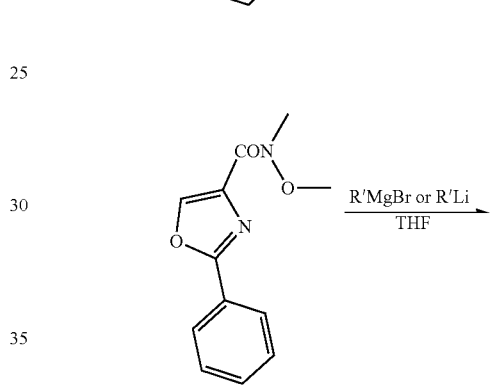
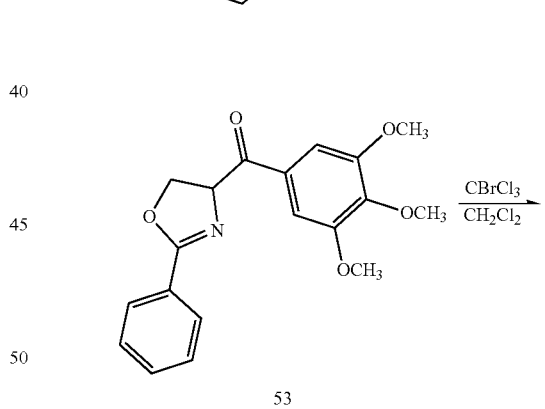
51
52
R = 3,4,5-triMeO-Ph
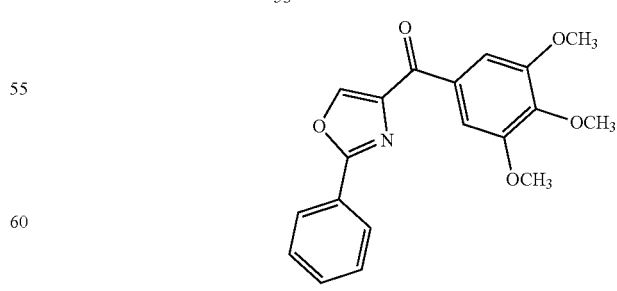
53
54
R' = 3,4,5-trMeO-Ph

Synthesis of (2-(4-bromophenyl)-1H-imidazol-4-yl)(3,4,5 trimethoxyphenyl)methanone (12Ia in the following scheme)

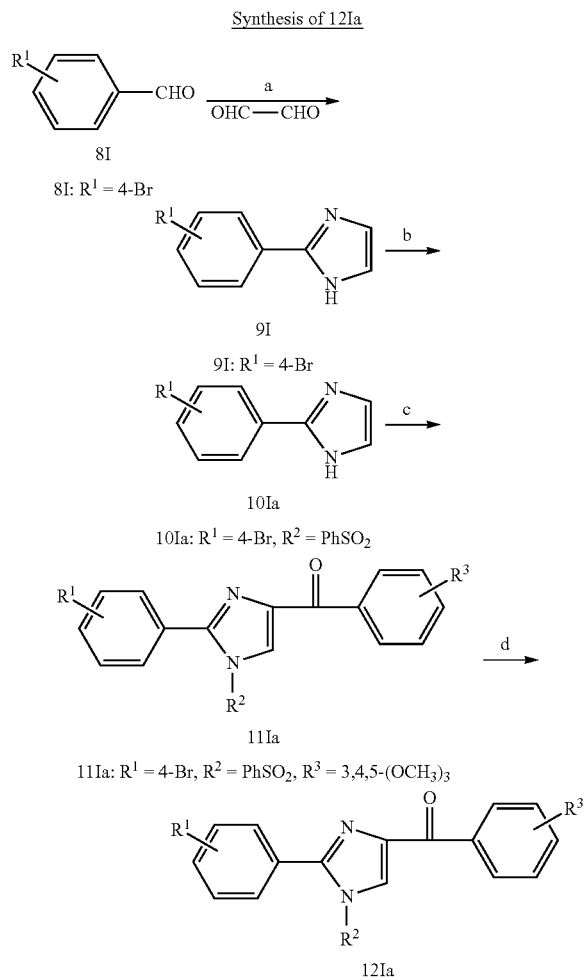

Synthesis of 9I

To a solution of appropriate benzaldehyde (e.g., 4-bromobenzaldehyde) (8I, 100 mmol) in ethanol (400 mL) at 0° C. was added a solution of 40% oxalaldehyde (glyoxal) in water (1.1 equiv) and a solution of 29% ammonium hydroxide in water (10 equiv). After stirring for 2-3 days at RT, the reaction mixture was concentrated and the residue was subjected to flash column chromatography with dichloromethane as eluent to yield compound 9I as a yellow powder. Yield: 10%-30%.

Synthesis of 10Ia

To a solution of imidazoles (9l) (2-(4-bromophenyl)-1H-imidazole) (10 mmol) in anhydrous THF (200 mL) at 0° C. was added sodium hydride (60% dispersion in mineral oil, 1.2 equiv) and stirred for 20 min. Benzenesulfonyl chloride (1.2 equiv) was added and the reaction mixture was stirred overnight. After dilution by 200 mL of saturated NaHCO$_3$ solution (aqueous), the reaction mixture was extracted by ethyl acetate (600 mL). The organic layer was dried over magnesium sulfate and concentrated. The residue was purified by flash column chromatography (hexane: ethyl acetate 2:1) to give a pale solid of compound 10la (e.g., 2-(4-bromophenyl)-1-(phenylsulfonyl)-1H-imidazole). Yield: 40%-95%.

Synthesis of 11Ia

To a solution of 2-(4-bromophenyl)-1-(phenylsulfonyl)-1H-imidazole (101a) (5.0 mmol) in anhydrous THF (30 mL) at −78° C. was added 1.7 M tert-butyllithium in pentane (1.2 equiv) and stirred for 10 min. 3,4,5-Trimethoxybenzoyl chloride (1.2 equiv) was added at −78° C. and stirred overnight. The reaction mixture was diluted with 100 mL of saturated NaHCO$_3$ solution (aqueous) and extracted by ethyl acetate (300 mL). The organic layer was dried over magnesium sulfate and concentrated. The residue was purified by flash column chromatography (hexane: ethyl acetate 3:1) to give a white solid of compound 111a (e.g., (2-(4-bromophenyl)-1-(phenylsulfonyl)-1H-imidazol-4-yl)(3,4,5-trimethoxyphenyl)methanone). Yield: 5%-45%.

Synthesis of 12Ia

To a solution of (2-(4-bromophenyl)-1-(phenylsulfonyl)-1H-imidazol-4-yl)(3,4,5-trimethoxyphenyl)methanone (111a), (2.0 mmol) in THF (25.0 mL) was added 1.0 M tetrabutyl ammonium fluoride (2 equiv) and stirred overnight. The reaction mixture was diluted by 60 mL of saturated NaHCO$_3$ solution (aqueous) and extracted by ethyl acetate (150 mL). The organic layer was dried over magnesium sulfate and concentrated. The residue was purified by flash column chromatography (hexane: ethyl acetate 4:1) or recrystallized from water and methanol to give a white solid of compound 12la ((2-(4-bromophenyl)-1H-imidazol-4-yl)(3,4,5-trimethoxyphenyl)methanone). Yield: 80-98%. mp 190-192° C. $^1$H NMR (500 MHz, CDCl$_3$) δ 7.99 (d, J=8.5 Hz, 2H), 7.92 (s, 1H), 7.70 (d, J=8.5 Hz, 2H), 7.32 (s, 2H), 4.03 (s, 3H), 4.00 (s, 6H). MS (ESI) calcd for C$_{19}$H$_{17}$BrN$_2$O$_4$ 416.0, found 417.0 [M+H]$^+$. HPLC2: t$_R$ 4.24 min, purity 98.8%.

Synthesis of (2-(p-Tolyl)-1H-imidazol-4-yl)(3,4,5-trimethoxyphenyl)methanone (12da in the Following Scheme)

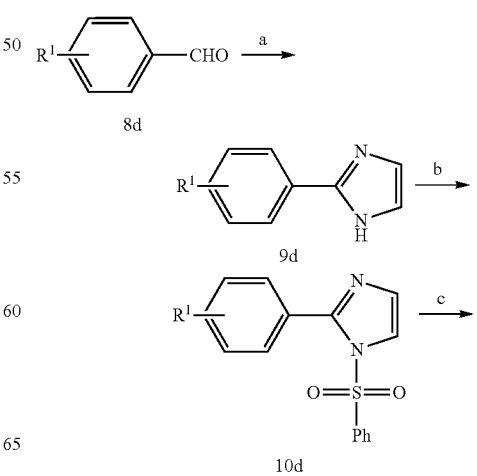

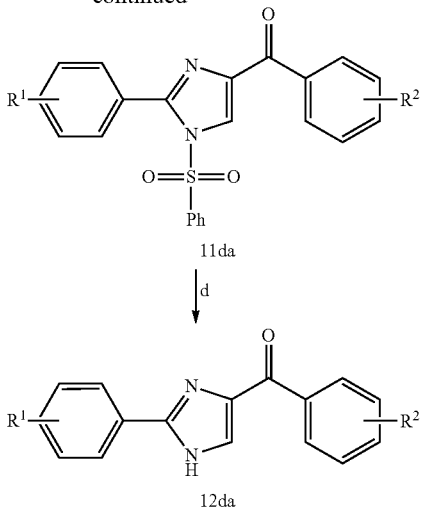

11da d: R¹ = 4-CH₃
R¹ and R² for 11 and 12:
da: R¹ = 4-CH₃; R² = 3,4,5-(OCH₃)₃

Synthesis of 9d

To a solution of 4-methylbenzaldehyde (8d) (100 mmol) in ethanol (350 mL) at 0° C. was added a solution of 40% oxalaldehyde in water (12.8 mL, 110 mmol) and a solution of 29% ammonium hydroxide in water (1000 mmol, 140 mL). After stirring for 2-3 days at RT, the reaction mixture was concentrated and the residue was subjected to flash column chromatography with dichloromethane as eluent to yield compound 9d (e.g., 2-(p-tolyl)-1H-imidazole) as a yellow powder. Yield: 20%-40%.

Synthesis of 10d

To a solution of 2-(p-tolyl)-1H-imidazole (9d) (20 mmol) in anhydrous THF (200 mL) at 0° C. was added sodium hydride (60% dispersion in mineral oil, 1.2 g, 30 mmol) and stirred for 30 min. Benzenesulfonyl chloride (2.82 mL, 22 mmol) was added and the reaction mixture was stirred overnight. After dilution by 100 mL of saturated NaHCO₃ solution (aqueous), the reaction mixture was extracted by ethyl acetate (500 mL). The organic layer was dried over magnesium sulfate and concentrated. The residue was purified by flash column chromatography (hexane: ethyl acetate 2:1) to give a pale solid 10d (e.g., 1-(phenylsulfonyl)-2-(p-tolyl)-1H-imidazole). Yield: 50%-70%.

Synthesis of 11da

To a solution of 1-(phenylsulfonyl)-2-(p-tolyl)-1H-imidazole (6.0 mmol) (10d) in anhydrous THF (30 mL) at −78° C. was added 1.7M tert-butyllithium in pentane (5.3 mL, 9.0 mmol) and stirred for 10 min. Appropriate substituted benzoyl chloride (7.2 mmol) was added at −78° C. and stirred for overnight. The reaction mixture was diluted with 100 mL of saturated NaHCO₃ solution (aqueous) and extracted by ethyl acetate (200 mL). The organic layer was dried over magnesium sulfate and concentrated. The residue was purified by flash column chromatography (hexane: ethyl acetate 4:1) to give a white solid of 11da (e.g., (1-(phenylsulfonyl)- 2-(p-tolyl)-1H-imidazol-4-yl)(3,4,5-trimethoxyphenyl) methanone). Yield: 15%-40%.

Synthesis of 12da

To a solution of (1-(phenylsulfonyl)-2-(p-tolyl)-1H-imidazol-4-yl)(3,4,5-trimethoxyphenyl)methanone (11da, 492 mg, 1.0 mmol) in THF (15.0 mL) was added 1.0 M tetrabutyl ammonium fluoride (2.0 mL, 2.0 mmol) and stirred overnight. The reaction mixture was diluted by 30 mL of saturated NaHCO₃ solution (aqueous) and extracted by ethyl acetate (80 mL). The organic layer was dried over magnesium sulfate and concentrated. The residue was recrystallized from water and methanol to give a white solid of 12da (2-(p-tolyl)-1H-imidazol-4-yl)(3,4,5-trimethoxyphenyl) methanone). Yield: 88.5%. mp 201-203° C. $^1$H NMR (500 MHz, CDCl₃) δ 10.40 (br, 1H), 7.88 (d, J=8.0 Hz, 2H), 7.82 (s, 1H), 7.31 (d, J=8.0 Hz, 2H), 7.24 (s, 2H), 3.96 (s, 3H), 3.94 (s, 6H), 2.43 (s, 3H). MS (ESI): calculated for $C_{20}H_{20}N_2O_4$, 352.10, found 375.2 [M+Na]⁺.HPLC2: $t_R$ 15.45 min, purity 97.4%.

Optically pure isomers of compounds 8a-8z (from Table 3 above) will also be prepared to investigate the importance of chirality at 4-position of thiazoline. This will be carried out using D- or L-cysteine to synthesize the chiral intermediate ketones from protected D- or L-cysteine. Condensation of the intermediate ketones with benzonitrile will afford R- or S-thiazoline isomers. Thiazoles can be prepared by dehydrogenation.

From previous studies on structure-relationship of thiazolidine carboxylic acid amides, reversed electronic effects of substituents on phenyl in C-2 position of thiazolidine ring resulted in significant different activity on prostate cancer cell lines. Derivatives with different aromatic ring substitutions from various substituted benzonitrile reactants will also be prepared (e.g., 4-dimethylamino-benzonitrile, 3-hydroxybenzonitrile, 4-methoxybenzonitrile, 3,4-dimethoxybenzonitrile, 3,4,5-trimethoxybenzonitrile, 4-acetamidobenzonitrile, 4-fluorobenzonitrile, 4-bromobenzonitrile, 4-nitrobenzonitrile, 4-cyanobenzonitrile, 3,5-difluorobenzonitrile, 4-methylbenzonitrile, 3-bromo-4-fluorobenzonitrile, 2,6-dichlorobenzonitrile, phenylbenzonitrile, indolenitrile and substituted indolylnitriles, pyridine-nitrile and substituted pyridinylnitriles, furan-nitrile and substituted furanylnitriles) to induce both electron withdrawing and electron donating substituents in ring substituent of C-2 position in thiazoline ring. It is believed that the best substituents of C-2 phenyl, indolyl, furanyl, thiophen-yl, and pyridinyl groups can be found after screening the resulting analogs.

Example 11: Indolyl A Ring Compounds

Figure 7:
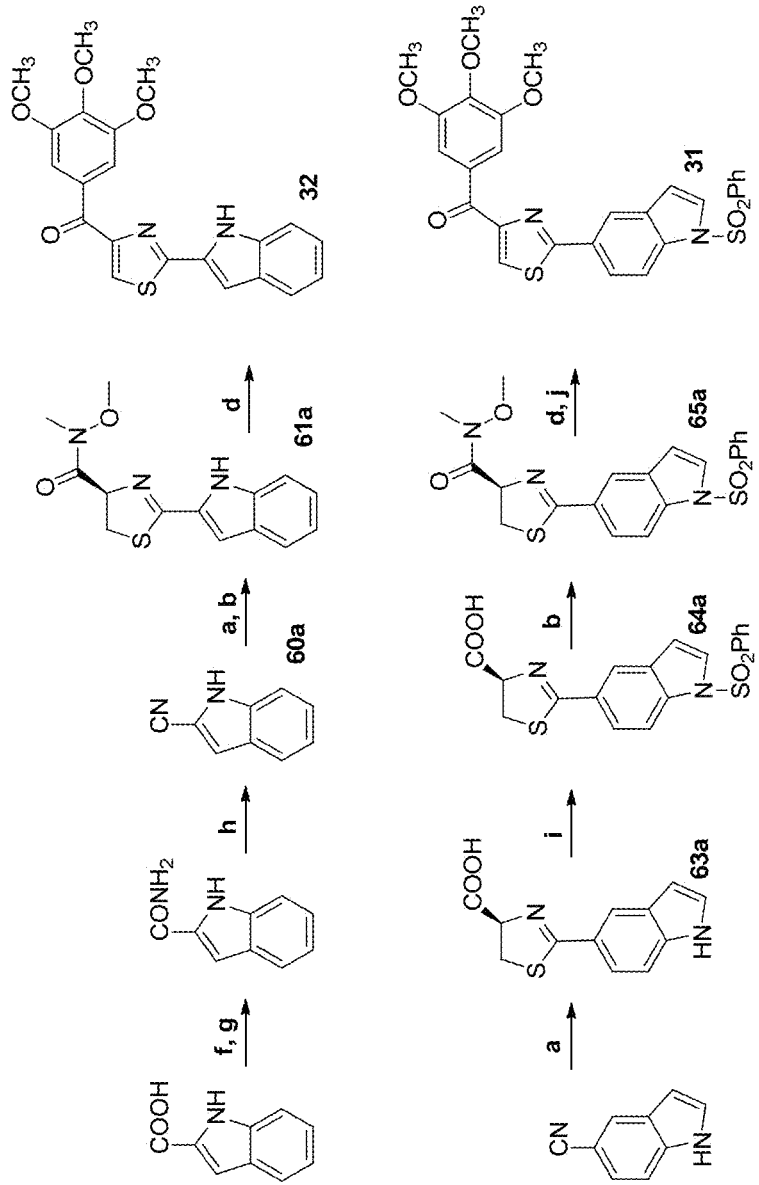
FIG. 7 depicts the synthetic scheme of compounds of this invention. Reagents and conditions: (a) L-cysteine, EtOH, 65° C.; (b) EDCI, HOBt, NMM, HNCH$_3$OCH$_3$, CH$_2$Cl$_2$; (c) TBDMSCl, imidazole, THF; (d) 3,4,5-trimethoxyphenyl-bromide, BuLi, THF; (e) TBAF, THF; (f) SOCl$_2$, Et$_2$O; (g) NH$_3$, MeOH; (h) POCl$_3$; (i) PhSO$_2$Cl, Bu$_4$NHSO$_4$, toluene, 50% NaOH; (j) 1 N NaOH, EtOH, reflux; (k) Boc$_2$O, 1 N NaOH, 1,4-dioxane; (l) CBrCl$_3$, DBU, CH$_2$Cl$_2$; (m) 4 N HCl in 1,4-dioxane; (n) NaH, DMF, MeI; (o) HCHO, NaBH$_3$CN, Et$_3$N.

Synthesis of (2-(1H-indol-2-yl)thiazol-4-yl)(3,4,5-trimethoxyphenyl)methanone (32) [FIG. 7]

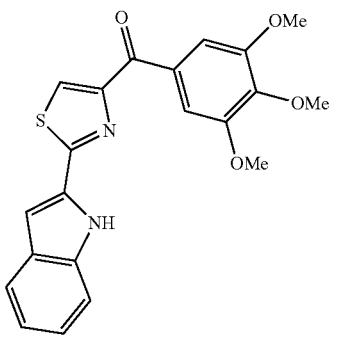

(32)

1H-Indole-2-carbonitrile (60a)

To a cooled solution of indole-2-carboxylic acid (2.0 g, 12.4 mmol) in 60 mL of anhydrous Et$_2$O was added 1.9 mL of SOCl$_2$ (26 mmol). After stirring for 40 min at RT, the ether was removed under reduced pressure at a temperature not exceeding 35° C. The obtained acyl chloride was dissolved in 40 mL of anhydrous Et$_2$O and the resulting solution was added immediately to a stirred solution of liquid ammonia in 80 ml of Et$_2$O. The reaction mixture was stirred at RT for 24 h. The solvent was then evaporated under reduced pressure, and the white indole-2-carboxamide was crystallized from 50% aq EtOH and dried in air, after which it was dissolved in POCl$_3$ and heated under reflux for 5 min. The cooled solution was poured onto crushed ice and aq NH$_4$OH was added to maintain a basic pH. The aqueous mixture was extracted with Et$_2$O, and the extracts were dried over Na$_2$SO$_4$ and evaporated. The brown indole-2-carbonitrile 60a (63.3% overall yield from indole-2-carboxylic acid) was obtained. $^1$H NMR (500 MHz, CDCl$_3$) δ 8.56 (br, s, 1H), 7.68 (d, 1H, J=8.0 Hz), 7.43-7.34 (m, 2H), 7.24-7.21 (m, 2H). MS (ESI) m/z 144.0 (M+H)$^+$, 140.8 (M−H)$^−$.

(R)-2-(1H-indol-2-yl)-N-methoxy-N-methyl-4,5-dihydrothiazole-4-carboxamide (61a) was synthesized using a method similar to that of 6a-6p (Scheme 3). 67.1% yield. $^1$H NMR (300 MHz, CDCl$_3$) δ 9.06 (s, br, 1H), 7.64 (d, 2H, J=8.1 Hz), 7.36-7.24 (m, 2H), 7.12 (dt, 1H, J=8.1 Hz, 1.2 Hz), 6.95 (d, 1H, J=1.8 Hz), 5.60 (t, br, 1H, J=8.7 Hz), 3.86 (s, 3H), 3.78 (t, 1H, J=10.2 Hz), 3.58 (dd, 1H, J=9.0 Hz, 10.2 Hz), 3.30 (s, 3H). MS (ESI) m/z 312.1 (M+Na)$^+$, 287.9 (M−H)$^−$.

(2-(1H-indol-2-yl)thiazol-4-yl)(3,4,5-trimethoxyphenyl) methanone (32) was synthesized from 61a using the same method as used for 8a-8z, Scheme 3, Method 1. 45.8% yield. $^1$H NMR (500 MHz, DMSO-d$_6$) δ 9.26 (s, 1H), 8.11 (s, 1H), 7.66 (d, 1H, J=8.0 Hz), 7.46 (s, 2H), 7.42 (d, 1H, J=8.0 Hz), 7.29 (t, 1H, J=7.5 Hz), 7.16 (t, 1H, J=7.5 Hz), 7.10 (s, 1H), 3.97 (s, 3H), 3.93 (s, 6H). MS (ESI) m/z 417.1 (M+Na)$^+$, 392.9 (M−H)$^−$.

Synthesis of (2-(1H-indol-5-yl)thiazol-4-yl)(3,4,5-trimethoxyphenyl)methanone (31) [FIG. 7]

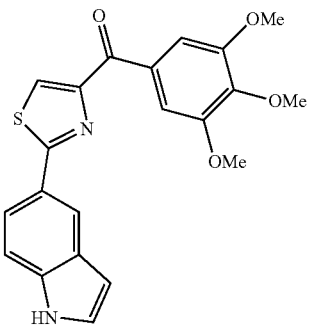

(31)

(R)-2-(1-(Phenylsulfonyl)-1H-indol-5-yl)-4,5-dihydrothiazole-4-carboxylic acid (64a)

(R)-2-(1H-Indol-5-yl)-4,5-dihydrothiazole-4-carboxylic acid 63a was synthesized from 1H-indole-5-carbonitrile using the same method as used for 42a of U.S. application Ser. No. 12/981,233 (now US2011/0257196) and U.S. application Ser. No. 1/216,927 (now US2012/0071524), incorporated herein by reference in their entirety. Briefly, benzonitrile (40 mmol) was combined with L-cysteine (45 mmol) in 100 mL of 1:1 MeOH/pH 6.4 phosphate buffer solution. The reaction was stirred at 40° C. for 3 days. The precipitate was removed by filtration, and MeOH was removed using rotary evaporation. To the remaining solution was added 1 M HCl to adjust to pH=2 under 0° C. The resulting precipitate was filtered to yield a white solid 2-phenyl-4,5-dihydrothiazole-4-carboxylic acid 42a, which was used directly to next step without purification. To a vigorously stirring solution of 63a (1 mmol) and tetrabutylammonium hydrogen sulfate (0.15 mmol) in toluene (10 mL) at 0° C. was added 50% aqueous sodium hydroxide (10 mL) and sulfonyl chloride (2 mmol). The resultant solution was stirred at RT for 6 h. Then 1 N HCl was added to acidify the mixture to pH=2 and extracted with CH$_2$Cl$_2$, the organic layer was separated and dried (MgSO$_4$); then evaporated to dryness to yield 64a, which were used in subsequent steps without further purification.

(R)—N-Methoxy-N-methyl-2-(1-(phenylsulfonyl)-1H-indol-5-yl)-4,5-dihydrothiazole-4-carboxamide (65a) was prepared from 64a a method similar to that of 6a-6p (Scheme 3). 57.1% yield. $^1$H NMR (500 MHz, CDCl$_3$) δ 7.92 (m, 2H), 7.77 (m, 3H), 7.51 (d, 1H, J=3.0 Hz), 7.46 (t, 1H), 7.35 (t, 1H), 6.61 (d, 1H), 5.58 (br, t, 1H) 3.82 (s, 3H), 3.73 (t, 1H), 3.43 (m, 1H), 3.21 (s, 3H). MS (ESI) m/z 452.1 (M+Na)$^+$.

(2-(1H-Indol-5-yl)thiazol-4-yl)(3,4,5-trimethoxyphenyl)methanone (31)

To a solution of n-BuLi (1.6 M, 1.7 mL) in 8 mL THF was added a solution of 3,4,5-trimethoxybromobenzene (2.47 mmol) in 3 mL THF under −78° C. The mixture was allowed to stir for 2 h and a solution of Weinreb amide 65a (1.24 mmol) in 3 mL THF was charged. The temperature was allowed to increase at RT and stirred overnight. The reaction mixture was quenched with satd. NH$_4$Cl, extracted with ethyl ether, dried with MgSO$_4$. The solvent was removed under reduced pressure to yield a crude product, which was refluxed in 1 N NaOH in 5 mL ethanol solution to obtain the deprotected compound 31 and purified by column chromatography to obtain pure compound as a light yellow solid (36.3%). $^1$H NMR (300 MHz, CDCl$_3$) δ 8.36 (br, s, 1H), 8.31 (s, 1H), 8.21 (s, 1H), 7.92, 7.89 (dd, 1H, J=1.8, 2.7 Hz), 7.46 (d, 1H,) 7.62 (s, 2H, J=8.7 Hz), 7.29 (t, 1H, J=2.7 Hz), 6.64 (br, 1H), 3.97 (s, 6H), 3.97 (s, 3H); MS (ESI) m/z 417.1(M+Na)$^+$, 392.9 (M−H)$^−$.

Synthesis of (2-Phenyl-thiazol-4-yl)-(3,4,5-trimethoxy-phenyl)-methanone (1-h)

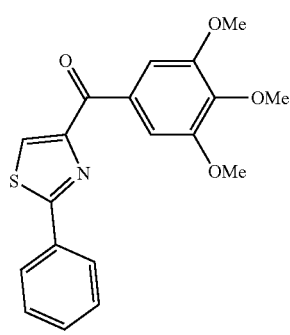

(1-h)

(2-Phenyl-thiazol-4-yl)-(3,4,5-trimethoxy-phenyl)-methanone (1-h)

A mixture of 2-phenyl-4,5-dihydrothiazole-4-carboxylic acid (5 mmol), EDCI (6 mmol) and HOBt (5 mmol) in CH$_2$Cl$_2$ (50 mL) was stirred for 10 min. To this solution, NMM (5 mmol) and HNCH$_3$OCH$_3$ (5 mmol) were added and stirring continued at RT for 6-8 h. The reaction mixture was diluted with CH$_2$Cl$_2$ (100 mL) and sequentially washed with water, satd. NaHCO$_3$, brine and dried over MgSO$_4$. The solvent was removed under reduced pressure to yield a crude product, which was purified by column chromatography to get 2-phenyl-4,5-dihydrothiazole-4-carboxylic acid methoxymethylamide. A solution of 2-phenyl-4,5-dihydrothiazole-4-carboxylic acid methoxymethylamide (1 equiv) in CH$_2$Cl$_2$ was cooled to 0° C., and distilled DBU (2 equiv) was added. Bromotrichloromethane (1.7 equiv) was then introduced dropwise via syringe over 10 min. The reaction mixtures were allowed to warm to RT and stirred overnight. Upon washing with satd. aqueous NH$_4$Cl (2×50 mL), the aqueous phase was extracted with EtOAc (3×50 mL). The combined organic layers were dried on MgSO$_4$, filtered and concentrated in vacuo. The residue was purified by flash chromatography as needed providing 2-phenyl-thiazole-4-carboxylic acid methoxymethylamide (73.6%). $^1$H NMR (300 MHz, CDCl$_3$) δ 8.01 (s, 1H), 7.99-7.96 (m, 2H), 7.47-7.44 (m, 3H), 3.88 (s, 3H), 3.49 (s, 3H). MS (ESI) m/z 271.0 (M+Na)$^+$. To a solution of 3,4,5-trimethoxyphenylmagnesium bromide (0.5N, 3 mL) in 2 mL THF was charged a solution of 2-phenyl-thiazole-4-carboxylic acid methoxymethylamide (1 mmol) in 3 mL THF at 0° C. The mixtures were stirred for 30 min until amides disappeared on TLC plates. The reaction mixture was quenched with satd. NH$_4$Cl, extracted with ethyl ether, dried with MgSO$_4$. The solvent was removed under reduced pressure to yield a crude product, which was purified by column chromatography to obtain pure compound 1-h. Yield: 27.3%. $^1$H NMR (300 MHz, CDCl$_3$) δ 8.29 (s, 1H), 8.03 (q, 2H), 7.80 (s, 2H), 7.49-7.47 (m, 3H), 3.96 (s, 6H), 3.97 (s, 3H). MS (ESI) m/z 378.1 (M+Na)$^+$.

Synthesis of (2-(1H-Indol-2-yl)thiazol-4-yl)(1H-indol-2-yl)methanone (8-8)

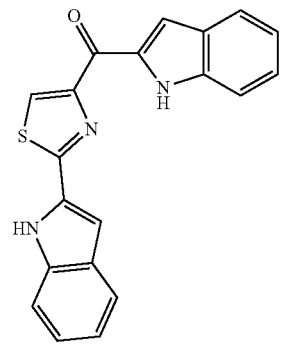

(8-8)

(2-(1H-Indol-2-yl)thiazol-4-yl)(1H-indol-2-yl)methanone (8-8) was prepared using the similar method as used of compound 1-h from 2-(1H-indol-2-yl)-4,5-dihydrothiazole-4-carboxylic acid and cysteine. $^1$H NMR (500 MHz, CDCl$_3$) δ 9.39 (s, 1H), 8.54 (s, 1H), 8.46 (s, 1H), 8.06 (s, 1H), 8.03 (dd, 1H), 7.66 (d, 1H), 7.51 (d, 1H), 7.41 (d, 1H), 7.33 (t, 1H), 7.29 (d, 1H), 7.15 (t, 1H), 7.09 (d, 1H), 6.72 (s, 1H). MS (ESI) m/z 366.1(M+Na)$^+$, 341.9 (M−H)$^−$.

Synthesis of (2-(1H-indol-2-yl)thiazol-4-yl)(1H-indol-5-yl)methanone (21-21)

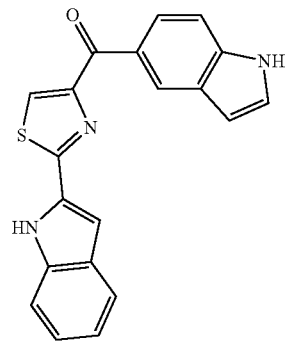

(21-21)

(2-(1H-indol-2-yl)thiazol-4-yl)(1H-indol-5-yl)methanone (21-21) was prepared using the similar method as used of compound 1-h from 2-(1H-indol-2-yl)-4,5-dihydrothiazole-4-carboxylic acid and cysteine. $^1$H NMR (500 MHz, CDCl$_3$) δ 9.60 (s, 1H), 9.26 (s, 1H), 8.31 (s, 1H), 8.03 (s, 1H), 7.83 (dd, 1H), 7.69 (d, 1H), 7.53-7.49 (m, 2H), 7.41 (t, 1H), 7.33 (t, 1H), 7.21-7.18 (m, 2H), 7.13 (s, 1H). MS (ESI) m/z 366.1(M+Na)$^+$, 341.9 (M−H)$^−$.

Example 12: Synthesis of Selected Indolyl-Benzoyl-Imidazole Compounds

Figure 8:
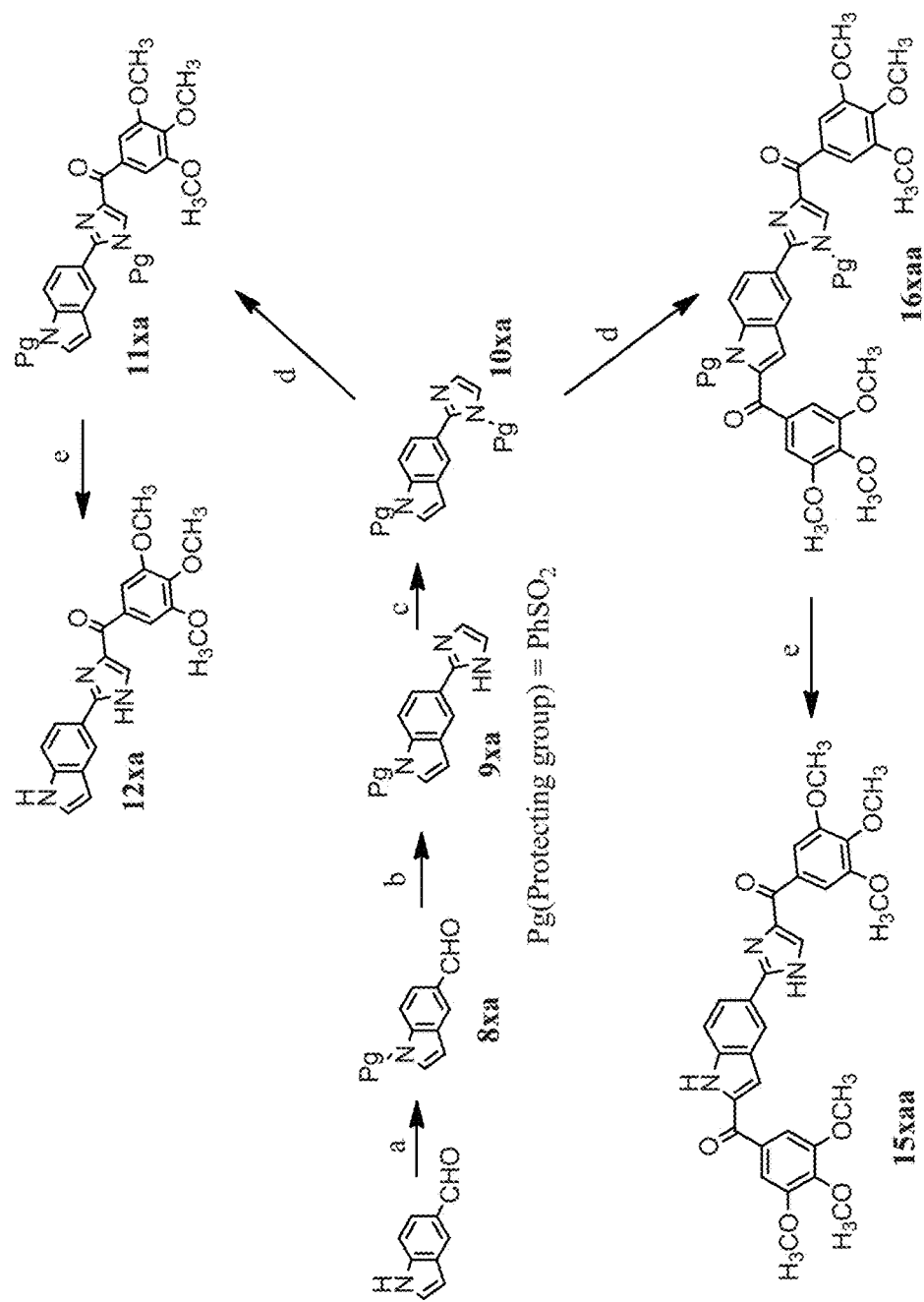
FIG. 8 depicts the synthetic scheme of compound 15xaa and 12xa. Reagents and conditions: (a) 1. KOH, ethanol; 2. PhSO$_2$Cl, acetone, RT; (b) NH$_4$OH, glyoxal, ethanol, RT; (c) NaH, PhSO$_2$Cl, THF, 0° C.—RT; (d) t-BuLi (1.7 M in pentane), 3,4,5-trimethoxybenzoyl chloride, THF, −78° C.; (e) NaOH, ethanol, H$_2$O, reflux.

The synthesis of 15xaa is outlined in FIG. 8. This route was originally designed for the synthesis of 12xa, but the nonselectivity of the benzoylation at the indole-2 and imidazole-4 positions resulted in the formation of 15xaa, which is a closely related but bulkier analog of 11xaa. The indole-5-carboxaldehyde was protected by a phenylsulfonyl group on the indole NH to afford intermediate 8xa. 8xa was reacted with glyoxal and ammonium hydroxide to generate the 2-aryl-imidazole 9xa. Protection of the imidazole NH with phenylsulfonyl gave the intermediate 10xaa which was coupled with 3,4,5-trimethoxybenzoyl chloride to produce 16xaa. Removal of the protecting group from 16xaa provided 15xaa.

Synthesis of 1-(Phenylsulfonyl)-1H-indole-5-carbaldehyde (8xa)

To a solution of indole-3-carboxaldehyde (100 mmol) in ethanol (500 mL) at room temperature was added potassium hydroxide (110 equiv), the mixture was stirred until total solubilization. The ethanol was completely removed in vacuum and acetone (250 mL) added followed by benzenesulfonyl chloride (110 equiv). The precipitate was filtered off and the filtrate was concentrated and recrystallized from methanol to give a white solid. Yield: 32.6% $^1$H NMR (500 MHz, CDCl$_3$) δ 10.17 (s, 1H), 8.25-8.39 (m, 2H), 7.97-8.09 (m, 3H), 7.69 (t, J=7.33 Hz, 1H), 7.59 (t, J=7.5 Hz, 2H), 7.39-7.54 (m, 2H). MS (ESI) calcd for $C_{15}H_{11}NO_3S$ 285.1, found 286.0 [M+H]$^+$.

Synthesis of (5-(4-(3,4,5-Trimethoxybenzoyl)-1H-imidazol-2-yl)-1H-indol-2-yl)(3,4,5-trimethoxyphenyl)methanone (15xaa)

To a solution of (1-(phenylsulfonyl)-2-(1-(phenylsulfonyl)-2-(3,4,5-trimethoxybenzoyl)-1H-indol-5-yl)-1H-imidazol-4-yl)(3,4,5-trimethoxyphenyl)methanone (16xaa) (1 mmol) in ethanol (20 mL) was added sodium hydroxide (10 equiv) and stirred overnight in darkness. The reaction mixture was diluted by 50 mL of water and extracted by ethyl acetate (250 mL). The organic layer was dried over magnesium sulfate and concentrated. The residue was purified by flash column chromatography (hexane: ethyl acetate 3:1) or recrystallized from water and methanol to give a white solid. Yield: 30-95%.

5-(1H-Imidazol-2-yl)-1-(phenylsulfonyl)-1H-indole (9xa)

Yield: 12.0%. $^1$H NMR (500 MHz, DMSO-d$_6$) δ 8.33 (d, J=2.9 Hz, 2H), 8.13 (d, J=7.8 Hz, 2H), 7.98-8.04 (m, 1H), 7.62-7.67 (m, 1H), 7.55 (d, J=7.82 Hz, 2H), 7.22-7.34 (m, 4H). MS (ESI) calcd for $C_{17}H_{13}N_3O_2S$ 323.1, found 324.0 [M+H]$^+$.

1-(Phenylsulfonyl)-5-(1-(phenylsulfonyl)-1H-imidazol-2-yl)-1H-indole (10xaa)

Yield: 23.6%. $^1$H NMR (500 MHz, CDCl$_3$) δ 8.01 (d, J=8.5 Hz, 1H), 7.95 (d, J=7.5 Hz, 2H), 7.73 (d, J=1.0 Hz, 1H), 7.70 (d, J=4.0 Hz, 1H), 7.63-7.66 (m, 2H), 7.52-7.56 (m, 3H), 7.31-7.34 (m, 3H), 7.22 (t, J=8.5 Hz, 2H), 7.17 (s, 1H), 6.14 (d, J=3.5 Hz, 1H). MS (ESI) calcd for $C_{23}H_{17}N_3O_4S_2$ 463.1, found 464.0 [M+H]$^+$.

(1-(Phenylsulfonyl)-2-(1-(phenylsulfonyl)-2-(3,4,5-trimethoxybenzoyl)-1H-indol-5-yl)-1H-imidazol-4-yl)(3,4,5-trimethoxyphenyl)methanone (16xaa)

Yield: 15.9%. $^1$H NMR (500 MHz, CDCl$_3$) δ 8.18-8.25 (m, 3H), 8.04 (d, J=8.1 Hz, 2H), 7.70-7.78 (m, 2H), 7.61-7.69 (m, 3H), 7.55 (t, J=7.7 Hz, 3H), 7.50 (s, 1H), 7.38 (s, 2H), 7.34 (s, 2H), 6.94 (s, 1H), 3.99-4.06 (m, 12H), 3.94-3.99 (m, 6H). MS (ESI) calcd for $C_{43}H_{37}N_3O_{12}S_2$ 851.2, found 852.1 [M+H]$^+$.

(5-(4-(3,4,5-Trimethoxybenzoyl)-1H-imidazol-2-yl)-1H-indol-2-yl)(3,4,5-trimethoxyphenyl)methanone (15xaa)

Yield: 45.9%; mp 239-241° C. $^1$H NMR (500 MHz, CDCl$_3$) δ 10.45 (s, 1H), 9.44 (s, 1H), 8.41 (s, 1H), 8.04 (d, J=8.5 Hz, 1H), 7.86 (s, 1H), 7.61 (d, J=8.5 Hz, 1H), 7.29 (s, 2H), 7.26 (s, 2H), 3.99 (s, 3H), 3.95-3.97 (m, 15H). MS (ESI) calcd for $C_{31}H_{29}N_3O_8$ 571.2, found 572.2 [M+H]$^+$. HPLC2: $t_R$ 4.09 min, purity 96.3%.

Figure 9:
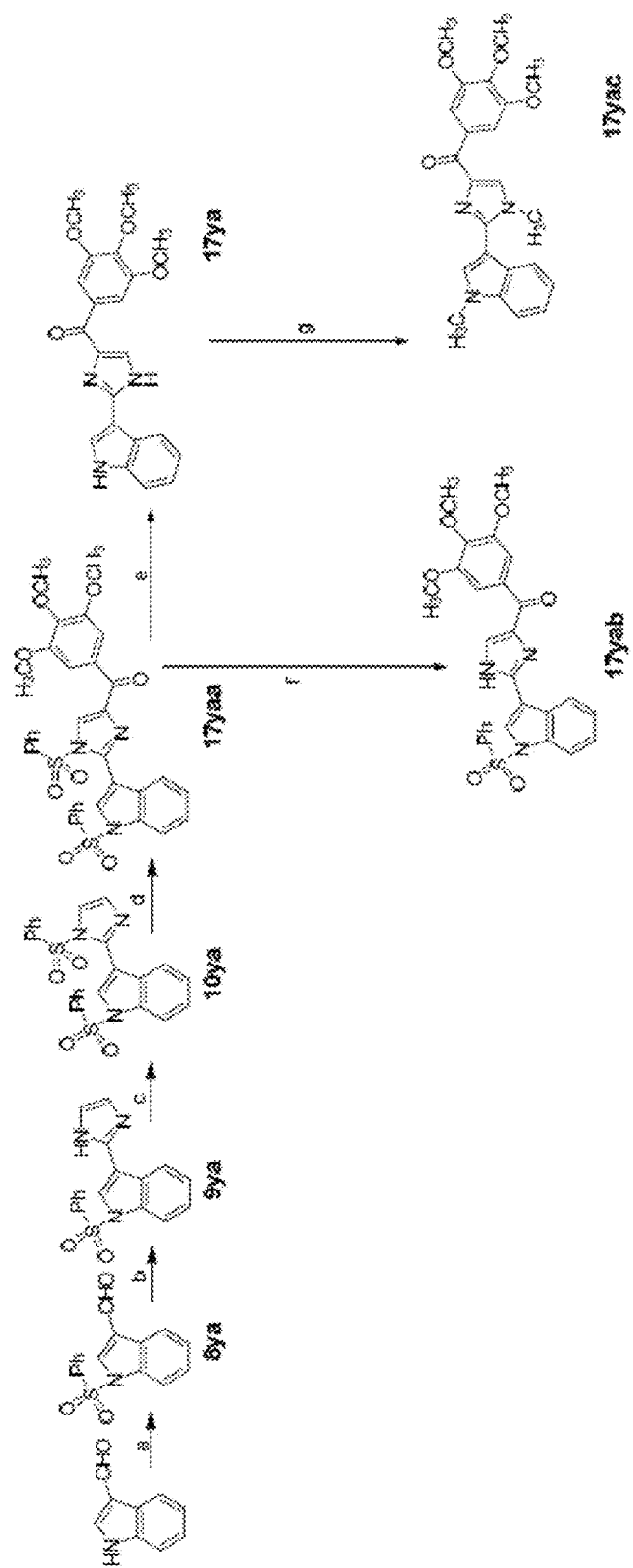
FIG. 9 depicts synthetic scheme of 17ya, 17yab and 17yac. Reagents and conditions: (a) 1. KOH, ethanol, 2. PhSO$_2$Cl, acetone, RT; (b) NH$_4$OH, glyoxal, ethanol, RT; (c) NaH, PhSO$_2$Cl, THF, 0° C.—RT; (d) t-BuLi (1.7 M in pentane), 3,4,5-trimethoxybenzoyl chloride, THF, −78° C.; (e) NaOH, ethanol, H$_2$O, reflux; (f) TBAF, THF, RT; (g) NaH, CH$_3$I, THF.
Figure 10A:
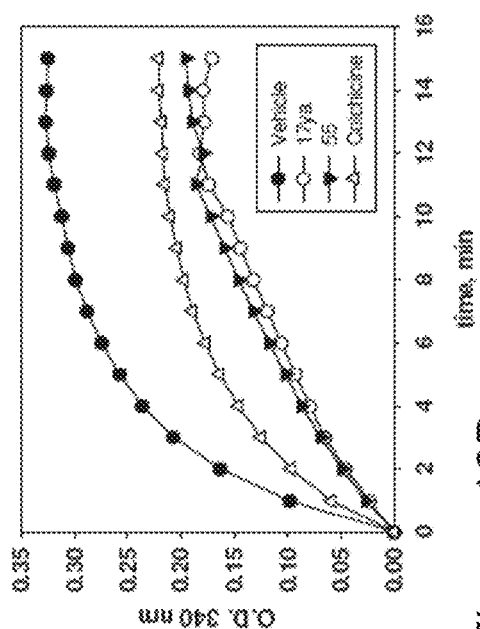
FIGS. 10A-D depict the effect of 17ya and 55 on tubulin polymerization. Compounds 17ya and 55 bind to colchicine-binding site on tubulin, and inhibit tubulin polymerization.
Figure 10B:
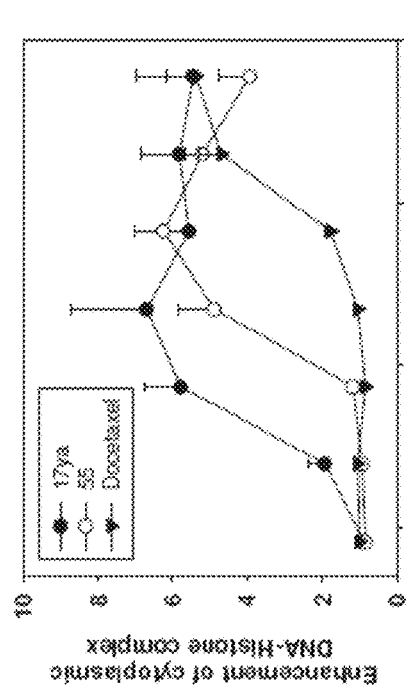
Figure 10C:
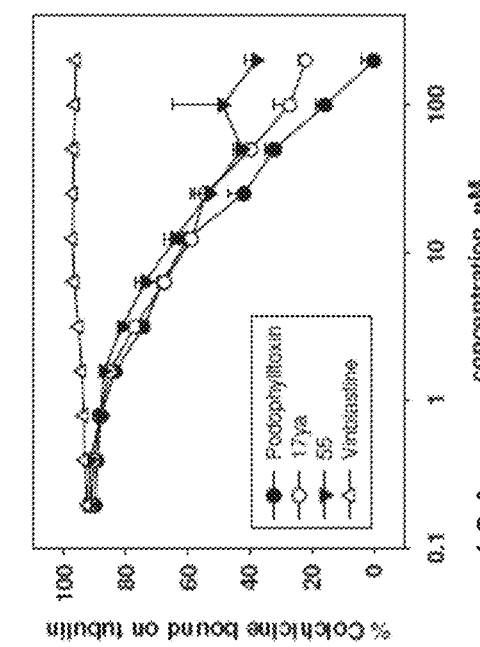
Figure 10D:
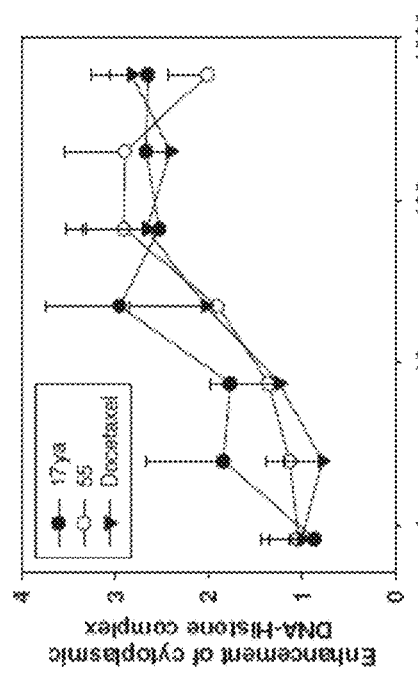

Example 13: Synthesis of (Indolyl)-1H-imidazol-4-yl)(3,4,5-trimethoxyphenyl)methanones (17ya), (17yab) and (17yac) (FIG. 9)

Synthesis of (2-(1H-indol-3-yl)-1H-imidazol-4-yl)(3,4,5-trimethoxyphenyl)methanone (17ya)

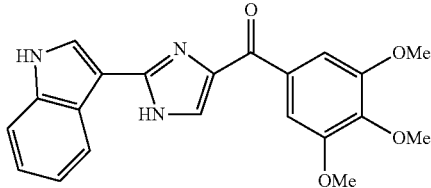

(17ya)

Synthesis of 1-(phenylsulfonyl)-1H-indole-3-carboxaldehyde (8ya)

To a solution of indole 3-carboxaldehyde (100 mmol) in ethanol (500 mL) at RT was added potassium hydroxide (1.1 equiv). The mixture was stirred until total solubilization. The ethanol was completely removed in vacuum and the residual was dissolved in acetone (250 mL) followed by adding benzenesulfonyl chloride (1.1 equiv, 110 mmol). The reaction mixture was stirred for half hour. The precipitate was filtered off and the filtrate was concentrated and recrystallized from methanol to give a white solid. Yield: 33%. $^1$H NMR (500 MHz, CDCl$_3$) δ 10.17 (s, 1H), 8.25-8.39 (m, 2H), 7.97-8.09 (m, 3H), 7.69 (t, J=7.33 Hz, 1H), 7.59 (t, J=7.5 Hz, 2H), 7.39-7.54 (m, 2H). MS (ESI) calcd for $C_{15}H_{11}NO_3S$ 285.1, found 286.0 [M+H]$^+$.

Synthesis of 3-(1H-imidazol-2-yl)-1-(phenylsulfonyl)-1H-indole (9ya)

To a solution of 1-(phenylsulfonyl)-1H-indole-3-carboxaldehyde (8ya) (100 mmol) in ethanol (400 mL) at 0° C. was added a solution of 40% oxalaldehyde (glyoxal) in water (1.1 equiv, 110 mmol) and a solution of 29% ammonium hydroxide in water (10 equiv, 1000 mmol). After stirring for 2-3 days at RT, the reaction mixture was quenched by water and extracted by dichloromethane. The organic layer was removed by vacuum and the residue was subjected to flash column chromatography with hexane/ethyl acetate (4:1-2:1) as eluent to yield the titled compound as a yellow powder. Yield: 12%. $^1$H NMR (500 MHz, DMSO-d$_6$) δ 8.33 (d, J=2.9 Hz, 2H), 8.13 (d, J=7.8 Hz, 2H), 7.98-8.04 (m, 1H), 7.62-7.67 (m, 1H), 7.55 (d, J=7.82 Hz, 2H), 7.22-7.34 (m, 4H). MS (ESI) calcd for $C_{17}H_{13}N_3O_2S$ 323.1, found 324.0 $[M+H]^+$.

Synthesis of 1-(phenylsulfonyl)-3-(1-(phenylsulfonyl)-1H-imidazol-2-yl)-1H-indole (10ya)

To a solution of 3-(1H-imidazol-2-yl)-1-(phenylsulfonyl)-1H-indole (9ya) (20 mmol) in anhydrous THF (300 mL) at 0° C. was added sodium hydride (60% dispersion in mineral oil, 1.2 equiv, 24 mmol) and stirred for 20 min. Benzenesulfonyl chloride (1.2 equiv, 24 mmol) was added and the reaction mixture was stirred overnight. After dilution by 200 mL of saturated NaHCO₃ solution (aqueous), the reaction mixture was extracted by ethyl acetate (600 mL). The organic layer was dried over magnesium sulfate and concentrated. The residue was purified by flash column chromatography (hexane: ethyl acetate 5:1) to give a white solid. Yield: 40%. $^1$H NMR (CDCl₃, 300 MHz) δ 8.02-8.08 (m, 4H), 7.72 (d, J=1.5 Hz, 1H), 7.35-7.60 (m, 8H), 7.23 (d, J=1.5 Hz, 1H), 7.10-7.16 (m, 3H). MS (ESI) calcd for $C_{23}H_{17}N_3O_4S_2$ 463.1, found 486.0 $[M+Na]^+$.

Synthesis of (1-(phenylsulfonyl)-2-(1-(phenylsulfonyl)-1H-indol-3-yl)-1H-imidazol-4-yl)(3,4,5-trimethoxyphenyl)methanone (17yaa)

To a solution of 1-(phenylsulfonyl)-3-(1-(phenylsulfonyl)-1H-imidazol-2-yl)-1H-indole (10ya) (5.0 mmol) in anhydrous THF (100 mL) at −78° C. was added 1.7 M tert-butyllithium in pentane (1.2 equiv, 6.0 mmol) and stirred for 10 min. A solution of 3,4,5-trimethoxybenzoyl chloride (1.2 equiv, 6.0 mmol) in THF was added at −78° C. and stirred overnight. The reaction mixture was quenched with 100 mL of saturated NaHCO₃ solution (aqueous) and extracted by ethyl acetate (300 mL). The organic layer was dried over magnesium sulfate and concentrated. The residue was purified by flash column chromatography (hexane: ethyl acetate 3:1) to give a white solid. Yield: 30%. $^1$H NMR (500 MHz, CDCl₃) δ 8.09 (d, J=10 Hz, 1H), 8.04 (d, J=10 Hz, 2H), 7.91 (s, 1H), 7.76 (d, J=5 Hz, 2H), 7.65 (t, J=10 Hz, 1H), 7.55-7.58 (m, 5H), 7.40 (s, 2H), 7.33-7.36 (m, 3H), 7.25 (t, J=10 Hz, 1H), 4.05 (s, 3H), 4.03 (s, 6H). MS (ESI) calcd for $C_{33}H_{27}N_3O_8$ 657.0, found 680.1 $[M+Na]^+$.

Synthesis of (2-(1H-indol-3-yl)-1H-imidazol-4-yl)(3,4,5-trimethoxyphenyl)methanone (17ya)

To a solution of (1-(phenylsulfonyl)-2-(1-(phenylsulfonyl)-1H-indol-3-yl)-1H-imidazol-4-yl)(3,4,5-trimethoxyphenyl)methanone (17yaa) (1 mmol) in ethanol (40 mL) and water (4 mL) was added sodium hydroxide (10 equiv, 10 mmol) and stirred overnight under refluxing condition in darkness. The reaction mixture was diluted by 50 mL of water and extracted by ethyl acetate (200 mL). The organic layer was dried over magnesium sulfate and concentrated. The residue was purified by flash column chromatography (hexane: ethyl acetate 1:1) to give a yellow solid. Yield: 60%. $^1$H NMR (500 MHz, CD₃OD) δ 8.31 (d, J=6.5 Hz, 1H), 7.99 (s, 1H), 7.90 (s, 1H), 7.48-7.52 (m, 3H), 7.24-7.28 (m, 2H), 4.00 (s, 6H), 3.93 (s, 3H). MS (ESI) calcd for $C_{21}H_{19}N_3O_4$ 377.1, found 400.1 $[M+Na]^+$. Mp 208-210° C.

Synthesis of (2-(1-(Phenylsulfonyl)-1H-indol-3-yl)-1H-imidazol-4-yl)(3,4,5-trimethoxyphenyl)methanone (17yab)

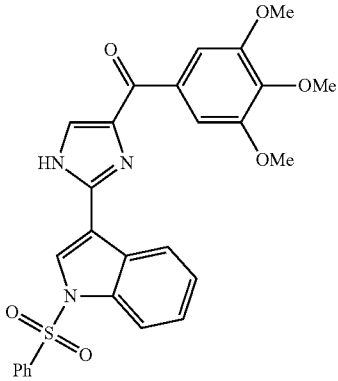

(17yab)

To a solution of compound 17yaa (66 mg) in THF (1.0 ml) was added 1.0 M tetrabutyl ammonium fluoride (0.4 mL, 0.4 mmol) and stirred overnight. The reaction mixture was diluted by 20 ml of saturated NaHCO₃ solution (aqueous) and extracted by ethyl acetate (20 mL). The organic layer was dried over magnesium sulfate and concentrated. The residue was purified by flash column chromatography (hexane:ethyl acetate, 2:1) to give a pale white solid. Yield: 45%. Mp 110-112° C. $^1$H NMR (CDCl₃, 500 MHz) δ 8.40-8.42 (m, 2H), 8.09 (d, J=8.0 Hz, 1H), 7.93-7.98 (m, 4H), 7.59 (t, J=7.5 Hz, 1H), 7.41-7.49 (m, 5H), 4.01 (s, 3H), 3.97 (s, 6H). MS (ESI) calcd for $C_{27}H_{23}N_3O_6S$ 517.1, found 540.0 $[M+Na]^+$. HPLC: $t_R$ 6.81 min, purity 96.3%.

Synthesis of (1-methyl-2-(1-(methyl)-1H-indol-3-yl)-1H-imidazol-4-yl)(3,4,5-trimethoxyphenyl)methanone (17yac)

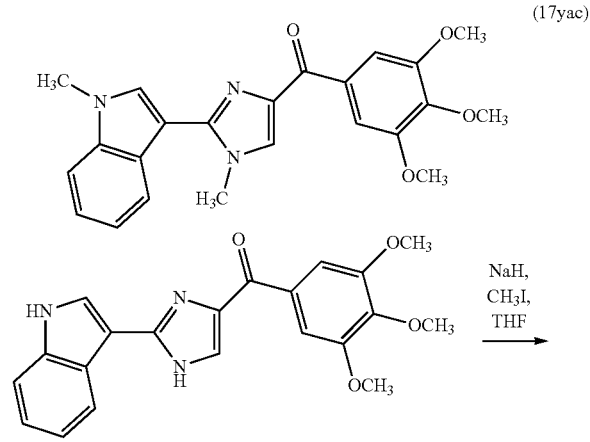

(17yac)

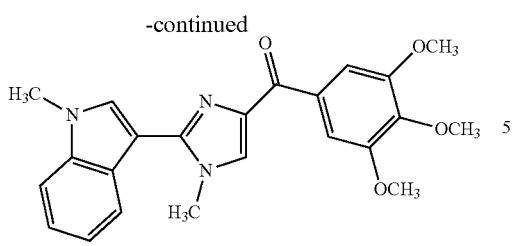

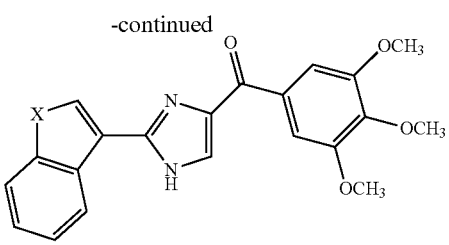

17ya (i, ii)

Reagents and conditions: (a) NH₄OH, glyoxal, ethanol, RT; (b) NaH, PhSO₂Cl, THF, 0° C.-RT; (c) t-BuLi (1.7M in Pentane), 3,4,5-trimethoxybenzoyl chloride, THF, -78° C.; (d) TBAF, THF, RT i: x = O
ii: x = S To a solution of 17ya (75 mg, 0.2 mmol) in anhydrous THF (20 ml) at 0° C. was added sodium hydride (60% dispersion in mineral oil, 20 mg, 0.5 mmol) and stirred for 20 min. Methyl iodide (70 mg, 0.5 mmol) was added, and the reaction mixture was stirred 1 h. After dilution by 20 ml of saturated NaHCO₃ solution (aqueous), the reaction mixture was extracted by ethyl acetate (60 ml). The organic layer was dried over magnesium sulfate and concentrated. The residue was recrystallized from water and methanol to give a white solid. 75% yield. Mp 164-166° C. $^1$H NMR (CDCl₃, 500 MHz) δ 8.30 (d, J=7.5 Hz, 1H), 8.01 (s, 1H), 7.87 (s, 1H), 7.41 (t, J=8.5 Hz, 1H), 7.39 (s, 1H), 7.35 (t, J=7.0 Hz, 1H), 7.23 (t, J=7.0 Hz, 1H), 3.98 (s, 6H), 3.95 (s, 3H), 3.91 (s, 3H), 3.89 (s, 3H). MS (ESI) calcd for $C_{23}H_{23}N_3O_4$ 405.2, found 406.4 [M+H]⁺. HPLC: $t_R$ 4.80 min, purity>99%.

Example 14: Synthesis of (Benzofuranyl-1H-Imidazol-4-yl)(3,4,5-Trimethoxyphenyl)Methanone (17ya (i)) and (Benzothiophenyl-1H-Imidazol-4-yl)(3,4,5-Trimethoxyphenyl)Methanones (17ya(ii))

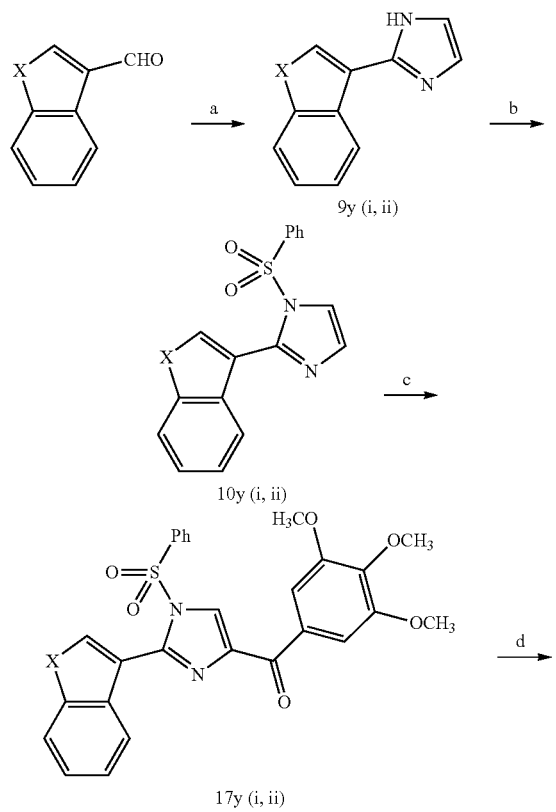

Synthesis of (2-(Benzofuran-3-yl)-1H-imidazol-4-yl)(3,4,5-trimethoxyphenyl)methanone (17ya(i)), and (2-(benzo[b]thiophen-3-yl)-1H-imidazol-4-yl)(3,4,5-trimethoxyphenyl)methanone (17ya(ii))

To a solution of compounds 10y (i, ii) (2.32 g, 5.0 mmol) in anhydrous THF (100 ml) at -78° C. was added 1.7 M tert-butyllithium in pentane (3.5 mL, 6.0 mmol) and stirred for 10 min. A solution of 3,4,5-trimethoxybenzoyl chloride (1.38 g, 6.0 mmol) in THF was added at -78° C. and stirred overnight. The reaction mixture was quenched with 100 ml of saturated NaHCO₃ solution (aqueous) and extracted by ethyl acetate (300 ml). The organic layer was dried over magnesium sulfate and concentrated. The residue was used for next step by adding 10 mL of 1.0 M tetrabutyl ammonium fluoride and stirred overnight. The reaction mixture was diluted by 200 ml of saturated NaHCO₃ solution (aqueous) and extracted by ethyl acetate (200 ml). The organic layer was dried over magnesium sulfate and concentrated. The residue was purified by flash column chromatography (hexane: ethyl acetate 3:1) to give a white solid. 17ya (i): 4.7% yield. Mp 208-210° C. $^1$H NMR (CDCl₃, 500 MHz) δ 8.77 (s, 1H), 8.12 (d, J=7.6 Hz, 1H), 7.90 (s, 1H), 7.632-7.65 (m, 1H), 7.44-7.49 (m, 2H), 7.29 (s, 2H), 3.99 (s, 3H), 3.93 (s, 6H). MS (ESI) calcd for $C_{21}H_{18}N_2O_5$ 378.1, found 377.1[M–H]⁻. HPLC1: $t_R$ 5.18 min, purity 98.8%. 17ya(ii): 3.2% yield. Mp 185-187° C. $^1$H NMR (CDCl₃, 500 MHz) δ 10.62 (s, 1H), 8.74 (d, J=5.0 Hz, 1H), 8.06 (s, 1H), 7.92-7.95 (m, 2H), 7.48-7.54 (m, 2H), 7.29 (s, 2H), 3.99 (s, 3H), 3.97 (s, 6H). MS (ESI) calcd for $C_{21}H_{18}N_2O_4S$ 394.1, found 392.8[M–H]⁻. HPLC: $t_R$ 5.38 min, purity 95.6%.

Example 15: Novel Anti-Tubulin Compounds Overcome P-Glycoprotein Mediated Multidrug Resistance The P-glycoprotein (P-gp) system appears to be a primary physiological mechanism of multidrug resistance (MDR) which acts as an ATP-dependent drug efflux pump, actively removing a variety of structurally diverse cytotoxic compounds. Enhanced efflux of these compounds reduces their intracellular accumulation and so reduces their cytotoxicity. Therefore, novel compounds which are not susceptible to drug resistance could be of high therapeutic and economic value. In addition to P-gp, clinically used antitubulin agents have other resistance mechanisms such as changes in microtubule dynamics and mutations in β-tubulin which are known to limit sensitivity to the taxanes. The anti-tubulin compounds of the invention were tested against an ovarian cancer cell line OVCAR-8 (parent) and P-gp over-expressing NCI/ADR-RES cell line (Table 7A).

Results:

TABLE 7A

Antiproliferative Activity of Selected Compounds against P-gp over-expressed MDR cell lines.

| Compound | | IC$_{50}$ (nM) | | Resistance factor |
|---|---|---|---|---|
| | | OVCAR-8 | NCI/ADR-RES | |
| 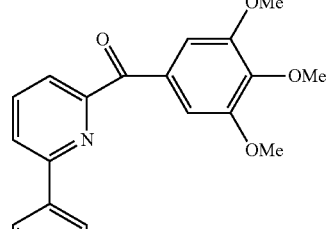 | 1-c | 33 ± 3 | 13 ± 0.8 | 0.4 |
| 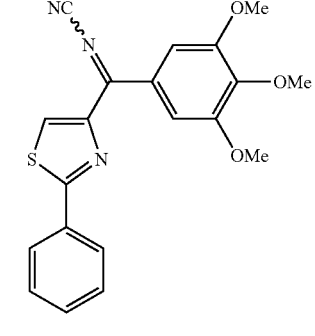 [SMILES: COc1cc(C(=NC#N)c2csc(-c3ccccc3)n2)cc(OC)c1OC] | 2-j | 34 ± 2 | 14 ± 1 | 0.4 |
| 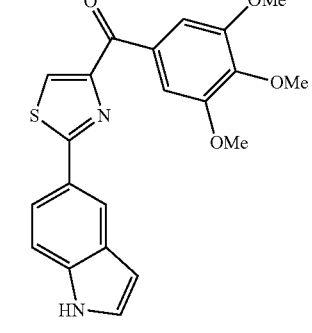 | 31 | 10 ± 3 | 4 ± 2 | 0.4 |
| 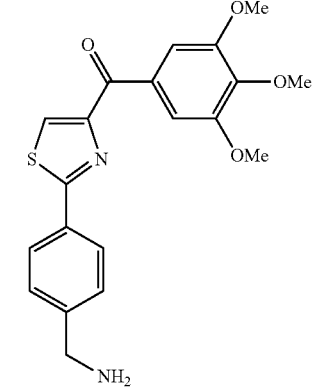 [SMILES: COc1cc(C(=O)c2csc(-c3ccc(CN)cc3)n2)cc(OC)c1OC] | 2-r | 26 ± 2 | 11 ± 2 | 0.4 |

TABLE 7A-continued

Antiproliferative Activity of Selected Compounds against P-gp over-expressed MDR cell lines.

| Compound | | IC$_{50}$ (nM) | | Resistance factor |
|---|---|---|---|---|
| | | OVCAR-8 | NCI/ADR-RES | |
| (structure: 3,4,5-trimethoxybenzoyl thiazole with 2-NH-phenyl) | 5-a | 46 ± 6 | 27 | 0.6 |
| (structure: 3,4,5-trimethoxybenzoyl thiazole with 2-NH-(4-Me-phenyl)) | 5-b | 28 | 21 | 0.8 |
| (structure: 3,4,5-trimethoxybenzoyl thiazole with 2-NH-(4-F-phenyl)) | 5-c | 44 ± 3 | 25 ± 6 | 0.6 |
| (structure: 3,4,5-trimethoxybenzoyl thiazole with 2-phenyl) | 1-h | 35 ± 2 | 13 ± 1 | 0.4 |
| paclitaxel* | | 4.7 ± 0.1 | 6263 ± 634 | 1333 |
| vinblastine | | 3.9 ± 0.1 | 582 ± 57 | 149 |
| colchicine | | 17 ± 1 | 1113 ± 79 | 65 |

Notably, the anti-tubulin compounds of the invention demonstrated equipotent antiproliferative effects against OVCAR-8 and NCI/ADR-RES cell lines, suggesting that they are not P-gp substrates and that they function in a P-gp-independent manner. This feature is distinct from that of paclitaxel, vinblastine, and colchicine in NCI/ADR-RES cells.

The phenyl amino thiazole compounds 5-a, 5-Hb, 5-c and 5-d demonstrated potent activity in a number of prostate cancer cell lines. Unexpectedly, the phenyl amino imidazole compound 5-e demonstrated no activity (IC$_{50}$>1000 nM in LNCaP, PC-3, DU-145, and PPC-1) in these prostate cancer cell lines. The positive controls for this experiment were 55 and 17ya which demonstrated IC$_{50}$ values between 7.5 nM and 24.1 nM in the same cell lines (Table 7B).

TABLE 7B

|  |  | IC$_{50}$ ± SEM (nM) | | | | | |
| --- | --- | --- | --- | --- | --- | --- | --- |
|  |  | B16-F1 | A375 | DU 145 | PC-3 | LNCaP | PPC-1 |
| 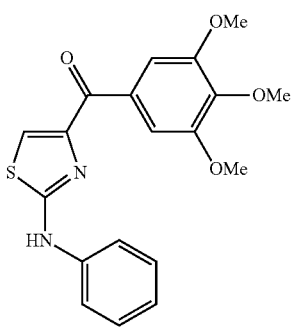 [SMILES: COc1cc(C(=O)c2csc(Nc3ccccc3)n2)cc(OC)c1OC] | 5-a | 65 ± 12 | 45 ± 8 | 70 ± 4 | 57 ± 3 | 51 ± 1 | 54 ± 1 |
| 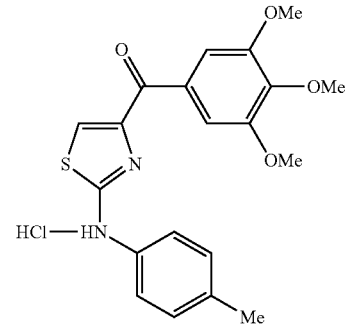 [SMILES: COc1cc(C(=O)c2csc(N(Cl)c3ccc(C)cc3)n2)cc(OC)c1OC] | 5-Hb | ND | ND | 35 ± 1 | 38 ± 2 | 35 ± 1 | 36 ± 1 |
| 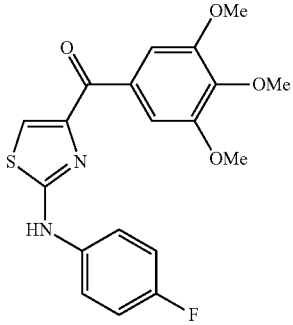 [SMILES: COc1cc(C(=O)c2csc(Nc3ccc(F)cc3)n2)cc(OC)c1OC] | 5-c | ND | ND | 63 ± 1 | 43 ± 1 | 41 ± 1 | 37 ± 1 |
| 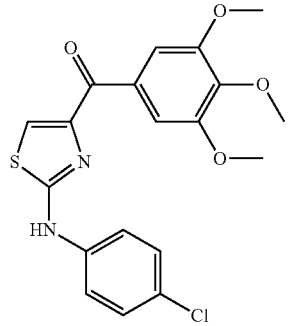 [SMILES: COc1cc(C(=O)c2csc(Nc3ccc(Cl)cc3)n2)cc(OC)c1OC] | 5-d | ND | 25 ± 7 | 73 ± 1 | 33 ± 1 | 45 ± 1 | 36 ± 1 |

TABLE 7B-continued
| | | IC$_{50}$ ± SEM (nM) | | | | | |
|---|---|---|---|---|---|---|---|
| | | B16-F1 | A375 | DU 145 | PC-3 | LNCaP | PPC-1 |
| 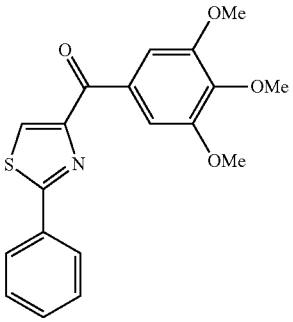 [SMILES: COc1cc(C(=O)c2csc(-c3ccccc3)n2)cc(OC)c1OC] | 1-h | 55 ± 5 | 28 ± 5 | 71 ± 4 | 21 ± 1 | 28 ± 4 | 43 ± 5 |
| 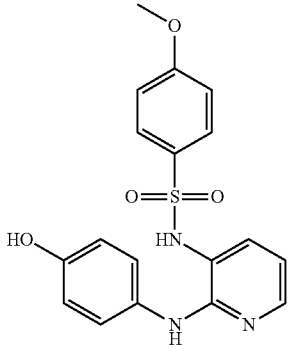 [SMILES: COc1ccc(S(=O)(=O)Nc2cccnc2Nc2ccc(O)cc2)cc1] | ABT-751 | 2127 ± 351 | 1111 ± 108 | 839 ± 719 | 786 ± 89 | 658 ± 117 | 701 ± 307 |
| 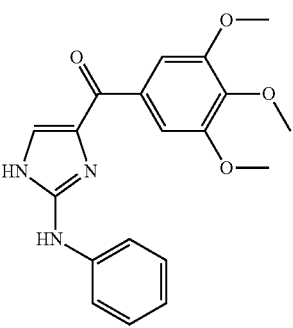 [SMILES: COc1cc(C(=O)c2c[nH]c(Nc3ccccc3)n2)cc(OC)c1OC] | 5-e | ND | ND | >1000 | >1000 | >1000 | >1000 |
| 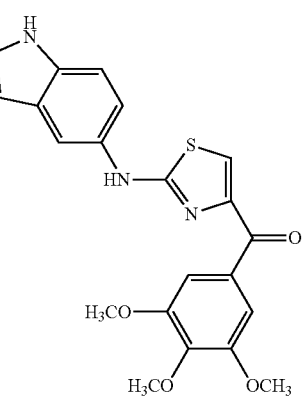 | 55 | ND | ND | 24 ± 6 | 12 ± 1 | 13 ± 1 | 15 ± 1 |

TABLE 7B-continued

| | | | IC$_{50}$ ± SEM (nM) | | | | |
|---|---|---|---|---|---|---|---|
| | | | B16-F1 | A375 | DU 145 | PC-3 | LNCaP | PPC-1 |
| [structure] | 17ya | ND | ND | 11 ± 1 | 5 ± 2 | 8 ± 2 | 8 ± 1 |

Example 16: Antiproliferative Activity of Compounds of the Invention

The antiproliferative activity of analogs prepared by the methods of the invention are shown in Table 8.

TABLE 8

| | | IC$_{50}$ (nM) | | | | | | |
|---|---|---|---|---|---|---|---|---|
| Structure | ID | LNCaP | PC-3 | DU 145 | PPC-1 | A375 | B16-F1 | WM164 |
| [structure] | 8-8 | 346 | 704 | 580 | 230 | 318 | 570 | 404 |
| [structure] | 9-9 | ~10000 | ~10000 | ~10000 | ~10000 | | | |
| [structure] | 10-10 | 658 | 786 | 839 | 701 | 1111 | 2127 | 661 |

TABLE 8-continued

| Structure | ID | IC₅₀ (nM) | | | | | | |
|---|---|---|---|---|---|---|---|---|
| | | LNCaP | PC-3 | DU 145 | PPC-1 | A375 | B16-F1 | WM164 |
| 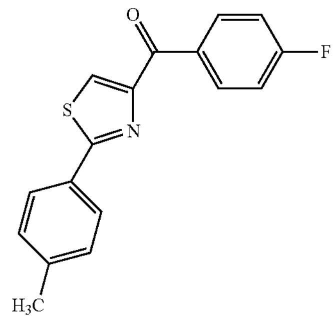 [SMILES: Cc1ccc(-c2nc(C(=O)c3ccc(F)cc3)cs2)cc1] | 11-11 | >10000 | >10000 | ~10000 | ~10000 | 3470 | 4900 | 4700 |
| 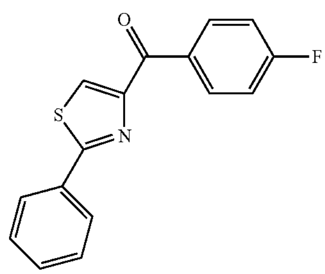 [SMILES: O=C(c1ccc(F)cc1)c1csc(-c2ccccc2)n1] | 12-12 | >10000 | >10000 | >10000 | >10000 | >10000 | >10000 | |
| 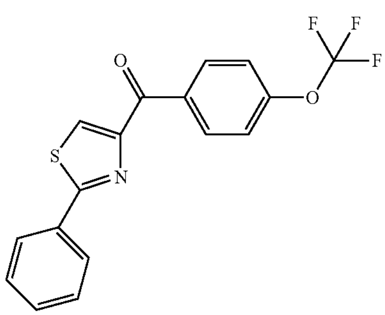 [SMILES: O=C(c1ccc(OC(F)(F)F)cc1)c1csc(-c2ccccc2)n1] | 13-13 | >10000 | >10000 | >10000 | >10000 | >10000 | >10000 | >10000 |
| 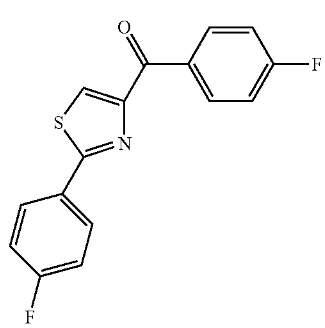 [SMILES: O=C(c1ccc(F)cc1)c1csc(-c2ccc(F)cc2)n1] | 14-14 | >10000 | >10000 | >10000 | >10000 | >10000 | >10000 | |

TABLE 8-continued

| | | IC$_{50}$ (nM) | | | | | | |
|---|---|---|---|---|---|---|---|---|
| Structure | ID | LNCaP | PC-3 | DU 145 | PPC-1 | A375 | B16-F1 | WM164 |
| | 16-16 | >10000 | >10000 | >10000 | >10000 | 15200 | 6900 | |
| | 17-17 | 2100 | 1900 | 2600 | 1300 | 4300 | 9800 | |
| | 18-18 | ~10000 | ~10000 | ~10000 | ~10000 | | | |
| | 19-19 | >20000 | >20000 | >20000 | >20000 | >20000 | >20000 | |
| | 20-20 | 1452 | >10000 | 642 | 633 | 2300 | 3100 | 1300 |

TABLE 8-continued
| | | IC₅₀ (nM) | | | | | | |
|---|---|---|---|---|---|---|---|---|
| Structure | ID | LNCaP | PC-3 | DU 145 | PPC-1 | A375 | B16-F1 | WM164 |
| 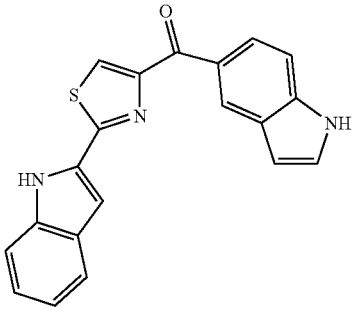 [SMILES: O=C(c1ccc2[nH]ccc2c1)c1csc(-c2cc3ccccc3[nH]2)n1] | 21-21 | 314 | 403 | 435 | 216 | 383 | 924 | 408 |
| 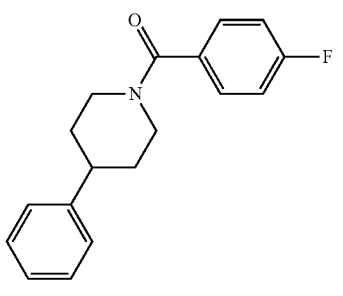 [SMILES: O=C(c1ccc(F)cc1)N1CCC(c2ccccc2)CC1] | 22-22 | >20000 | >20000 | >20000 | >20000 | >20000 | >20000 | |
| 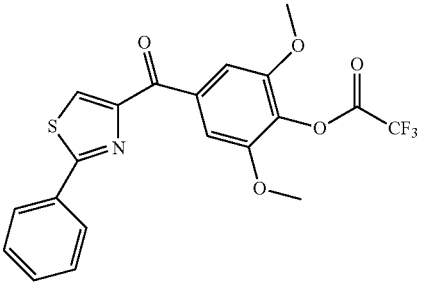 [SMILES: COc1cc(C(=O)c2csc(-c3ccccc3)n2)cc(OC)c1OC(=O)C(F)(F)F] | 23-23 | ~10000 | ~10000 | ~10000 | ~10000 | | | |
| 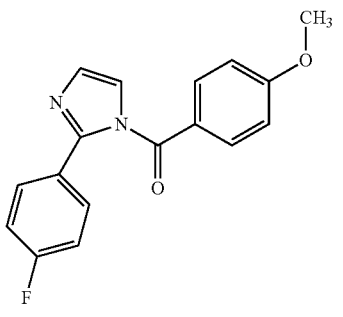 [SMILES: COc1ccc(C(=O)n2ccnc2-c2ccc(F)cc2)cc1] | 24-24 | >10000 | >10000 | >10000 | >10000 | >10000 | >10000 | >10000 |
| 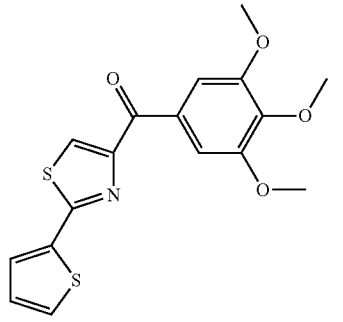 [SMILES: COc1cc(C(=O)c2csc(-c3cccs3)n2)cc(OC)c1OC] | 25-25 | 48 | 44 | 24 | 13 | 20 | 38 | |

TABLE 8-continued

| Structure | ID | IC$_{50}$ (nM) | | | | | | |
|---|---|---|---|---|---|---|---|---|
| | | LNCaP | PC-3 | DU 145 | PPC-1 | A375 | B16-F1 | WM164 |
| (structure) | 26-26 | 23 | 16 | 16 | 15 | 11 | 14 | |
| (structure) | 29-29 | 1788 | >10000 | >10000 | >10000 | >10000 | >10000 | |
| (structure) | 30-30 | >10000 | >10000 | >10000 | >10000 | >10000 | >10000 | |
| (structure) | 32-32 | 1664 | 2291 | 4601 | 1170 | 2700 | >10000 | 2600 |

TABLE 8-continued

| | | IC$_{50}$ (nM) | | | | | | |
|---|---|---|---|---|---|---|---|---|
| Structure | ID | LNCaP | PC-3 | DU 145 | PPC-1 | A375 | B16-F1 | WM164 |
| | 33-33 | >2000 | >2000 | >2000 | >2000 | 9800 | >20000 | |
| | 34-34 | >10000 | >10000 | >10000 | >10000 | >10000 | >10000 | >10000 |
| | 35-35 | 1500 | 40100 | 21900 | 15000 | | | |
| | 39-39 | 4300 | 32500 | 16800 | 21400 | | | |
| | 40-40 | 13400 | 19600 | 18400 | 6200 | | | |

TABLE 8-continued

| | | IC₅₀ (nM) | | | | | | |
|---|---|---|---|---|---|---|---|---|
| Structure | ID | LNCaP | PC-3 | DU 145 | PPC-1 | A375 | B16-F1 | WM164 |
| | 41-41 | 15750 | 18170 | 17040 | >20000 | | | |
| | 42-42 | 43590 | 23790 | 24880 | >20000 | | | |
| | 43-43 | 12690 | 14720 | 17210 | >20000 | | | |
| | 17ya | 12 | 10 | 17 | 21 | 17.35 | 32.94 | 12.08 |
| | 17yab | 233.7 | 148.3 | 592.1 | 208.9 | 481.2 | 538.7 | 467.6 |
| | 15xaa | 1068 | 2628 | 5917 | 4575 | 1800 | 1390 | 1700 |

TABLE 8-continued

| | | IC$_{50}$ (nM) | | | | | | |
|---|---|---|---|---|---|---|---|---|
| Structure | ID | LNCaP | PC-3 | DU 145 | PPC-1 | A375 | B16-F1 | WM164 |
| 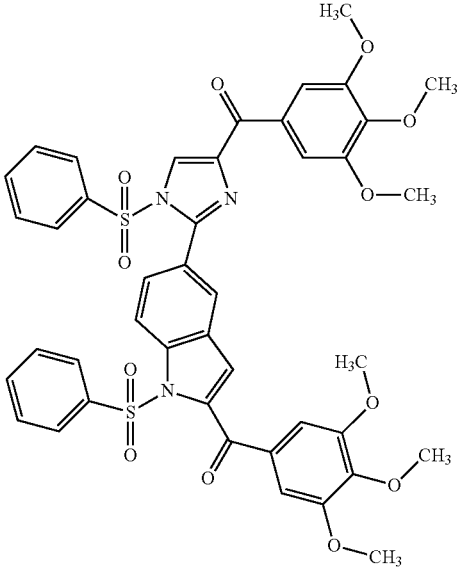 [SMILES: COc1cc(C(=O)c2cn(S(=O)(=O)c3ccccc3)c(-c3ccc4c(c3)cc(C(=O)c3cc(OC)c(OC)c(OC)c3)n4S(=O)(=O)c3ccccc3)n2)cc(OC)c1OC] | 16xaa | >10000 | >10000 | >10000 | >10000 | >10000 | >10000 | >10000 |

Example 17: In Vitro and In Vivo Pharmacology of Compounds 17ya, 12fa, and 55

Materials and Methods

Cell Culture and Cytotoxicity Assay of Prostate Cancer.

All prostate cancer cell lines (LNCaP, PC-3, and DU145, PPC-1) were obtained from ATCC (American Type Culture Collection, Manassas, Va., USA). Human PC-3_TxR, was resistant to paclitaxel and used as a MDR model compared with PC-3. Cell culture supplies were purchased from Cellgro Mediatech (Herndon, Va., USA). All cell lines were used to test the antiproliferative activity of compounds 17ya, 12fa (((2-(4-Chlorophenyl)-1H-imidazol-4-yl)(3,4,5-trimethoxyphenyl)methanone), and 55 ((2-(1H-indol-5-ylamino)thiazol-4-yl)(3,4,5-trimethoxyphenyl)methanone) by sulforhodamine B (SRB) assay. All cancer cell lines were maintained in RPMI 1640 media with 2 mM glutamine and 10% fetal bovine serum (FBS).

In Vitro Microtubule Polymerization Assay.

Porcine brain tubulin (0.4 mg) (Cytoskeleton, Denver, Colo.) was mixed with 1 and 5 µM of the test compound or vehicle (DMSO) and incubated in 100 µL of buffer (80 mM PIPES, 2.0 mM MgCl$_2$, 0.5 mM EGTA, pH 6.9 and 1 mM GTP). The absorbance at 340 nm wavelength was monitored every min for 15 min (SYNERGY 4 Microplate Reader, Bio-Tek Instruments, Winooski, Vt.). The spectrophotometer was maintained at 37° C. for tubulin polymerization.

Metabolic Incubations.

Metabolic stability studies were conducted by incubating 0.5 µM of test compounds in a total reaction volume of 1 mL containing 1 mg/mL microsomal protein in reaction buffer [0.2 M of phosphate buffer solution (pH 7.4), 1.3 mM NADP$^+$, 3.3 mM glucose-6-phosphate, and 0.4 U/mL glucose-6-phosphate dehydrogenase] at 37° C. in a shaking water bath. The NADPH regenerating system (solution A and B) was obtained from BD Biosciences (Bedford, Mass.). For glucuronidation studies, 2 mM UDP-glucuronic acid (Sigma, St. Louis, Mo.) cofactor in deionized water was incubated with 8 mM MgCl$_2$, 25 µg of alamethicin (Sigma, St. Louis, Mo.) in deionized water, and NADPH regenerating solutions (BD Biosciences, Bedford, Mass.) as described previously. The total DMSO concentration in the reaction solution was approximately 0.5% (v/v). Aliquots (100 µL) from the reaction mixtures used to determine metabolic stability were sampled at 5, 10, 20, 30, 60, and 90 min. Acetonitrile (150 µL) containing 200 nM of the internal standard was added to quench the reaction and to precipitate the proteins. Samples were then centrifuged at 4,000 g for 30 min at RT, and the supernatant was analyzed directly by LC-MS/MS.

Analytical Method.

Sample solution (10 µL) was injected into an Agilent series HPLC system (Agilent 1100 Series Agilent 1100 Chemstation, Agilent Technology Co, Ltd). All analytes were separated on a narrow-bore C18 column (Alltech Alltima HP, 2.1×100 mm, 3 µm, Fisher, Fair Lawn, N.J.). Two gradient modes were used. For metabolic stability studies, gradient mode was used to achieve the separation of analytes using mixtures of mobile phase A [ACN/H$_2$O (5%/95%, v/v) containing 0.1% formic acid] and mobile phase B [ACN/H$_2$O (95%/5%, v/v) containing 0.1% formic acid] at a flow rate of 300 µL/min. Mobile phase A was used at 10% from 0 to 1 min followed by a linearly programmed gradient to 100% of mobile phase B within 4 min, 100% of mobile phase B was maintained for 0.5 min before a quick ramp to 10% mobile phase A. Mobile phase A was continued for another 10 min towards the end of analysis.

A triple-quadruple mass spectrometer, API Qtrap 4000™ (Applied Biosystems/MDS SCIEX, Concord, Ontario, Canada), operating with a TurbolonSpray source was used. The spraying needle voltage was set at 5 kV for positive mode. Curtain gas was set at 10; Gas 1 and gas 2 were set 50. Collision-Assisted-Dissociation (CAD) gas at medium and the source heater probe temperature at 500° C. Multiple reaction monitoring (MRM) mode, scanning m/z 378→210 (17ya), m/z 373→205 (12fa), m/z 410→242 (55) and m/z 309→171 (internal standard), was used to obtain the most sensitive signals. Data acquisition and quantitative processing were accomplished using Analyst™ software, Ver. 1.4.1 (Applied Biosystems).

Aqueous Solubility.

The solubility of drugs was determined by Multiscreen Solubility Filter Plate (Millipore Corporate, Billerica, Mass.) coupled with LC-MS/MS. Briefly, 198 μL of phosphate buffered saline (PBS) buffer (pH 7.4) was loaded into 96-well plate, and 2 μL of 10 mM test compounds (in DMSO) was dispensed and mixed with gentle shaking (200-300 rpm) for 1.5 hours at RT (N=3). The plate was centrifuged at 800 g for 10 min, and the filtrate was used to determine its concentration and solubility of test compound by LC-MS/MS as described previously.

Pharmacokinetic Study.

Male ICR mice (n=3 per group) 6 to 8 weeks of age were purchased from Harlan Inc., and used to examine the pharmacokinetics (PK) of 17ya, 12fa, and 55. All compounds (10 mg/kg) were dissolved in DMSO/PEG300 (1/9) and administered by a single intravenously (i.v.) injection (50 μL) into the tail vein. Blood samples were collected at 5, 15, and 30 min, 1, 1.5, 2, 3, 4, 8, 12, and 24 h after i.v. administration. Mice were given (p.o.) by oral gavage at 20 mg/kg (in Tween80/DMSO/H$_2$O, 2/2/6) of each test compound to evaluate their oral bioavailability. Blood samples were collected at 0.5, 1, 1.5, 2, 3, 4, 8, 12, and 24 h after p.o. administration.

Female Sprague-Dawley rats (n=3; 254±4 g) were purchased from Harlan Inc. (Indianapolis, Ind.). Rat thoracic jugular vein catheters were purchased from Braintree Scientific Inc. (Braintree, Mass.). On arrival at the animal facility, the animals were acclimated for 3 days in a temperature-controlled room (20-22° C.) with a 12 h light/dark cycle before any treatment. Compounds 17ya, 12fa, and 55 were administered i.v. into the thoracic jugular vein at a dose of 5 mg/kg (in DMSO/PEG300, 1/9). An equal volume of heparinized saline was injected to replace the removed blood, and blood samples (250 μL) were collected via the jugular vein catheter at 10, 20, 30 min, and 1, 2, 4, 8, 12, 24 h. Rats were given (p.o.) by oral gavage at 10 mg/kg (in Tween80/DMSO/H$_2$O, 2/2/6) of each test compound to evaluate their oral bioavailability. All blood samples (250 μL) after oral administration were collected via the jugular vein catheter at 30, 60, 90 min, 120 min, 150 min, 180 min, 210 min, 240 min, and 8, 12, 24 h. Heparinized syringes and vials were prepared prior to blood collection. Plasma samples were prepared by centrifuging the blood samples at 8,000 g for 5 min. All plasma samples were stored immediately at −80° C. until analyzed.

Analytes were extracted from 100 μL of plasma with 200 μL of acetonitrile containing 200 nM the internal standard. The samples were thoroughly mixed, centrifuged, and the organic extract was transferred to autosampler for LC-MS/MS analysis.

PC-3_TxR Xenograft Studies.

PC-3_TxR cells (10×10$^7$ per mL) were prepared in RPMI1640 growth media containing 10% FBS, and mixed with Matrigel (BD Biosciences, San Jose, Calif.) at 1:1 ratio. Tumors were established by injecting 100 μL of the mixture (5×10$^6$ cells per animal) subcutaneously (s.c.) into the flank of 6-8-week-old male athymic nude mice. Length and width of tumors were measured and the tumor volume (mm$^3$) was calculated by the formula, $7r/6 \times L \times W^2$, where length (L) and width (W) were determined in mm. When the tumor volumes reached 300 mm$^3$, the animals bearing PC-3_TxR tumors were treated with vehicle [Tween80/DMSO/H$_2$O (2/2/6)], or 17ya (10 mg/kg) orally. The dosing schedule was 3 times a week for four weeks.

Results 17a and 55 Exhibit Broad Cytotoxicity in Cells, Including Multidrug-Resistant Cells.

The ability of 17ya and 55 to inhibit the growth of cancer cell lines was evaluated using SRB assay (Table 9). Both compounds inhibited the growth of several human cancer cell lines, including five prostate and one glioma cancer cell lines, with IC$_{50}$ values in the low nanomolar range. 17ya exhibited 1.7-4.3 fold higher potency than 55 in these cell lines. Paclitaxel-resistant PC-3 (PC-3/TxR) cell line that over-expresses P-glycoprotein (P-gp), was used to study the effect of drug resistance on 17ya and 55 and to compare against its parent, PC-3 cell line. The IC$_{50}$ values of docetaxel were 1.2±0.1 nM and 17.7±0.7 nM in PC-3 and PC-3/TxR cells, respectively. 17ya and 55 were both equipotent against parent PC-3 and PC-3/TxR, whereas paclitaxel and docetaxel exhibited relative resistance of 85- and 15-fold, respectively. These data indicate that both 17ya and 55 circumvent P-gp-mediated drug resistance.

TABLE 9

Cytotoxicity data of 17ya and 55

| Cell line | Type | 17ya Cytotoxicity [IC$_{50}$ values, mean ± SD nM] | 55 Cytotoxicity [IC$_{50}$ values, mean ± SD nM] |
|---|---|---|---|
| PC-3 | Prostate | 5.2 ± 0.2 | 16 ± 1.5 |
| PC-3/TxR | Prostate | 2.1 ± 0.1 (0.4) | 6.7 ± 0.5 (0.4) |

TABLE 9-continued

Cytotoxicity data of 17ya and 55

| | | | |
|---|---|---|---|
| LNCaP | Prostate | 12 ± 0.1 | 27 ± 0.6 |
| Du-145 | Prostate | 17 ± 0.2 | 38 ± 0.6 |
| PPC-1 | Prostate | 21 ± 0.1 | 36 ± 0.4 |
| U87MG | Glioma | 10 ± 1.6 | 22 ± 3.0 |

| Cell line | Cytotoxicity [IC$_{50}$ values, mean ± SD nM] Paclitaxel |
|---|---|

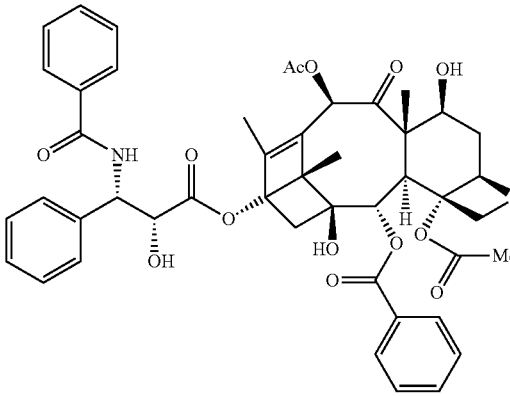

| | |
|---|---|
| PC-3 | 0.6 ± 0.05 |
| PC-3/TxR | 51 ± 2.3 (85) |
| LNCaP | 1.7 ± 0.2 |
| Du-145 | 5.1 ± 0.1 |
| PPC-1 | 2.3 ± 0.8 |
| U87MG | NR |

IC$_{50}$ values (mean ± SD) were determined after 96 h treatment (N = 3). Paclitaxel was used as a positive control. Data in parentheses indicated resistance factor when compared IC$_{50}$ values in PC-3 and PC-3/TxR. NR, Not Reported.

17ya and 55 bind to colchicine-binding site on tubulin, inhibit tubulin polymerization, and induce cell apoptosis (FIG. 10). A competitive mass binding assay was developed to study the interaction of small molecule inhibitors with tubulin. In this study, varying concentrations of 17ya or 55 were used to compete with colchicine-tubulin binding. Both compounds competed effectively with colchicine for tubulin binding (FIG. 10A); however, their competitive binding curves deviated substantially from zero at higher concentrations when compared to podophylltoxin, a known potent colchicine-site binding ligand. This suggests that both 17ya and 55 exhibited less affinity than podophylltoxin or they partially bind to the colchicine-binding site. Vinblastine, the negative control, did not inhibit the colchicine-tubulin binding, successfully demonstrating the specificity of this competitive mass binding assay.

Porcine brain tubulin (>97% pure) was incubated with 17ya or 55 (5 µM) to test their effect on tubulin polymerization (FIG. 10B). 17ya and 55 inhibited tubulin polymerization by 47% and 40% at 15 min, respectively. Colchicine at 5 µM was used as a positive control and inhibited tubulin polymerization by 32%. These data suggest that both 17ya and 55 have slightly greater inhibition of tubulin polymerization than colchicine. Therefore, the molecular mechanism of these compounds is binding to the colchicine-binding site, inhibiting tubulin polymerization, and inducing cytotoxicity.

PC-3 and PC-3/TxR cells were exposed to 0.8 to 600 nmol/L of 17ya, 55, or docetaxel for 24 h. The levels of DNA-histone complexes were used to represent cell apoptosis. Both 17ya and 55 were equally potent to induce cell apoptosis in PC-3 (FIG. 10C) and PC-3/TxR (FIG. 10D) in 24 h. Though, docetaxel was highly potent to induce apoptosis of PC-3 cells, it was weaker in PC-3/TxR cells due to over-expression of P-gp.

17ya and 55 Exhibited Favorable Drug-Like Properties.

Drug-like properties, such as metabolic stability, permeability, aqueous solubility, and drug-drug interactions, were examined for 17ya and 55 (Table 10A). 17ya exhibited greater metabolic stability, and aqueous solubility than 55. Both chemicals exhibited more than adequate permeability values, suggesting their potential to be orally used. In addition, both 17ya and 55 showed high IC$_{50}$ values in micromolar range on CYP enzyme inhibition assays, indicating that both compounds may avoid drug-drug interactions through main CYP liver enzymes. Overall, both compounds exhibited favorable drug-like properties.

TABLE 10A

Drug-like properties of compound 17a and 55. Metabolic stability, permeability, solubility, and potential drug-drug interactions were evaluated. Each value represents the mean from duplicate studies.

| Measurment | Units | 17ya | 55 | positive controls (mean) |
|---|---|---|---|---|
| Metabolic stability | | | | |
| half-life in human liver microsomes | min | >60 | 28 | Verapamil (12) |
| Permeability | | | | |
| P$_{app(A \to B)}$ in CaCO-2 assay | 10$^{-6}$ cm/s | 36 | 99 | Propranolol (19) |
| Aqueous solubility | µg/mL | >75 | 19 | 1 h (1.1) |
| Drug-drug interactions | | | | |
| IC$_{50}$ value in Cyp3A4 (substrate: Testosterone) | µM | 20 | 5.5 | Ketoconazole (0.02) |

TABLE 10A-continued

Drug-like properties of compound 17a and 55. Metabolic stability, permeability, solubility, and potential drug-drug interactions were evaluated. Each value represents the mean from duplicate studies.

| Measurment | Units | 17ya | 55 | positive controls (mean) |
|---|---|---|---|---|
| $IC_{50}$ value in Cyp2D6 (substrate: Dextromethorphan) | μM | >50 | 34 | Quinindine (0.1) |
| $IC_{50}$ value in Cyp2C19 (substrate: (S)-mephenytoin) | μM |  | 6.6 | 5.3 | Ticlopidine (0.37) |
| $IC_{50}$ value in Cyp2C9 (substrate: Diclofenac) | μM | 17 | 4.9 | Sulfaphenazole (0.5) |
| $IC_{50}$ value in Cyp1A2 (substrate: Phenacetin) | μM | 9.2 | 8.1 | Furafylline (2.2) |

TABLE 10B

Summary of drug-like and pharmacokinetic properties of 17ya, 12fa, 55, and 1-h

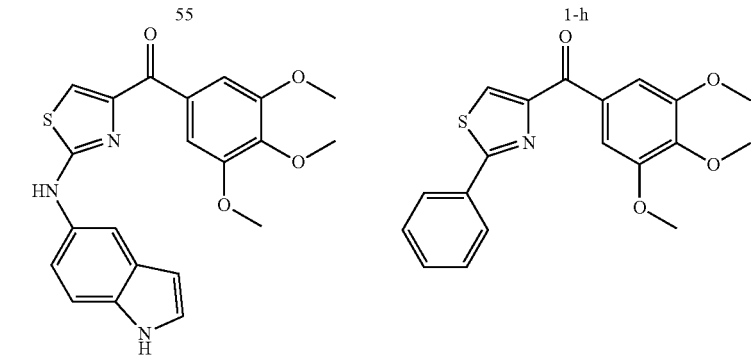

| | | 17ya | 12fa |
|---|---|---|---|
| Molecular weight | | 377 | 372 |
| $IC_{50}$ in PC3 (nM) | nM | 10 | 35 |
| Half-life in HLM (Phase I) | min | ~80 | 44 |
| Half-life in HLM (Phase I +II) | min | ~90 | NA |
| Solubility | μg/mL | >75 | 12 |
| RatPK_IV5mgk_Cl | mL/min/kg | | 16 |
| RatPK_IV5mgk_V | L/kg | | 1.9 |
| RatPK_PO10mgk_Cmax | ng/mL | | 1109 |
| RatPK_PO10mgk_AUC | min*μg/mL | | 218 |
| RatPK_Bioavailability | % F | | 35 |
| MousePK_IV10mgk_Cl | mL/min/kg | | 61 |
| MousePK_IV10mgk_V | L/kg | | 4 |
| MousePK_PO20mgk_Cmax | ng/mL | | 2592 |
| MousePK_PO20mgk_AUC | min*μg/mL | | 201 |
| MousePK_Bioavailability | % F | | 62 |

| | | 55 | 1-h |
|---|---|---|---|
| Molecular weight | | 409 | 355 |
| $IC_{50}$ in PC3 (nM) | nM | 28 | 21 |
| Half-life in HLM (Phase I) | min | 30 | 17 |
| Half-life in HLM (Phase I +II) | min | 43 | 17 |
| Solubility | μg/mL | 19 | 1 |
| RatPK_IV5mgk_Cl | mL/min/kg | | 7.7 (2.5 mpk) |
| RatPK_IV5mgk_V | L/kg | | 4.9 (2.5 mpk) |
| RatPK_PO10mgk_Cmax | ng/mL | | 212 |
| RatPK_PO10mgk_AUC | min*μg/mL | | 37 |
| RatPK_Bioavailability | % F | | 3.3 |
| MousePK_IV10mgk_Cl | mL/min/kg | | 130 |

TABLE 10B-continued

Summary of drug-like and pharmacokinetic properties of 17ya, 12fa, 55, and 1-h

| | | |
|---|---|---|
| MousePK_IV10mgk_V | L/kg | 4.9 |
| MousePK_PO20mgk_Cmax | ng/mL | NA |
| MousePK_PO20mgk_AUC | min*µg/mL | NA |
| MousePK_Bioavailability | % F | NA |

As shown in Table 10B, 17ya had a half-life of 80 min by phase I reaction, suggesting that 17ya was stable in phase I metabolic processes. The half-life (90 min) in the presence of UDP-glucuronic acid was similar to that observed in its absence. These data suggested that 17ya is stable in human liver microsomes, and it was hoped that low clearance and long half-life will be obtained in human. On the other hand, 55 exhibited 30 and 43 min as half lives when it was in the presence and absence of UDP-glucuronic acid, respectively. Compound 12fa shows the half-life with 44 in phase I. These data suggested that all three compounds showed acceptable stability in human liver microsomes, and 17ya is more stable than 12fa and 55. When investigating their metabolism, it was found that 12fa and 55 exhibited higher levels of ketone-reduction (data not shown), suggesting that 12fa and 55 are more labile than 17ya.

Compound 17ya exhibited great aqueous solubility, compounds 12fa and 55 showed acceptable solubility.

Compound 17ya contained an imidazole ring, and this ring improved aqueous solubility, resulting in >75 µg/mL aqueous solubility (Table 10A or 10B). Compounds 12fa and 55 exhibited less aqueous solubility, and exhibited 12 and 19 µg/mL, respectively. Overall, 17ya demonstrated a great aqueous solubility, and 12fa and 55 showed acceptable aqueous solubility, and much improved over 1-h. The greater solubility of 12fa translated into much improved oral bioavailability compared to 1-h (35% vs. 3.3% in rat). Similarly for 17ya and 55, aqueous solubility correlated with much improved oral bioavailability as discussed infra (Table 11).

Pharmacokinetic Studies of 17ya and 55 in Mice, Rats and Dogs.

The pharmacokinetic parameters of 17ya and 55 given in a single (i.v. or p.o.) dose in ICR mice, Sprague-Dawley rats, and beagle dogs are summarized in Table 11. 17ya exhibited low clearance in mice and rats, suggesting that 17ya exhibited metabolic stability, and minimal first-pass metabolism in these species. In addition, 17ya had moderate volume of distribution in mice and rats, indicating that it may properly distribute into tissues, including tumors. Unlike in mice and rats, surprisingly, the total clearance of 17ya in dogs was high. Two abundant metabolites in dog plasma, a hydroxylated metabolite and an unknown metabolite with +34 m/z of the parent (data not shown), were consistent with those found in dog liver microsomes. In summary, higher clearance and lower oral exposure was obtained for 17ya compared to 55 in dogs, but not in mice and rats. In addition, 17ya exhibited abundant metabolites only in dog liver microsomes, but not in mouse, rat or human liver microsomes (data not shown). 17ya showed acceptable 21%, 36%, and 50% oral bioavailability in rats, mice, and dogs, respectively. Meanwhile, 55 had low clearance in rats, and moderate clearance in mice and dogs. Similar to 17ya, 55 exhibited moderate volume of distribution in these species. 55 had constant oral bioavailability rates among three species (24%-36%). These properties indicate that both 17ya and 55 are potential orally available tubulin inhibitors.

TABLE 11

Pharmacokinetic studies of compounds 17ya and 55 in mice, rats, and dogs.

| | 17ya | | 55 | |
|---|---|---|---|---|
| | IV | PO | IV | PO |
| Mouse PK (N = 3) | | | | |
| Dose, mg/kg | 10 | 20 | 10 | 20 |
| Clearance, mL/min/kg | 19 | NR | 40 | NR |
| Vss, L/kg | 2.9 | NR | 1.3 | NR |
| $t_{1/2}$, min | 101 | 339 | 46 | 126 |
| AUC, min * µg/mL | 540 | 384 | 249 | 171 |
| $C_{max}$, ng/mL | 4800 | 1560 | 7739 | 1253 |
| F, % | | 36% | | 34% |
| Rat PK (N = 3) | | | | |
| Dose, mg/kg | 5 | 10 | 5 | 10 |
| Clearance, mL/min/kg | 9.5 ± 2.3 | NR | 10 ± 1.4 | NR |
| Vss, L/kg | 1.8 ± 0.2 | NR | 1.0 ± 0.1 | NR |
| $t_{1/2}$, min | 139 ± 24 | 206 ± 12 | 73 ± 5.0 | 350 ± 214 |
| AUC, min * µg/mL | 553 ± 143 | 233 ± 134 | 509 ± 73 | 246 ± 163 |
| $C_{max}$, ng/mL | 3672 ± 519 | 999 ± 445 | 4609 ± 55 | 757 ± 520 |
| F, % | | 21% | | 24% |
| Dog PK (N = 4) | | | | |
| Dose, mg/kg | 2 | 5 | 2 | 5 |
| Clearance, mL/min/kg | 109 ± 29 | NR | 15 ± 3.2 | NR |
| Vss, L/kg | 94 ± 95 | NR | 0.9 ± 0.2 | NR |
| $t_{1/2}$, min | 2757 ± 1573 | 1695 ± 439 | 82 ± 15 | 191 ± 9.0 |

TABLE 11-continued

Pharmacokinetic studies of compounds 17ya and 55 in mice, rats, and dogs.

|  | 17ya | | 55 | |
| --- | --- | --- | --- | --- |
|  | IV | PO | IV | PO |
| AUC, min * μg/mL | 18.5 ± 4.7 | 23.1 ± 11.3 | 141 ± 30 | 128 ± 154 |
| $C_{max}$, ng/mL | 400 ± 118 | 210 ± 133 | 2552 ± 576 | 862 ± 1010 |
| F, % |  | 50% |  | 36% |

17ya and 55 Inhibit Paclitaxel Resistant Prostate (PC-3/TxR) Xenografts Growth.

Figure 11A:
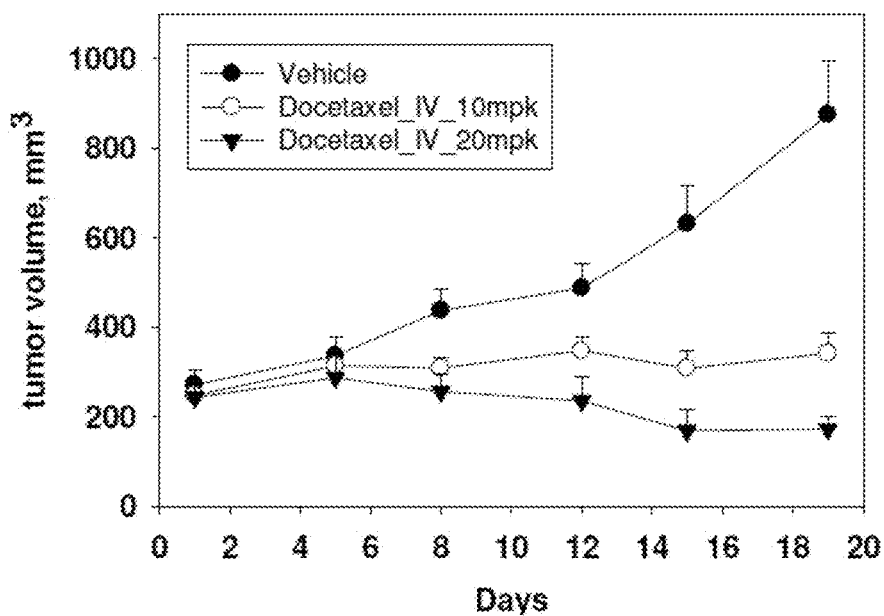
FIGS. 11A-D depict in vivo anticancer efficacy.
Figure 11B:
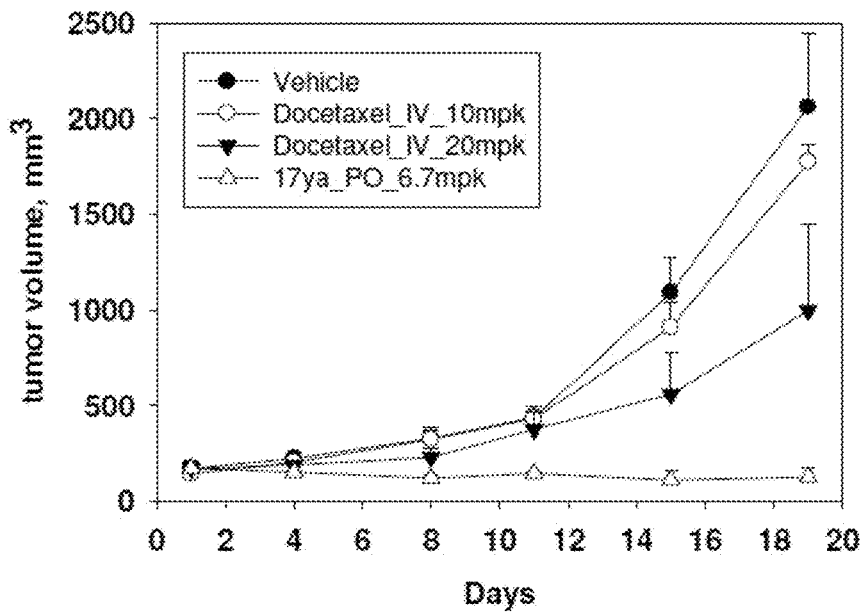

PC-3 (FIG. 11A) and paclitaxel-resistant prostate cancer (PC-3/TxR) (FIG. 11B) cells were inoculated in nude mice and the tumor volumes were allowed to reach about 150-300 mm³. Docetaxel (10 or 20 mg/kg), which is in clinic for prostate cancer, was used to evaluate its effectiveness in models of P-gp-mediated drug resistance in vivo. PC-3/TxR tumor was found to be fast-growing and the volume reached 1500-2500 mm³ at the termination of the study. Though 10 and 20 mg/kg intravenously administered docetaxel exhibited a dose response in both models (FIGS. 11A and 11B), the tumor growth inhibition (TGI) effect decreased from 84% TGI in PC-3 tumors to 14% TGI in PC-3/TxR tumors when intravenously dosed at 10 mg/kg (Table 12). In addition, at the higher dose (20 mg/kg), docetaxel elicited partial regression (>100% TGI) of PC-3 tumors, but barely 56% TGI in PC-3/TxR tumors. The effectiveness of docetaxel in PC-3/TxR tumors was dramatically decreased when compared to that in PC-3 tumors, suggesting that the efficacy was impaired by P-gp-mediated drug resistance, and these results are in very good agreement with our in vitro cytotoxicity or apoptosis data. In contrast to the lack of efficacy of docetaxel in PC-3/TxR tumors, orally administered 17ya (6.7 mg/kg) demonstrated more than 100% TGI without an effect on their body weights (FIG. 11B and Table 12). In addition, 2 out of 4 nude mice bearing PC-3/TxR tumors were tumor free on day 19 (data not shown).

The PC-3/TxR xenograft model was further utilized to evaluate efficacies of 17ya (in other dosing schedules) and 55. The maximal tolerated dose (body weight loss >20%) of 17ya was found to be 10 mg/kg, when orally dosed once daily for four days; or at 3.3 mg/kg twice a day (b.i.d.) for five days (data not shown.

Figure 11C:
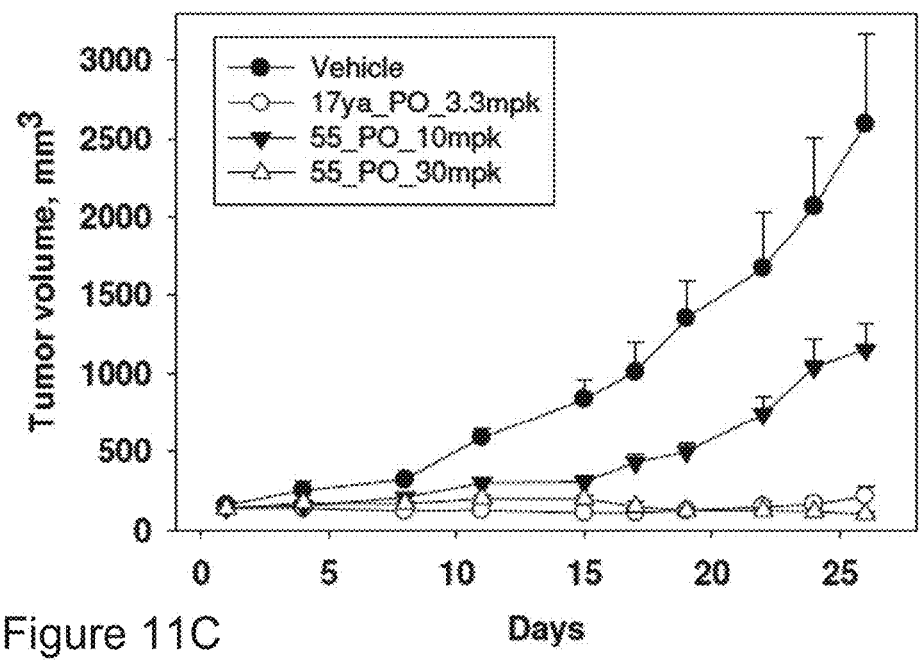
Figure 11D:
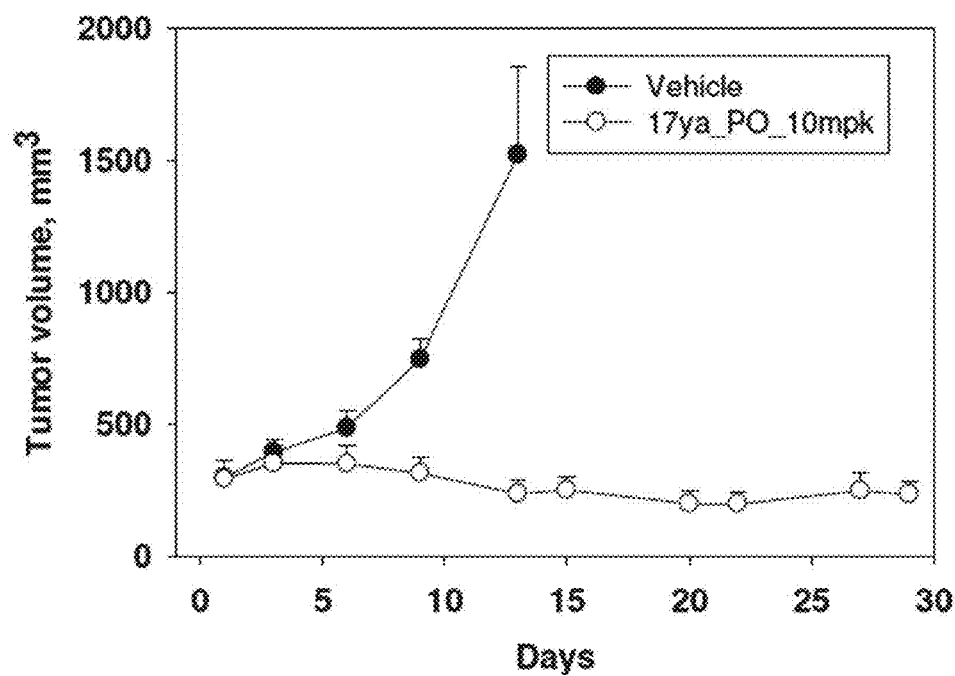

As shown in FIG. 11C, 3.3 mg/kg of 17ya was dosed b.i.d. for first consecutive four days in the first week, and the schedule was then changed to once daily between weeks 2 and 4. The result shows that partial regression was obtained during day 4-19, and the TGI was 97%, and one of the seven mice was tumor free on day 26. Higher dose (10 mg/kg) with lower dosing frequency (q2d) of 17ya (FIG. 11D) elicited partial regression during days 13 to 29. These data suggest that regimens with optimized doses and dosing schedules will facilitate 17ya to successfully inhibit PC-3/TxR tumors. 55, was orally administered to nude mice with 10 or 30 mg/kg b.i.d., and five times a week between weeks 1 and 4. As shown in FIG. 11C, the inhibition profiles exhibit a dose-response in PC-3/TxR tumor. The TGI value was 59% for the treatment group with a lower dose (10 mg/kg). Moreover, the higher dose (30 mg/kg) started to show partial regression (>100% TGI) from day 19 to the termination of the study (day 26). Some mice in the vehicle group lost body weight at the endpoint, in part, due to cancer cachexia. On the contrary, mice treated with 17ya (3.3 mg/kg) or 55 (30 mg/kg) were gaining weight (Table 12), suggesting that these optimized doses of 17ya or 55 may be well-tolerated and were preventive of cancer cachexia.

TABLE 12

Antitumor activity of compounds 17ya and 55 versus concomitantly evaluated docetaxel in vivo.

| | Dosing Schedule | End point | Number End/Start | Body weight (g) | | Tumor size (mm³) | | TGI (%) |
| --- | --- | --- | --- | --- | --- | --- | --- | --- |
| | | | | Start | End | Start | End | |
| PC-3 xenograft | | | | | | | | |
| Vehicle_IV | day 1 and 9 | day 19 | 6/6 | 30 ± 2 | 32 ± 4 | 271 ± 83 | 875 ± 292 | — |
| Docetaxel_IV_10mpk | day 1 and 9 | day 19 | 5/5 | 29 ± 2 | 24 ± 2 | 247 ± 49 | 341 ± 101 | 84 |
| Docetaxel_IV_20mpk | day 1 and 9 | day 19 | 5/5 | 28 ± 3 | 24 ± 3 | 243 ± 68 | 172 ± 62 | >100 |
| PC-3/TxR xenograft | | | | | | | | |
| Vehible_IV | day 1 and 9 | day 19 | 5/5 | 33 ± 1 | 26 ± 5 | 171 ± 57 | 2061 ± 858 | — |
| Docetaxel_IV_10mpk | day 1 and 9 | day 19 | 4/4 | 31 ± 2 | 25 ± 2 | 143 ± 20 | 1774 ± 183 | 14 |
| Docetaxel_IV_20mpk | day 1 and 9 | day 19 | 4/4 | 30 ± 1 | 25 ± 4 | 170 ± 86 | 999 ± 905 | 56 |
| 17ya_PO_6.7mpk | qd × 5/w | day 19 | 4/4 | 33 ± 3 | 34 ± 3 | 172 ± 69 | 126 ± 100 | >100 |
| Vehicle_PO | b.i.d × 5/w | day 26 | 6/7 | 30 ± 2 | 25 ± 2 | 156 ± 30 | 2591 ± 1423 | — |
| 55_PO_10mpk | b.i.d × 5/w | day 26 | 7/7 | 29 ± 2 | 26 ± 3 | 143 ± 44 | 1152 ± 433 | 59 |
| 55_PO_30mpk | b.i.d × 5/w | day 26 | 7/7 | 29 ± 3 | 30 ± 2 | 134 ± 34 | 101 ± 19 | >100 |
| 17ya_PO_3.3mpk[a] | qd × 5/w | day 26 | 7/7 | 29 ± 2 | 30 ± 2 | 139 ± 44 | 214 ± 172 | 97 |
| Vehicle_PO | q2d × 3/w | day 29 | 5/5 | 24 ± 2 | 21 ± 1 | 299 ± 40 | 1521 ± 580 | — |
| 17ya_PO_10mpk | q2d × 3/w | day 29 | 5/5 | 24 ± 2 | 28 ± 2 | 294 ± 156 | 237 ± 103 | >100 |

Dosing schedule: qd × 5/w = one administration given on five consecutive days per week; b.i.d. × 5/w = two administrations given on five consecutive days per week; or q2d × 3/w = every other day administration or three times a week.
[a]Dose schedule was two administrations given on four consecutive days of the first week, and dose schedule was changed (because of toxicity) to one administration given on five consecutive days per week for the second to fourth week.

Brain Penetration of 17ya and 55 in Nude Mice.

Whole brain concentrations in nude mice at 1 h and 4 h after oral administration of 20 mg/kg 17ya or 55 were determined (Table 13). The ratios of brain to plasma concentrations were determined and compared to docetaxel in the nude mice. 55 exhibited greater brain penetration than 17ya and docetaxel. 17ya only exhibited slightly greater brain/plasma concentration ratios than docetaxel at both 1 and 4 h. The brain concentrations of 55 reached 14 to 19% of plasma concentrations at 1 h and 4 h, respectively, showing a 3.2-fold higher brain/plasma ratio at both 1 h and 4 h compared to docetaxel. These data suggest that 55 exhibited potentially favorable properties to treat glioma, since it has greater brain penetration and high potency (22 nM, Table 9) in glioma cells.

TABLE 13

Brain-Blood Barrier (BBB) studies of compounds 17ya and 55. Brain and plasma concentrations were determined in nude mice at 1 and 4 h after administration of docetaxel (IP, 10 mpk), 17ya (PO, 20 mpk), and 55 (PO, 20 mpk). Each value represents the mean ± SD from 3 nude mice.

| Measurment | Docetaxel | | 17ya | | 55 | |
| --- | --- | --- | --- | --- | --- | --- |
| | 1 hr | 4 hr | 1 hr | 4 hr | 1 hr | 4 hr |
| Brain (ng/mL) | 33 ± 14 | 20 ± 9 | 124 ± 108 | 49 ± 32 | 180 ± 44 | 73 ± 18 |
| Plasma (ng/mL) | 768 ± 92 | 345 ± 94 | 2058 ± 1252 | 570 ± 438 | 1669 ± 867 | 380 ± 32 |
| Brain/plasma (%) | 4.4 ± 2.0 | 6.0 ± 2.9 | 5.4 ± 1.9 | 8.9 ± 1.7 | 14 ± 7.9 | 19 ± 3.1 |

Example 18: Vascular Disrupting Activity of Compounds 17ya and 55

Method

Cells.

HUVECs (Human Umbilical Vein Endothelial Cells) were cultured and grown in EGM-2 BulletKit (Lonza, Cat No. CC-3162), which contains growth supplements including hydrocortisone, human fibroblast growth factor-basic with heparin (hFGF-B), vascular endothelial growth factor (VEGF), insulin-like growth factor 1 (IGF-1), ascorbic acid, heparin, fetal bovine serum, human epidermal growth factor (hEGF), and GA-1000 (gentamicin and amphotericin B) in Endothelial Cell Basal Medium-2. Cells between the third and fifth passages were used for experiments. PC-3 human prostate cancer cells and T47D human breast cancer cells were cultured in RPMI-1640 medium with 5% fetal bovine serum.

Cell Growth Inhibition Studies.

Cytotoxic or antiproliferative activity of test compounds was investigated in several cell lines using the sulforhodamine B (SRB) assay. Cultured cells were plated into 96-well plates and incubated in medium containing different concentrations of the test compounds for 24 h or 48 h. Cells were stained with sulphorhodamine B (SRB) solution. The optical density was determined at 540 nm on a microplate reader (Dynex Technologies, Chantilly, Va.). Plots of percent inhibition of cell growth versus drug concentration were constructed, and the concentration that inhibited cell growth by 50% relative to the vehicle control ($IC_{50}$) was determined by nonlinear least squares regression using WinNonlin software (Pharsight Corporation, Cary, N.C.).

Capillary Formation and Disruption Assays.

Capillary formation assays were performed in 96-well plates by plating 12,000 cells/wells of HUVECs on a Matrigel layer (BD Biosciences). In order to evaluate the anti-capillary action, capillaries were allowed to form over a 16 h period before the addition of test compound or vehicle-control. In addition, capillary formation inhibitory effect of test compound was investigated by treating HUVEC cells with test compounds before capillary formation. Images were acquired immediately following compound addition, 5, 10, 15, and 25 h after exposure to test compound. Capillary formation was quantified by counting the number of tubes and nodes having at least three edges.

Endothelial Monolayer Permeability Assay.

The permeability of an endothelial cell monolayer was assessed in the transwell system. HUVECs were plated at $2\times10^6$ cells per insert of 24 well plates in EGM-2 medium and incubated for 72 h to reach 100% confluency. Test compounds were diluted in EGM-2 medium and added to the upper chamber of the apparatus. Following 1, 2, and 4 h of incubation, the compounds were removed and 75 μg/mL of FITC-conjugated dextran (MW 40,000) was added for 5 minutes. Fluorescent measurements of the lower chamber were taken after excitation at 485 nm and emission was measured at 520 nm using a BioTek Synergy 4 Microplate Reader.

Result

17ya and 55 Exhibited High Antiproliferative Activity Against Endothelial Cells.

Figure 12A:
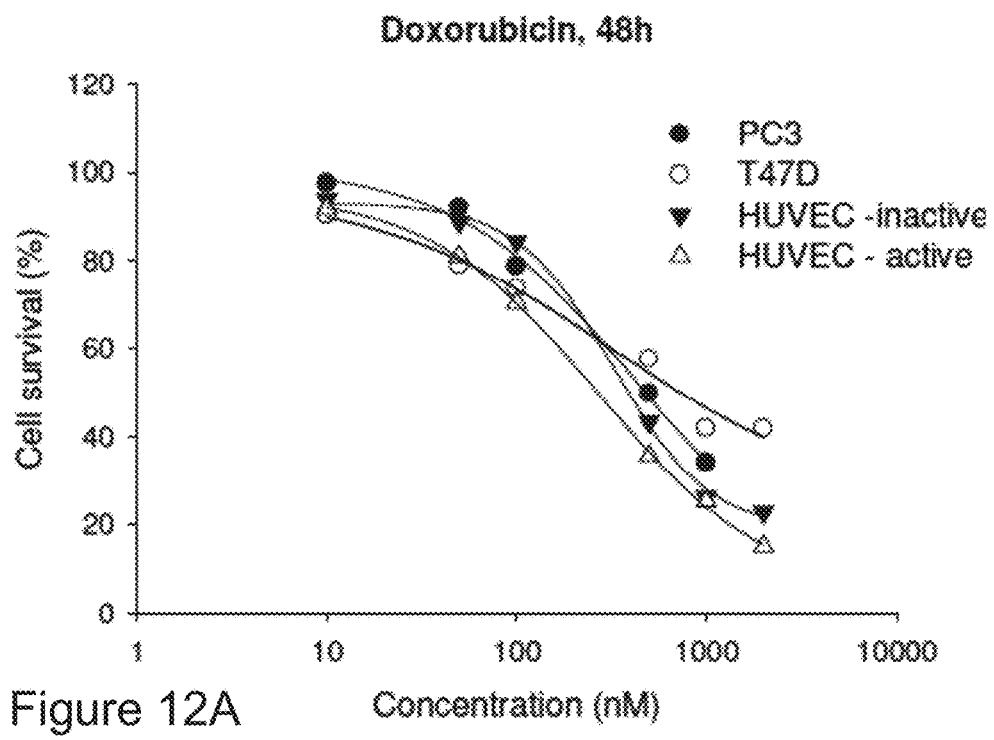
FIGS. 12A-B depict the potent endothelial cell growth inhibition of compound 17ya. Cell growth inhibition of doxorubicin (FIG. 12A) and compound 17ya (FIG. 12B) was investigated in several cell lines by SRB study. HUVEC-active and HUVEC-inactive treatments represent growth factor-supplemented and growth factor-deprived endothelial cell cultures, respectively.
Figure 12B:
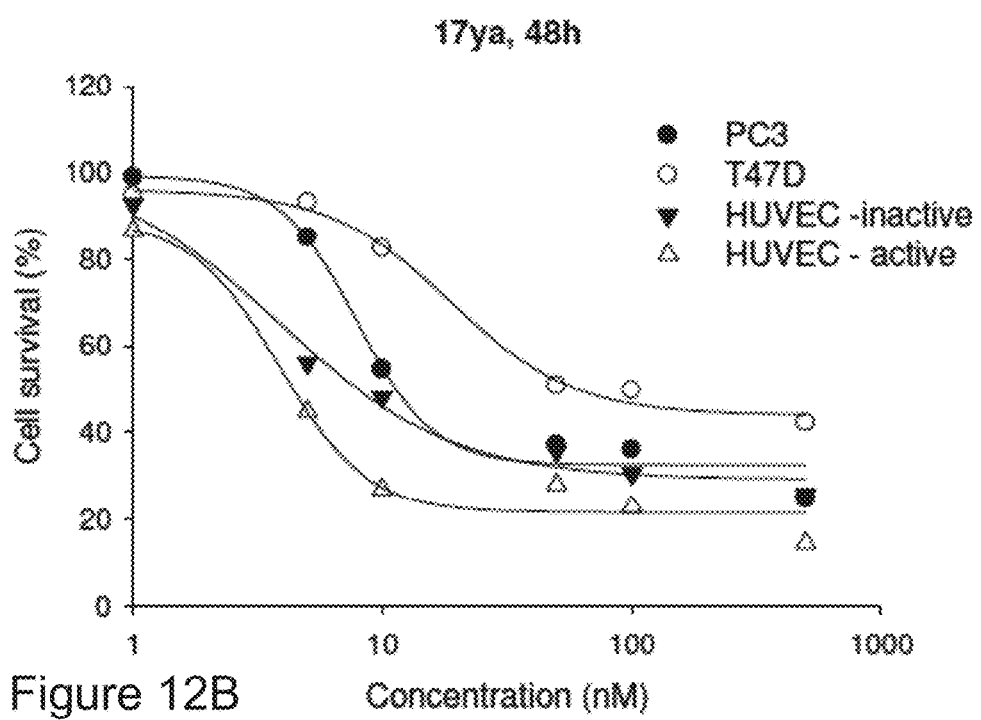

17ya and 55 were evaluated for cytotoxic activity against growth factor-supplemented endothelial cells and growth factor-deprived endothelial cell cultures. Combretastatin A-4 (CA4) and doxorubicin were used as positive and negative control, respectively. Compound 17ya exhibited higher potency than compound 55 against actively proliferating endothelial cells (Table 14 and FIG. 12). Both 17ya and 55 exhibited selectivity for endothelial cells showing lower $IC_{50}$ values compared to one of the prostate cancer cells. CA4, 17ya and 55 were 8, 5 and 3 times more active against endothelial cells than against cancer cells, respectively, while doxorubicin was not specific to endothelial cells (Table 14 and FIG. 12). However no selectivity was observed between quiescent and active endothelial cells with these compounds (data not shown).

TABLE 14

Endothelial cell growth inihibition of 17ya and 55 (N = 3).

| | CA4 | Doxorubicin |
|---|---|---|
| | 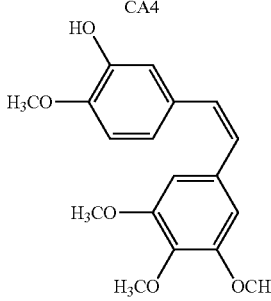 | 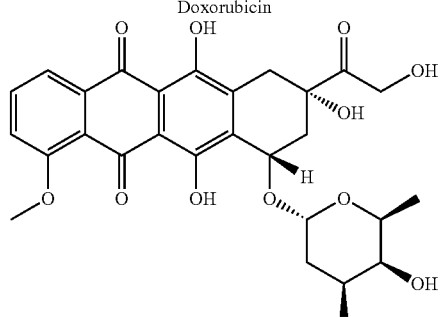 |
| PC3 | 3.2 | 397.0 |
| T47D | 6.0 | 352.8 |
| HUVEC | 1.2 | 273.6 |
| Selectivity ratio*, cancer cells/ HUVEC | 7.6 | 1.4 |
| | 17ya | 55 |
| | 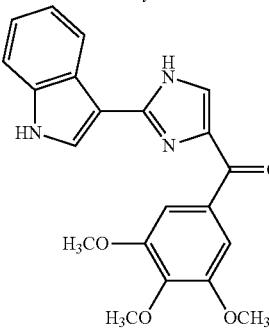 | 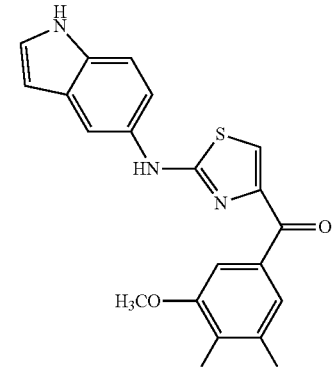 |
| PC3 | 7.8 | 23.3 |
| T47D | 18.0 | 37.4 |
| HUVEC | 2.8 | 9.7 |
| Selectivity ratio*, cancer cells/ HUVEC | 4.6 | 3.1 |

*To obtain the selectivity ratio between cancer cells and HUVEC cells, the mean $IC_{50}$ (nM) values of test compounds in PC3 and T47D cells were used.

17ya Disrupts the Formation of Endothelial Capillaries but does not Disrupt Preformed Capillaries.

The activity of 17ya was investigated on endothelial cells engaged in capillary tube formation in vitro. Endothelial cells were placed on a Matrigel matrix and the formation and construction of capillary tubes in the presence or absence of compounds were observed (CA4, doxorubicin, and 17ya).

To avoid confusion between early stage of tube formation and disruption of tube construction, HUVEC cells on matrix in the presence of drug treatment were incubated for 15 h. Then disruption of capillary was determined by counting the number of tubes and nodes in each treatment group. On the other hand, to evaluate the effect of test compound in preformed capillaries, HUVEC cells on matrix were allowed to form capillary tube for 16 h and the capillaries were treated with test compounds.

As a result, the number of tubes and nodes was gradually decreased over time due to deficiency or consumption of nutrient by HUVEC cells (FIG. 13). This trend was observed in every drug treatment group (FIG. 13). In order to examine the difference between untreated and pretreated capillaries 15 h incubation groups were compared (FIG. 13).

Figure 14:
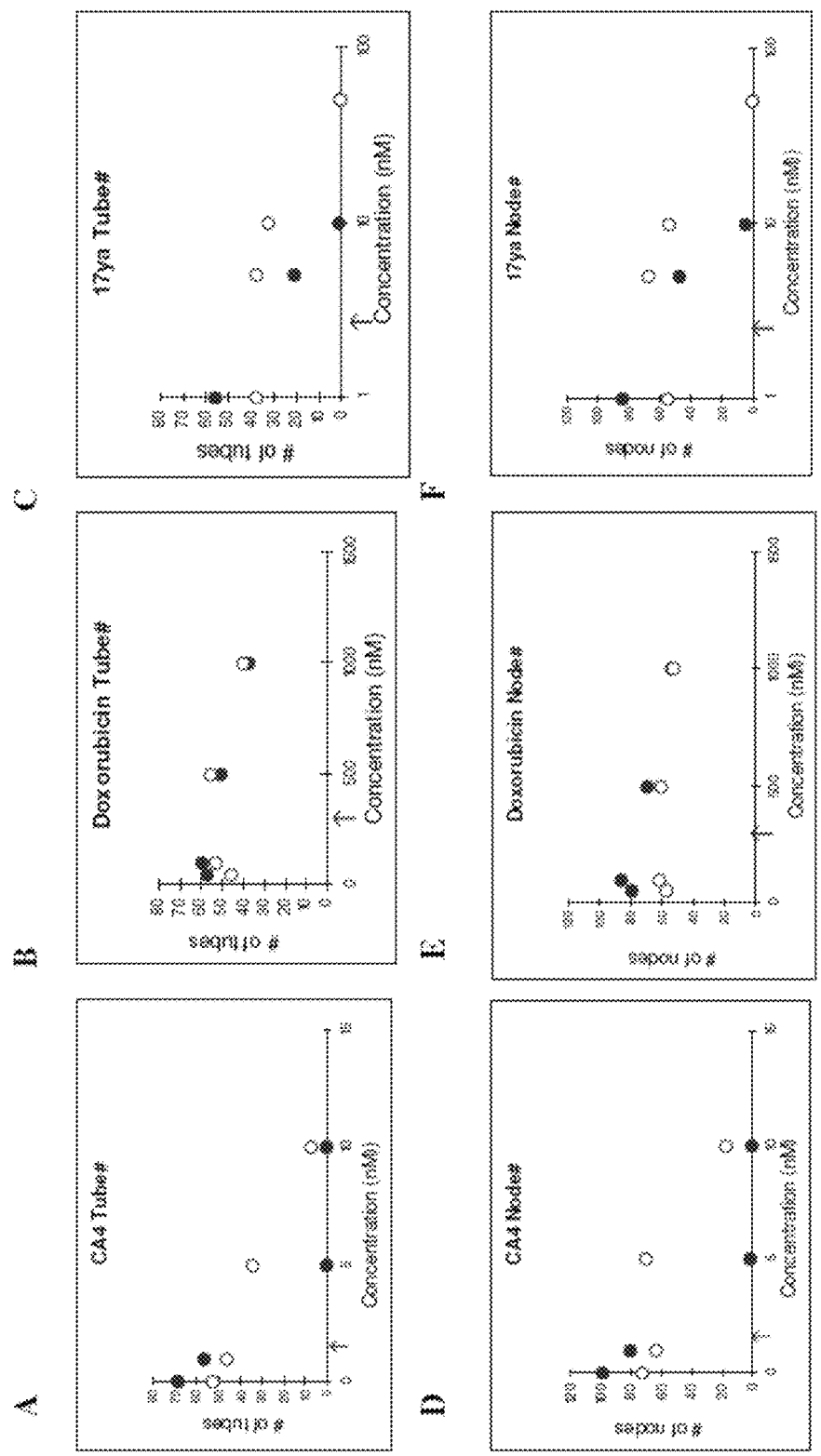
FIG. 14 depicts the inhibition of the endothelial capillary formation and disruption of preformed capillaries. Inhibition of capillary formation (●) and disruption of preformed capillary (○) were compared in an in vitro study using HUVEC cells after 15 h CA4 (A and D), DOX (B and E), and 17ya (C and F) treatment. Arrow shows the $IC_{50}$ value of each compound in HUVEC cell growth inhibition.

Endothelial cells that were exposed to various concentrations of 17ya (0 to 50 μM) plated on Matrigel matrix resulted in inhibition of tube formation in a dose dependent manner. 17ya with approximate $IC_{50}$ value of 5 nM in cell growth inhibition studies inhibited more than 50% of tube formation compared to vehicle-control (FIG. 14). 17ya at 10 nM completely inhibited the tube formation (FIG. 14). However, in the preformed capillaries, the 10 nM 17ya treatment group did not disrupt the capillary structure by 15 h (FIG. 13). These results suggest that 17ya inhibits the formation of endothelial capillaries significantly but is less effective to disrupt preformed capillaries. Similar result was observed in CA4 treatment group (FIG. 14). However, doxorubicin did not affect the capillary construction at toxic concentration.

17ya and 55 Increased the Permeability of Endothelial Cell Monolayers.

Antitubulin agents could modify the integrity of endothelial cell layers lining blood vessels by targeting cytoskeleton of the endothelial cells. Thus, the vascular disruption effect of antitubulin agent is known to increase the permeability of blood vessel and thus could lead to protein leakage and high blood viscosity. This could result in reduction of blood flow, causing subsequent tumor death from hypoxia and nutrient deprivation.

Figure 15:
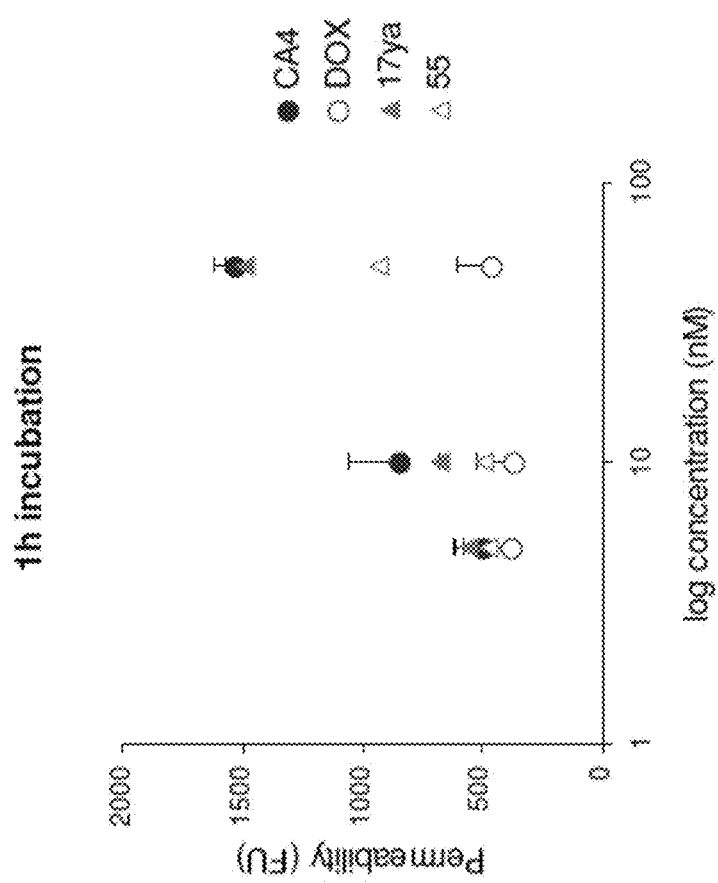
FIG. 15 depicts the increased permeability of endothelial cell monolayers by 17ya and 55. Confluent HUVEC monolayers were exposed to test compound. The leakage of FITC-conjugated dextran through the monolayer was assessed by relative fluorescence measurements at λ=485 nm excitation and λ=530 nm emission in a receiver to determine changes in monolayer permeability following exposure.

The effect of 17ya and 55 was evaluated on vascular permeability using in vitro study using transwell system with confluent HUVEC monolayers. The change in permeability by test compound was measured by the leakage of dextran (MW 40,000) after 1, 2, and 4 h of drug treatment. CA4 was used as a positive control. CA4, 17ya, and 55 resulted in increased permeability and the effect was more pronounced at 1 h incubation (data was not shown). 17ya showed a potency similar to CA4 (FIG. 15). Doxorubicin did not induce any change in the permeability of endothelial cell monolayer (FIG. 15).

Figure 16:
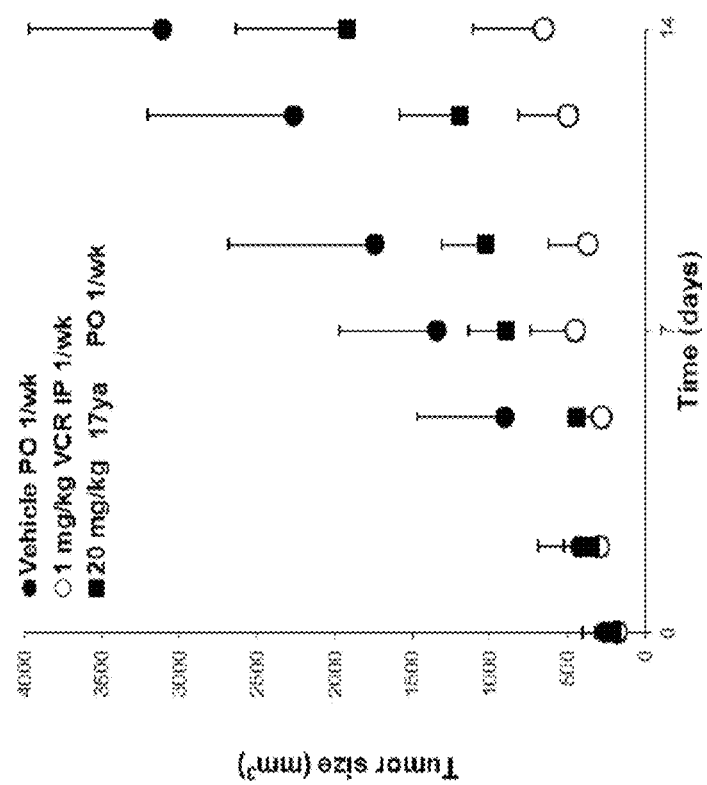
FIG. 16 depicts in vivo anti-cancer efficacy of 17ya in HL60 leukemia cell xenografts.
Figure 17A:
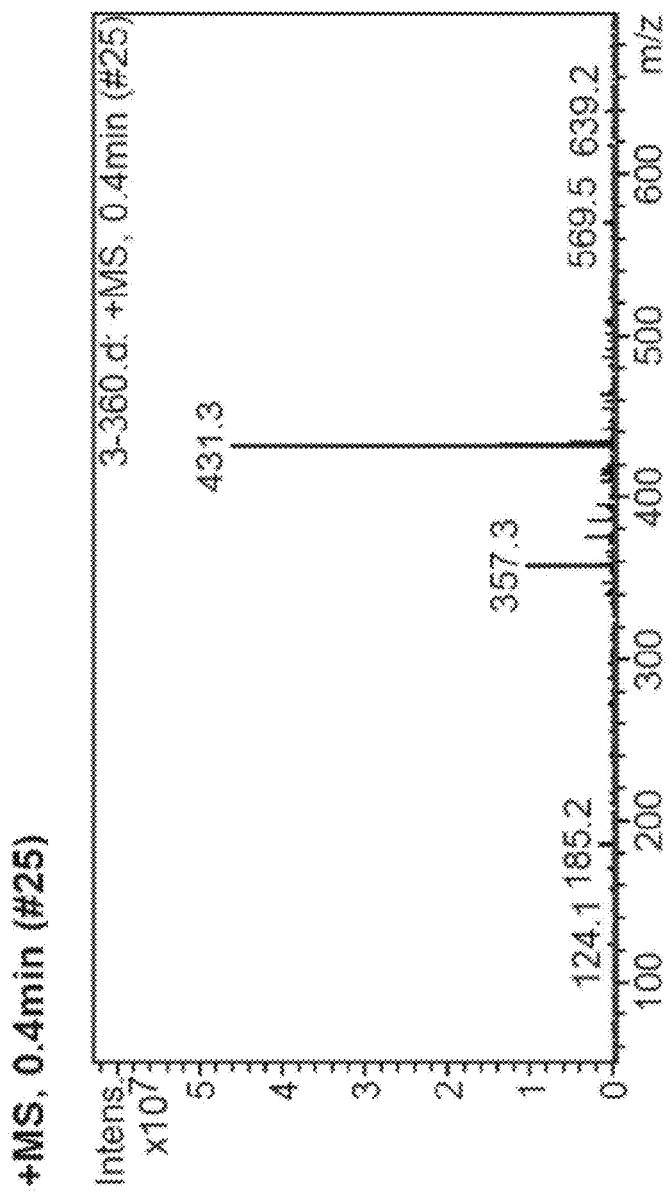
Figure 17B:
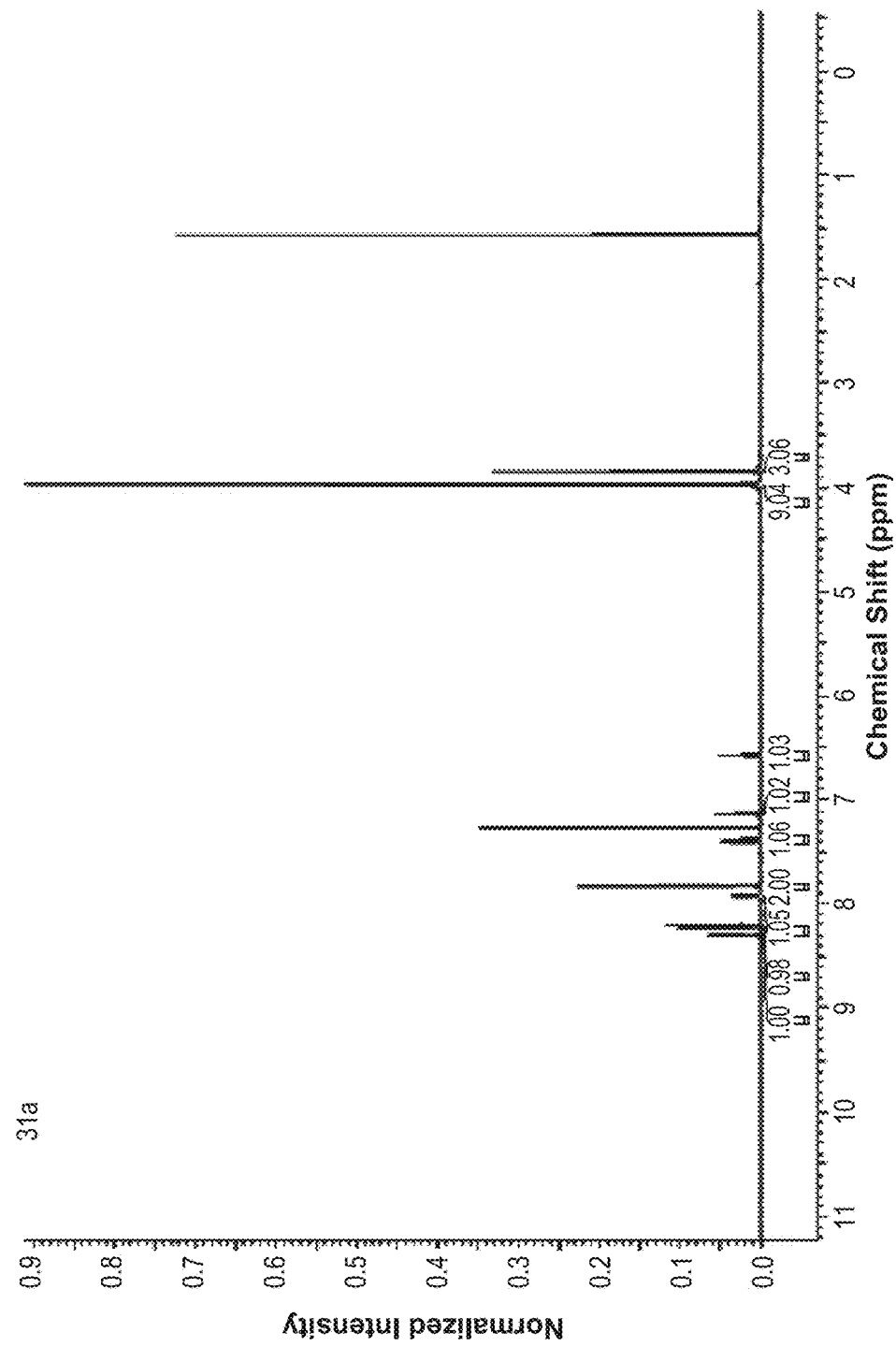
Figure 17C:
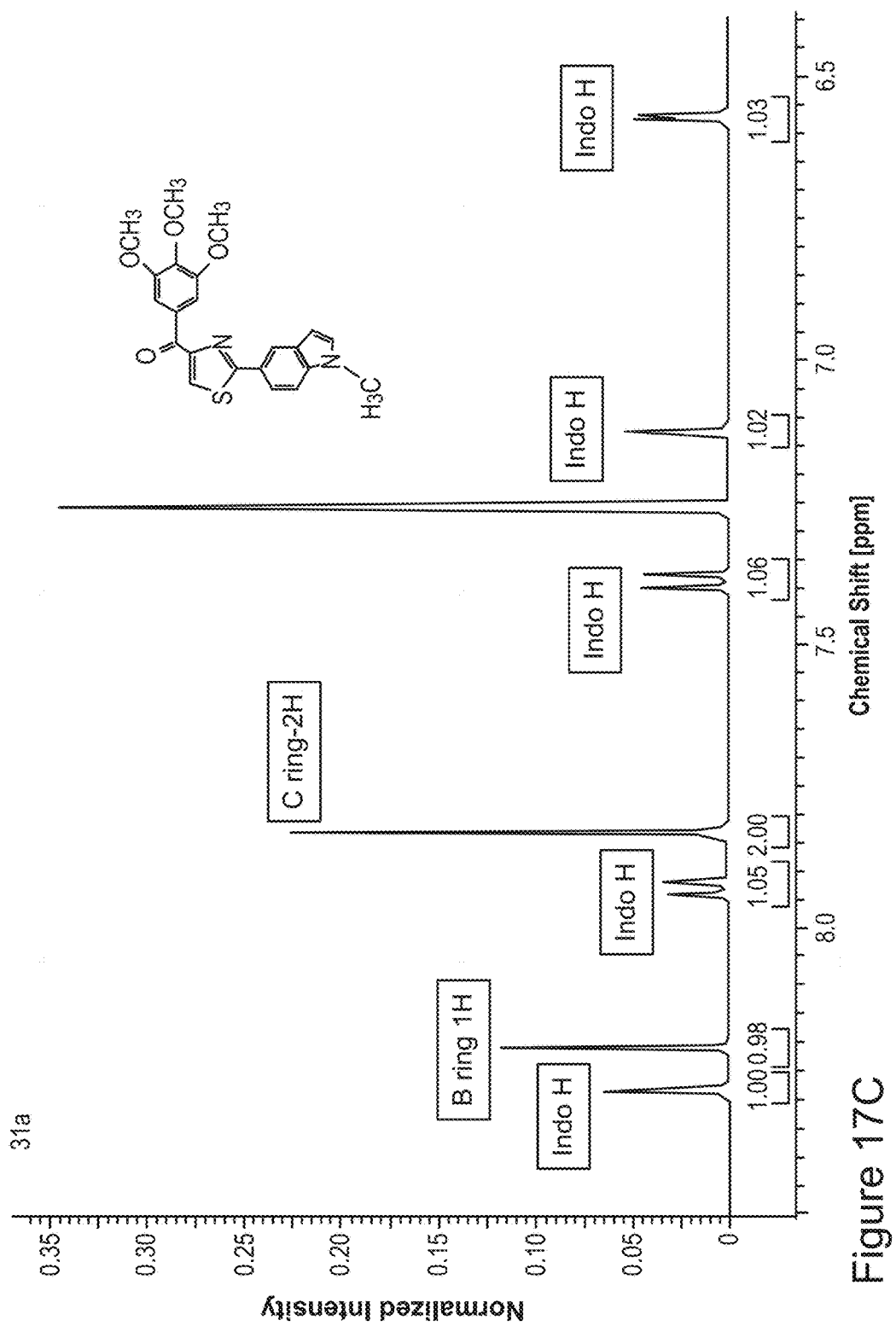
Figure 17D:
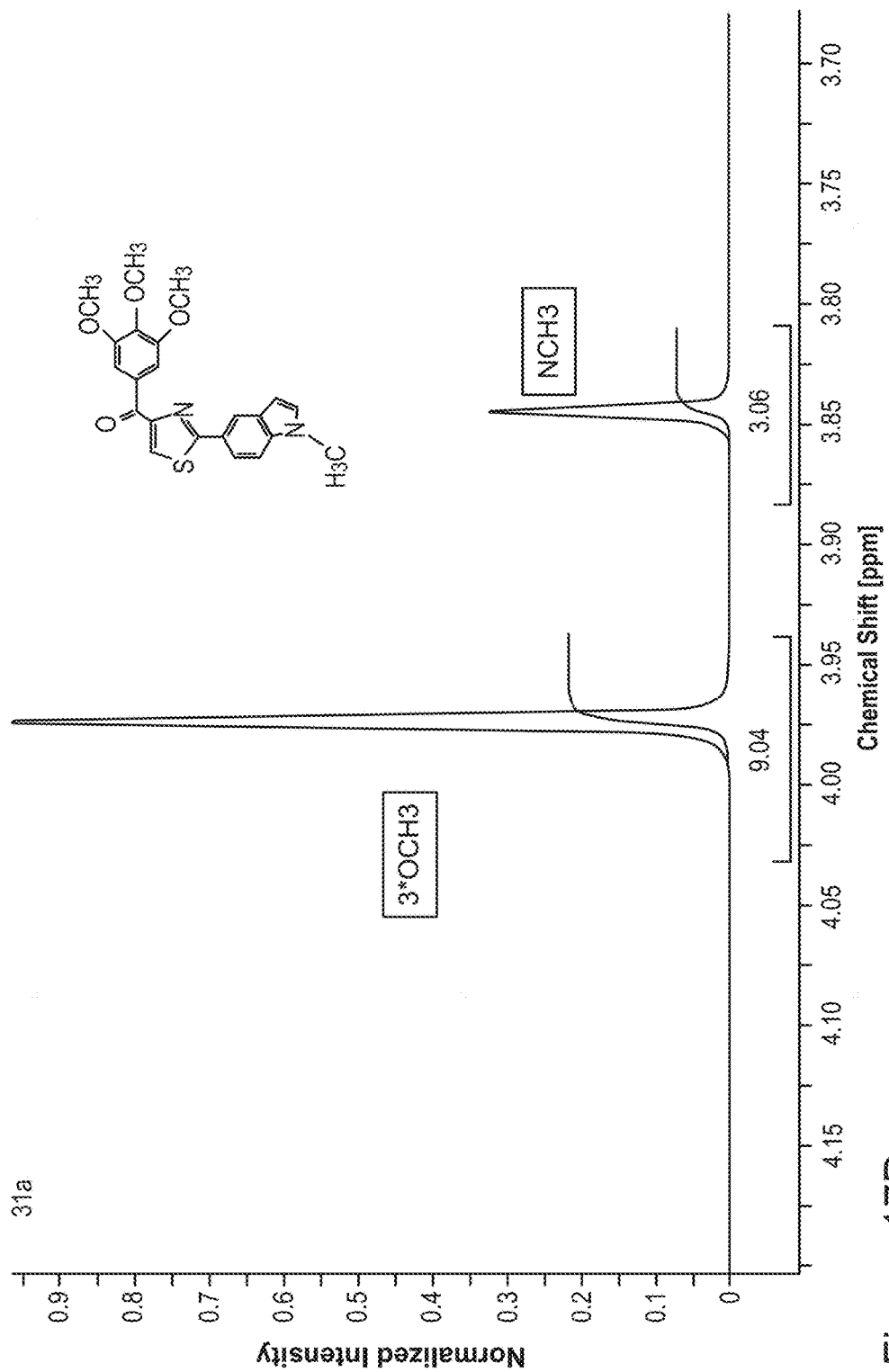

Example 19: In Vivo Effacacy of 17ya in Leukemia (HL60) Xenograft (FIG. 16)

HL60 cells (10×10$^7$ per mL) were prepared in RPMI1640 growth media containing 10% FBS, and mixed with Matrigel (BD Biosciences, San Jose, Calif.) at 1:1 ratio. Tumors were established by injecting 100 μL of the mixture (5×10$^6$ cells per animal) subcutaneously into the flank of 6-8-week-old male athymic nude mice. Length and width of tumors were measured and the tumor volume (mm$^3$) was calculated by the formula, $\pi/6 \times L \times W^2$, where length (L) and width (W) were determined in mm. When the tumor volumes reached 200 mm$^3$ approximately, the animals bearing HL60 tumors were treated with vehicle [Tween80/DMSO/H$_2$O (2/2/6)], or 17ya (20 mg/kg) orally. The dosing schedule was once a week for two weeks. Vincristine (1 mg/mL) was administrated via intraperitoneal injection once a week.

Results

Human promyelocytic leukemia cells, HL60 cells were inoculated in nude mice and the tumor volumes were allowed to reach about 200 mm$^3$. Vincristine (1 mg/kg), which is in clinic for hematological cancers including leukemia, was used to evaluate the response of this in vivo model against a positive control drug. The tumor volumes (mm$^3$) were plotted against time and are the means±SD from four to five animals. HL60 tumor was found to be fast-growing and the volume reached 2000-3000 mm$^3$ within two weeks. Though 1 mg/kg intraperitoneal injection of vincristine exhibited very potent tumor growth inhibitory effect (FIG. 16) and the tumor growth inhibition (TGI) was 84%. Orally administered 17ya (20 mg/kg) showed 40% tumor growth inhibition. The size of HL60 tumors was maintained up to 5 days after 17ya treatment without dramatic increase but during the next 2 days tumor sizes increased significantly (60-100%). It suggests that a more frequent dosing schedule could enhance the tumor growth inhibitory effect of 17ya.

Example 20: Synthesis of a Derivative of Compound 31

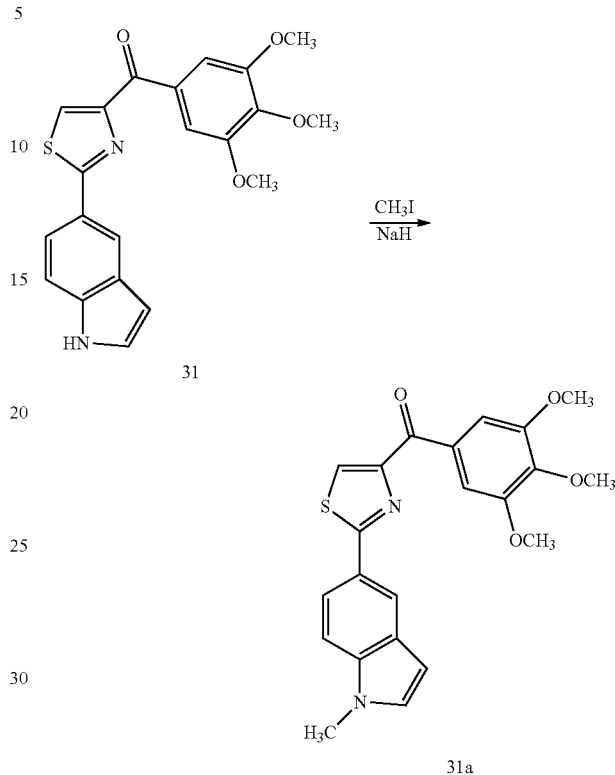

Compound 31a was synthesized by the addition of sodium hydride (60% dispersion in mineral oil, 20 mg, 0.5 mmol) to 31 and stirred for 20 min. Methyl iodide (70 mg, 0.5 mmol) was added, and the reaction mixture was stirred 1 h. After dilution by 20 ml of saturated NaHCO$_3$ solution (aqueous), the reaction mixture was extracted by ethyl acetate (60 ml). The organic layer was dried over magnesium sulfate and concentrated. The residue was recrystallized from water and methanol to give a white solid of 31a. (2-(1-Methyl-1H-indol-5-yl)thiazol-4-yl)(3,4,5-trimethoxyphenyl)methanone (Compound 31a): Yield: 75% $^1$H NMR (300 MHz, CDCl$_3$) δ 8.28 (br, 1H), 8.21 (br, 1H), 7.95-7.91 (dd, 1H), 7.83 (s, 2H), 7.38 (d, 1H), 7.25 (t, 1H), 6.67 (t, br, 1H), 3.98 (s, 9H), 3.85 (s, 3H). MS (ESI) m/z 431.3.

Example 21: In Vitro and In Vivo Pharmacology of Compounds 17ya, 31, and 31a

Materials and Methods Cell Culture and Cytotoxicity Assay of Prostate, Lung, Colon, Breast, Uterine and Ovarian Cancers.

All cancer cell lines (PC-3-prostate cancer, PC-3/TXR prostate cancer-multidrug resistant (MDR), A549-lung cancer, C26-colon cancer, MCF7-breast cancer, MES-SA-uterine cancer and MES-SA/DX5-uterine cancer-MDR) were obtained from ATCC (American Type Culture Collection, Manassas, Va., USA) unless otherwise specified. Both ovarian cell lines (OVCAR8-ovarian cancer and NCI/ADR-RES-ovarian cancer-MDR) were obtained from National Cancer Institutes (NCI). Human PC-3_TxR, was resistant to paclitaxel and used as a MDR model compared with PC-3. Human MES-SA/DX5 was resistant to doxorubicin and used as a MDR model compared with MES-SA. Human NCI/ADR-RES was resistant to Adriamycin and used as a MDR model compared with OVCAR8. Cell culture supplies were purchased from Cellgro Mediatech (Herndon, Va., USA). All cell lines were used to test the antiproliferative activity of compounds 17ya (2-(1H-indol-3-yl)imidazol-4-yl)(3,4,5-trimethoxyphenyl)methanone, 31 (2-(1H-indol-5-yl)thiazol-4-yl)(3,4,5-trimethoxyphenyl)methanone, and 31a (2-(1-methyl-1H-indol-5-yl)thiazol-4-yl)(3,4,5-trimethoxyphenyl)methanone by sulforhodamine B (SRB) assay. All cancer cell lines were maintained in RPMI 1640 media with 2 mM glutamine and 10% fetal bovine serum (FBS).

Metabolic Incubations.

Metabolic stability studies were conducted for compound 17ya and 31 by incubating 0.5 µM of test compounds in a total reaction volume of 1 mL containing 1 mg/mL microsomal protein in reaction buffer [0.2 M of phosphate buffer solution (pH 7.4), 1.3 mM $NADP^+$, 3.3 mM glucose-6-phosphate, and 0.4 U/mL glucose-6-phosphate dehydrogenase] at 37° C. in a shaking water bath. The NADPH regenerating system (solution A and B) was obtained from BD Biosciences (Bedford, Mass.). For glucuronidation studies, 2 mM UDP-glucuronic acid (Sigma, St. Louis, Mo.) cofactor in deionized water was incubated with 8 mM $MgCl_2$, 25 µg of alamethicin (Sigma, St. Louis, Mo.) in deionized water, and NADPH regenerating solutions (BD Biosciences, Bedford, Mass.) as described previously. The total DMSO concentration in the reaction solution was approximately 0.5% (v/v). Aliquots (100 µL) from the reaction mixtures used to determine metabolic stability were sampled at 5, 10, 30, 60, 90 and 120 min. Acetonitrile (150 µL) containing 200 nM of the internal standard was added to quench the reaction and to precipitate the proteins. Samples were then centrifuged at 4,000 g for 30 min at RT, and the supernatant was analyzed directly by LC-MS/MS.

Analytical Method.

Sample solution (10 µL) was injected into an Agilent series HPLC system (Agilent 1100 Series Agilent 1100 Chemstation, Agilent Technology Co, Ltd). All analytes were separated on a narrow-bore C18 column (Alltech Alltima HP, 2.1×100 mm, 3 m, Fisher, Fair Lawn, N.J.). Two gradient modes were used. For metabolic stability studies, gradient mode was used to achieve the separation of analytes using mixtures of mobile phase A [ACN/$H_2O$ (5%/95%, v/v) containing 0.1% formic acid] and mobile phase B [ACN/$H_2O$ (95%/5%, v/v) containing 0.1% formic acid] at a flow rate of 300 µL/min. Mobile phase A was used at 10% from 0 to 1 min followed by a linearly programmed gradient to 100% of mobile phase B within 4 min, 100% of mobile phase B was maintained for 0.5 min before a quick ramp to 10% mobile phase A. Mobile phase A was continued for another 10 min towards the end of analysis.

A triple-quadruple mass spectrometer, API Qtrap 4000™ (Applied Biosystems/MDS SCIEX, Concord, Ontario, Canada), operating with a TurbolonSpray source was used. The spraying needle voltage was set at 5 kV for positive mode. Curtain gas was set at 10; Gas 1 and gas 2 were set 50. Collision-Assisted-Dissociation (CAD) gas at medium and the source heater probe temperature at 500° C. [Multiple reaction monitoring (MRM) mode, scanning m/z 378→210 (17ya), m/z 373→205 (12fa), m/z 410→242 (55) and m/z 309-171 (internal standard), was used to obtain the most sensitive signals. Data acquisition and quantitative processing were accomplished using Analyst™ software, Ver. 1.4.1 (Applied Biosystems).

Aqueous Solubility.

The solubility of drugs was determined by Multiscreen Solubility Filter Plate (Millipore Corporate, Billerica, Mass.) coupled with LC-MS/MS. Briefly, 198 µL of phosphate buffered saline (PBS) buffer (pH 7.4) was loaded into 96-well plate, and 2 µL of 10 mM test compounds (in DMSO) was dispensed and mixed with gentle shaking (200-300 rpm) for 1.5 hours at RT (N=3). The plate was centrifuged at 800 g for 10 min, and the filtrate was used to determine its concentration and solubility of test compound by LC-MS/MS as described previously.

Pharmacokinetic Study.

Female Sprague-Dawley rats (n=3; 254±4 g) were purchased from Harlan Inc. (Indianapolis, Ind.). Rat thoracic jugular vein catheters were purchased from Braintree Scientific Inc. (Braintree, Mass.). On arrival at the animal facility, the animals were acclimated for 3 days in a temperature-controlled room (20-22° C.) with a 12 h light/dark cycle before any treatment. Compounds 17ya and 31 were administered i.v. into the thoracic jugular vein at a dose of 5 mg/kg (in DMSO/PEG300, 1/9). An equal volume of heparinized saline was injected to replace the removed blood, and blood samples (250 µL) were collected via the jugular vein catheter at 10, 20, 30 min, and 1, 2, 4, 8, 12, 24 h. Rats were given (p.o.) by oral gavage at 10 mg/kg (in Tween80/DMSO/$H_2O$, 2/2/6) of each test compound to evaluate their oral bioavailability. All blood samples (250 µL) after oral administration were collected via the jugular vein catheter at 30, 60, 90 min, 120 min, 150 min, 180 min, 210 min, 240 min, and 8, 12, 24 h. Heparinized syringes and vials were prepared prior to blood collection. Plasma samples were prepared by centrifuging the blood samples at 8,000 g for 5 min. All plasma samples were stored immediately at −80° C. until analyzed.

Analytes were extracted from 100 µL of plasma with 200 µL of acetonitrile containing 200 nM the internal standard. The samples were thoroughly mixed, centrifuged, and the organic extract was transferred to autosampler for LC-MS/MS analysis.

Results

Compounds 17ya, 31 and 31a Exhibit Broad Cytotoxicity in Cancer Cells, Including Multidrug-Resistant Cancer Cells.

The ability of 17ya, 31 and 31a to inhibit the growth of cancer cell lines was evaluated using an SRB assay (Table 15). All three compounds inhibited the growth of several human cancer cell lines, including prostate, lung, colon, breast, uterine, doxorubicin-resistant uterine, ovarian and adriamycin-resistant ovarian cancer cell lines, with $IC_{50}$ values in the low nanomolar range.

Doxorubicin-resistant MES-SA (MES-SA/DX5) cell line and adriamycin-resistant OVCAR8 (NCI/ADR-RES) cell line that express high levels of mdr-1 mRNA resulting in the over-expression of P-glycoprotein (P-gp), were used to study the effect of 17ya, 31 and 31a on multi-drug resistant cell lines and to compare results against parent lines, MES-SA cell line and OVCAR8 cell line, respectively. The $IC_{50}$ values of docetaxel (DTX) were 0.1 nM and 26 nM in MES-SA and MES-SA/DX5 cells, respectively, and 0.4 nM and 2471 nM in OVCAR8 and NCI/ADR-RES cells, respectively, demonstrating a signigicant reduction of effectiveness in drug-resistant cancer cells. Docetaxel exhibited relative resistance of 4260-fold (resistance factor; MES-SA vs. MES-SA/Dx5) and 6042.5-fold (resistance factor; OVCAR8 vs. NCI/ADR-RES), respectively. In contrast, compounds 17ya, 31 and 31a were equipotent against parent MES-SA or OVCAR8 cell lines and MES-SA/DX5 or NCI/ADR-RES multidrug resistant cell lines, respectively.

Uniformly, 17ya, 31 and 31a demonstrated at least an order of magnitude (i.e., 10-fold) increased potency compared to DTX in multidrug resistant cells lines. (Table 15) These data indicate that 17ya, 31 and 31a circumvent P-gp-mediated drug resistance.

Compounds 17ya, 31 and 31a Exhibited Favorable Drug-Like Properties.

Drug-like properties, such as metabolic stability, bioavailability (AUC; min*µg/mL), clearance (Cl; mL/min/kg) and steady-state volume of distribution (Vss; L/kg) were exam-

TABLE 15

Cytotoxicity data of 17ya, 31 and 31a
$IC_{50}$ (nM) in the SRB

| | | DTX | 17ya | 31 |
|---|---|---|---|---|
| PC3 | Prostate | 1-5 | 7-10 | 7 |
| A549 | Lung | 0.2 | 22 | 9 |
| C26 | Colon | 4 | 7 | 5 |
| MCF7 | Breast | 0.1 | 13 | 11 |
| MES-SA | Uterine | 0.1 | 9 | 6 |
| MES-SA/DX5 | | 426 | 14 | 8 |
| OVCAR8 | Ovary | 0.4 | 12 | 11 |
| NCI/ADR-RES | | 2471 | 19 | 5 |

| | | 31a |
|---|---|---|
| PC3 | Prostate | 5 |
| A549 | Lung | 21 |
| C26 | Colon | 16 |
| MCF7 | Breast | 22 |
| MES-SA | Uterine | 18 |
| MES-SA/DX5 | | 18 |
| OVCAR8 | Ovary | 16 |
| NCI/ADR-RES | | 14 |

$IC_{50}$ values are expressed in nM and were determined after 96 h treatment (N = 3). Docetaxel was used as a positive control.

Figure 18:
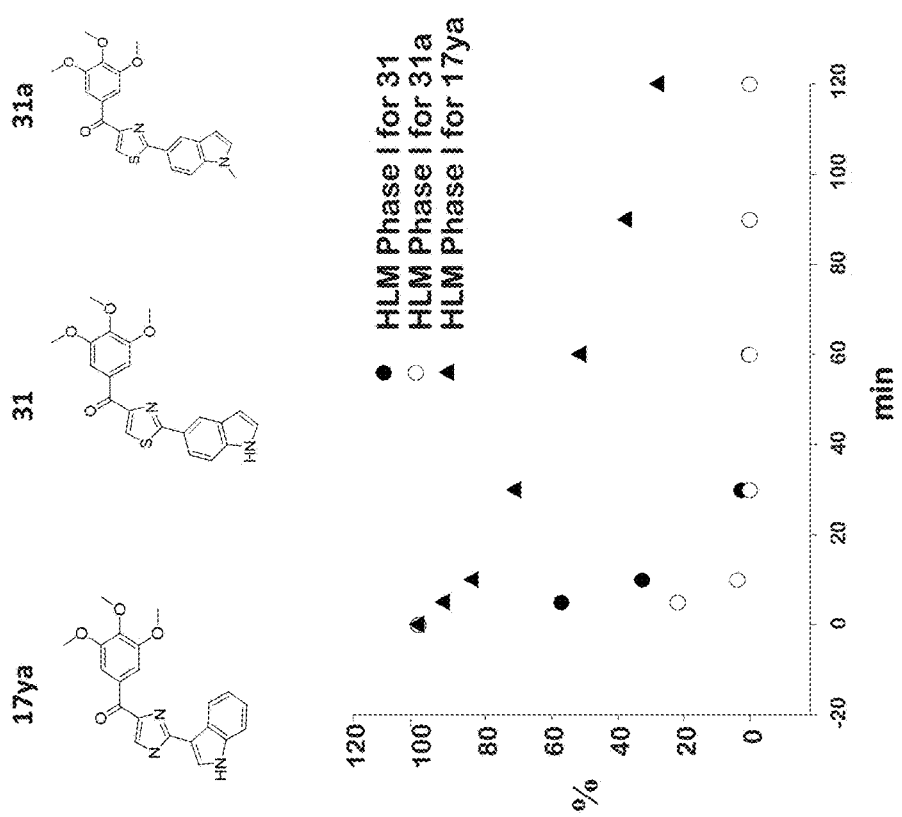
FIG. 18 depicts metabolic stability in human liver microsomes (HLM), Phase I conditions, of compounds 17ya (▲), 31 (•) and 31a (○).
Figure 19A:
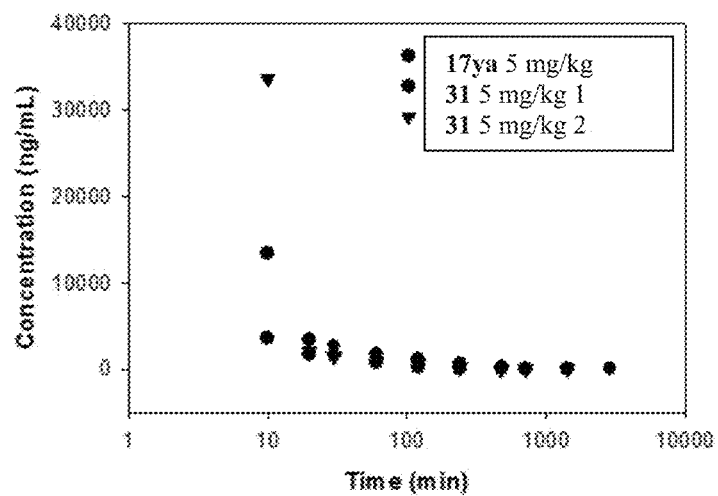
FIGS. 19A-C depict pharmacokinetics for 17ya (•) and 31 (•-colored and ▼) at 5 mg/kg dosages.
Figure 19B:
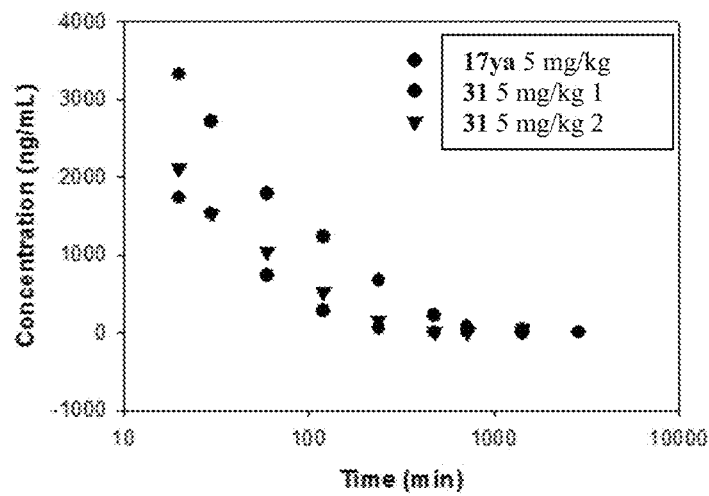
Figure 19C:
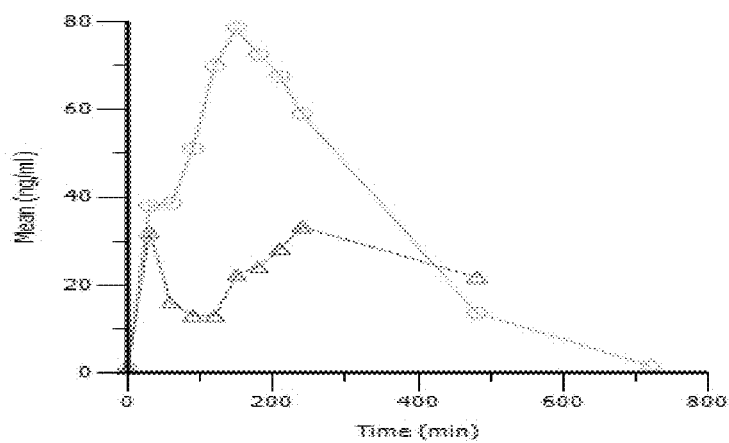

As shown in FIG. 18, 17ya had a half-life that was much longer than 31 or 31a as seen by the larger area under the curve in in vitro phase I reactions with human liver microsomes. This suggested that 17ya was stable in phase I metabolic processes. These data suggested that all three compounds showed acceptable stability in human liver microsomes, and 17ya is more stable than 31 or 31a.

ined for 17ya, 31 and 31a (metabolic stability only for 31a) (FIGS. 18, 19A, 19B and 19C; Table 16). 17ya exhibited superior metabolic stability compared with 31 and 31a (FIG. 18). As seen in the concentration time plots, 17ya also demonstrated superior stability in vivo when injected (FIGS. 19A, 19B) and dose orally (FIG. 19C) compared to 31 (Table 16).

TABLE 16

Pharmacokinetic properties of compounds 17ya and 31.

|  | 17ya | 31 | | | |
|---|---|---|---|---|---|
|  |  | 10 min-48 h | | 20 min-48 h | |
| AUC (min * µg/mL) | 553 | 828 | 3210 | 210 | 249 |
| CI (mL/min/kg) | 10 | 6 | 1 | 23 | 18 |
| Vss (L/kg) | 1.8 | 0.8 | 0.03 | 12 | 5 |

Example 22: Xenograft Efficacy Studies Using Compound 17ya to Treat Multi-Drug Resistant (MDR) and Non-MDR Tumors Materials and Methods Cell culture of prostate, lung, colon, breast, uterine and ovarian cancer cell lines was as above in Example 21. Additionaly, MCF7 (breast) cells were obtained from ATCC (American Type Culture Collection, Manassas, Va., USA). Cell lines were used to develop xenografts in order to test in vivo the anti-tumor growth activity of compound 17ya (2-(1H-indol-3-yl)imidazol-4-yl)(3,4,5-trimethoxyphenyl) methanone.

Xenograft Studies.

PC-3, PC-3_TxR, MES-SA/DX5, OVCAR8, NCI/ADR-RES, A549, C26 and MCF7 cells ($10 \times 10^7$ per mL) were prepared in RPMI1640 growth media containing 10% FBS, and mixed with Matrigel (BD Biosciences, San Jose, Calif.) at 1:1 ratio. Tumors were established by injecting 100 µL of the mixture ($5 \times 10^6$ cells per animal) subcutaneously (s.c.) into the flank of 6-8-week-old male athymic nude mice. Length and width of tumors were measured and the tumor volume ($mm^3$) was calculated by the formula, $\pi/6 \times L \times W^2$, where length (L) and width (W) were determined in mm. When the tumor volumes reached 300 $mm^3$, the animals bearing tumors were treated with vehicle [Tween80/DMSO/$H_2O$ (2/2/6)] or docetaxel (DTX) (10 mg/kg once per week) or 17ya intravenously or orally. The dosing schedule for 17ya included trials at 7 mg/kg once per week; 10 mg/kg once per week; 15 mg/kg once per week; 15 mg/kg twice per week; 15 mg/kg three times per week; and 20 mg/kg once per week.

Results

Compound 17ya Inhibits Tumor Growth in Nude Mice Bearing Prostate, Paclitaxel Resistant Prostate (PC3/TXR), Ovarian, Adriamycin-Resistant Ovarian (NCI/ADR-RES), Doxorubicin-Resistant Uterine (MES-SA/DX5), Lung and Colon Cancer Xenografts.

PC3, paclitaxel-resistant prostate cancer (PC-3/TxR), doxorubicin-resistant uterine cancer (MES-SA/DX5), ovarian cancer, adriamycin-resistant ovarian cancer (NCI/ADR-RES), lung cancer and colon cancer cells were inoculated in nude mice and the tumor volumes were allowed to reach about 150-300 $mm^3$. Docetaxel (10 mg/kg), which is in the clinic for prostate cancer, was used as a positive control to evaluate its effectiveness in models of parental and P-gp-mediated drug resistant xenografts in vivo.

The results of these studies are summarized in Table 17 below.

TABLE 17

|  |  |  |  |  | Dose (mg/kg) |  | TGI (%) |
|---|---|---|---|---|---|---|---|
| DTX | PC3 | Prostate | IV | 10 | 1/wk | 84 |
|  | PC3/TXR | Prostate (MDR) | IV | 10 | 1/wk | 14 |
|  | MES-SA/DX5 | Uterine (MDR) | IV | 10 | 1/wk | 47 |
|  | OVCAR8 | Ovary | IV | 10 | 1/wk | 22 |
|  | A549 | Lung | IV | 10 | 1/wk | 44 |
|  | C26 | Colon | IV | 10 | 1/wk | 35 |
|  | MCF7 | Breast | IV | 10 | 1/wk | <5 |
| GTx230 | PC3 | Prostate | IV | 10 | 1/wk | 72 |
|  | PC3 | Prostate | PO | 15 | 2/wk | 83 |
|  | PC3/TXR | Prostate (MDR) | PO | 20 | 1/wk | >100 |
|  | OVCAR8 | Ovary | PO | 20 | 1/wk | 8 |
|  | OVCAR8 | Ovary | PO | 15 | 2/wk | 63 |
|  | NCI/ADR-RES | Ovary (MDR) | PO | 15 | 1/wk | 99.6 |
|  | MES-SA/DX5 | Uterine (MDR) | PO | 20 | 1/wk | 60 |
|  | MES-SA/DX5 | Uterine (MDR) | PO | 15 | 2/wk | 72 |
|  | A549 | Lung | PO | 20 | 1/wk | 62 |
|  | C26 | Colon | PO | 20 | 1/wk | 61 |

Non-MDR Xenografts:

Ten (10) mg/kg intravenously administered docetaxel exhibited tumor growth inhibition (TGI) in xenografts: PC-3 (prostate) xenografts of 84%, and to a lesser extent in OVCAR8 (ovarian; TGI of 22%, A549 (lung; TGI of 44%) and C26 (colon; TGI of 35%). DTX administration exhibited less than 5% TGI in breast cancer xenografts. In comparison, Table 17 shows that intravenous or oral administration of 17ya (10/15/20 mg/kg) exhibited reduced tumor growth over a wide range of tumor types including xenografts of: PC3 (prostate; TGI of 72% and 83%), OVCAR8 (ovarian; TGI of 63%), A549 (lung; TGI of 62%) and C26 (colon; TGI of 61%). Thus, compound 17ya was effective in a range of tumor types and particularly showed significantly greater TGI than DTX in ovarian, lung, and colon cancers.

17ya Exhibited Greater Effectiveness than DTX in Drug-Resistant Prostate Tumors.

Comparison of prostate and prostate-MDR tumor growth showed that administration of DTX (10 mg/kg) resulted in a significantly decreased TGI effect from 84% TGI in PC-3 tumors compared with only 14% TGI in PC-3/TxR tumors (Table 17). Thus, the effectiveness of docetaxel in PC-3/TxR tumors was dramatically decreased when compared to that in PC-3 tumors, suggesting that the efficacy of DTX was impaired by P-gp-mediated drug resistance. In contrast to the lack of efficacy of docetaxel in PC-3/TxR tumors, orally administered 17ya (20 mg/kg) demonstrated more than 100% TGI in PC3/TXr xenografts.

In addition, 17ya showed effective tumor growth inhibition (TGI) in MDR-xenografts from NCI/ADR-RES (adriamycin resistant ovarian cancer cells) of 99.6% TGI, and for MES-SA/DX5 (doxorubicin resistant uterine cancer cells) the efficacy was 60% and 72% TGI. (Table 17).

Effectiveness of 17ya in PC3 and PC3/TXR Xenografts (Prostate Cancer and Paclitaxel-Resistant Prostate Cancer, Respectively).

Figure 20A:
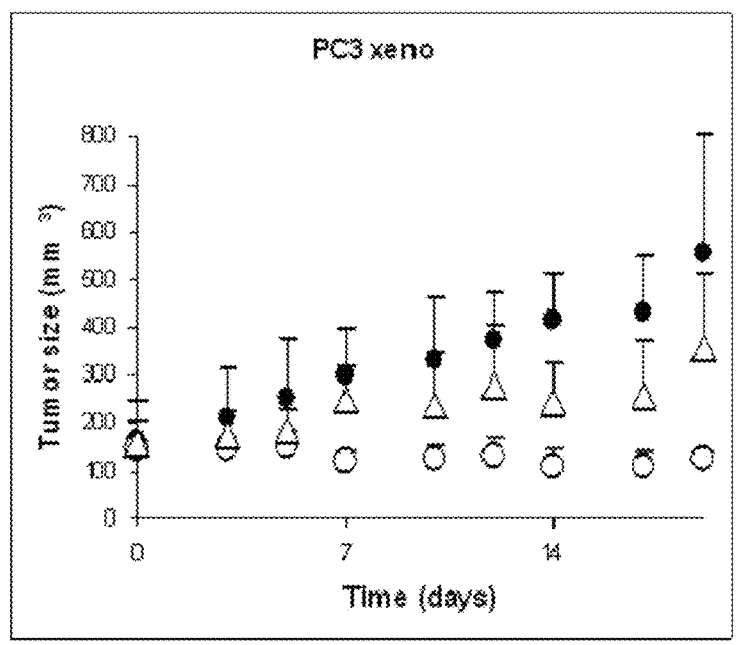
FIGS. 20A-D depict in vivo anti-cancer efficacy of compound 17ya in PC3 and PC3/TXR (prostate cancer and multidrug-resistant prostate cancer) xenograft studies.
Figure 20B:
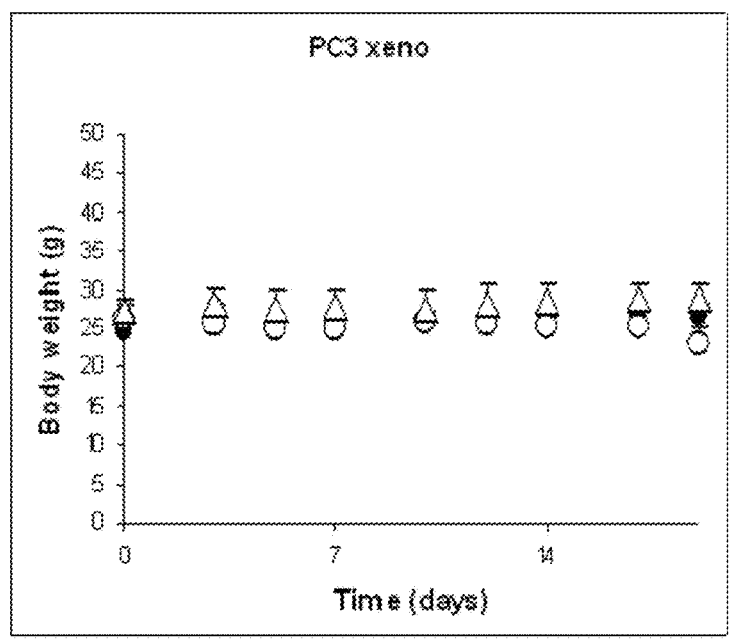

Intravenously administered 17ya at 7 mg/kg once per week or orally administered 17ya at 15 mg/kg once per week in mice bearing PC3 xenografts demonstrated dose responsive reduction (7 mg/kg) and essentially no growth (15 mg/kg) in PC3 tumors (FIG. 20A). The efficacy of 17ya to inhibit tumor growth did not effect body weights during this same time period (FIG. 20B).

Figure 20C:
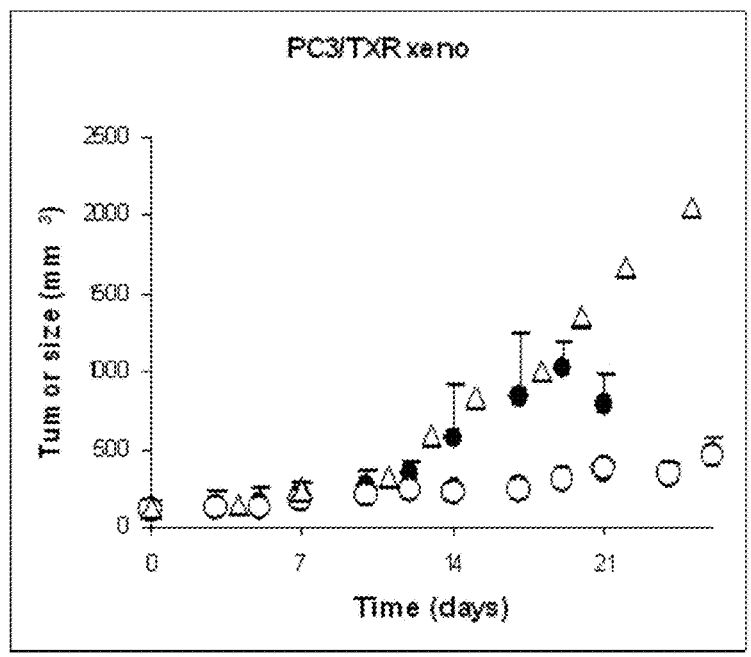
Figure 20D:
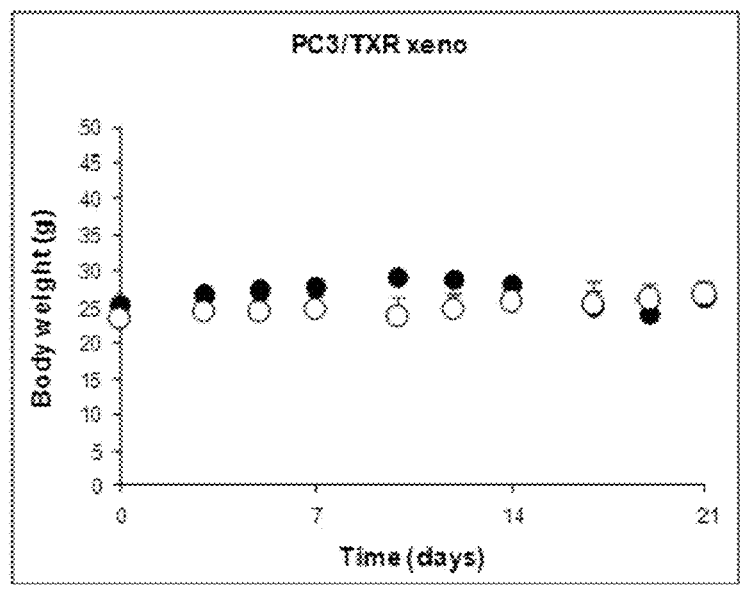

Similarly, orally administered 17ya, 15 mg/kg once per week, exhibited dose responsive inhibition of PC3/TXR tumor growth (FIG. 20C) in the absence of body weight changes during the same time period (FIG. 20D).

Effectiveness of 17ya in NCI/ADR-RES Xenografts (Adriamycin-Resistant Ovarian Cancer).

Figure 21A:
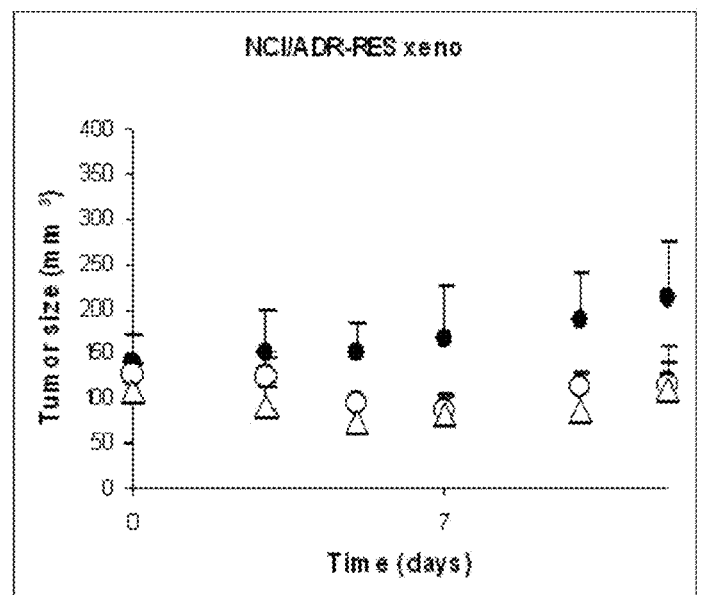
FIGS. 21A-B depict in vivo anti-cancer efficacy of compound 17ya in NCI/ADR-RES (multidrug-resistant ovarian cancer) xenograft studies. Nude mice bearing NCI/ADR-RES (ovarian adriamycin-(multidrug) resistant) tumors were orally administered 15 mg/kg 17ya (○) one time per week, orally administered 15 mg/kg 17ya (Δ) three times per week, or orally administered vehicle alone (•) one time per week, and the effect on tumor size (FIG. 21A) and body weight (FIG. 21B) was measured over time.
Figure 21B:
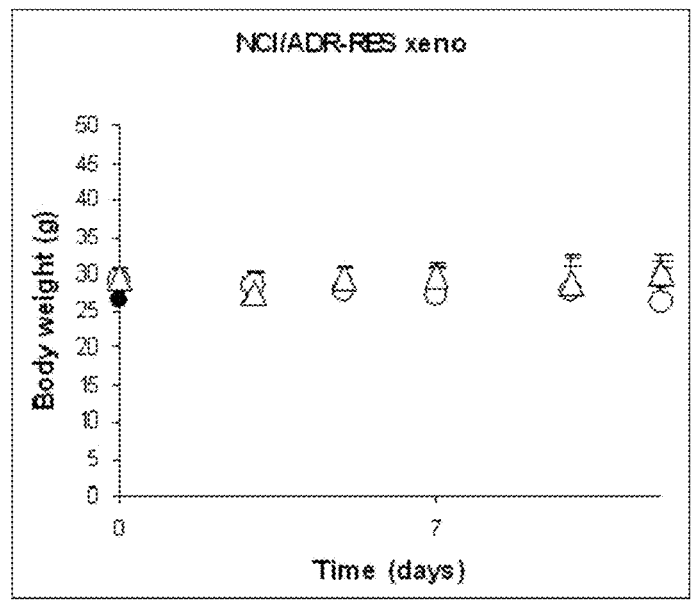

Orally administered 17ya at 15 mg/kg once per week or three-times per week in mice bearing NCI/ADR-RES xenografts demonstrated dose responsive inhibition of tumor growth and reduction of tumor size (FIG. 21A). The efficacy of 17ya to inhibit tumor growth did not effect body weights during this same time period (FIG. 21B).

Effectiveness of 17ya in MES-SA/DX5 Xenografts (Doxorubicin-Resistant Uterine Cancer)

Figure 22A:
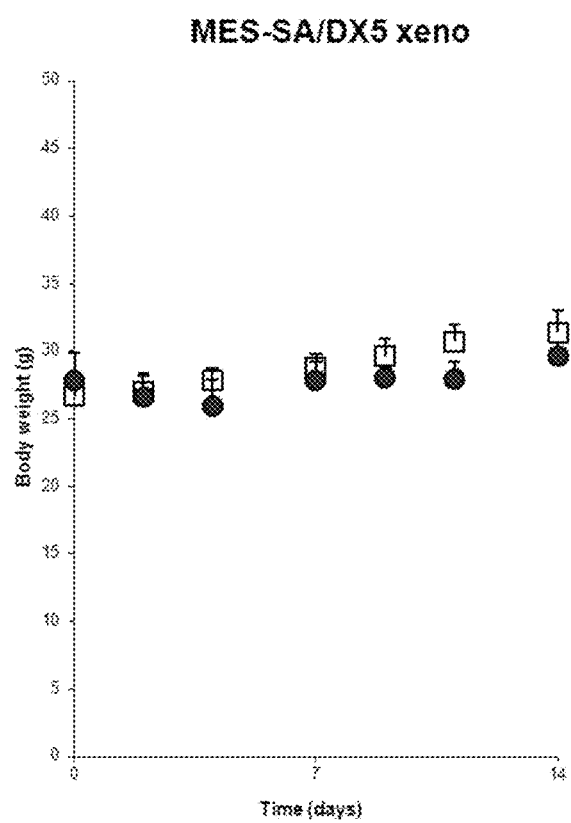
FIGS. 22A-B depict in vivo anti-cancer efficacy of compound 17ya in MES-SA/DX5 (multidrug-resistant uterine cancer) xenograft studies. Nude mice bearing MES-SA/DX5 (uterine doxorubicin-(multidrug) resistant) tumors were orally administered 15 mg/kg 17ya (•) two times per week, orally administered 20 mg/kg 17ya (•-blue) one time per week, intravenously administered 10 mg/kg DTX (▲-orange) one time per week, orally administered vehicle alone (□) two times per week, or orally administered vehicle alone (■) one time per week, and the effect on tumor size (FIG. 22B) and body weight (FIG. 22A) was measured over time.
Figure 22B:
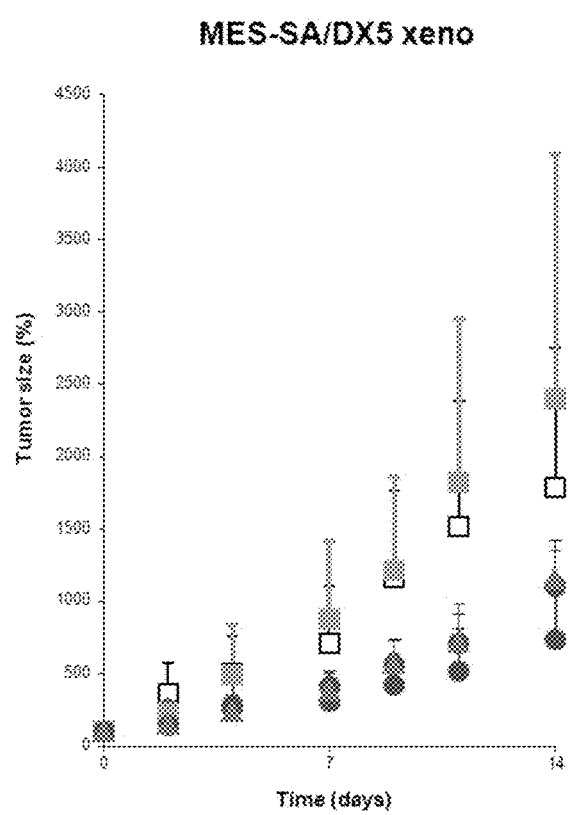

Orally administered 17ya at either 15 mg/kg twice per week or 20 mg/kg once per week, in mice bearing MES-SA/DX5 xenografts demonstrated dose responsive inhibition of tumor growth in comparison with vehicle alone (FIG. 22B). The efficacy of 17ya to inhibit tumor growth did not affect body weights during this same time period (FIG. 22A). Using the data for FIG. 22B, comparison of the different 17ya dosages with intravenously administered DTX at 10 mg/kg once a week showed 17ya at 15 mg/kg twice per week to be the most effective dosage for tumor growth inhibition (72%). 17ya at 20 mg/kg once per week showed 60% tumor growth inhibition, while DTX showed only 47% tumor growth inhibition.

Dosage Regime of 17ya Effects Tumor Growth Inhibition in OVCAR8 Xenografts (Ovarian Cancer)

Figure 23A:
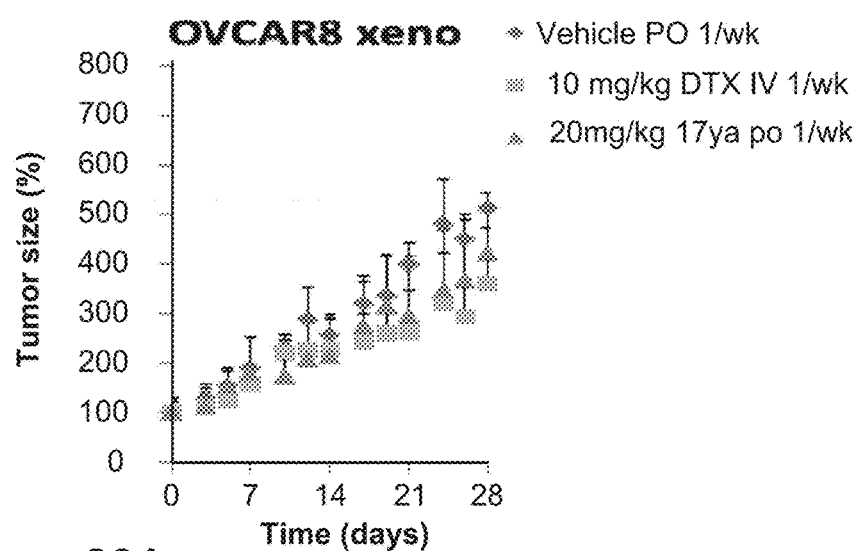
FIGS. 23A-C depict in vivo anti-cancer efficacy of compound 17ya at different dosages in OVCAR8 (ovarian cancer) xenograft studies. Nude mice bearing OVCAR8 (ovarian) tumors orally administered 20 mg/kg 17ya (•-red) one time per week, intravenously administered 10 mg/kg DTX (○) one time per week or orally administered vehicle alone (•-black) one time per week (FIG. 23A), showed minimal reduction of tumor size at the 20 mg/kg 17ya dose administered. In contrast, nude mice bearing OVCAR8 (ovarian) tumors orally administered 15 mg/kg 17ya (•-red) two times per week or orally administered vehicle alone (•-black) two times per week (FIG. 23B), showed significant reduction of tumor size using the 15 mg/kg 17ya dosage regime. Comparison of body weight over time showed a minimal increase in body weight over the same time period.
Figure 23B:
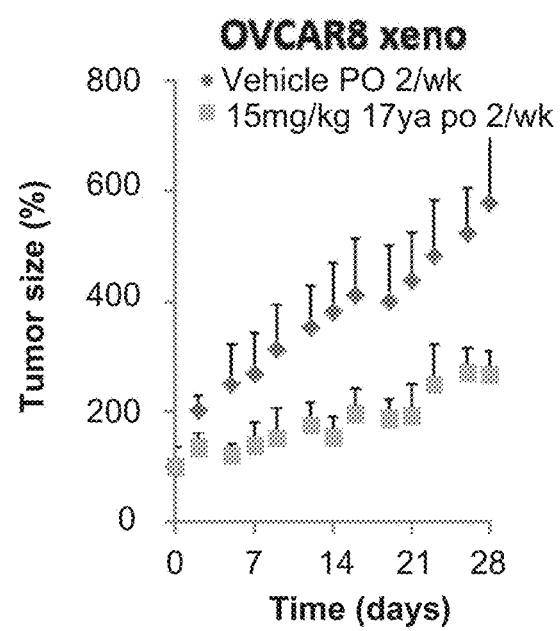
Figure 23C:
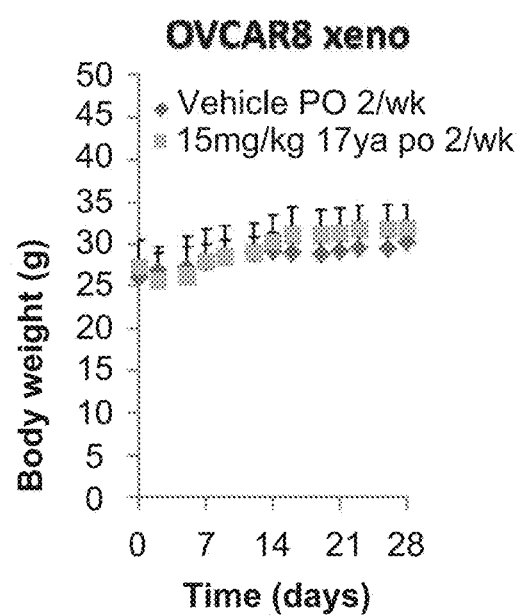

The effectiveness of 17ya to reduce tumor size of ovarian xenoraphs was markedly increased with a twice weekly dosage regime. While orally administered 17ya at 20 mg/kg once per week in mice bearing OVCAR8 xenografts showed minimal reduction of tumor size (8%), orally administered 17ya at 15 mg/kg twice per week, exhibited significant tumor size reduction (63%) compared with vehicle alone (FIGS. 23A and 23B). The effectiveness of intravenously administered DTX at 10 mg/kg once per week was significantly less (22%; FIG. 23A) than the twice-weekly dose regime of 17ya (63%). The twice-weekly 17ya dose regime showed minimal weight increase over the same time period compared with vehicle alone (FIG. 23C).

All of the features described herein (including any accompanying claims, abstract and drawings), and/or all of the steps of any method or process so disclosed, may be combined with any of the above aspects in any combination, except combinations where at least some of such features and/or steps are mutually exclusive. Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of treating, suppressing, reducing the severity, reducing the risk, or inhibiting cancer comprising administering a compound 17ya represented by the structure:

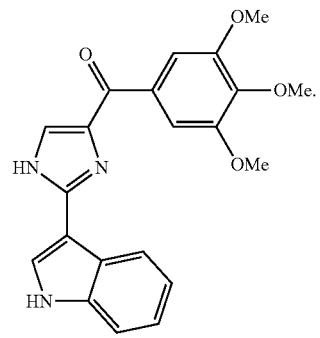

(17ya)

or an N-oxide thereof, or a pharmaceutically acceptable salt thereof, to a subject having cancer under conditions effective to treat the cancer.

2. The method of claim 1, wherein said cancer is selected from the group consisting of prostate cancer, drug-resistant prostate cancer, breast cancer, ovarian cancer, drug-resistant ovarian cancer, skin cancer, melanoma, drug-resistant melanoma, lung cancer, colon cancer, glioma, leukemia, lymphoma, renal cancer, CNS cancer, uterine cancer, drug-resistant uterine cancer, and combinations thereof.

3. The method of claim 2, wherein said cancer is melanoma cancer.

4. The method of claim 2, wherein said cancer is metastatic melanoma.

5. The method of claim 2, wherein said cancer is prostate cancer.

6. The method of claim 5, wherein said prostate cancer is drug-resistant prostate cancer.

7. The method of claim 2, wherein said cancer is ovarian cancer.

8. The method of claim 7, wherein said ovarian cancer is drug-resistant ovarian cancer.

9. The method of claim 2, wherein said cancer is uterine cancer.

10. The method of claim 9, wherein said uterine cancer is drug-resistant uterine cancer.

11. The method of claim 2, wherein said cancer is lung cancer.

12. The method of claim 2, wherein said cancer is colon cancer.

13. The method of claim 2, wherein said administering is carried out in combination with another cancer therapy.

14. A method of treating a drug resistant tumor or tumors comprising administering a compound 17ya represented by the structure:

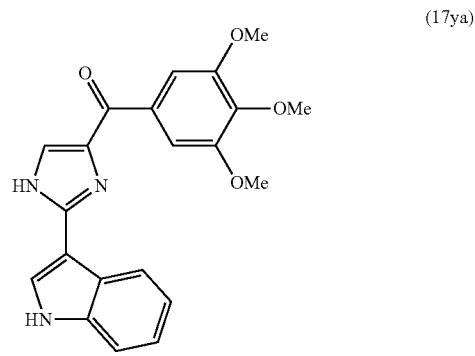 [SMILES: COc1cc(C(=O)c2c[nH]c(-c3c[nH]c4ccccc34)n2)cc(OC)c1OC]

(17ya)

or an N-oxide thereof, or a pharmaceutically acceptable salt thereof, to a subject suffering from cancer under conditions effective to treat the drug resistant tumor or tumors.

15. The method of claim 14, wherein said tumor is a melanoma cancer tumor.

16. The method of claim 14, wherein said tumor is a metastatic melanoma tumor.

17. The method of claim 14, wherein said tumor is a prostate cancer tumor.

18. The method of claim 14, wherein said tumor is an ovarian cancer tumor.

19. The method of claim 14, wherein said tumor is an uterine tumor, breast cancer tumor or glioma tumor.

20. The method of claim 14, wherein said administering is carried out in combination with another cancer therapy.

21. A method of destroying a cancerous cell comprising providing a compound 17ya represented by the structure:

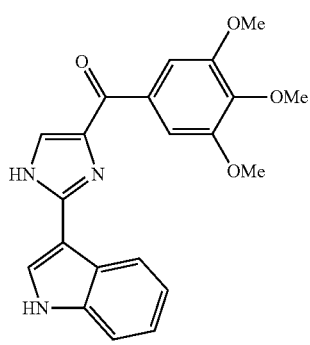

(17ya)

or an N-oxide thereof, or a pharmaceutically acceptable salt thereof and contacting the cancerous cell with said compound under conditions effective to kill the cancer cell.

22. A method of inhibiting, preventing, or slowing the progress of vascularization of a tumor comprising administering a compound 17ya represented by the structure:

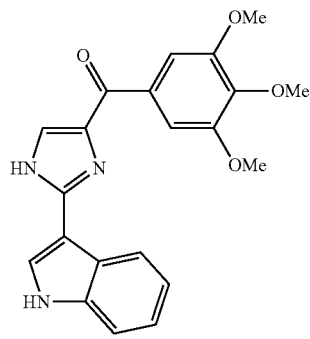

(17ya)

or an N-oxide thereof, or a pharmaceutically acceptable salt thereof, to a subject having cancer under conditions effective to inhibit, prevent or slow the progress of vascularization of said tumor.

23. The method of claim 22, wherein said tumor is selected from the group consisting of prostate cancer tumor, drug-resistant prostate cancer tumor, breast cancer tumor, glioma tumor, ovarian cancer tumor, drug-resistant ovarian cancer tumor, skin cancer tumor, melanoma tumor, drug-resistant melanoma tumor, lung cancer tumor, colon cancer tumor, lymphoma tumor, renal cancer tumor, CNS cancer tumor, uterine cancer tumor, drug-resistant uterine cancer tumor, and combinations thereof.

24. The method of claim 22, wherein said method further inhibits, prevents, or slows the progress of vascularization of a metastatic tumor.

25. The method of claim 24, wherein said tumor is selected from the group consisting of prostate cancer tumor, drug-resistant prostate cancer tumor, breast cancer tumor, glioma tumor, ovarian cancer tumor, drug-resistant ovarian cancer tumor, skin cancer tumor, melanoma tumor, drug-resistant melanoma tumor, lung cancer tumor, colon cancer tumor, leukemia tumor, lymphoma tumor, renal cancer tumor, CNS cancer tumor, uterine cancer tumor, drug-resistant uterine cancer tumor, and combinations thereof.

* * * * *